US012779016B2

(12) United States Patent
Bloom

(10) Patent No.: US 12,779,016 B2
(45) Date of Patent: Nov. 3, 2026

(54) APPETITE SUPPRESSING COMPOUNDS

(71) Applicant: IP2IPO INNOVATIONS LIMITED, London (GB)

(72) Inventor: Stephen Robert Bloom, London (GB)

(73) Assignee: IP2IPO Innovations Limited, London (GB)

( * ) Notice: Subject to any disclaimer, the term of this patent is extended or adjusted under 35 U.S.C. 154(b) by 1048 days.

(21) Appl. No.: 17/618,368

(22) PCT Filed: Jun. 12, 2020

(86) PCT No.: PCT/GB2020/051426
§ 371 (c)(1),
(2) Date: Dec. 10, 2021

(87) PCT Pub. No.: WO2020/249967
PCT Pub. Date: Dec. 17, 2020

(65) Prior Publication Data

US 2022/0257719 A1 Aug. 18, 2022

(30) Foreign Application Priority Data

Jun. 12, 2019 (GB) ..................................... 1908426

(51) Int. Cl.
*A61K 38/22* (2006.01)
*A61K 38/26* (2006.01)
*A61P 3/04* (2006.01)
*C07K 14/575* (2006.01)

(52) U.S. Cl.
CPC .............. *A61K 38/22* (2013.01); *A61K 38/26* (2013.01); *A61P 3/04* (2018.01); *C07K 14/575* (2013.01)

(58) Field of Classification Search
CPC ........... A61K 38/22; A61K 38/26; A61P 3/04; C07K 14/575
See application file for complete search history.

(56) References Cited

U.S. PATENT DOCUMENTS

| | | | |
|---|---|---|---|
| 4,179,337 A | 12/1979 | Davis et al. | |
| 5,700,486 A | 12/1997 | Canal et al. | |
| 5,936,092 A | 8/1999 | Shen et al. | |
| 5,939,380 A | 8/1999 | Wang | |
| 5,993,414 A | 11/1999 | Haller | |
| 6,093,692 A | 7/2000 | Shen et al. | |
| 6,225,445 B1 | 5/2001 | Shen et al. | |
| 6,355,478 B1 | 3/2002 | Baez et al. | |
| 6,410,707 B2 | 6/2002 | Wagner et al. | |
| 6,436,091 B1 | 8/2002 | Harper et al. | |
| 6,447,743 B1 | 9/2002 | Devic et al. | |
| 8,603,969 B2 | 12/2013 | Levy et al. | |
| 2011/0092416 A1 | 4/2011 | Doyle et al. | |
| 2016/0263197 A1* | 9/2016 | Oestergaard | A61K 38/22 |
| 2017/0137486 A1 | 5/2017 | Bloom | |
| 2018/0117170 A1 | 5/2018 | Macielag et al. | |

FOREIGN PATENT DOCUMENTS

| | | |
|---|---|---|
| CN | 102027007 A | 4/2011 |
| CN | 102741278 A | 10/2012 |
| CN | 102905722 A | 1/2013 |
| CN | 103459416 A | 12/2013 |
| JP | 2021505656 A | 2/2021 |
| JP | 2022536761 A | 8/2022 |
| WO | WO 2003/026591 A2 | 4/2003 |
| WO | WO-03057235 A2 | 7/2003 |
| WO | WO 2004/062685 A2 | 7/2004 |
| WO | WO 2005/077094 A2 | 8/2005 |
| WO | WO 2006/066024 A2 | 6/2006 |
| WO | WO 2009/138511 A1 | 11/2009 |
| WO | WO 2011/058165 A1 | 5/2011 |
| WO | WO 2011/092473 A1 | 8/2011 |
| WO | WO 2012/006566 A2 | 1/2012 |
| WO | WO 2012/101413 A1 | 8/2012 |
| WO | WO 2015/177572 A1 | 11/2015 |
| WO | WO 2015/177573 A1 | 11/2015 |
| WO | WO-2020249967 A1 | 12/2020 |

OTHER PUBLICATIONS

Definition of Derivative, Online Medical Dictionary, 2005.*
Barlow, S. E. et al., "Obesity Evaluation and Treatment: Expert Committee Recommendations," Pediatrics, vol. 102, No. 3, Sep. 3, 1998, pp. 1-11.
Buchwald, H., et al.; "Long-term, continuous intravenous heparin administration by an implantable infusion pump in ambulatory patients with recurrent venous thrombosis," Surgery; 88(4):507-516 (1980).
Byrn, S., et al., "Pharmaceutical solids: a strategic approach to regulatory considerations", Pharmaceutical Research (1995); 12(7): 945-954.
Jameson & Wolf, "The antigenic index: a novel algorithm for predicting antigenic determinants," Comput. Appl. Biosci., vol. 4(1), 1988, pp. 181-186.
Jequier, E., "Energy, obesity, and body weight standards," American Journal of Clinical Nutrition, vol. 45, May 1987, pp. 1035-1036.
Kolaskar & Tongaonkar, "A semi-empirical method for prediction of antigenic determinants on protein antigens," FEBS Lett., vol. 10, No. 276(1-2), Dec. 1990, pp. 172-174.
Kopelman, P.G., "Obesity as a medical problem," Nature, vol. 404, Apr. 6, 2000, pp. 635-643.
Langer R. "New Methods of Drug Delivery." Science. Sep. 28, 1990;249(4976): 1527-1533.
National Institutes of Health, "Executive Summary," Obesity Research, vol. 6, Suppl. 2, Sep. 1998, pp. 51S-179S.

(Continued)

*Primary Examiner* — Erinne R Dabkowski
(74) *Attorney, Agent, or Firm* — COOLEY LLP

(57) ABSTRACT

PYY-derived compounds comprising residues changed from the naturally-occurring peptide sequence and substituted, for example at their gamma-carboxylic acid groups, epsilon-amino groups or alpha-amino groups, with fatty dioic acid groups either directly or via short pendant oligopeptides. Related methods, compositions and uses, in particular for use in appetite suppression and the treatment or prevention of diabetes or obesity.

5 Claims, 24 Drawing Sheets

Specification includes a Sequence Listing.

(56) References Cited

OTHER PUBLICATIONS

Pellequer & Westhof, "Preditop: A program for antigenicity prediction," J. Mol. Graph., vol. 11, No. 3, 1993, pp. 204-210 (10 pages total).
Rissanen, A. et al., "Risk of disability and mortality due to overweight in a Finnish population," British Medical Journal, vol. 301, Oct. 13, 1990, pp. 835-837.
Saudek, C.D., et al.; "A preliminary trial of the programmable implantable medication system for insulin delivery," N Engl J Med.; 321(9):574-579 (1989).
Sefton, M.V.; "Implantable pumps," Crit Rev Biomed Eng.; 14(3):201-240 (1987).
Wang, Y. et al., "Parenteral Formulations of Proteins and Peptides: Stability and Stabilizers," Journal of Parenteral Science and Technology, Technical Report No. 10, Supplement 1988, vol. 42, No. 2S, pp. S2-S25.
Batterham, R. L. et al., "Gut hormone $PYY_{3-36}$ physiologically inhibits food intake," *letters to nature*, Aug. 8, 2002, pp. 650-654, vol. 48.
Batterham, R. L. et al., "Inhibition of Food Intake in Obese Subjects by Peptide $YY_{3-36}$," *The New England Journal of Medicine*, Sep. 4, 2003, pp. 941-948, vol. 349, No. 10.
De Silva, A. et al., "Gut Hormones and Appetite Control: A Focus on PYY and GLP-1 as Therapeutic Targets in Obesity," *Gut and Liver*, Jan. 2012, pp. 10-20, vol. 6, No. 1.
Dumont, Y. et al., "Characterization of a Selective Neuropeptide Y/Peptide $YYY_2$ Receptor Radioligand: $[^{125}I]PYY_{3-36}$," Society for Neuroscience Abstracts, 1993, one page, vol. 19 (abstract only).
International Preliminary Report on Patentability Chapter I, Patent Cooperation Treaty Application No. PCT/GB2020/051426, Dec. 23, 2021, 10 pages.
International Search Report and Written Opinion, Patent Cooperation Treaty Application No. PCT/GB2020/051426, Sep. 16, 2020, 14 pages.
Kenchaiah, S. et al., "Obesity and the Risk of Heart Failure," *The New England Journal of Medicine*, vol. 347, No. 5, Aug. 1, 2002, pp. 305-313.
Lim, E.L. et al., "Reversal of type 2 diabetes: normalisation of beta cell function in association with decreased pancreas and liver triacylglycerol," *Diabetologia*, vol. 54, Jun. 9, 2011, pp. 2506-2514.
Lyznicki, J. M. et al., "Obesity: assessment and management in primary care," *American Family Physician*, vol. 63, No. 11, Jun. 2001, pp. 2185-2196.
Massie, B., "Obesity and Heart Failure—Risk Factor or Mechanism? ", The New England Journal of Medicine, 2002, 347, pp. 358-359.
Niida, A., et al., "Antiobesity and emetic effects of a short-length peptide YY analog and its PEGylated and alkylated derivatives," *Bioorganic &Medicinal Chemistry*, vol. 26, Issue 3, Feb. 1, 2018, pp. 566-572.
Nishizawa, N., et al., "Antiobesity Effect of a Short-Length Peptide YY Analogue after Continuous Administration in Mice," *ACS Medical Chemistry Letters*, 2017, vol. 8, No. 6, pp. 628-631.
Tan, T., et al., "The Effect of a Subcutaneous Infusion of GLP-1, Oxm, and PYY on Energy Intake and Expenditure in Obese Volunteers," *The Journal of Clinical Endocrinology & Metabolism*, 2017, vol. 102, No. 7, pp. 2364-2372.
UK Search Report, UK Intellectual Property Office Patent Application No. GB1908426.8, Dec. 23, 2019, 5 pages.

* cited by examiner

| | | SEQ ID NO | -5 | -4 | -3 | -2 | -1 | 1 | 2 | 3 | 4 | 5 | 6 | 7 | 8 | 9 | 10 | 11 | 12 | 13 | 14 |
|---|---|---|---|---|---|---|---|---|---|---|---|---|---|---|---|---|---|---|---|---|---|
| | hPYY | 22 | | | | | | Tyr | Pro | Ile | Lys | Pro | Glu | Ala | Pro | Gly | Glu | Asp | Ala | Ser | Pro |
| Y | 1592 | 47 | | | | | Lys *1 | Gly | Pro | Ile | Lys | Pro | Glu | Ala | Pro | Gly | Glu | Gly | Ala | Ser | Pro |
| Y | 1593 | 48 | | | | | | Lys *1 | Pro | Ile | Lys | Pro | Glu | Ala | Pro | Gly | Glu | Gly | Ala | Ser | Pro |
| Y | 1594 | 49 | | | | | | | Pro | Ile | Lys | Pro | Lys *1 | Ala | Pro | Gly | Glu | Gly | Ala | Ser | Pro |
| Y | 1595 | 50 | | | | | | | Pro | Ile | Lys | Pro | Glu | Lys *1 | Pro | Gly | Glu | Gly | Ala | Ser | Pro |
| Y | 1596 | 51 | | | | | | | Pro | Ile | Lys | Pro | Glu | Ala | Pro | Gly | Lys *1 | Gly | Ala | Ser | Pro |
| Y | 1597 | 52 | | | | | | | Pro | Ile | Lys | Pro | Glu | Ala | Pro | Gly | Glu | Lys *1 | Ala | Ser | Pro |
| Y | 1598 | 53 | | | | | | | Pro | Ile | Lys | Pro | Glu | Ala | Pro | Gly | Glu | Gly | Ala | Ser | Pro |
| Y | 1599 | 54 | | | | | | | Pro | Ile | Lys | Pro | Glu | Ala | Pro | Gly | Glu | Gly | Ala | Ser | Pro |
| Y | 1600 | 55 | | | | | | | Pro | Ile | Lys | Pro | Glu | Ala | Pro | Gly | Glu | Gly | Ala | Ser | Pro |
| Y | 1601 | 56 | | | | | | | Pro | Ile | Lys | Pro | Glu | Ala | Pro | Gly | Glu | Gly | Ala | Ser | Pro |
| Y | 1602 | 57 | | | | | | | Pro | Ile | Lys | Pro | Glu | Ala | Pro | Gly | Glu | Gly | Ala | Ser | Pro |
| Y | 1603 | 58 | | | | | | | Pro | Ile | Lys | Pro | Glu | Ala | Pro | Gly | Glu | Gly | Ala | Ser | Pro |
| Y | 1604 | 59 | | | | | | | Pro | Ile | Lys | Pro | Glu | Ala | Pro | Gly | Glu | Gly | Ala | Ser | Pro |
| Y | 1605 | 60 | | | | | | | Pro | Ile | Lys | Pro | Glu | Ala | Pro | Gly | Glu | Gly | Ala | Ser | Pro |
| Y | 1606 | 61 | | | | | | | Pro | Ile | Lys | Pro | Glu | Ala | Pro | Gly | Glu | Gly | Ala | Ser | Pro |
| Y | 1607 | 62 | | | | | | | Pro | Ile | Lys | Pro | Glu | Lys *53 | Pro | Gly | Glu | Gly | Ala | Ser | Pro |
| Y | 1608 | 63 | | | | | | | Pro | Ile | Lys | Pro | Glu | Lys *2 | Pro | Gly | Glu | Gly | Ala | Ser | Pro |
| Y | 1609 | 64 | | | | | | | Pro | Ile | Lys | Pro | Glu | Lys *3 | Pro | Gly | Glu | Gly | Ala | Ser | Pro |
| Y | 1610 | 65 | | | | | | | Pro | Ile | Lys | Pro | Glu | Lys *4 | Pro | Gly | Glu | Gly | Ala | Ser | Pro |
| Y | 1611 | 66 | | | | | | | Pro | Ile | Lys | Pro | Glu | Lys *5 | Pro | Gly | Glu | Gly | Ala | Ser | Pro |
| Y | 1612 | 67 | | | | | | | Pro | Ile | Lys | Pro | Glu | Lys *2 | Pro | Gly | Glu | Gly | Ala | Ser | Pro |
| Y | 1613 | 68 | | | | | | | Pro | Ile | Lys | Pro | Glu | Lys *3 | Pro | Gly | Glu | Gly | Ala | Ser | Pro |
| Y | 1614 | 69 | | | | | | | Pro | Ile | Lys | Pro | Glu | Lys *6 | Pro | Gly | Glu | Gly | Ala | Ser | Pro |
| Y | 1615 | 70 | | | | | | | Pro | Ile | Lys | Pro | Glu | Lys *7 | Pro | Gly | Glu | Gly | Ala | Ser | Pro |
| Y | 1616 | 71 | | | | | | | Pro | Ile | Lys | Pro | Glu | Lys *8 | Pro | Gly | Glu | Gly | Ala | Ser | Pro |
| Y | 1617 | 72 | | | | | | | Pro | Ile | Lys | Pro | Glu | Lys *54 | Pro | Gly | Glu | Gly | Ala | Ser | Pro |
| Y | 1618 | 73 | | | | | | | Pro | Ile | Lys | Pro | Glu | Lys *9 | Pro | Gly | Glu | Gly | Ala | Ser | Pro |
| Y | 1619 | 74 | | | | | Lys *2 | Gly | Pro | Ile | Lys | Pro | Glu | Ala | Pro | Gly | Glu | Gly | Ala | Ser | Pro |
| Y | 1620 | 75 | | | | | | Lys *2 | Pro | Ile | Lys | Pro | Glu | Ala | Pro | Gly | Glu | Gly | Ala | Ser | Pro |
| Y | 1621 | 76 | | | | | | | Pro | Ile | Lys | Pro | Lys *2 | Ala | Pro | Gly | Glu | Gly | Ala | Ser | Pro |
| Y | 1622 | 77 | | | | | | | Pro | Ile | Lys | Pro | Glu | Ala | Pro | Gly | Lys *2 | Gly | Ala | Ser | Pro |

Figure 1
Part 1

| 15 | 16 | 17 | 18 | 19 | 20 | 21 | 22 | 23 | 24 | 25 | 26 | 27 | 28 | 29 | 30 | 31 | 32 | 33 | 34 | 35 | 36 | | | | |
|---|---|---|---|---|---|---|---|---|---|---|---|---|---|---|---|---|---|---|---|---|---|---|---|---|---|
| Glu | Glu | Leu | Asn | Arg | Tyr | Tyr | Ala | Ser | Leu | Arg | His | Tyr | Leu | Asn | Leu | Val | Thr | Arg | Gln | Arg | Tyr | NH2 | | | hPYY |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1592 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1593 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1594 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1595 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1596 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1597 |
| Glu | Glu | Leu | Lys *1 | His | Tyr | Tyr | Ala | Ala | Leu | Arg | His | Phe | Leu | Asn | His | Val | Thr | Arg | Gln | Arg | Tyr | NH2 | | Y | 1598 |
| Glu | Glu | Leu | Leu | Lys *1 | Tyr | Tyr | Ala | Ala | Leu | Arg | His | Phe | Leu | Asn | His | Val | Thr | Arg | Gln | Arg | Tyr | NH2 | | Y | 1599 |
| Glu | Glu | Leu | Leu | His | Tyr | Tyr | Lys *1 | Ala | Leu | Arg | His | Phe | Leu | Asn | His | Val | Thr | Arg | Gln | Arg | Tyr | NH2 | | Y | 1600 |
| Glu | Glu | Leu | Leu | His | Tyr | Tyr | Ala | Lys *1 | Leu | Arg | His | Phe | Leu | Asn | His | Val | Thr | Arg | Gln | Arg | Tyr | NH2 | | Y | 1601 |
| Glu | Glu | Leu | Leu | His | Tyr | Tyr | Ala | Ala | Leu | Lys *1 | His | Phe | Leu | Asn | His | Val | Thr | Arg | Gln | Arg | Tyr | NH2 | | Y | 1602 |
| Glu | Glu | Leu | Leu | His | Tyr | Tyr | Ala | Ala | Leu | Arg | Lys *1 | Phe | Leu | Asn | His | Val | Thr | Arg | Gln | Arg | Tyr | NH2 | | Y | 1603 |
| Glu | Glu | Leu | Leu | His | Tyr | Tyr | Ala | Ala | Leu | Arg | His | Lys *1 | Leu | Asn | His | Val | Thr | Arg | Gln | Arg | Tyr | NH2 | | Y | 1604 |
| Glu | Glu | Leu | Leu | His | Tyr | Tyr | Ala | Ala | Leu | Arg | His | Phe | Leu | Asn | Lys *1 | Val | Thr | Arg | Gln | Arg | Tyr | NH2 | | Y | 1605 |
| Glu | Glu | Leu | Leu | His | Tyr | Tyr | Ala | Ala | Leu | Arg | His | Phe | Leu | Asn | Lys *2 | Val | Thr | Arg | Gln | Arg | Tyr | NH2 | | Y | 1606 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1607 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1608 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1609 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1610 |
| Glu | Glu | Ile | Leu | Lys | Tyr | Tyr | Ile | Glu | Leu | Arg | His | Phe | Leu | Asn | His | Leu | Thr | Arg | Gln | Arg | Tyr | NH2 | | Y | 1611 |
| Glu | Glu | Ile | Leu | Lys | Tyr | Tyr | Ile | Glu | Leu | Arg | His | Phe | Leu | Asn | His | Leu | Thr | Arg | Gln | Arg | Tyr | NH2 | | Y | 1612 |
| Glu | Glu | Ile | Leu | Lys | Tyr | Tyr | Ile | Glu | Leu | Arg | His | Phe | Leu | Asn | His | Leu | Thr | Arg | Gln | Arg | Tyr | NH2 | | Y | 1613 |
| Glu | Glu | Ile | Leu | Lys | Tyr | Tyr | Ile | Glu | Leu | Arg | His | Phe | Leu | Asn | His | Leu | Thr | Arg | Gln | Arg | Tyr | NH2 | | Y | 1614 |
| Glu | Glu | Ile | Leu | Lys | Tyr | Tyr | Ile | Glu | Leu | Arg | His | Phe | Leu | Asn | His | Leu | Thr | Arg | Gln | Arg | Tyr | NH2 | | Y | 1615 |
| Glu | Glu | Ile | Leu | Lys | Tyr | Tyr | Ile | Glu | Leu | Arg | His | Phe | Leu | Asn | His | Leu | Thr | Arg | Gln | Arg | Tyr | NH2 | | Y | 1616 |
| Glu | Glu | Ile | Leu | Lys | Tyr | Tyr | Ile | Glu | Leu | Arg | His | Phe | Leu | Asn | His | Leu | Thr | Arg | Gln | Arg | Tyr | NH2 | | Y | 1617 |
| Glu | Glu | Ile | Leu | Lys | Tyr | Tyr | Ile | Glu | Leu | Arg | His | Phe | Leu | Asn | His | Leu | Thr | Arg | Gln | Arg | Tyr | NH2 | | Y | 1618 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1619 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1620 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1621 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1622 |

Figure 1
Part 2

| | | SEQ ID NO | -5 | -4 | -3 | -2 | -1 | 1 | 2 | 3 | 4 | 5 | 6 | 7 | 8 | 9 | 10 | 11 | 12 | 13 | 14 |
|---|---|---|---|---|---|---|---|---|---|---|---|---|---|---|---|---|---|---|---|---|---|
| Y | 1623 | 78 | | | | | | | Pro | Ile | Lys | Pro | Glu | Ala | Pro | Gly | Glu | Lys *2 | Ala | Ser | Pro |
| Y | 1624 | 79 | | | | | | | Pro | Ile | Lys | Pro | Glu | Ala | Pro | Gly | Glu | Gly | Ala | Ser | Pro |
| Y | 1625 | 80 | | | | | | | Pro | Ile | Lys | Pro | Glu | Ala | Pro | Gly | Glu | Gly | Ala | Ser | Pro |
| Y | 1626 | 81 | | | | | | | Pro | Ile | Lys | Pro | Glu | Ala | Pro | Gly | Glu | Gly | Ala | Ser | Pro |
| Y | 1627 | 82 | | | | | | | Pro | Ile | Lys | Pro | Glu | Ala | Pro | Gly | Glu | Gly | Ala | Ser | Pro |
| Y | 1628 | 83 | | | | | | | Pro | Ile | Lys | Pro | Glu | Ala | Pro | Gly | Glu | Gly | Ala | Ser | Pro |
| Y | 1629 | 84 | | | | | | | Pro | Ile | Lys | Pro | Glu | Ala | Pro | Gly | Glu | Gly | Ala | Ser | Pro |
| Y | 1630 | 85 | | | | | | | Pro | Ile | Lys | Pro | Glu | Ala | Pro | Gly | Glu | Gly | Ala | Ser | Pro |
| Y | 1631 | 86 | | | | | | | Pro | Ile | Lys | Pro | Glu | Ala | Pro | Gly | Glu | Gly | Ala | Ser | Pro |
| Y | 1632 | 87 | | | | | | | Pro | Ile | Lys | Pro | Lys *11 | Ala | Pro | Gly | Glu | Gly | Ala | Ser | Pro |
| Y | 1633 | 88 | | | | | | | Pro | Ile | Lys | Pro | Glu | Ala | Pro | Gly | Lys *11 | Gly | Ala | Ser | Pro |
| Y | 1634 | 89 | | | | | | | Pro | Ile | Lys | Pro | Glu | Ala | Pro | Gly | Glu | Lys *12 | Ala | Ser | Pro |
| Y | 1635 | 90 | | | | | | | Pro | Ile | Lys | Pro | Glu | Lys *12 | Pro | Gly | Glu | Gly | Ala | Ser | Pro |
| Y | 1636 | 91 | | Glu *10 | Gly | Ser | Gly | Gly | Pro | Ile | Lys | Pro | Glu | Ala | Pro | Gly | Glu | Gly | Ala | Ser | Pro |
| Y | 1637 | 92 | | Glu *10 | Gly | Ser | Gly | Gly | Pro | Ile | Lys | Pro | Glu | Ala | Pro | Gly | Glu | Gly | Ala | Ser | Pro |
| Y | 1638 | 93 | | | | | Lys *53 | Gly | Pro | Ile | Lys | Pro | Glu | Ala | Pro | Gly | Glu | Gly | Ala | Ser | Pro |
| Y | 1639 | 94 | | | | | Lys *53 | Gly | Pro | Ile | Lys | Pro | Glu | Ala | Pro | Gly | Glu | Gly | Ala | Ser | Pro |
| Y | 1640 | 95 | | | | | | Lys *53 | Pro | Ile | Lys | Pro | Glu | Ala | Pro | Gly | Glu | Gly | Ala | Ser | Pro |
| Y | 1641 | 96 | | | | | | Lys *53 | Pro | Ile | Lys | Pro | Glu | Ala | Pro | Gly | Glu | Gly | Ala | Ser | Pro |
| Y | 1642 | 97 | | | | | | | Pro | Ile | Lys | Pro | Glu | Ala | Pro | Gly | Lys *53 | Gly | Ala | Ser | Pro |
| Y | 1643 | 98 | | | | | | | Pro | Ile | Lys | Pro | Glu | Ala | Pro | Gly | Lys *53 | Gly | Ala | Ser | Pro |
| Y | 1644 | 99 | | | | | | | Pro | Ile | Lys | Pro | Glu | Ala | Pro | Gly | Glu | Gly | Ala | Ser | Pro |
| Y | 1645 | 100 | | | | | | | Pro | Ile | Lys | Pro | Glu | Ala | Pro | Gly | Glu | Gly | Ala | Ser | Pro |
| Y | 1646 | 101 | | | | | | | Pro | Ile | Lys | Pro | Glu | Lys *53 | Pro | Gly | Glu | Gly | Ala | Ser | Pro |
| Y | 1647 | 102 | | | | | | | Pro | Ile | Lys | Pro | Glu | Lys *55 | Pro | Gly | Glu | Gly | Ala | Ser | Pro |
| Y | 1648 | 103 | | | | | | | Pro | Ile | Lys | Pro | Glu | Lys *13 | Pro | Gly | Glu | Gly | Ala | Ser | Pro |
| Y | 1649 | 104 | | | | | | | Pro | Ile | Lys | Pro | Glu | Lys *14 | Pro | Gly | Glu | Gly | Ala | Ser | Pro |
| Y | 1650 | 105 | | | | | | | Pro | Ile | Lys | Pro | Glu | Lys *7 | Pro | Gly | Lys | Gly | Ala | Ser | Pro |
| Y | 1651 | 106 | | | | | | | Pro | Ile | Lys | Pro | Glu | Lys *7 | Pro | Gly | Lys | Asp | Ala | Ser | Pro |
| Y | 1652 | 107 | | | | | | | Pro | Ile | Lys | Pro | Glu | Lys *7 | Pro | Gly | Glu | Gly | Ala | Ser | Pro |
| Y | 1653 | 108 | | | | | | | Pro | Ile | Lys | Pro | Glu | Lys *7 | Pro | Gly | Glu | Asn | Ala | Ser | Pro |
| Y | 1654 | 109 | | | | | | | Pro | Ile | Lys | Pro | Glu | Ala | Pro | Lys *53 | Glu | Gly | Ala | Ser | Pro |

Figure 1
Part 3

| 15 | 16 | 17 | 18 | 19 | 20 | 21 | 22 | 23 | 24 | 25 | 26 | 27 | 28 | 29 | 30 | 31 | 32 | 33 | 34 | 35 | 36 | | | | |
|---|---|---|---|---|---|---|---|---|---|---|---|---|---|---|---|---|---|---|---|---|---|---|---|---|---|
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1623 |
| Glu | Glu | Leu | Lys *2 | His | Tyr | Tyr | Ala | Ala | Leu | Arg | His | Phe | Leu | Asn | His | Val | Thr | Arg | Gln | Arg | Tyr | NH2 | | Y | 1624 |
| Glu | Glu | Leu | Leu | Lys *2 | Tyr | Tyr | Ala | Ala | Leu | Arg | His | Phe | Leu | Asn | His | Val | Thr | Arg | Gln | Arg | Tyr | NH2 | | Y | 1625 |
| Glu | Glu | Leu | Leu | His | Tyr | Tyr | Lys *2 | Ala | Leu | Arg | His | Phe | Leu | Asn | His | Val | Thr | Arg | Gln | Arg | Tyr | NH2 | | Y | 1626 |
| Glu | Glu | Leu | Leu | His | Tyr | Tyr | Ala | Lys *2 | Leu | Arg | His | Phe | Leu | Asn | His | Val | Thr | Arg | Gln | Arg | Tyr | NH2 | | Y | 1627 |
| Glu | Glu | Leu | Leu | His | Tyr | Tyr | Ala | Ala | Leu | Lys *2 | His | Phe | Leu | Asn | His | Val | Thr | Arg | Gln | Arg | Tyr | NH2 | | Y | 1628 |
| Glu | Glu | Leu | Leu | His | Tyr | Tyr | Ala | Ala | Leu | Arg | Lys *2 | Phe | Leu | Asn | His | Val | Thr | Arg | Gln | Arg | Tyr | NH2 | | Y | 1629 |
| Glu | Glu | Leu | Leu | His | Tyr | Tyr | Ala | Ala | Leu | Arg | His | Lys *2 | Leu | Asn | His | Val | Thr | Arg | Gln | Arg | Tyr | NH2 | | Y | 1630 |
| Glu | Glu | Leu | Leu | His | Tyr | Tyr | Ala | Ala | Leu | Arg | His | Phe | Leu | Asn | Lys *2 | Val | Thr | Arg | Gln | Arg | Tyr | NH2 | | Y | 1631 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1632 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1633 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1634 |
| Glu | Glu | Ile | Leu | Lys | Tyr | Tyr | Ile | Glu | Leu | Arg | His | Phe | Leu | Asn | His | Leu | Thr | Arg | Gln | Arg | Tyr | NH2 | | Y | 1635 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1636 |
| Glu | Glu | Ile | Leu | Lys | Tyr | Tyr | Ile | Glu | Leu | Arg | His | Phe | Leu | Asn | His | Leu | Thr | Arg | Gln | Arg | Tyr | NH2 | | Y | 1637 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1638 |
| Glu | Glu | Ile | Leu | Lys | Tyr | Tyr | Ile | Glu | Leu | Arg | His | Phe | Leu | Asn | His | Leu | Thr | Arg | Gln | Arg | Tyr | NH2 | | Y | 1639 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1640 |
| Glu | Glu | Ile | Leu | Lys | Tyr | Tyr | Ile | Glu | Leu | Arg | His | Phe | Leu | Asn | His | Leu | Thr | Arg | Gln | Arg | Tyr | NH2 | | Y | 1641 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1642 |
| Glu | Glu | Ile | Leu | Lys | Tyr | Tyr | Ile | Glu | Leu | Arg | His | Phe | Leu | Asn | His | Leu | Thr | Arg | Gln | Arg | Tyr | NH2 | | Y | 1643 |
| Glu | Glu | Leu | Lys *53 | His | Tyr | Tyr | Ala | Ala | Leu | Arg | His | Phe | Leu | Asn | His | Val | Thr | Arg | Gln | Arg | Tyr | NH2 | | Y | 1644 |
| Glu | Glu | Ile | Lys *53 | Lys | Tyr | Tyr | Ile | Glu | Leu | Arg | His | Phe | Leu | Asn | His | Leu | Thr | Arg | Gln | Arg | Tyr | NH2 | | Y | 1645 |
| Glu | Glu | Ile | Leu | Lys | Tyr | Tyr | Ile | Glu | Leu | Arg | His | Phe | Leu | Asn | His | Leu | Thr | Arg | Gln | Arg | Tyr | NH2 | | Y | 1646 |
| Glu | Glu | Ile | Leu | Lys | Tyr | Tyr | Ile | Glu | Leu | Arg | His | Phe | Leu | Asn | His | Leu | Thr | Arg | Gln | Arg | Tyr | NH2 | | Y | 1647 |
| Glu | Glu | Ile | Leu | Lys | Tyr | Tyr | Ile | Glu | Leu | Arg | His | Phe | Leu | Asn | His | Leu | Thr | Arg | Gln | Arg | Tyr | NH2 | | Y | 1648 |
| Glu | Glu | Ile | Leu | Lys | Tyr | Tyr | Ile | Glu | Leu | Arg | His | Phe | Leu | Asn | His | Leu | Thr | Arg | Gln | Arg | Tyr | NH2 | | Y | 1649 |
| Glu | Glu | Leu | Ala | His | Tyr | Tyr | Ile | Glu | Leu | Arg | His | Phe | Leu | Asn | Lys | Val | Thr | Arg | Gln | Arg | Tyr | NH2 | | Y | 1650 |
| Glu | Glu | Ile | Leu | Arg | Tyr | Tyr | Ile | Glu | Leu | Arg | His | Phe | Leu | Asn | His | Leu | Thr | Arg | Gln | Arg | Tyr | NH2 | | Y | 1651 |
| Glu | Glu | Ile | Leu | His | Tyr | Tyr | Ala | Ala | Leu | Arg | His | Phe | Leu | Asn | His | Leu | Thr | Arg | Gln | Arg | Tyr | NH2 | | Y | 1652 |
| Glu | Glu | Ile | Leu | Lys | Tyr | Tyr | Ile | Glu | Leu | Arg | His | Phe | Leu | Asn | His | Leu | Thr | Arg | Gln | Arg | Tyr | NH2 | | Y | 1653 |
| Glu | Glu | Ile | Leu | Lys | Tyr | Tyr | Ile | Glu | Leu | Arg | His | Phe | Leu | Asn | His | Leu | Thr | Arg | Gln | Arg | Tyr | NH2 | | Y | 1654 |

Figure 1
Part 4

| | | SEQ ID NO | -5 | -4 | -3 | -2 | -1 | 1 | 2 | 3 | 4 | 5 | 6 | 7 | 8 | 9 | 10 | 11 | 12 | 13 | 14 |
|---|---|---|---|---|---|---|---|---|---|---|---|---|---|---|---|---|---|---|---|---|---|
| Y | 1655 | 110 | | | | | | | Pro | Ile | Lys | Pro | Glu | Ala | Pro | Gly | Glu | Gly | Lys *53 | Ser | Pro |
| Y | 1656 | 111 | | | | | | | Pro | Ile | Lys | Pro | Glu | Lys *56 | Pro | Gly | Glu | Gly | Ala | Ser | Pro |
| Y | 1657 | 112 | | | | | | | Pro | Ile | Lys | Pro | Glu | Lys *15 | Pro | Gly | Glu | Gly | Ala | Ser | Pro |
| Y | 1658 | 113 | | | | | | | Pro | Ile | Lys | Pro | Glu | Lys *16 | Pro | Gly | Glu | Gly | Ala | Ser | Pro |
| Y | 1659 | 114 | | | | | | | Pro | Ile | Lys | Pro | Glu | Lys *57 | Pro | Gly | Glu | Gly | Ala | Ser | Pro |
| Y | 1660 | 115 | | | | | | | Pro | Ile | Lys | Pro | Glu | Ala | Pro | Gly | Glu | Gly | Ala | Ser | Pro |
| Y | 1661 | 116 | | | | | | | Pro | Ile | Lys | Pro | Glu | Ala | Pro | Gly | Glu | Gly | Ala | Ser | Pro |
| Y | 1662 | 117 | | | | | | | Pro | Ile | Lys | Pro | Glu | Ala | Pro | Gly | Glu | Gly | Ala | Ser | Lys *2 |
| Y | 1663 | 118 | | | | | | | Pro | Ile | Lys | Pro | Glu | Ala | Pro | Gly | Glu | Gly | Ala | Lys *2 | Pro |
| Y | 1664 | 119 | | | | | | | Pro | Ile | Lys | Pro | Glu | Ala | Pro | Gly | Glu | Gly | Lys *2 | Ser | Pro |
| Y | 1665 | 120 | | | | | | | Pro | Ile | Lys | Pro | Glu | Ala | Pro | Lys *2 | Glu | Gly | Ala | Ser | Pro |
| Y | 1666 | 121 | | | | | | | Pro | Ile | Lys *2 | Pro | Glu | Ala | Pro | Gly | Glu | Gly | Ala | Ser | Pro |
| Y | 1667 | 122 | | | | | | | Pro | Lys *2 | Lys | Pro | Glu | Ala | Pro | Gly | Glu | Gly | Ala | Ser | Pro |
| Y | 1668 | 123 | | | | | Gly *10 | Ser | Pro | Ile | Lys | Pro | Glu | Ala | Pro | Gly | Glu | Gly | Ala | Ser | Pro |
| Y | 1669 | 124 | | | | | Gly *10 | Thr | Pro | Ile | Lys | Pro | Glu | Ala | Pro | Gly | Glu | Gly | Ala | Ser | Pro |
| Y | 1670 | 125 | | | | | Gly *10 | Tyr | Pro | Ile | Lys | Pro | Glu | Ala | Pro | Gly | Glu | Gly | Ala | Ser | Pro |
| Y | 1671 | 126 | | | | Glu *10 | Gly | Ser | Pro | Ile | Lys | Pro | Glu | Ala | Pro | Gly | Glu | Gly | Ala | Ser | Pro |
| Y | 1672 | 127 | | | Ser *10 | Gly | Gly | Ser | Pro | Ile | Lys | Pro | Glu | Ala | Pro | Gly | Glu | Gly | Ala | Ser | Pro |
| Y | 1673 | 128 | | | | Lys *17 | Gly | Ser | Pro | Ile | Lys | Pro | Glu | Ala | Pro | Gly | Glu | Gly | Ala | Ser | Pro |
| Y | 1674 | 129 | | | | | | Lys *10 | Pro | Ile | Lys | Pro | Glu | Ala | Pro | Gly | Glu | Gly | Ala | Ser | Pro |
| Y | 1675 | 130 | | | | | | Lys *17 | Pro | Ile | Lys | Pro | Glu | Ala | Pro | Gly | Glu | Gly | Ala | Ser | Pro |
| Y | 1676 | 131 | | | | | Lys *17 | Gly | Pro | Ile | Lys | Pro | Glu | Ala | Pro | Gly | Glu | Gly | Ala | Ser | Pro |
| Y | 1677 | 132 | | | | | Lys *17 | Ser | Pro | Ile | Lys | Pro | Glu | Ala | Pro | Gly | Glu | Gly | Ala | Ser | Pro |
| Y | 1678 | 133 | | | | Lys *17 | Ser | Gly | Pro | Ile | Lys | Pro | Glu | Ala | Pro | Gly | Glu | Gly | Ala | Ser | Pro |
| Y | 1679 | 134 | | | | Lys *17 | Thr | Gly | Pro | Ile | Lys | Pro | Glu | Ala | Pro | Gly | Glu | Gly | Ala | Ser | Pro |
| Y | 1680 | 135 | | | | Lys *18 | Ser | Gly | Pro | Ile | Lys | Pro | Glu | Ala | Pro | Gly | Glu | Gly | Ala | Ser | Pro |
| Y | 1681 | 136 | | | | | Lys *10 | Gly | Pro | Ile | Lys | Pro | Glu | Ala | Pro | Gly | Glu | Gly | Ala | Ser | Pro |
| Y | 1682 | 137 | | | | | Lys *19 | Gly | Pro | Ile | Lys | Pro | Glu | Ala | Pro | Gly | Glu | Gly | Ala | Ser | Pro |
| Y | 1683 | 138 | | | | | Lys *20 | Gly | Pro | Ile | Lys | Pro | Glu | Ala | Pro | Gly | Glu | Gly | Ala | Ser | Pro |
| Y | 1684 | 139 | | | | Lys *58 | Ser | Gly | Pro | Ile | Lys | Pro | Glu | Ala | Pro | Gly | Glu | Gly | Ala | Ser | Pro |
| Y | 1685 | 140 | | | | Lys *58 | Thr | Gly | Pro | Ile | Lys | Pro | Glu | Ala | Pro | Gly | Glu | Gly | Ala | Ser | Pro |
| Y | 1686 | 141 | | | | Lys *59 | Ser | Gly | Pro | Ile | Lys | Pro | Glu | Ala | Pro | Gly | Glu | Gly | Ala | Ser | Pro |

Figure 1
Part 5

| 15 | 16 | 17 | 18 | 19 | 20 | 21 | 22 | 23 | 24 | 25 | 26 | 27 | 28 | 29 | 30 | 31 | 32 | 33 | 34 | 35 | 36 | | | | |
|---|---|---|---|---|---|---|---|---|---|---|---|---|---|---|---|---|---|---|---|---|---|---|---|---|---|
| Glu | Glu | Ile | Leu | Lys | Tyr | Tyr | Ile | Glu | Leu | Arg | His | Phe | Leu | Asn | His | Leu | Thr | Arg | Gln | Arg | Tyr | NH2 | | Y | 1655 |
| Glu | Glu | Ile | Leu | Lys | Tyr | Tyr | Ile | Glu | Leu | Arg | His | Phe | Leu | Asn | His | Leu | Thr | Arg | Gln | Arg | Tyr | NH2 | | Y | 1656 |
| Glu | Glu | Ile | Leu | Lys | Tyr | Tyr | Ile | Glu | Leu | Arg | His | Phe | Leu | Asn | His | Leu | Thr | Arg | Gln | Arg | Tyr | NH2 | | Y | 1657 |
| Glu | Glu | Ile | Leu | Lys | Tyr | Tyr | Ile | Glu | Leu | Arg | His | Phe | Leu | Asn | His | Leu | Thr | Arg | Gln | Arg | Tyr | NH2 | | Y | 1658 |
| Glu | Glu | Ile | Leu | Lys | Tyr | Tyr | Ile | Glu | Leu | Arg | His | Phe | Leu | Asn | His | Leu | Thr | Arg | Gln | Arg | Tyr | NH2 | | Y | 1659 |
| Glu | Lys *2 | Leu | Leu | His | Tyr | Tyr | Ala | Ala | Leu | Arg | His | Phe | Leu | Asn | His | Val | Thr | Arg | Gln | Arg | Tyr | NH2 | | Y | 1660 |
| Lys *2 | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1661 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1662 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1663 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1664 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1665 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1666 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1667 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1668 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1669 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1670 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1671 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1672 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1673 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1674 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1675 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1676 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1677 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1678 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1679 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1680 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1681 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1682 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1683 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1684 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1685 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1686 |

Figure 1
Part 6

| | | SEQ ID NO | -5 | -4 | -3 | -2 | -1 | 1 | 2 | 3 | 4 | 5 | 6 | 7 | 8 | 9 | 10 | 11 | 12 | 13 | 14 |
|---|---|---|---|---|---|---|---|---|---|---|---|---|---|---|---|---|---|---|---|---|---|
| Y | 1687 | 142 | | | | | | Lys *21 | Pro | Ile | Lys | Pro | Glu | Ala | Pro | Gly | Glu | Gly | Ala | Ser | Pro |
| Y | 1688 | 143 | | | | | | Lys *22 | Pro | Ile | Lys | Pro | Glu | Ala | Pro | Gly | Glu | Gly | Ala | Ser | Pro |
| Y | 1689 | 144 | | | | Glu *10 | Ser | Gly | Pro | Ile | Lys | Pro | Glu | Ala | Pro | Gly | Glu | Gly | Ala | Ser | Pro |
| Y | 1690 | 145 | | | | Glu *19 | Ser | Gly | Pro | Ile | Lys | Pro | Glu | Ala | Pro | Gly | Glu | Gly | Ala | Ser | Pro |
| Y | 1691 | 146 | | | | Glu *10 | Thr | Gly | Pro | Ile | Lys | Pro | Glu | Ala | Pro | Gly | Glu | Gly | Ala | Ser | Pro |
| Y | 1692 | 147 | Glu | Tyr | Glu | Lys *10 | Glu | Tyr | Pro | Ile | Lys | Pro | Glu | Ala | Pro | Gly | Glu | Gly | Ala | Ser | Pro |
| Y | 1693 | 148 | | | | | Lys *53 | Gly | Pro | Ile | Lys | Pro | Glu | Ala | Pro | Gly | Glu | Gly | Ala | Ser | Pro |
| Y | 1694 | 149 | | | | | Lys *53 | Gly | Pro | Ile | Lys | Pro | Glu | Ala | Pro | Gly | Glu | Asn | Ala | Ser | Pro |
| Y | 1695 | 150 | | | | | Lys *53 | Gly | Pro | Ile | Lys | Pro | Glu | Ala | Pro | Gly | Lys | Asp | Ala | Ser | Pro |
| Y | 1696 | 151 | Glu | Tyr | Glu | Lys *19 | Glu | Tyr | Pro | Ile | Lys | Pro | Glu | Ala | Pro | Gly | Glu | Gly | Ala | Ser | Pro |
| Y | 1697 | 152 | Glu | Tyr | Glu | Lys *21 | Glu | Tyr | Pro | Ile | Lys | Pro | Glu | Ala | Pro | Gly | Glu | Gly | Ala | Ser | Pro |
| Y | 1698 | 153 | | | | Lys *10 | Glu | Tyr | Pro | Ile | Lys | Pro | Glu | Ala | Pro | Gly | Glu | Gly | Ala | Ser | Pro |
| Y | 1699 | 154 | | | | Lys *21 | Glu | Tyr | Pro | Ile | Lys | Pro | Glu | Ala | Pro | Gly | Glu | Gly | Ala | Ser | Pro |
| Y | 1700 | 155 | | | | | Glu *23 | Tyr | Pro | Ile | Lys | Pro | Glu | Ala | Pro | Gly | Glu | Gly | Ala | Ser | Pro |
| Y | 1701 | 156 | Tyr | Glu | Lys *2 | Glu | Tyr | Glu | Pro | Ile | Lys | Pro | Glu | Ala | Pro | Gly | Glu | Gly | Ala | Ser | Pro |
| Y | 1702 | 157 | Tyr | Glu | Lys *10 | Glu | Tyr | Glu | Pro | Ile | Lys | Pro | Glu | Ala | Pro | Gly | Glu | Gly | Ala | Ser | Pro |
| Y | 1703 | 158 | | | Lys *10 | Glu | Tyr | Glu | Pro | Ile | Lys | Pro | Glu | Ala | Pro | Gly | Glu | Gly | Ala | Ser | Pro |
| Y | 1704 | 159 | | Glu | Tyr | Glu | Lys *10 | Glu | Pro | Ile | Lys | Pro | Glu | Ala | Pro | Gly | Glu | Gly | Ala | Ser | Pro |
| Y | 1705 | 160 | | | | Gly *10 | Gly | Thr | Pro | Ile | Lys | Pro | Glu | Ala | Pro | Gly | Glu | Gly | Ala | Ser | Pro |
| Y | 1706 | 161 | Glu *11 | Gly | Ser | Gly | Gly | Ala | Pro | Ile | Lys | Pro | Glu | Ala | Pro | Gly | Glu | Gly | Ala | Ser | Pro |
| Y | 1707 | 162 | Glu *11 | Gly | Ser | Gly | Gly | Val | Pro | Ile | Lys | Pro | Glu | Ala | Pro | Gly | Glu | Gly | Ala | Ser | Pro |
| Y | 1708 | 163 | | Glu *11 | Gly | Ser | Gly | Ala | Pro | Ile | Lys | Pro | Glu | Ala | Pro | Gly | Glu | Gly | Ala | Ser | Pro |
| Y | 1709 | 164 | | | Glu *11 | Gly | Ser | Ala | Pro | Ile | Lys | Pro | Glu | Ala | Pro | Gly | Glu | Gly | Ala | Ser | Pro |
| Y | 1710 | 165 | Tyr | Glu | Lys *10 | Glu | Tyr | Ala | Pro | Ile | Lys | Pro | Glu | Ala | Pro | Gly | Glu | Gly | Ala | Ser | Pro |
| Y | 1711 | 166 | | | | | | Ala *10 | Pro | Ile | Lys | Pro | Glu | Ala | Pro | Gly | Glu | Gly | Ala | Ser | Pro |
| Y | 1712 | 167 | | | | Ser *10 | Gly | Ala | Pro | Ile | Lys | Pro | Glu | Ala | Pro | Gly | Glu | Gly | Ala | Ser | Pro |
| Y | 1713 | 168 | | | | | | | Pro | Ile | Lys | Pro | Glu *23 | Ala | Pro | Gly | Glu | Gly | Ala | Ser | Pro |
| Y | 1714 | 169 | | | | | | | Pro | Ile | Lys | Pro | Glu | Ala | Pro | Gly | Glu *23 | Gly | Ala | Ser | Pro |
| Y | 1715 | 170 | | | | | | | Pro | Ile | Lys | Pro | Glu | Ala | Pro | Gly | Glu | Gly | Ala | Ser | Pro |
| Y | 1716 | 171 | | | | | | | Pro | Ile | Lys | Pro | Glu | Ala | Pro | Gly | Glu | Gly | Ala | Ser | Pro |
| Y | 1717 | 172 | | | | | | | Pro | Ile | Lys | Pro | Glu | Cys *24 | Pro | Gly | Glu | Gly | Ala | Ser | Pro |
| Y | 1718 | 173 | | | | | | | Pro | Ile | Lys | Pro | Glu | Ala | Pro | Gly | Lys *53 | Asp | Ala | Ser | Pro |

Figure 1
Part 7

| 15 | 16 | 17 | 18 | 19 | 20 | 21 | 22 | 23 | 24 | 25 | 26 | 27 | 28 | 29 | 30 | 31 | 32 | 33 | 34 | 35 | 36 | | | | |
|---|---|---|---|---|---|---|---|---|---|---|---|---|---|---|---|---|---|---|---|---|---|---|---|---|---|
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1687 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1688 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1689 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1690 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1691 |
| Glu | Glu | Ile | Leu | Lys | Tyr | Tyr | Ile | Glu | Leu | Arg | His | Phe | Leu | Asn | His | Leu | Thr | Arg | Gln | Arg | Tyr | NH2 | | Y | 1692 |
| Glu | Glu | Ile | Leu | His | Tyr | Tyr | Ala | Ala | Leu | Arg | His | Phe | Leu | Asn | His | Leu | Thr | Arg | Gln | Arg | Tyr | NH2 | | Y | 1693 |
| Glu | Glu | Ile | Leu | Lys | Tyr | Tyr | Ile | Glu | Leu | Arg | His | Phe | Leu | Asn | His | Leu | Thr | Arg | Gln | Arg | Tyr | NH2 | | Y | 1694 |
| Glu | Glu | Ile | Leu | Arg | Tyr | Tyr | Ile | Ala | Leu | Arg | His | Phe | Leu | Asn | His | Leu | Thr | Arg | Gln | Arg | Tyr | NH2 | | Y | 1695 |
| Glu | Glu | Ile | Leu | Lys | Tyr | Tyr | Ile | Glu | Leu | Arg | His | Phe | Leu | Asn | His | Leu | Thr | Arg | Gln | Arg | Tyr | NH2 | | Y | 1696 |
| Glu | Glu | Ile | Leu | Lys | Tyr | Tyr | Ile | Glu | Leu | Arg | His | Phe | Leu | Asn | His | Leu | Thr | Arg | Gln | Arg | Tyr | NH2 | | Y | 1697 |
| Glu | Glu | Ile | Leu | Lys | Tyr | Tyr | Ile | Glu | Leu | Arg | His | Phe | Leu | Asn | His | Leu | Thr | Arg | Gln | Arg | Tyr | NH2 | | Y | 1698 |
| Glu | Glu | Ile | Leu | Lys | Tyr | Tyr | Ile | Glu | Leu | Arg | His | Phe | Leu | Asn | His | Leu | Thr | Arg | Gln | Arg | Tyr | NH2 | | Y | 1699 |
| Glu | Glu | Ile | Leu | Lys | Tyr | Tyr | Ile | Glu | Leu | Arg | His | Phe | Leu | Asn | His | Leu | Thr | Arg | Gln | Arg | Tyr | NH2 | | Y | 1700 |
| Glu | Glu | Ile | Leu | Lys | Tyr | Tyr | Ile | Glu | Leu | Arg | His | Phe | Leu | Asn | His | Leu | Thr | Arg | Gln | Arg | Tyr | NH2 | | Y | 1701 |
| Glu | Glu | Ile | Leu | Lys | Tyr | Tyr | Ile | Glu | Leu | Arg | His | Phe | Leu | Asn | His | Leu | Thr | Arg | Gln | Arg | Tyr | NH2 | | Y | 1702 |
| Glu | Glu | Ile | Leu | Lys | Tyr | Tyr | Ile | Glu | Leu | Arg | His | Phe | Leu | Asn | His | Leu | Thr | Arg | Gln | Arg | Tyr | NH2 | | Y | 1703 |
| Glu | Glu | Ile | Leu | Lys | Tyr | Tyr | Ile | Glu | Leu | Arg | His | Phe | Leu | Asn | His | Leu | Thr | Arg | Gln | Arg | Tyr | NH2 | | Y | 1704 |
| Glu | Glu | Ile | Leu | Lys | Tyr | Tyr | Ile | Glu | Leu | Arg | His | Phe | Leu | Asn | His | Leu | Thr | Arg | Gln | Arg | Tyr | NH2 | | Y | 1705 |
| Glu | Glu | Ile | Leu | Lys | Tyr | Tyr | Ile | Glu | Leu | Arg | His | Phe | Leu | Asn | His | Leu | Thr | Arg | Gln | Arg | Tyr | NH2 | | Y | 1706 |
| Glu | Glu | Ile | Leu | Lys | Tyr | Tyr | Ile | Glu | Leu | Arg | His | Phe | Leu | Asn | His | Leu | Thr | Arg | Gln | Arg | Tyr | NH2 | | Y | 1707 |
| Glu | Glu | Ile | Leu | Lys | Tyr | Tyr | Ile | Glu | Leu | Arg | His | Phe | Leu | Asn | His | Leu | Thr | Arg | Gln | Arg | Tyr | NH2 | | Y | 1708 |
| Glu | Glu | Ile | Leu | Lys | Tyr | Tyr | Ile | Glu | Leu | Arg | His | Phe | Leu | Asn | His | Leu | Thr | Arg | Gln | Arg | Tyr | NH2 | | Y | 1709 |
| Glu | Glu | Ile | Leu | Lys | Tyr | Tyr | Ile | Glu | Leu | Arg | His | Phe | Leu | Asn | His | Leu | Thr | Arg | Gln | Arg | Tyr | NH2 | | Y | 1710 |
| Glu | Glu | Ile | Leu | Lys | Tyr | Tyr | Ile | Glu | Leu | Arg | His | Phe | Leu | Asn | His | Leu | Thr | Arg | Gln | Arg | Tyr | NH2 | | Y | 1711 |
| Glu | Glu | Ile | Leu | Lys | Tyr | Tyr | Ile | Glu | Leu | Arg | His | Phe | Leu | Asn | His | Leu | Thr | Arg | Gln | Arg | Tyr | NH2 | | Y | 1712 |
| Glu | Glu | Ile | Leu | Lys | Tyr | Tyr | Ile | Glu | Leu | Arg | His | Phe | Leu | Asn | His | Leu | Thr | Arg | Gln | Arg | Tyr | NH2 | | Y | 1713 |
| Glu | Glu | Ile | Leu | Lys | Tyr | Tyr | Ile | Glu | Leu | Arg | His | Phe | Leu | Asn | His | Leu | Thr | Arg | Gln | Arg | Tyr | NH2 | | Y | 1714 |
| Glu *23 | Glu | Ile | Leu | Lys | Tyr | Tyr | Ile | Glu | Leu | Arg | His | Phe | Leu | Asn | His | Leu | Thr | Arg | Gln | Arg | Tyr | NH2 | | Y | 1715 |
| Glu | Glu *23 | Ile | Leu | Lys | Tyr | Tyr | Ile | Glu | Leu | Arg | His | Phe | Leu | Asn | His | Leu | Thr | Arg | Gln | Arg | Tyr | NH2 | | Y | 1716 |
| Glu | Glu | Ile | Leu | Lys | Tyr | Tyr | Ile | Glu | Leu | Arg | His | Phe | Leu | Asn | His | Leu | Thr | Arg | Gln | Arg | Tyr | NH2 | | Y | 1717 |
| Glu | Glu | Leu | Asn | His | Tyr | Tyr | Ala | Ala | Leu | Arg | His | Phe | Leu | Asn | Arg | Val | Thr | Arg | Gln | Arg | Tyr | NH2 | | Y | 1718 |

Figure 1
Part 8

| | | SEQ ID NO | -5 | -4 | -3 | -2 | -1 | 1 | 2 | 3 | 4 | 5 | 6 | 7 | 8 | 9 | 10 | 11 | 12 | 13 | 14 |
|---|---|---|---|---|---|---|---|---|---|---|---|---|---|---|---|---|---|---|---|---|---|
| Y | 1719 | 174 | | | | | | | Pro | Ile | Lys | Pro | Glu | Ala | Pro | Gly | Lys *53 | Asp | Ala | Ser | Pro |
| Y | 1720 | 175 | | | | | | | Pro | Ile | Lys | Pro | Glu | Ala | Pro | Gly | Lys *53 | Asp | Ala | Ser | Pro |
| Y | 1721 | 176 | | | | | | | Pro | Ile | Lys | Pro | Glu | Ala | Pro | Gly | Lys *53 | Glu | Ala | Ser | Pro |
| Y | 1722 | 177 | | | | | | | Pro | Ile | Lys | Pro | Glu | Ala | Pro | Gly | Lys *53 | Asn | Ala | Ser | Pro |
| Y | 1723 | 178 | | | | | | | Pro | Ile | Lys | Pro | Glu | Ala | Pro | Gly | Lys *13 | Asn | Ala | Ser | Pro |
| Y | 1724 | 179 | | | | | | | Pro | Ile | Lys | Pro | Glu | Ala | Pro | Gly | Lys *53 | Gly | Ala | Ser | Pro |
| Y | 1725 | 180 | | | | | | | Pro | Ile | Lys | Pro | Glu | Lys *53 | Pro | Gly | Glu | Gly | Ala | Ser | Pro |
| Y | 1726 | 181 | | | | | | | Pro | Ile | Lys | Pro | Glu | Lys *53 | Pro | Gly | Glu | Asp | Ala | Ser | Pro |
| Y | 1727 | 182 | | | | | | | Pro | Ile | Lys | Pro | Glu | Lys *53 | Pro | Gly | Glu | Asp | Ala | Ser | Pro |
| Y | 1728 | 183 | | | | | | | Pro | Ile | Lys | Pro | Glu | Lys *53 | Pro | Gly | Glu | Asp | Ala | Ser | Pro |
| Y | 1729 | 184 | | | | | | | Pro | Ile | Lys | Pro | Glu | Lys *53 | Pro | Gly | Glu | Glu | Ala | Ser | Pro |
| Y | 1730 | 185 | | | | | | | Pro | Ile | Lys | Pro | Glu | Lys *53 | Pro | Gly | Glu | Asn | Ala | Ser | Pro |
| Y | 1731 | 186 | | | | | | | Pro | Ile | Lys | Pro | Glu | Lys *53 | Pro | Gly | Glu | Asn | Ala | Ser | Pro |
| Y | 1732 | 187 | | | | | | | Pro | Ile | Lys | Pro | Glu | Lys *53 | Pro | Gly | Glu | Gly | Ala | Ser | Pro |
| Y | 1733 | 188 | | | | | | | Pro | Ile | Lys | Pro | Glu | Ala | Pro | Lys *25 | Glu | Gly | Ala | Ser | Pro |
| Y | 1734 | 189 | | | | | | | Pro | Ile | Lys | Pro | Glu | Ala | Pro | Lys *26 | Glu | Gly | Ala | Ser | Pro |
| Y | 1735 | 190 | | | | | | | Pro | Ile | Lys | Pro | Glu | Ala | Pro | Lys *27 | Glu | Gly | Ala | Ser | Pro |
| Y | 1736 | 191 | | | | | | | Pro | Ile | Lys | Pro | Glu | Ala | Pro | Lys *60 | Glu | Asn | Ala | Ser | Pro |
| Y | 1737 | 192 | | | | | | | Pro | Ile | Lys | Pro | Glu | Ala | Pro | Lys *28 | Glu | Asn | Ala | Ser | Pro |
| Y | 1738 | 193 | | | | | | | Pro | Ile | Lys | Pro | Glu | Ala | Pro | Lys *29 | Glu | Asn | Ala | Ser | Pro |
| Y | 1739 | 194 | | | | | | | Pro | Ile | Lys | Pro | Glu | Ala | Pro | Gly | Lys *25 | Gly | Ala | Ser | Pro |
| Y | 1740 | 195 | | | | | | | Pro | Ile | Lys | Pro | Glu | Ala | Pro | Gly | Lys *44 | Gly | Ala | Ser | Pro |
| Y | 1741 | 196 | | | | | | | Pro | Ile | Lys | Pro | Glu | Ala | Pro | Gly | Lys *27 | Gly | Ala | Ser | Pro |
| Y | 1742 | 197 | | | | | | | Pro | Ile | Lys | Pro | Glu | Ala | Pro | Gly | Lys *25 | Asn | Ala | Ser | Pro |
| Y | 1743 | 198 | | | | | | | Pro | Ile | Lys | Pro | Glu | Ala | Pro | Gly | Lys *26 | Asn | Ala | Ser | Pro |
| Y | 1744 | 199 | | | | | | | Pro | Ile | Lys | Pro | Glu | Ala | Pro | Gly | Lys *27 | Asn | Ala | Ser | Pro |
| Y | 1745 | 200 | | | | | | | Pro | Ile | Lys | Pro | Glu | Ala | Pro | Lys *30 | Glu | Gly | Ala | Ser | Pro |
| Y | 1746 | 201 | | | | | | | Pro | Ile | Lys | Pro | Glu | Ala | Pro | Lys *31 | Glu | Gly | Ala | Ser | Pro |
| Y | 1747 | 202 | | | | | | | Pro | Ile | Lys | Pro | Glu | Ala | Pro | Lys *18 | Glu | Gly | Ala | Ser | Pro |
| Y | 1748 | 203 | | | | | | | Pro | Ile | Lys | Pro | Glu | Ala | Pro | Lys *28 | Glu | Gly | Ala | Ser | Pro |
| Y | 1749 | 204 | | | | | | | Pro | Ile | Lys | Pro | Glu | Ala | Pro | Lys *32 | Glu | Gly | Ala | Ser | Pro |
| Y | 1750 | 205 | | | | | | | Pro | Ile | Lys | Pro | Glu | Ala | Pro | Lys *33 | Glu | Gly | Ala | Ser | Pro |

Figure 1
Part 9

| 15 | 16 | 17 | 18 | 19 | 20 | 21 | 22 | 23 | 24 | 25 | 26 | 27 | 28 | 29 | 30 | 31 | 32 | 33 | 34 | 35 | 36 | | | | |
|---|---|---|---|---|---|---|---|---|---|---|---|---|---|---|---|---|---|---|---|---|---|---|---|---|---|
| Glu | Glu | Leu | Val | His | Tyr | Tyr | Ile | Ala | Leu | Arg | His | Phe | Leu | Asn | His | Val | Thr | Arg | Gln | Arg | Tyr | NH2 | | Y | 1719 |
| Glu | Glu | Ile | Leu | His | Tyr | Tyr | Ala | Ala | Leu | Arg | His | Tyr | Leu | Asn | His | Leu | Thr | Arg | Gln | Arg | Tyr | NH2 | | Y | 1720 |
| Glu | Glu | Ile | Leu | Lys | Tyr | Tyr | Ile | Glu | Leu | Arg | His | Phe | Leu | Asn | His | Leu | Thr | Arg | Gln | Arg | Tyr | NH2 | | Y | 1721 |
| Glu | Glu | Ile | Leu | Lys | Tyr | Tyr | Ile | Glu | Leu | Arg | His | Phe | Leu | Asn | His | Leu | Thr | Arg | Gln | Arg | Tyr | NH2 | | Y | 1722 |
| Glu | Glu | Ile | Leu | Lys | Tyr | Tyr | Ile | Glu | Leu | Arg | His | Phe | Leu | Asn | His | Leu | Thr | Arg | Gln | Arg | Tyr | NH2 | | Y | 1723 |
| Glu | Glu | Ile | Leu | His | Tyr | Tyr | Ala | Ala | Leu | Arg | His | Phe | Leu | Asn | His | Leu | Thr | Arg | Gln | Arg | Tyr | NH2 | | Y | 1724 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1725 |
| Glu | Glu | Leu | Asn | His | Tyr | Tyr | Ala | Ala | Leu | Arg | His | Phe | Leu | Asn | Arg | Val | Thr | Arg | Gln | Arg | Tyr | NH2 | | Y | 1726 |
| Glu | Glu | Leu | Val | His | Tyr | Tyr | Ile | Ala | Leu | Arg | His | Phe | Leu | Asn | His | Val | Thr | Arg | Gln | Arg | Tyr | NH2 | | Y | 1727 |
| Glu | Glu | Ile | Leu | His | Tyr | Tyr | Ala | Ala | Leu | Arg | His | Tyr | Leu | Asn | His | Leu | Thr | Arg | Gln | Arg | Tyr | NH2 | | Y | 1728 |
| Glu | Glu | Ile | Leu | Lys | Tyr | Tyr | Ile | Glu | Leu | Arg | His | Phe | Leu | Asn | His | Leu | Thr | Arg | Gln | Arg | Tyr | NH2 | | Y | 1729 |
| Glu | Glu | Ile | Leu | Lys | Tyr | Tyr | Ile | Glu | Leu | Arg | His | Phe | Leu | Asn | His | Leu | Thr | Arg | Gln | Arg | Tyr | NH2 | | Y | 1730 |
| Glu | Glu | Ile | Leu | Lys | Tyr | Tyr | Ile | Glu | Leu | Arg | His | Phe | Leu | Asn | His | Leu | Thr | Arg | Gln | Arg | Tyr | NH2 | | Y | 1731 |
| Glu | Glu | Ile | Leu | His | Tyr | Tyr | Ala | Ala | Leu | Arg | His | Phe | Leu | Asn | His | Leu | Thr | Arg | Gln | Arg | Tyr | NH2 | | Y | 1732 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1733 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1734 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1735 |
| Glu | Glu | Ile | Leu | Lys | Tyr | Tyr | Ile | Glu | Leu | Arg | His | Phe | Leu | Asn | His | Leu | Thr | Arg | Gln | Arg | Tyr | NH2 | | Y | 1736 |
| Glu | Glu | Ile | Leu | Lys | Tyr | Tyr | Ile | Glu | Leu | Arg | His | Phe | Leu | Asn | His | Leu | Thr | Arg | Gln | Arg | Tyr | NH2 | | Y | 1737 |
| Glu | Glu | Ile | Leu | Lys | Tyr | Tyr | Ile | Glu | Leu | Arg | His | Phe | Leu | Asn | His | Leu | Thr | Arg | Gln | Arg | Tyr | NH2 | | Y | 1738 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1739 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1740 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1741 |
| Glu | Glu | Ile | Leu | Lys | Tyr | Tyr | Ile | Glu | Leu | Arg | His | Phe | Leu | Asn | His | Leu | Thr | Arg | Gln | Arg | Tyr | NH2 | | Y | 1742 |
| Glu | Glu | Ile | Leu | Lys | Tyr | Tyr | Ile | Glu | Leu | Arg | His | Phe | Leu | Asn | His | Leu | Thr | Arg | Gln | Arg | Tyr | NH2 | | Y | 1743 |
| Glu | Glu | Ile | Leu | Lys | Tyr | Tyr | Ile | Glu | Leu | Arg | His | Phe | Leu | Asn | His | Leu | Thr | Arg | Gln | Arg | Tyr | NH2 | | Y | 1744 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1745 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1746 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1747 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1748 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1749 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1750 |

Figure 1
Part 10

| | | SEQ ID NO | -5 | -4 | -3 | -2 | -1 | 1 | 2 | 3 | 4 | 5 | 6 | 7 | 8 | 9 | 10 | 11 | 12 | 13 | 14 |
|---|---|---|---|---|---|---|---|---|---|---|---|---|---|---|---|---|---|---|---|---|---|
| Y | 1751 | 206 | | | | | | | Pro | Ile | Lys | Pro | Glu | Ala | Pro | Lys *34 | Glu | Gly | Ala | Ser | Pro |
| Y | 1752 | 207 | | | | | | | Pro | Ile | Lys | Pro | Glu | Ala | Pro | Lys *61 | Glu | Gly | Ala | Ser | Pro |
| Y | 1753 | 208 | | | | | | | Pro | Ile | Lys | Pro | Glu | Ala | Pro | Lys *35 | Glu | Gly | Ala | Ser | Pro |
| Y | 1754 | 209 | | | | | | | Pro | Ile | Lys | Pro | Glu | Ala | Pro | Lys *2 | Glu | Glu | Ala | Ser | Pro |
| Y | 1755 | 210 | | | | | | | Pro | Ile | Lys | Pro | Glu | Ala | Pro | Lys *2 | Glu | Gly | Ala | Ser | Pro |
| Y | 1756 | 211 | | | | | | | Pro | Ile | Lys | Pro | Glu | Ala | Pro | Cys *36 | Glu | Gly | Ala | Ser | Pro |
| Y | 1757 | 212 | | | | | | | Pro | Ile | Lys | Pro | Glu | Ala | Pro | Cys *36 | Glu | Glu | Ala | Ser | Pro |
| Y | 1758 | 213 | | | | | | | Pro | Ile | Lys | Pro | Glu | Ala | Pro | Cys *36 | Glu | Gly | Ala | Ser | Pro |
| Y | 1759 | 214 | | | | | | | Pro | Ile | Lys | Pro | Glu | Ala | Pro | Gly | Cys *36 | Glu | Ala | Ser | Pro |
| Y | 1760 | 215 | | | | | | | Cys | Ile | Lys | Pro | Glu | Ala | Pro | Lys *2 | Glu | Gly | Ala | Ser | Pro |
| Y | 1761 | 216 | | | | | | | Pro | Ile | Lys | Cys | Glu | Ala | Pro | Lys *2 | Glu | Gly | Ala | Ser | Pro |
| Y | 1762 | 217 | | | | | | | Pro | Ile | Lys | Pro | Glu | Ala | Pro | Lys *37 | Glu | Gly | Ala | Ser | Pro |
| Y | 1763 | 218 | | | | | | | Pro | Ile | Lys | Pro | Glu | Ala | Pro | Lys *38 | Glu | Gly | Ala | Ser | Pro |
| Y | 1764 | 219 | | | | | | | Pro | Ile | Lys | Pro | Glu | Ala | Pro | Lys *2 | Glu | Asp | Ala | Ser | Pro |
| Y | 1765 | 220 | | | | | | | Pro | Ile | Lys | Pro | Glu | Ala | Pro | Lys *2 | Glu | Asp | Ala | Ser | Pro |
| Y | 1766 | 221 | | | | | | | Pro | Ile | Lys | Pro | Glu | Ala | Pro | Lys *2 | Glu | Asn | Ala | Ser | Pro |
| Y | 1767 | 222 | | | | | | | Pro | Ile | Lys | Pro | Glu | Ala | Pro | Lys *2 | Glu | Asn | Ala | Ser | Pro |
| Y | 1768 | 223 | | | | | | | Pro | Ile | Lys | Pro | Glu | Ala | Pro | Lys *2 | Glu | Gly | Ala | Ser | Pro |
| Y | 1769 | 224 | | | | | | | Pro | Ile | Lys | Pro | Glu | Ala | Pro | Lys *39 | Glu | Gly | Ala | Ser | Pro |
| Y | 1770 | 225 | | | | | | | Pro | Ile | Lys | Pro | Glu | Lys *39 | Pro | Gly | Glu | Gly | Ala | Ser | Pro |
| Y | 1771 | 226 | | | | | | | Pro | Ile | Lys | Pro | Glu | Ala | Pro | Gly | Lys *39 | Gly | Ala | Ser | Pro |
| Y | 1772 | 227 | | | | | | | Pro | Ile | Lys | Pro | Glu | Ala | Pro | Gly | Glu | Lys *39 | Ala | Ser | Pro |
| Y | 1773 | 228 | | Gly *18 | Ser | Gly | Ser | Gly | Pro | Ile | Lys | Pro | Glu | Ala | Pro | Gly | Glu | Gly | Ala | Ser | Pro |
| Y | 1774 | 229 | Gly *18 | Ser | Gly | Ser | Gly | Tyr | Pro | Ile | Lys | Pro | Glu | Ala | Pro | Gly | Glu | Gly | Ala | Ser | Pro |
| Y | 1775 | 230 | | | | | | Lys *39 | Pro | Ile | Lys | Pro | Glu | Ala | Pro | Gly | Glu | Gly | Ala | Ser | Pro |
| Y | 1776 | 231 | Lys *40 | Gly | Pro | Pro | Pro | Ser | Pro | Ile | Lys | Pro | Glu | Ala | Pro | Gly | Glu | Gly | Ala | Ser | Pro |
| Y | 1777 | 232 | Lys *41 | Gly | Pro | Pro | Pro | Ser | Pro | Ile | Lys | Pro | Glu | Ala | Pro | Gly | Glu | Gly | Ala | Ser | Pro |
| Y | 1778 | 233 | | | | Lys *40 | Ser | Gly | Pro | Ile | Lys | Pro | Glu | Ala | Pro | Gly | Glu | Gly | Ala | Ser | Pro |
| Y | 1779 | 234 | | | | Lys *41 | Ser | Gly | Pro | Ile | Lys | Pro | Glu | Ala | Pro | Gly | Glu | Gly | Ala | Ser | Pro |
| Y | 1780 | 235 | | | Asn *10 | Thr | Ser | Gly | Pro | Ile | Lys | Pro | Glu | Ala | Pro | Gly | Glu | Gly | Ala | Ser | Pro |
| Y | 1781 | 236 | | | | | Lys *42 | Tyr | Pro | Ile | Lys | Pro | Glu | Ala | Pro | Gly | Glu | Gly | Ala | Ser | Pro |
| Y | 1782 | 237 | | | | Lys *42 | Pro | Tyr | Pro | Ile | Lys | Pro | Glu | Ala | Pro | Gly | Glu | Gly | Ala | Ser | Pro |

Figure 1
Part 11

| 15 | 16 | 17 | 18 | 19 | 20 | 21 | 22 | 23 | 24 | 25 | 26 | 27 | 28 | 29 | 30 | 31 | 32 | 33 | 34 | 35 | 36 | | | | |
|---|---|---|---|---|---|---|---|---|---|---|---|---|---|---|---|---|---|---|---|---|---|---|---|---|---|
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1751 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1752 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1753 |
| Glu | Glu | Ile | Leu | Lys | Tyr | Tyr | Ile | Glu | Leu | Arg | His | Phe | Leu | Asn | His | Leu | Thr | Arg | Gln | Arg | Tyr | NH2 | | Y | 1754 |
| Glu | Glu | Ile | Leu | Lys | Tyr | Tyr | Ile | Glu | Leu | Arg | His | Phe | Leu | Asn | His | Leu | Thr | Arg | Gln | Arg | Tyr | NH2 | | Y | 1755 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1756 |
| Glu | Glu | Ile | Leu | Lys | Tyr | Tyr | Ile | Glu | Leu | Arg | His | Phe | Leu | Asn | His | Leu | Thr | Arg | Gln | Arg | Tyr | NH2 | | Y | 1757 |
| Glu | Glu | Ile | Leu | Lys | Tyr | Tyr | Ile | Glu | Leu | Arg | His | Phe | Leu | Asn | His | Leu | Thr | Arg | Gln | Arg | Tyr | NH2 | | Y | 1758 |
| Glu | Glu | Ile | Leu | Lys | Tyr | Tyr | Ile | Glu | Leu | Arg | His | Phe | Leu | Asn | His | Leu | Thr | Arg | Gln | Arg | Tyr | NH2 | | Y | 1759 |
| Glu | Glu | Leu | Leu | His | Tyr | Tyr | Ala | Ala | Leu | Arg | His | Cys | Leu | Asn | His | Val | Thr | Arg | Gln | Arg | Tyr | NH2 | | Y | 1760 |
| Glu | Glu | Leu | Leu | His | Tyr | Tyr | Ala | Ala | Cys | Arg | His | Phe | Leu | Asn | His | Val | Thr | Arg | Gln | Arg | Tyr | NH2 | | Y | 1761 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1762 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1763 |
| Glu | Glu | Leu | Val | His | Tyr | Tyr | Ile | Ala | Leu | Arg | His | Phe | Leu | Asn | His | Val | Thr | Arg | Gln | Arg | Tyr | NH2 | | Y | 1764 |
| Glu | Glu | Ile | Leu | His | Tyr | Tyr | Ala | Ala | Leu | Arg | His | Tyr | Leu | Asn | His | Leu | Thr | Arg | Gln | Arg | Tyr | NH2 | | Y | 1765 |
| Glu | Glu | Ile | Leu | Lys | Tyr | Tyr | Ile | Glu | Leu | Arg | His | Phe | Leu | Asn | His | Leu | Thr | Arg | Gln | Arg | Tyr | NH2 | | Y | 1766 |
| Glu | Glu | Ile | Leu | Lys | Tyr | Tyr | Ile | Glu | Leu | Arg | His | Phe | Leu | Asn | His | Leu | Thr | Arg | Gln | Arg | Tyr | NH2 | | Y | 1767 |
| Glu | Glu | Ile | Leu | His | Tyr | Tyr | Ala | Ala | Leu | Arg | His | Phe | Leu | Asn | His | Leu | Thr | Arg | Gln | Arg | Tyr | NH2 | | Y | 1768 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1769 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1770 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1771 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1772 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1773 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1774 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1775 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1776 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1777 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1778 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1779 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1780 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1781 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1782 |

Figure 1
Part 12

| | | SEQ ID NO | -5 | -4 | -3 | -2 | -1 | 1 | 2 | 3 | 4 | 5 | 6 | 7 | 8 | 9 | 10 | 11 | 12 | 13 | 14 |
|---|---|---|---|---|---|---|---|---|---|---|---|---|---|---|---|---|---|---|---|---|---|
| Y | 1783 | 238 | | | | | | | Pro | Ile | Lys | Pro | Glu | Ala | Pro | Gly | Lys *42 | Gly | Ala | Ser | Pro |
| Y | 1784 | 239 | | | | | | | Pro | Ile | Lys | Pro | Glu | Ala | Pro | Lys *42 | Glu | Gly | Ala | Ser | Pro |
| Y | 1785 | 240 | | | | | | | Pro | Ile | Lys | Pro | Glu | Lys *42 | Pro | Gly | Glu | Gly | Ala | Ser | Pro |
| Y | 1786 | 241 | | | | | | | Pro | Ile | Lys | Pro | Glu | Ala | Pro | Gly | Lys *28 | Gly | Ala | Ser | Pro |
| Y | 1787 | 242 | | | | | | | Pro | Ile | Lys | Pro | Glu | Lys *28 | Pro | Gly | Glu | Gly | Ala | Ser | Pro |
| Y | 1788 | 243 | | | | | | | Pro | Ile | Lys | Pro | Glu | Ala | Pro | Gly | Lys *34 | Gly | Ala | Ser | Pro |
| Y | 1789 | 244 | | | | | | | Pro | Ile | Lys | Pro | Glu | Lys *26 | Pro | Gly | Glu | Gly | Ala | Ser | Pro |
| Y | 1790 | 245 | | | | | | Lys *42 | Pro | Ile | Lys | Pro | Glu | Ala | Pro | Gly | Glu | Gly | Ala | Ser | Pro |
| Y | 1791 | 246 | | | | | | Lys *26 | Pro | Ile | Lys | Pro | Glu | Ala | Pro | Gly | Glu | Gly | Ala | Ser | Pro |
| Y | 1792 | 247 | | | | | | Lys *28 | Pro | Ile | Lys | Pro | Glu | Ala | Pro | Gly | Glu | Gly | Ala | Ser | Pro |
| Y | 1793 | 248 | | | | | Lys *44 | Tyr | Pro | Ile | Lys | Pro | Glu | Ala | Pro | Gly | Glu | Gly | Ala | Ser | Pro |
| Y | 1794 | 249 | | | | | Lys *43 | Tyr | Pro | Ile | Lys | Pro | Glu | Ala | Pro | Gly | Glu | Gly | Ala | Ser | Pro |
| Y | 1795 | 250 | | | | | Glu *23 | Tyr | Pro | Ile | Lys | Pro | Glu | Ala | Pro | Gly | Glu | Gly | Ala | Ser | Pro |
| Y | 1796 | 251 | | | | | Glu *45 | Tyr | Pro | Ile | Lys | Pro | Glu | Ala | Pro | Gly | Glu | Gly | Ala | Ser | Pro |
| Y | 1797 | 252 | | | | | | | Pro | Ile | Lys | Pro | Glu | Ala | Pro | Gly | Lys *46 | Gly | Ala | Ser | Pro |
| Y | 1798 | 253 | | | | | | | Pro | Ile | Lys | Pro | Glu | Ala | Pro | Gly | Lys *47 | Gly | Ala | Ser | Pro |
| Y | 1799 | 254 | | | | | | | Pro | Ile | Lys | Pro | Glu | Ala | Pro | Gly | Lys *2 | Gly | Ala | Ser | Pro |
| Y | 1800 | 255 | | | | | | | Pro | Ile | Lys | Pro | Glu | Ala | Pro | Gly | Lys *48 | Gly | Ala | Ser | Pro |
| Y | 1801 | 256 | | | | | | | Pro | Ile | Lys | Pro | Glu | Ala | Pro | Gly | Lys *49 | Gly | Ala | Ser | Pro |
| Y | 1802 | 257 | | | | | | | Pro | Ile | Lys | Pro | Glu | Ala | Pro | Gly | Lys *50 | Gly | Ala | Ser | Pro |
| Y | 1803 | 258 | | | | | | | Pro | Ile | Lys | Pro | Glu | Ala | Pro | Gly | Lys *13 | Gly | Ala | Ser | Pro |
| Y | 1804 | 259 | | | | | | | Pro | Ile | Lys | Pro | Glu | Ala | Pro | Gly | Lys *62 | Gly | Ala | Ser | Pro |
| Y | 1805 | 260 | | | | | | | Pro | Ile | Lys | Pro | Glu | Ala | Pro | Gly | Lys *63 | Gly | Ala | Ser | Pro |
| Y | 1806 | 261 | | | | | | Lys *53 | Pro | Ile | Lys | Pro | Glu | Ala | Pro | Gly | Glu | Gly | Ala | Ser | Pro |
| Y | 1807 | 262 | | | | | | Lys *13 | Pro | Ile | Lys | Pro | Glu | Ala | Pro | Gly | Glu | Gly | Ala | Ser | Pro |
| Y | 1808 | 263 | | | | | | Lys *50 | Pro | Ile | Lys | Pro | Glu | Ala | Pro | Gly | Glu | Gly | Ala | Ser | Pro |
| Y | 1809 | 264 | | | | | | Lys *13 | Pro | Ile | Lys | Pro | Glu | Ala | Pro | Gly | Glu | Gly | Ala | Ser | Pro |
| Y | 1810 | 265 | | | | | Glu *51 | Tyr | Pro | Ile | Lys | Pro | Glu | Ala | Pro | Gly | Glu | Gly | Ala | Ser | Pro |
| Y | 1811 | 266 | | | | | | Lys *2 | Pro | Ile | Lys | Pro | Glu | Ala | Pro | Gly | Glu | Gly | Ala | Ser | Pro |
| Y | 1812 | 267 | | | | | | Lys *52 | Pro | Ile | Lys | Pro | Glu | Ala | Pro | Gly | Glu | Gly | Ala | Ser | Pro |
| Y | 1813 | 268 | | | | | | Lys *42 | Pro | Ile | Lys | Pro | Glu | Ala | Pro | Gly | Glu | Gly | Ala | Ser | Pro |
| Y | 1814 | 269 | | | | | | Lys *41 | Pro | Ile | Lys | Pro | Glu | Ala | Pro | Gly | Glu | Gly | Ala | Ser | Pro |

Figure 1
Part 13

| 15 | 16 | 17 | 18 | 19 | 20 | 21 | 22 | 23 | 24 | 25 | 26 | 27 | 28 | 29 | 30 | 31 | 32 | 33 | 34 | 35 | 36 | | | | |
|---|---|---|---|---|---|---|---|---|---|---|---|---|---|---|---|---|---|---|---|---|---|---|---|---|---|
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1783 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1784 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1785 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1786 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1787 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1788 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1789 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1790 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1791 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1792 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1793 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1794 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1795 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1796 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1797 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1798 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1799 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1800 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1801 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1802 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1803 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1804 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1805 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1806 |
| Glu | Glu | Leu | Leu | His | Tyr | Tyr | Ala | Ala | Leu | Arg | His | Phe | Leu | Asn | His | Val | Thr | Arg | Gln | Arg | Tyr | NH2 | | Y | 1807 |
| Glu | Glu | Ile | Leu | Lys | Tyr | Tyr | Ile | Glu | Leu | Arg | His | Phe | Leu | Asn | His | Leu | Thr | Arg | Gln | Arg | Tyr | NH2 | | Y | 1808 |
| Glu | Glu | Ile | Leu | Lys | Tyr | Tyr | Ile | Glu | Leu | Arg | His | Phe | Leu | Asn | His | Leu | Thr | Arg | Gln | Arg | Tyr | NH2 | | Y | 1809 |
| Glu | Glu | Ile | Leu | Lys | Tyr | Tyr | Ile | Glu | Leu | Arg | His | Phe | Leu | Asn | His | Leu | Thr | Arg | Gln | Arg | Tyr | NH2 | | Y | 1810 |
| Glu | Glu | Ile | Leu | Lys | Tyr | Tyr | Ile | Glu | Leu | Arg | His | Phe | Leu | Asn | His | Leu | Thr | Arg | Gln | Arg | Tyr | NH2 | | Y | 1811 |
| Glu | Glu | Ile | Leu | Lys | Tyr | Tyr | Ile | Glu | Leu | Arg | His | Phe | Leu | Asn | His | Leu | Thr | Arg | Gln | Arg | Tyr | NH2 | | Y | 1812 |
| Glu | Glu | Ile | Leu | Lys | Tyr | Tyr | Ile | Glu | Leu | Arg | His | Phe | Leu | Asn | His | Leu | Thr | Arg | Gln | Arg | Tyr | NH2 | | Y | 1813 |
| Glu | Glu | Ile | Leu | Lys | Tyr | Tyr | Ile | Glu | Leu | Arg | His | Phe | Leu | Asn | His | Leu | Thr | Arg | Gln | Arg | Tyr | NH2 | | Y | 1814 |

Figure 1
Part 14

| | | SEQ ID NO | -5 | -4 | -3 | -2 | -1 | 1 | 2 | 3 | 4 | 5 | 6 | 7 | 8 | 9 | 10 | 11 | 12 | 13 | 14 |
|---|---|---|---|---|---|---|---|---|---|---|---|---|---|---|---|---|---|---|---|---|---|
| Y | 1815 | 270 | | | | | Lys *28 | Tyr | Pro | Ile | Lys | Pro | Glu | Ala | Pro | Gly | Glu | Gly | Ala | Ser | Pro |
| Y | 1816 | 271 | | | | | | Lys *53 | Pro | Ile | Lys | Pro | Glu | Ala | Pro | Gly | Glu | Gly | Ala | Ser | Pro |
| Y | 1817 | 272 | | | | | | Lys *53 | Pro | Ile | Lys | Pro | Glu | Ala | Pro | Gly | Glu | Gly | Ala | Ser | Pro |
| Y | 1818 | 273 | | | | | | Lys *53 | Pro | Ile | Lys | Pro | Glu | Ala | Pro | Gly | Glu | Asn | Ala | Ser | Pro |
| Y | 1819 | 274 | | | | | | Lys *53 | Pro | Ile | Lys | Pro | Glu | Ala | Pro | Gly | Glu | Gly | Ala | Ser | Pro |
| Y | 1820 | 275 | | | | | | Lys *53 | Pro | Ile | Lys | Pro | Glu | Ala | Pro | Gly | Glu | Gly | Ala | Ser | Pro |
| Y | 1821 | 276 | | | | | | | Pro | Ile | Lys | Pro | Glu | Ala | Pro | Gly | Lys *50 | Gly | Ala | Ser | Pro |
| Y | 1822 | 277 | | | | | | | Pro | Ile | Lys | Pro | Glu | Ala | Pro | Gly | Lys *50 | Gly | Ala | Ser | Pro |
| Y | 1823 | 278 | | | | | | | Pro | Ile | Lys | Pro | Glu | Ala | Pro | Gly | Lys *2 | Gly | Ala | Ser | Pro |
| Y | 1824 | 279 | | | | | | | Pro | Ile | Lys | Pro | Glu | Ala | Pro | Gly | Lys *2 | Gly | Ala | Ser | Pro |
| Y | 1825 | 280 | | | | | | Lys *53 | Pro | Ile | Lys | Pro | Glu | Ala | Pro | Gly | Glu | Gly | Ala | Ser | Pro |
| Y | 1826 | 281 | | | | | | | Pro | Ile | Lys | Pro | Glu | Ala | Pro | Gly | Lys *2 | Gly | Ala | Ser | Pro |
| Y | 1827 | 282 | | | | | | | Pro | Ile | Lys | Pro | Glu | Ala | Pro | Gly | Lys *63 | Gly | Ala | Ser | Pro |

Figure 1
Part 15

| 15 | 16 | 17 | 18 | 19 | 20 | 21 | 22 | 23 | 24 | 25 | 26 | 27 | 28 | 29 | 30 | 31 | 32 | 33 | 34 | 35 | 36 | | | | |
|---|---|---|---|---|---|---|---|---|---|---|---|---|---|---|---|---|---|---|---|---|---|---|---|---|---|
| Glu | Glu | Ile | Leu | Lys | Tyr | Tyr | Ile | Glu | Leu | Arg | His | Phe | Leu | Asn | His | Leu | Thr | Arg | Gln | Arg | Tyr | NH2 | | Y | 1815 |
| Glu | Glu | Ile | Leu | Lys | Tyr | Tyr | Ile | Glu | Leu | Arg | His | Phe | Leu | Asn | His | Leu | Thr | Arg | Gln | Arg | Tyr | NH2 | | Y | 1816 |
| Glu | Glu | Ile | Leu | Lys | Tyr | Tyr | Ile | Glu | Leu | Arg | His | Phe | Leu | Asn | His | Leu | Thr | Arg | Gln | Arg | Tyr | NH2 | | Y | 1817 |
| Glu | Glu | Ile | Leu | Lys | Tyr | Tyr | Ile | Glu | Leu | Arg | His | Phe | Leu | Asn | His | Leu | Thr | Arg | Gln | Arg | Tyr | NH2 | | Y | 1818 |
| Glu | Glu | Ile | Leu | His | Tyr | Tyr | Ile | Glu | Leu | Arg | His | Phe | Leu | Asn | His | Leu | Thr | Arg | Gln | Arg | Tyr | NH2 | | Y | 1819 |
| Glu | Glu | Ile | Leu | Lys | Tyr | Tyr | Ala | Ala | Leu | Arg | His | Phe | Leu | Asn | His | Leu | Thr | Arg | Gln | Arg | Tyr | NH2 | | Y | 1820 |
| Glu | Glu | Leu | Leu | His | Tyr | Tyr | Ala | Ala | Leu | Arg | His | Phe | Leu | Asn | His | Val | Thr | Arg | Gln | Marg | Tyr | NH2 | | Y | 1821 |
| Glu | Glu | Leu | Leu | His | Tyr | Tyr | Ala | Ala | Leu | Arg | His | Phe | Leu | Asn | His | Leu | Thr | Arg | Gln | Arg | Tyr | NH2 | | Y | 1822 |
| Glu | Glu | Leu | Leu | His | Tyr | Tyr | Ala | Ala | Leu | Arg | His | Phe | Leu | Asn | His | Val | Thr | Arg | Gln | Marg | Tyr | NH2 | | Y | 1823 |
| Glu | Glu | Leu | Leu | His | Tyr | Tyr | Ala | Ala | Leu | Arg | His | Phe | Leu | Asn | His | Leu | Thr | Arg | Gln | Arg | Tyr | NH2 | | Y | 1824 |
| Glu | Glu | Ile | Leu | Lys | Tyr | Tyr | Ile | Glu | Leu | Arg | His | Phe | Leu | Asn | His | Leu | Thr | Arg | Gln | Marg | Tyr | NH2 | | Y | 1825 |
| Glu | Glu | Leu | Leu | His | Tyr | Tyr | Ala | Ala | Leu | Arg | His | Phe | Leu | Asn | His | Val | Thr | Arg | Gln | | | | | Y | 1826 |
| Glu | Glu | Leu | Leu | His | Tyr | Tyr | Ala | Ala | Leu | Arg | His | Phe | Leu | Asn | His | Val | Thr | Arg | Gln | | | | | Y | 1827 |

Figure 1
Part 16

| | | human cAMP inhibition | Solubility at 50mg/ml pH4 | Food intake in rat (g) | | | | | Weight Loss in rat (g) | | | | | Longevity | |
|---|---|---|---|---|---|---|---|---|---|---|---|---|---|---|---|
| | | | | 0-24h | 0-48h | 0-72h | 0-96h | 0-7d | 0-24h | 0-48h | 0-72h | 0-96h | 0-7d | Food intake | weight loss |
| Y | 1592 | 41 | | -16 | -17 | -15 | -13 | -11 | -9 | -10 | -7 | -6 | -6 | 0.9 | 1.0 |
| Y | 1593 | 16 | 1 | -15 | -18 | -19 | -19 | -13 | -6 | -11 | -12 | -10 | -10 | 0.7 | 1.0 |
| Y | 1594 | 39.6 | | -2 | 0 | 0 | -1 | 0 | 0 | -4 | -3 | -3 | -4 | 0.0 | 0.0 |
| Y | 1595 | 0.4 | 1 | -18 | -27 | -25 | -21 | -12 | -13 | -19 | -11 | -8 | -3 | 0.6 | 0.4 |
| Y | 1596 | 4.2 | 1 | -13 | -15 | -13 | -10 | -6 | -8 | -9 | -4 | -4 | -4 | 0.6 | 1.0 |
| Y | 1597 | 15.0 | 1 | -10 | -9 | -9 | -8 | -9 | -3 | -2 | -6 | -3 | -4 | 1.1 | 1.4 |
| Y | 1598 | 27 | 1 | -11 | -19 | -22 | -25 | -30 | -5 | -10 | -9 | -10 | -8 | 1.2 | 0.9 |
| Y | 1599 | 10.9 | 1 | -5 | -3 | -4 | -2 | 2 | -3 | -2 | -2 | 2 | 3 | 0.0 | 0.0 |
| Y | 1600 | 20 | 1 | -5 | -6 | -8 | -9 | -14 | -1 | -3 | -2 | -1 | -2 | 1.6 | 1.7 |
| Y | 1601 | 30.0 | 1 | -5 | -3 | -2 | -2 | -2 | -1 | -2 | 0 | 1 | 3 | 0.0 | 0.0 |
| Y | 1602 | 50.8 | 1 | -5 | -5 | -3 | -3 | -4 | -3 | -6 | -5 | -4 | -4 | 0.0 | 0.0 |
| Y | 1603 | 24.4 | 1 | -4 | -5 | -6 | -8 | -12 | -2 | -3 | -1 | -4 | -5 | 1.6 | 1.3 |
| Y | 1604 | 70.9 | 1 | -3 | -3 | -4 | -4 | -5 | 1 | -1 | 2 | 2 | -1 | 0.0 | 0.0 |
| Y | 1605 | 41 | 1 | -3 | -4 | -4 | -3 | -2 | -1 | -2 | -2 | -2 | -1 | 0.0 | 0.0 |
| Y | 1606 | 3.8 | 1 | -14 | -24 | -26 | -26 | -25 | -8 | -16 | -15 | -11 | -9 | 1.0 | 0.8 |
| Y | 1607 | 4.0 | 1 | -14 | -22 | -22 | -19 | -19 | -3 | -11 | -7 | -3 | -1 | 1.0 | 0.3 |
| Y | 1608 | 4.6 | 1 | -9 | -12 | -10 | -7 | 2 | -2 | -6 | -3 | -2 | 2 | -0.3 | -1.0 |
| Y | 1609 | 9.4 | 1 | -11 | -20 | -19 | -17 | -10 | -6 | -12 | -8 | -3 | -2 | 0.6 | 0.7 |
| Y | 1610 | 4.7 | 1 | -13 | -21 | -20 | -17 | -9 | -3 | -13 | -10 | -7 | 2 | 0.5 | -0.3 |
| Y | 1611 | 0.4 | 1 | -11 | -11 | -14 | -15 | -19 | -5 | -5 | -7 | -6 | -4 | 1.3 | 0.8 |
| Y | 1612 | 2.2 | 5 | -10 | -17 | -13 | -10 | -4 | -5 | -10 | -3 | -2 | 5 | 0.4 | -2.0 |
| Y | 1613 | 4.1 | 5 | -17 | -25 | -22 | -19 | -10 | -10 | -16 | -9 | -8 | -1 | 0.5 | 0.2 |
| Y | 1614 | 3.9 | 1 | -14 | -21 | -18 | -15 | -7 | -11 | -13 | -6 | -2 | 1 | 0.5 | -0.4 |
| Y | 1615 | 3.0 | 1 | -16 | -29 | -27 | -27 | -20 | -10 | -17 | -15 | -14 | -1 | 0.8 | 0.1 |
| Y | 1616 | 7.9 | 1 | -11 | -19 | -18 | -17 | -8 | 0 | -11 | -10 | -12 | 0 | 0.5 | 0.0 |
| Y | 1617 | 5.0 | 1 | 0 | 1 | 6 | 10 | 16 | -2 | -3 | 0 | 1 | 5 | 0.0 | 0.0 |
| Y | 1618 | 4.4 | 1 | -14 | -23 | -19 | -15 | -3 | -8 | -11 | -7 | -10 | 6 | 0.2 | -0.6 |
| Y | 1619 | 18.1 | 1 | -13 | -21 | -20 | -15 | -12 | -3 | -13 | -6 | -3 | -4 | 0.8 | 1.2 |
| Y | 1620 | 14 | 1 | -11 | -19 | -17 | -15 | -14 | -5 | -8 | -8 | -6 | -5 | 0.9 | 0.7 |
| Y | 1621 | 14 | 1 | -12 | -21 | -21 | -18 | -17 | -4 | -13 | -5 | -6 | -6 | 0.9 | 1.0 |

Figure 2
Part 1

| | | human cAMP inhibition | Solubility at 50mg/ml pH4 | Food intake in rat (g) | | | | | Weight Loss in rat (g) | | | | | Longevity | |
|---|---|---|---|---|---|---|---|---|---|---|---|---|---|---|---|
| | | | | 0-24h | 0-48h | 0-72h | 0-96h | 0-7d | 0-24h | 0-48h | 0-72h | 0-96h | 0-7d | Food intake | weight loss |
| Y | 1622 | 1.7 | 1 | -19 | -33 | -31 | -31 | -26 | -14 | -21 | -13 | -12 | -9 | 0.8 | 0.7 |
| Y | 1623 | 19 | 1 | -12 | -15 | -15 | -14 | -11 | -5 | -6 | -7 | -6 | -2 | 0.8 | 0.4 |
| Y | 1624 | 11.2 | 1 | -9 | -16 | -14 | -13 | -5 | -2 | -10 | -9 | -5 | -1 | 0.4 | 0.2 |
| Y | 1625 | 12.9 | 1 | -9 | -9 | -8 | -6 | -2 | -2 | -4 | -3 | -3 | 3 | 0.3 | -1.0 |
| Y | 1626 | 11.5 | 1 | -5 | -8 | -6 | -6 | -3 | 2 | -1 | -1 | 0 | 6 | 0.0 | 0.0 |
| Y | 1627 | 23.1 | 1 | -1 | -1 | 0 | 1 | 9 | 1 | 1 | 0 | -1 | 5 | 0.0 | 0.0 |
| Y | 1628 | 200 | 1 | 0 | -2 | -1 | -1 | 1 | 4 | 2 | 0 | 0 | 3 | 0.0 | 0.0 |
| Y | 1629 | 13.7 | 1 | -3 | -5 | -4 | -6 | -4 | 2 | 0 | 1 | -1 | 5 | 0.0 | 0.0 |
| Y | 1630 | 0.0 | 1 | 1 | 2 | 4 | 4 | 10 | 3 | 1 | 0 | 2 | 3 | 0.0 | 0.0 |
| Y | 1631 | 3.2 | 1 | -7 | -12 | -12 | -12 | -6 | 0 | -7 | -6 | -3 | 2 | 0.5 | -0.6 |
| Y | 1632 | 14 | 1 | -11 | -14 | -14 | -11 | -9 | -5 | -9 | -10 | -6 | -6 | 0.8 | 1.1 |
| Y | 1633 | 3.5 | 1 | -15 | -27 | -32 | -29 | -17 | -7 | -14 | -16 | -12 | -6 | 0.6 | 0.5 |
| Y | 1634 | 30 | 1 | -15 | -16 | 0 | -16 | -15 | -7 | -7 | 0 | -10 | -8 | 1.0 | 0.7 |
| Y | 1635 | 18.3 | 1 | -10 | -17 | -16 | -14 | -7 | -1 | -9 | -11 | -8 | 1 | 0.5 | -0.1 |
| Y | 1636 | 5.7 | 1 | -10 | -9 | -10 | -11 | -8 | -6 | -5 | -8 | -6 | -3 | 0.8 | 0.4 |
| Y | 1637 | 213 | 1 | -9 | -20 | -22 | -22 | -22 | -6 | -13 | -13 | -10 | -8 | 1.0 | 0.7 |
| Y | 1638 | 9 | 1 | -7 | -6 | -7 | -7 | -6 | -5 | -3 | -5 | -6 | -3 | 0.9 | 0.5 |
| Y | 1639 | 437 | 1 | -12 | -20 | -21 | -19 | -16 | -5 | -13 | -13 | -10 | -6 | 0.8 | 0.6 |
| Y | 1640 | 3.8 | 1 | -10 | -4 | -3 | -3 | -1 | -1 | -2 | -2 | -4 | -1 | 0.0 | 0.0 |
| Y | 1641 | 0.7 | 5 | -15 | -20 | -24 | -26 | -30 | -10 | -12 | -13 | -13 | -8 | 1.1 | 0.6 |
| Y | 1642 | 3.0 | 1 | -11 | -14 | -14 | -14 | -11 | -12 | -10 | -13 | -11 | -10 | 0.8 | 0.9 |
| Y | 1643 | 2.7 | 1 | -13 | -15 | -16 | -17 | -20 | -7 | -10 | -11 | -7 | -8 | 1.2 | 1.2 |
| Y | 1644 | 12.3 | 1 | -5 | -7 | -6 | -7 | -10 | -2 | -2 | -2 | -1 | -2 | 1.4 | 1.3 |
| Y | 1645 | 4.4 | 1 | -12 | -15 | -16 | -17 | -18 | -9 | -11 | -12 | -10 | -7 | 1.1 | 0.7 |
| Y | 1646 | 1.1 | 1 | -16 | -19 | -20 | -20 | -25 | -5 | -14 | -13 | -11 | -6 | 1.2 | 0.6 |
| Y | 1647 | 3.1 | 1 | -12 | -13 | -15 | -17 | -18 | -5 | -10 | -12 | -13 | -4 | 1.1 | 0.3 |
| Y | 1648 | 5.6 | | -8 | -11 | -13 | -14 | -16 | -3 | -9 | -9 | -7 | 0 | 1.1 | 0.0 |
| Y | 1649 | 1.9 | 1 | -12 | -9 | -9 | -7 | -9 | -5 | -7 | -6 | -7 | -7 | 1.3 | 1.0 |
| Y | 1650 | 0.0 | | -4 | -7 | -5 | 1 | 9 | 7 | 2 | 2 | 3 | 7 | 0.0 | 0.0 |
| Y | 1651 | 1.4 | 1 | -17 | -24 | -23 | -19 | -8 | -9 | -13 | -12 | -8 | 1 | 0.4 | -0.1 |

Figure 2
Part 2

| | | human cAMP inhibition | Solubility at 50mg/ml pH4 | Food intake in rat (g) | | | | | Weight Loss in rat (g) | | | | | Longevity | |
|---|---|---|---|---|---|---|---|---|---|---|---|---|---|---|---|
| | | | | 0-24h | 0-48h | 0-72h | 0-96h | 0-7d | 0-24h | 0-48h | 0-72h | 0-96h | 0-7d | Food intake | weight loss |
| Y | 1652 | 5.5 | | -9 | -15 | -12 | -8 | 1 | -1 | -8 | -4 | -6 | 2 | -0.1 | -0.3 |
| Y | 1653 | 4.4 | | -13 | -16 | -14 | -10 | 19 | -4 | -9 | -9 | -9 | 2 | -1.9 | -0.2 |
| Y | 1654 | 8.0 | 1 | -17 | -22 | -23 | -18 | -10 | -7 | -12 | -12 | -8 | -7 | 0.6 | 0.9 |
| Y | 1655 | 68.0 | | -3 | -3 | -5 | -3 | -5 | -3 | -5 | -7 | -4 | -5 | 0.0 | 0.0 |
| Y | 1656 | 3.0 | 1 | -15 | -20 | -24 | -22 | -19 | -7 | -14 | -13 | -12 | -8 | 0.9 | 0.7 |
| Y | 1657 | 2.7 | | -10 | -13 | -14 | -13 | -11 | 5 | -6 | -7 | -4 | -2 | 0.8 | 0.5 |
| Y | 1658 | 1.6 | | -10 | -8 | -9 | -6 | 0 | -2 | -2 | -6 | -3 | -2 | 0.0 | 0.7 |
| Y | 1659 | 0.0 | | -5 | -7 | -8 | -6 | -6 | 8 | -4 | -6 | -2 | 3 | 1.0 | -1.5 |
| Y | 1660 | 42.5 | 1 | -3 | -4 | 0 | -10 | -14 | 0 | -1 | 0 | -6 | -5 | 1.4 | 0.8 |
| Y | 1661 | 27.9 | | -4 | -3 | 0 | -7 | -8 | -2 | 1 | 0 | -4 | -4 | 1.2 | 0.9 |
| Y | 1662 | 6.9 | 1 | -17 | -25 | 0 | -21 | -18 | -12 | -12 | 0 | -7 | -9 | 0.9 | 1.3 |
| Y | 1663 | 22.5 | | -5 | -4 | 0 | -7 | -7 | -5 | -2 | 0 | -4 | -7 | 1.0 | 1.9 |
| Y | 1664 | 55.5 | | -3 | -2 | 0 | -2 | 1 | -5 | -1 | 0 | -3 | -1 | 0.0 | 0.0 |
| Y | 1665 | 2.5 | 2 | -19 | -31 | -25 | -29 | -21 | -14 | -18 | -8 | -12 | -12 | 0.7 | 1.0 |
| Y | 1666 | 42.4 | | -3 | -4 | 0 | -3 | -1 | -2 | -4 | 0 | -1 | -2 | 0.0 | 0.0 |
| Y | 1667 | 28.1 | | -9 | -10 | 0 | -6 | -2 | -6 | -5 | 0 | -1 | -1 | 0.0 | 0.0 |
| Y | 1668 | 84 | 2 | -2 | -2 | 0 | -4 | -4 | 1 | 1 | 0 | -5 | -7 | 1.2 | 1.4 |
| Y | 1669 | 26.2 | | -2 | -2 | 0 | -4 | -2 | -4 | 0 | 0 | -2 | -2 | 0.0 | 0.0 |
| Y | 1670 | 0.0 | | -1 | -2 | 0 | -4 | -3 | 3 | 4 | 0 | 2 | 2 | 0.0 | 0.0 |
| Y | 1671 | 92 | 4 | -7 | -11 | 0 | -13 | -10 | -4 | -6 | 0 | -3 | -4 | 0.8 | 1.6 |
| Y | 1672 | 9.0 | | -5 | -4 | 0 | -1 | 2 | -6 | -3 | 0 | -3 | -3 | 0.0 | 0.0 |
| Y | 1673 | 15 | 3 | -15 | -24 | 0 | -20 | -17 | -16 | -17 | 0 | -10 | -8 | 0.9 | 0.8 |
| Y | 1674 | 24.0 | | -7 | -6 | 0 | -9 | -9 | -3 | -1 | 0 | -3 | -4 | 1.0 | 1.6 |
| Y | 1675 | 29.4 | | -12 | -11 | 0 | -7 | -4 | -8 | -4 | 0 | -1 | -1 | 0.6 | 0.7 |
| Y | 1676 | 25.8 | | -15 | -19 | 0 | -17 | -14 | -10 | -9 | 0 | -4 | -1 | 0.8 | 0.3 |
| Y | 1677 | 92 | 3 | -13 | -18 | 0 | -17 | -14 | -5 | -5 | 0 | -4 | -3 | 0.8 | 0.7 |
| Y | 1678 | 12 | 5 | -11 | -16 | -10 | -19 | -23 | -4 | -8 | -5 | -7 | -8 | 1.2 | 1.1 |
| Y | 1679 | 33.5 | | -9 | -8 | 0 | -8 | -6 | -4 | -1 | 0 | -3 | -4 | 0.7 | 1.7 |
| Y | 1680 | 16.8 | | -10 | -10 | 0 | -12 | -12 | -4 | -1 | 0 | 1 | -2 | 1.0 | -3.7 |
| Y | 1681 | 34 | 1 | -13 | -11 | 0 | -12 | -11 | -8 | -5 | 0 | -6 | -7 | 0.9 | 1.3 |

Figure 2
Part 3

| | | human cAMP inhibition | Solubility at 50mg/ml pH4 | Food intake in rat (g) | | | | | Weight Loss in rat (g) | | | | | Longevity | |
|---|---|---|---|---|---|---|---|---|---|---|---|---|---|---|---|
| | | | | 0-24h | 0-48h | 0-72h | 0-96h | 0-7d | 0-24h | 0-48h | 0-72h | 0-96h | 0-7d | Food intake | weight loss |
| Y | 1682 | 7.8 | | -7 | -4 | 0 | 3 | 8 | -3 | 1 | 0 | 1 | -1 | 0.0 | 0.0 |
| Y | 1683 | 7.9 | 1 | -13 | -11 | 0 | -12 | -9 | -9 | -1 | 0 | -4 | -4 | 0.8 | 1.0 |
| Y | 1684 | 28.9 | | -7 | -5 | 0 | -4 | -1 | -5 | -2 | 0 | 0 | -3 | 0.0 | 0.0 |
| Y | 1685 | 22 | 1 | -7 | -7 | 0 | -9 | -9 | -3 | -3 | 0 | -3 | -8 | 1.0 | 2.4 |
| Y | 1686 | 25.3 | | -9 | -6 | 0 | -7 | -7 | -3 | 1 | 0 | 1 | -1 | 0.0 | 0.0 |
| Y | 1687 | 31.8 | | -14 | -13 | 0 | -10 | -9 | -9 | -6 | 0 | 1 | -3 | 0.9 | -2.5 |
| Y | 1688 | 7.7 | 3 | -8 | -9 | 0 | -3 | 1 | -5 | -5 | 0 | -3 | -6 | 0.0 | 0.0 |
| Y | 1689 | 0.0 | | -4 | -8 | -9 | -6 | -2 | 4 | -2 | -2 | 3 | 3 | 0.0 | 0.0 |
| Y | 1690 | 0.0 | | -2 | -5 | -3 | -3 | 0 | 1 | -1 | 2 | 2 | 5 | 0.0 | 0.0 |
| Y | 1691 | 0.0 | | -2 | -5 | -5 | -3 | -1 | 3 | -1 | -1 | 1 | 1 | 0.0 | 0.0 |
| Y | 1692 | 354 | | -6 | -9 | 0 | -11 | -19 | -4 | -4 | 0 | -2 | -5 | 1.8 | 3.0 |
| Y | 1693 | 293 | 2 | -11 | -10 | 0 | -12 | -22 | -7 | -6 | 0 | -5 | -11 | 1.9 | 2.1 |
| Y | 1694 | 9 | 3 | -18 | -23 | 0 | -25 | -32 | -13 | -15 | 0 | -10 | -11 | 1.3 | 1.1 |
| Y | 1695 | 20 | 1 | -11 | -15 | 0 | -17 | -27 | -6 | -6 | 0 | -3 | -10 | 1.6 | 3.1 |
| Y | 1696 | 139 | 5 | -7 | -10 | 0 | -17 | -25 | -6 | -5 | 0 | -5 | -4 | 1.5 | 0.8 |
| Y | 1697 | 553 | | -6 | -10 | 0 | -15 | -26 | 0 | 1 | 0 | 2 | -1 | 1.8 | -0.6 |
| Y | 1698 | 783 | 5 | -14 | -15 | 0 | -15 | -22 | -8 | -8 | 0 | -7 | -10 | 1.5 | 1.3 |
| Y | 1699 | 72.4 | | -6 | -7 | 0 | -7 | -16 | -1 | -4 | 0 | 0 | -5 | 0.0 | 0.0 |
| Y | 1700 | 6.8 | 5 | -22 | -43 | 0 | -48 | -53 | -15 | -23 | 0 | -15 | -15 | 1.1 | 1.0 |
| Y | 1701 | 1158 | 5 | -3 | -5 | 0 | -8 | -19 | -2 | -3 | 0 | -1 | -6 | 2.4 | 7.7 |
| Y | 1702 | 377 | | -4 | -8 | 0 | -11 | -20 | -2 | -3 | 0 | 0 | -4 | 1.9 | -11.0 |
| Y | 1703 | 123 | 5 | -8 | -13 | 0 | -15 | -25 | -3 | -8 | 0 | -8 | -11 | 1.6 | 1.4 |
| Y | 1704 | 3626 | 5 | -7 | -11 | 0 | -18 | -30 | -2 | -5 | 0 | -1 | -7 | 1.6 | 5.0 |
| Y | 1705 | 0.0 | | -8 | -9 | 0 | -4 | -10 | -6 | -3 | 0 | 4 | 0 | 0.0 | 0.0 |
| Y | 1706 | 125 | 5 | 0 | -1 | -1 | -1 | 0 | 0 | -6 | -3 | -4 | -1 | 0.0 | 0.0 |
| Y | 1707 | 0.0 | | -3 | -4 | -5 | -4 | -4 | 1 | -2 | 0 | 0 | 2 | 0.0 | 0.0 |
| Y | 1708 | 0.0 | | -3 | -4 | -5 | -5 | -25 | 2 | -2 | -2 | 0 | 0 | 0.0 | 0.0 |
| Y | 1709 | 0.0 | | 0 | 0 | 0 | 0 | 0 | 1 | 0 | -3 | 1 | 0 | 0.0 | 0.0 |
| Y | 1710 | 195 | | -3 | -6 | -9 | -10 | -14 | 0 | -2 | -4 | -2 | -1 | 1.4 | 0.5 |
| Y | 1711 | 0.0 | | 0 | 0 | 1 | 1 | 4 | 0 | 0 | 0 | 3 | 4 | 0.0 | 0.0 |

Figure 2
Part 4

| | | human cAMP inhibition | Solubility at 50mg/ml pH4 | Food intake in rat (g) | | | | | Weight Loss in rat (g) | | | | | Longevity | |
|---|---|---|---|---|---|---|---|---|---|---|---|---|---|---|---|
| | | | | 0-24h | 0-48h | 0-72h | 0-96h | 0-7d | 0-24h | 0-48h | 0-72h | 0-96h | 0-7d | Food intake | weight loss |
| Y | 1712 | 9.6 | | -2 | -4 | -4 | -4 | -6 | 2 | -2 | 1 | 3 | 1 | 0.0 | 0.0 |
| Y | 1713 | 9 | | -15 | -21 | 0 | -19 | -29 | -7 | -11 | 0 | -4 | -10 | 1.5 | 2.3 |
| Y | 1714 | 5.4 | | -14 | -17 | -13 | -9 | -1 | -9 | -13 | -12 | -7 | -5 | 0.1 | 0.7 |
| Y | 1715 | 32.5 | | -4 | -3 | 0 | -2 | -9 | -3 | -1 | 0 | 1 | -3 | 0.0 | 0.0 |
| Y | 1716 | 0.0 | | 0 | 1 | 0 | -1 | -8 | 2 | 1 | 0 | 3 | -1 | 0.0 | 0.0 |
| Y | 1717 | 8.6 | 1 | -21 | -31 | -28 | -28 | -24 | -17 | -21 | -16 | -13 | -8 | 0.9 | 0.6 |
| Y | 1718 | 2.9 | | -8 | -4 | 1 | 5 | 17 | 1 | -3 | 1 | 4 | 10 | 0.0 | 0.0 |
| Y | 1719 | 15.2 | | -4 | -5 | -3 | -2 | -3 | -1 | -4 | 1 | -1 | 0 | 0.0 | 0.0 |
| Y | 1720 | 0.0 | | -8 | -13 | -3 | 2 | 11 | 1 | -7 | -4 | -2 | 0 | 0.0 | 0.0 |
| Y | 1721 | 4.4 | | -11 | -10 | -7 | -4 | 1 | -5 | -7 | -5 | -4 | -1 | 0.0 | 0.0 |
| Y | 1722 | 4.2 | | -16 | -16 | -12 | -12 | -9 | -7 | -9 | -6 | -5 | -2 | 0.7 | 0.4 |
| Y | 1723 | 4.9 | | -19 | -23 | -19 | -17 | -12 | -10 | -18 | -11 | -11 | -6 | 0.7 | 0.5 |
| Y | 1724 | 6.3 | | 0 | 0 | 0 | 0 | 0 | 0 | 0 | 0 | 0 | 0 | 0.0 | 0.0 |
| Y | 1725 | 7.3 | | -9 | -6 | -2 | 3 | 13 | -4 | -7 | -7 | 0 | 1 | 0.0 | 0.0 |
| Y | 1726 | 2.7 | | -2 | 2 | 6 | 9 | 16 | 5 | 3 | 2 | 5 | 11 | 0.0 | 0.0 |
| Y | 1727 | 0.0 | | -6 | -5 | -3 | 0 | 5 | 2 | -2 | 1 | 5 | 6 | 0.0 | 0.0 |
| Y | 1728 | 0.0 | | -4 | -5 | 0 | 2 | 7 | 9 | -2 | -3 | 0 | 5 | 0.0 | 0.0 |
| Y | 1729 | 2.1 | | -15 | -16 | -11 | -11 | -6 | -6 | -11 | -8 | -3 | 0 | 0.5 | 0.1 |
| Y | 1730 | 2.2 | | -11 | -10 | -8 | -8 | -7 | -1 | -6 | -4 | -1 | -2 | 0.9 | 1.7 |
| Y | 1731 | 0.0 | | -13 | -12 | -8 | -6 | -2 | -7 | -6 | -5 | 0 | 1 | 0.0 | 0.0 |
| Y | 1732 | 0.0 | | -6 | -7 | -4 | -2 | 0 | 5 | -5 | -6 | 1 | 1 | 0.0 | 0.0 |
| Y | 1733 | 8.5 | | | | | | | | | | | | | |
| Y | 1734 | 7.5 | | | | | | | | | | | | | |
| Y | 1735 | 3.7 | | | | | | | | | | | | | |
| Y | 1736 | 9.0 | | | | | | | | | | | | | |
| Y | 1737 | 6.7 | | | | | | | | | | | | | |
| Y | 1738 | 6.2 | | | | | | | | | | | | | |
| Y | 1739 | 2.2 | | | | | | | | | | | | | |
| Y | 1740 | 3.5 | | | | | | | | | | | | | |
| Y | 1741 | 3.0 | | | | | | | | | | | | | |

Figure 2
Part 5

| | | human cAMP inhibition | Solubility at 50mg/ml pH4 | Food intake in rat (g) | | | | | Weight Loss in rat (g) | | | | | Longevity | |
|---|---|---|---|---|---|---|---|---|---|---|---|---|---|---|---|
| | | | | 0-24h | 0-48h | 0-72h | 0-96h | 0-7d | 0-24h | 0-48h | 0-72h | 0-96h | 0-7d | Food intake | weight loss |
| Y | 1742 | 3.1 | | | | | | | | | | | | | |
| Y | 1743 | 5.4 | | | | | | | | | | | | | |
| Y | 1744 | 1.6 | | | | | | | | | | | | | |
| Y | 1745 | 22.1 | | | | | | | | | | | | | |
| Y | 1746 | 11.2 | | | | | | | | | | | | | |
| Y | 1747 | 26.7 | | | | | | | | | | | | | |
| Y | 1748 | 19.3 | | | | | | | | | | | | | |
| Y | 1749 | 7.6 | | | | | | | | | | | | | |
| Y | 1750 | 2.4 | | | | | | | | | | | | | |
| Y | 1751 | 8.8 | | | | | | | | | | | | | |
| Y | 1752 | 2.3 | | | | | | | | | | | | | |
| Y | 1753 | 21.8 | | | | | | | | | | | | | |
| Y | 1754 | 5.1 | 1 | | | | | | | | | | | | |
| Y | 1755 | 2.0 | 1 | | | | | | | | | | | | |
| Y | 1756 | 11.2 | | | | | | | | | | | | | |
| Y | 1757 | 5.4 | 1 | | | | | | | | | | | | |
| Y | 1758 | 3.9 | 1 | | | | | | | | | | | | |
| Y | 1759 | 2.5 | 1 | | | | | | | | | | | | |
| Y | 1760 | 77.0 | | | | | | | | | | | | | |
| Y | 1761 | 492 | | | | | | | | | | | | | |
| Y | 1762 | 1.4 | | | | | | | | | | | | | |
| Y | 1763 | 2.7 | | | | | | | | | | | | | |
| Y | 1764 | 7.8 | | | | | | | | | | | | | |
| Y | 1765 | 6.3 | 1 | | | | | | | | | | | | |
| Y | 1766 | 3.8 | 1 | | | | | | | | | | | | |
| Y | 1767 | 2.9 | 1 | | | | | | | | | | | | |
| Y | 1768 | 4.6 | 1 | | | | | | | | | | | | |
| Y | 1769 | 30.2 | | | | | | | | | | | | | |
| Y | 1770 | 24.8 | | | | | | | | | | | | | |
| Y | 1771 | 14.1 | | | | | | | | | | | | | |

Figure 2
Part 6

| | | human cAMP inhibition | Solubility at 50mg/ml pH4 | Food intake in rat (g) | | | | | Weight Loss in rat (g) | | | | | Longevity | |
|---|---|---|---|---|---|---|---|---|---|---|---|---|---|---|---|
| | | | | 0-24h | 0-48h | 0-72h | 0-96h | 0-7d | 0-24h | 0-48h | 0-72h | 0-96h | 0-7d | Food intake | weight loss |
| Y | 1772 | 39.6 | | | | | | | | | | | | | |
| Y | 1773 | 21.2 | | | | | | | | | | | | | |
| Y | 1774 | 40.9 | | | | | | | | | | | | | |
| Y | 1775 | 48.2 | | | | | | | | | | | | | |
| Y | 1776 | 49.0 | 1 | | | | | | | | | | | | |
| Y | 1777 | 53.7 | 1 | | | | | | | | | | | | |
| Y | 1778 | 21.1 | 1 | | | | | | | | | | | | |
| Y | 1779 | 32.5 | 1 | | | | | | | | | | | | |
| Y | 1780 | 14.4 | 1 | | | | | | | | | | | | |
| Y | 1781 | 11.3 | 1 | | | | | | | | | | | | |
| Y | 1782 | 12.2 | 1 | | | | | | | | | | | | |
| Y | 1783 | 3.5 | 1 | | | | | | | | | | | | |
| Y | 1784 | 3.7 | 1 | | | | | | | | | | | | |
| Y | 1785 | 2.9 | 1 | | | | | | | | | | | | |
| Y | 1786 | 13.4 | | | | | | | | | | | | | |
| Y | 1787 | 12.4 | | | | | | | | | | | | | |
| Y | 1788 | 5.7 | | | | | | | | | | | | | |
| Y | 1789 | 4.7 | | | | | | | | | | | | | |
| Y | 1790 | 11.1 | | | | | | | | | | | | | |
| Y | 1791 | 20.9 | | | | | | | | | | | | | |
| Y | 1792 | 15.8 | | | | | | | | | | | | | |
| Y | 1793 | 13.0 | | | | | | | | | | | | | |
| Y | 1794 | 11.7 | | | | | | | | | | | | | |
| Y | 1795 | 5.6 | | | | | | | | | | | | | |
| Y | 1796 | 5.8 | | | | | | | | | | | | | |
| Y | 1797 | 11.2 | | | | | | | | | | | | | |
| Y | 1798 | 2.3 | | | | | | | | | | | | | |
| Y | 1799 | 3.7 | | | | | | | | | | | | | |
| Y | 1800 | 1.2 | 1 | | | | | | | | | | | | |
| Y | 1801 | 4.3 | 1 | | | | | | | | | | | | |

Figure 2
Part 7

| | | human cAMP inhibition | Solubility at 50mg/ml pH4 | Food intake in rat (g) | | | | | Weight Loss in rat (g) | | | | | Longevity | |
|---|---|---|---|---|---|---|---|---|---|---|---|---|---|---|---|
| | | | | 0-24h | 0-48h | 0-72h | 0-96h | 0-7d | 0-24h | 0-48h | 0-72h | 0-96h | 0-7d | Food intake | weight loss |
| Y | 1802 | 0.6 | 1 | | | | | | | | | | | | |
| Y | 1803 | 3.7 | 1 | | | | | | | | | | | | |
| Y | 1804 | 0.7 | 1 | | | | | | | | | | | | |
| Y | 1805 | 2.4 | 1 | | | | | | | | | | | | |
| Y | 1806 | 1.4 | 1 | | | | | | | | | | | | |
| Y | 1807 | 0.7 | 1 | | | | | | | | | | | | |
| Y | 1808 | 1.7 | 1 | | | | | | | | | | | | |
| Y | 1809 | 1.4 | 1 | | | | | | | | | | | | |
| Y | 1810 | 7.8 | 5 | | | | | | | | | | | | |
| Y | 1811 | 16.1 | 1 | | | | | | | | | | | | |
| Y | 1812 | 12.1 | 1 | | | | | | | | | | | | |
| Y | 1813 | 4.4 | 1 | | | | | | | | | | | | |
| Y | 1814 | 8.7 | 1 | | | | | | | | | | | | |
| Y | 1815 | 23.0 | 4 | | | | | | | | | | | | |
| Y | 1816 | 1.3 | 1 | | | | | | | | | | | | |
| Y | 1817 | 1.8 | 1 | | | | | | | | | | | | |
| Y | 1818 | 0.9 | 1 | | | | | | | | | | | | |
| Y | 1819 | 2.3 | 3 | | | | | | | | | | | | |
| Y | 1820 | 0.4 | 1 | | | | | | | | | | | | |

Figure 2
Part 8

APPETITE SUPPRESSING COMPOUNDS

CROSS-REFERENCE TO RELATED APPLICATIONS

This application is the National Stage of International Application No. PCT/GB2020/051426, filed on Jun. 12, 2020, which claims the benefit of and priority to Great Britain Patent Application No. 1908426.8, filed on Jun. 12, 2019, the contents of which are incorporated by reference in their entirety.

SEQUENCE LISTING

The instant application contains a Sequence Listing which has been submitted via EFS-Web and is hereby incorporated by reference in its entirety. Said ASCII copy, created on Dec. 10, 2021, is named 50867US_CRF_sequencelisting.txt, and is 205,137 bytes in size.

FIELD OF THE INVENTION

This application relates to compounds which are analogues of peptide YY (PYY), and which are useful in treating disorders such as diabetes and obesity, either alone or in combination with other agents, especially in combination with GLP-1 analogues.

BACKGROUND OF THE INVENTION

According to the National Health and Nutrition Examination Survey (NHANES, 2011 to 2012), over two thirds of adults in the United States are overweight or obese. In the United States, 78% percent of males and 74% percent of women, of the age of 20 or older, are either overweight or obese. In addition, a large percentage of children in the United States are overweight or obese.

The cause of obesity is complex and multi-factorial. Increasing evidence suggests that obesity is not a simple problem of self-control but is a complex disorder involving appetite regulation and energy metabolism. In addition, obesity is associated with a variety of conditions associated with increased morbidity and mortality in a population. Although the etiology of obesity is not definitively established, genetic, metabolic, biochemical, cultural and psychosocial factors are believed to contribute. In general, obesity has been described as a condition in which excess body fat puts an individual at a health risk.

There is strong evidence that obesity is associated with increased morbidity and mortality. Disease risk, such as cardiovascular disease risk and type-2 diabetes disease risk, increases independently with increased body mass index (BMI). Indeed, this risk has been quantified as a five percent increase in the risk of cardiac disease for females, and a seven percent increase in the risk of cardiac disease for males, for each point of a BMI greater than 24.9 (see Kenchaiah et al., *N. Engl. J. Med.* 347:305, 2002; Massie, *N. Engl. J. Med.* 347:358, 2002).

Diabetes is a chronic syndrome of impaired carbohydrate, protein, and fat metabolism owing to insufficient secretion of insulin or to target tissue insulin resistance. It occurs in two major forms: insulin-dependent diabetes mellitus (type 1 diabetes) and non-insulin dependent diabetes mellitus (type 2 diabetes). Diabetes type 1, or insulin dependent diabetes mellitus (IDDM) is caused by the destruction of β cells, which results in insufficient levels of endogenous insulin. Diabetes type 2, or non-insulin dependent diabetes, results from a defect in both the body's sensitivity to insulin, and a relative deficiency in insulin production. According to the National Diabetes Statistics Report, 2014 around 28.9 million adults in the United States aged 20 and over have diabetes (2009-2012 National Health and Nutrition Examination Survey estimates applied to 2012 U.S. Census data). In adults 90 to 95% of the diabetes is type 2 diabetes.

There is substantial evidence that weight loss in obese persons reduces important disease risk factors. Even a small weight loss, such as 10% of the initial body weight in both overweight and obese adults has been associated with a decrease in risk factors such as hypertension, hyperlipidemia, and hyperglycemia. It has been shown that considerable weight loss can effectively cure type 2 diabetes (Lim et al, Diabetologia June 2011).

Although diet and exercise provide a simple process to decrease weight gain, overweight and obese individuals often cannot sufficiently control these factors to effectively lose weight. Pharmacotherapy is available; several weight loss drugs have been approved by the Food and Drug Administration that can be used as part of a comprehensive weight loss program. However, many of these drugs have serious adverse side effects. When less invasive methods have failed, and the patient is at high risk for obesity related morbidity or mortality, weight loss surgery is an option in carefully selected patients with clinically severe obesity. However, these treatments are high-risk, and suitable for use in only a limited number of patients. It is not only obese subjects who wish to lose weight. People with weight within the recommended range, for example, in the upper part of the recommended range, may wish to reduce their weight, to bring it closer to the ideal weight. Thus, a need remains for agents that can be used to effect weight loss in overweight and obese subjects as well as in subjects who are of normal weight.

PYY is a 36-amino acid peptide produced by the L cells of the gut, with highest concentrations found in the large bowel and the rectum. Two endogenous forms, PYY and PYY 3-36, are released into the circulation. PYY 3-36 is further produced by cleavage of the Tyr-Pro amino terminal residues of PYY by the enzyme dipeptidyl peptidase IV (DPP-IV). PYY 3-36 binds to the Y2 receptor of the Y family of receptors (De Silva and Bloom, Gut Liver, 2012, 6, p10-20). Studies have shown that peripheral administration of PYY 3-36 to rodents and humans leads to marked inhibition of food intake, leading to the prospect that analogues of PYY may be useful in treating conditions such as obesity (see, e.g. Batterham et al, Nature, 2002, 418, p650-654; Batterham et al, New England Journal of Medicine, 2003, 349, p941-948).

PYY has also been implicated in altering the metabolism of subjects and has been proposed as a treatment for type-2 diabetes, following evidence that it is able to restore impaired insulin and glucagon secretion in type-2 diabetes. The relationship between obesity and diabetes is complex because being overweight increases diabetic risk and being diabetic increases the likelihood of being overweight. The nexus between the two conditions is one in which PYY plays an increasingly recognized role.

WO2011/092473 and WO2012/101413 (Imperial Innovations Limited) disclose certain analogues of PYY. However, there remains a need for further compounds which have suitable properties so that they are effective as therapeutic agents in treating or preventing disorders of energy metabolism such as obesity and/or diabetes.

Despite significant advances, the process of identifying substances useful as drugs remains a complex and, in many cases, unpredictable field. In order to be useful as therapeutic agents, compounds must possess a suitable range of properties. In addition to having good efficacy at the biological target of interest, compounds must have good in vivo pharmacokinetic properties, low toxicity and an acceptable side effect profile. For example, even with commercial agents such as liraglutide, side effects can include nausea and vomiting, and concerns have also been raised with regard to thyroid cancer and pancreatitis.

Thus, there remains a need for further compounds which are useful for the treatment of disorders and diseases such as diabetes and obesity. For example, it would be desirable to identify peptides having beneficial properties such as an improved activity profile, and/or which have reduced side effects. If a compound decreases food intake less, then it is expected that the compound will have fewer side effects such as nausea. Alternatively, or additionally, it would be desirable for a peptide to be identified that has these and other biological effects for a sustained period. A compound that has a longer period of activity can be administered less frequently and at lower dose, which contributes to improved convenience for the subject, to fewer side effects and to lower cost.

SUMMARY OF THE INVENTION

According to a first aspect of the invention there is provided a compound of formula I, II or III:

$$C—NH_2 \quad \text{Formula I;}$$

$$B—C—NH_2 \quad \text{Formula II;}$$

$$A\text{-}B—C—NH \quad \text{Formula III;}$$

wherein C is a peptide sequence:

```
                                              [SEQ ID NO: 1]
Xaa2-Xaa3-Xaa4-Xaa5-Xaa6-Xaa7-Pro8-Xaa9-Xaa10-

Xaa11-Xaa12-Xaa13-Xaa14-Xaa15-Xaa16-Xaa17-Xaa18-

Xaa19-Tyr20-Tyr21-Xaa22-Xaa23-Xaa24-Xaa25-Xaa26-

Xaa27-Leu28-Asn29-Xaa30-Xaa31-Thr32-Arg33-Gln34-

Arg35-Tyr36
```

wherein:

- Xaa2 is Pro or Cys;
- Xaa3 is Lys substituted at its ε-amino group or Ile;
- Xaa4 is Lys substituted at its ε-amino group or Lys;
- Xaa5 is Pro or Cys;
- Xaa6 is Glu substituted at its γ carboxylic acid group, Lys substituted at its ε-amino group or Glu;
- Xaa7 is Lys substituted at its ε-amino group, Cys substituted at its β-thiol group, Ala or Cys
- Xaa9 is Lys substituted at its ε-amino group, Cys substituted at its β-thiol group, Gly or Cys;
- Xaa10 is Glu substituted at its γ carboxylic acid group, Lys substituted at its ε-amino group, Cys substituted at its β-thiol group, Lys, Glu or Cys;
- Xaa11 is Lys substituted at its ε-amino group, Asp, Gly, Asn or Glu;
- Xaa12 is Lys substituted at its ε-amino group or Ala;
- Xaa13 is Lys substituted at its ε-amino group or Ser;
- Xaa14 is Lys substituted at its ε-amino group or Pro;
- Xaa15 is Lys substituted at its ε-amino group or Glu;
- Xaa16 is Lys substituted at its ε-amino group or Glu;
- Xaa17 is Leu or Ile;
- Xaa18 is Lys substituted at its ε-amino group, Asn, Leu, Ala or Val;
- Xaa19 is Lys substituted at its ε-amino group, Arg, Lys or His;
- Xaa22 is Lys substituted at its ε-amino group, Ala, or Ile;
- Xaa23 is Lys substituted at its ε-amino group, Ala or Glu;
- Xaa24 is Leu or Cys;
- Xaa25 is Lys substituted at its ε-amino group or Arg;
- Xaa26 is Lys substituted at its ε-amino group or His;
- Xaa27 is Lys substituted at its ε-amino group, Tyr, Phe or Cys;
- Xaa30 is Lys substituted at its ε-amino group, Arg, Lys or His; and
- Xaa31 is Val or Leu;

wherein B is a peptide residue selected from:

Lys substituted at its ε-amino group, Ala substituted at its α-amino group, Tyr, Val, Ala, Ser, Gly, Lys and Glu;

wherein A is a peptide sequence:

```
                                 [SEQ ID NO: 2]
Xaa51-Xaa52-Xaa53-Xaa54-Xaa55-Xaa56;

                                 [SEQ ID NO: 3]
Xaa52-Xaa53-Xaa54-Xaa55-Xaa56;

                                 [SEQ ID NO: 4]
Xaa53-Xaa54-Xaa55-Xaa56

Xaa54-Xaa55-Xaa56;

Xaa55-Xaa56;
or

Xaa56;
```

Wherein:

- Xaa51 is Glu substituted at its α-amino group or Glu;
- Xaa52 is Glu substituted at its α-amino group, Lys substituted at its ε-amino group, Gly or Tyr;
- Xaa53 is Glu substituted at its α-amino group, Gly substituted at its α-amino group, Ser, Asn, Gly, Glu or Tyr;
- Xaa54 is Glu substituted at its γ-carboxylic acid group, Glu substituted at its α-amino group, Lys substituted at its ε-amino group, Ser substituted at its α-amino group, Asn substituted at its a-amino group, Ser, Gly, Glu, Tyr, Pro, Asn or His;
- Xaa55 is Glu substituted at its γ-carboxylic acid group, Glu substituted at its α-amino group, Lys substituted at its ε-amino group, Ser substituted at its α-amino group, Gly, Ser, Glu, Pro, His, Asn or Thr;
- Xaa56 is Lys substituted at its ε-amino group, Glu substituted at its γ-carboxylic acid group, Gly substituted at its α-amino group, Gly, Ser, Pro, His, Thr, Tyr or Glu;

wherein the compound has a single substitution at one of the amino acid residues indicated above and wherein the substituent is selected from:

(a) a group of the formula:

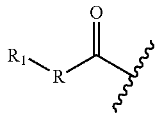

wherein the substituent is attached to the α-amino group of said substituted residue or wherein the substituted residue is Lys and the substituent is attached to the γ-amino group of the Lys residue; R is a $C_8$-$C_{28}$ alkylene or alkenylene chain and $R_1$ is $CO_2H$.

(b) Z—Cys-S— wherein Z is a group of the formula

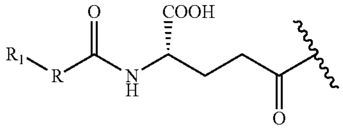

wherein R is a $C_8$-$C_{28}$ alkylene or alkenylene chain and $R_1$ is $CO_2H$, (c) Z—Cys-S— wherein Z is a group of the formula

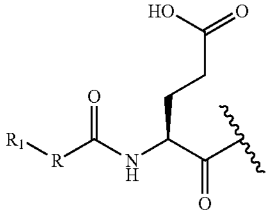

wherein R is a $C_8$-$C_{28}$ alkylene or alkenylene chain and $R_1$ is $CO_2H$; or (d) X-Q-;

wherein Q is a peptide sequence or single amino acid residue selected from:

```
                                        [SEQ ID NO: 5]
Xaa65-Xaa64-Xaa63-Xaa62-Xaa61,

                                        [SEQ ID NO: 6]
Xaa64-Xaa63-Xaa62-Xaa61,

Xaa63-Xaa62-Xaa61,

Xaa62-Xaa61
and

Xaa61;
```

and X is group of the formula

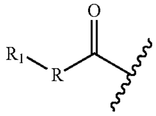
,
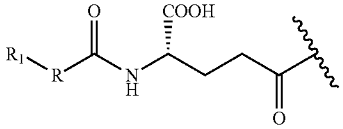
or
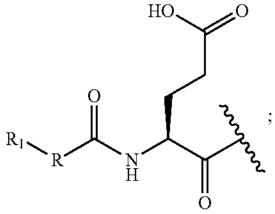
;

wherein R: is a $C_8$-$C_{28}$ alkylene or alkenylene chain and $R_1$ is $CO_2H$;

or a salt or derivative thereof.

According to a second aspect of the invention, there is provided a composition comprising a compound, derivative or salt of the first aspect of the invention together with a pharmaceutically acceptable carrier and optionally a further therapeutic agent (for example an appetite suppressor which is a GLP-1 derivative).

According to a third aspect of the invention, there is provided a compound, derivative or salt of the first aspect of the invention, or a composition of the second aspect of the invention, for use as a medicament, e.g. for use in the prevention or treatment of diabetes, obesity, heart disease, stroke or non-alcoholic fatty liver disease, improving insulin release in a subject, improving carbohydrate metabolism in a subject, improving the lipid profile of a subject, improving carbohydrate tolerance in a subject, reducing appetite, reducing food intake, reducing calorie intake, and/or for use as a cytoprotective agent.

According to a forth aspect of the invention, there is provided a method of treating or preventing a disease or disorder or other non-desired physiological state in a subject comprising administration of a therapeutically effective amount of a compound, derivative or salt of the first aspect of the invention, or of a composition of the second aspect of the invention, e.g. in a method of treating or preventing diabetes, obesity, heart disease, stroke or non-alcoholic fatty liver disease, improving carbohydrate metabolism in a subject, improving the lipid profile of a subject, improving carbohydrate tolerance in a subject, reducing appetite, reducing food intake, reducing calorie intake, and/or providing cytoprotection in a subject.

According to a fifth aspect of the invention, there is provided a compound, derivative or salt of the first aspect of the invention, or a pharmaceutical composition of the second aspect of the invention, for use in the prevention or treatment of diabetes, obesity, heart disease, stroke and non-alcoholic fatty liver disease, improving insulin release in a subject, improving carbohydrate metabolism in a subject, improving the lipid profile of a subject, reducing appetite, reducing food intake, reducing calorie intake, improving carbohydrate tolerance in a subject, and/or for use as a cytoprotective agent.

According to a sixth aspect of the invention, there is provided a method of treating or preventing diabetes, obesity, heart disease, stroke or non-alcoholic fatty liver disease in a subject, improving insulin release in a subject, improving carbohydrate metabolism in a subject, improving the lipid profile of a subject, improving carbohydrate tolerance in a subject, reducing appetite, reducing food intake, reducing calorie intake, and/or providing cytoprotection in a subject, comprising administration of a therapeutically effective amount of a compound, derivative or salt of the first aspect of the invention, or of a composition of the second aspect of the invention.

According to a seventh aspect of the invention, there is provided use of a compound, derivative or salt of the first aspect of the invention for the manufacture of a medicament for the prevention or treatment of diabetes, obesity, heart disease, stroke and non-alcoholic fatty liver disease, improving insulin release in a subject, improving carbohydrate metabolism in a subject, improving the lipid profile of a subject, improving carbohydrate tolerance in a subject, reducing appetite, reducing food intake, reducing calorie intake, and/or for use as a cytoprotective agent.

According to an eighth aspect of the invention, there is provided a method of causing weight loss or preventing weight gain in a subject for cosmetic purposes comprising administration of an effective amount of a compound, derivative or salt of the first aspect of the invention, or of a composition of the second aspect of the invention.

The present invention is based on the discovery that analogues of PYY in which specific amino acid residues are deleted and/or substituted can also be administered to a subject in order to cause decreased food intake, decreased caloric intake, decreased appetite and an alteration in energy metabolism. In many cases the PYY analogues of the present invention exhibit improved potency and/or longer duration of action and/or fewer side effects than native PYY.

The compounds of the present invention are also especially suitable for use in combination therapies with agonists of the GLP-1 receptor. This is because PYY and GLP-1 analogues have broadly compatible and similar chemistries which lend them to being formulated in combination, so they can be conveniently administered as a single injection. Additionally, PYY analogues and GLP-1 analogues inhibit appetite by different and separate mechanisms, and so a patient receiving a combination therapy is less liable to 'escape' the desired pharmaceutical effect than would be the case if treated with either agent alone. Lastly, the different mechanisms of action allow for an additive or synergistic effect on appetite suppression, making a more potent therapy.

BRIEF DESCRIPTION OF THE DRAWINGS

FIG. 1 is a table listing the amino acid sequences of some PYY analogues (SEQ ID NOs: 47-282) that relate to specific preferred embodiments of the invention. The naturally occurring sequence of human PYY (hPYY) (SEQ ID NO: 22) is included on the first line for reference. Derivatisation in the amino acid sequences given in FIG. 1 are indicated by '*n'. These derivatives are described in Table 1 below:

TABLE 1

| | |
|---|---|
| Lys *1 | Lys residue with a hexadecanedioic acid moiety attached to its ε-amino group |
| Lys *2 | Lys residue with the C terminus of peptide sequence γGlu*-Gly-Ser-Gly [SEQ ID NO: 7] attached to its ε-amino group, wherein γGlu* is a γGlu residue with an octadecanedioic acid moiety attached to its α-amino group |
| Lys *3 | Lys residue with the C terminus of peptide sequence γGlu*-Gly-Ser-Gly-Ser [SEQ ID NO: 8] attached to its ε-amino group, wherein γGlu* is a γGlu residue with an octadecanedioic acid moiety attached to its α-amino group |
| Lys *4 | Lys residue with the C terminus of peptide sequence γGlu*-Pro-Thr-Gly [SEQ ID NO: 9] attached to its ε-amino group, wherein γGlu* is a γGlu residue with an octadecanedioic acid moiety attached to its α-amino group |
| Lys *5 | Lys residue with the C terminus of peptide sequence Ser*-Gly attached to its ε-amino group, wherein Ser* is a Ser residue with an octadecanedioic acid moiety attached to its α-amino group |
| Lys *6 | Lys residue with the C terminus of peptide sequence γGlu*-Gly-Thr-Gly-Thr [SEQ ID NO: 10] attached to its ε-amino group, wherein γGlu* is a γGlu residue with an octadecanedioic acid moiety attached to its α-amino group |
| Lys *7 | Lys residue with the C terminus of peptide sequence γGlu*-Gly-Thr attached to its ε-amino group, wherein γGlu* is a γGlu residue with an octadecanedioic acid moiety attached to its α-amino group |
| Lys *8 | Lys residue with the C terminus of peptide sequence γGlu*-Tyr-Gly attached to its ε-amino group, wherein γGlu* is a γGlu residue with an octadecanedioic acid moiety attached to its α-amino group |
| Lys *9 | Lys residue with the C terminus of peptide sequence γGlu*-Ser-Gly-Gly-Gly [SEQ ID NO: 11] attached to its ε-amino group, wherein γGlu* is a γGlu residue with an octadecanedioic acid moiety attached to its α-amino group |
| Glu *10 | γGlu residue with an octadecanedioic acid moiety attached to its α-amino group |
| Asn *10 | Asn residue with an octadecanedioic acid moiety attached to its α-amino group |
| Gly *10 | Gly residue with an octadecanedioic acid moiety attached to its α-amino group |
| Ser *10 | Ser residue with an octadecanedioic acid moiety attached to its α-amino group |
| Ala *10 | Lys residue with an octadecanedioic acid moiety attached to its α-amino group |
| Lys *10 | Lys residue with an octadecanedioic acid moiety attached to its ε-amino group |
| Lys *11 | Lys residue with the C terminus of peptide sequence γGlu*-Gly-Ser-Gly-Glu [SEQ ID NO: 12] attached to its ε-amino group, wherein γGlu* is a γGlu residue with an octadecanedioic acid moiety attached to its α-amino group |
| Glu *11 | Glu residue with an octadecanedioic acid moiety attached to its α-amino group |
| Lys *12 | Lys residue with the C terminus of peptide sequence γGlu*-Gly-Ser-Gly-Asp [SEQ ID NO: 13] attached to its ε-amino group, wherein γGlu* is a γGlu residue with an octadecanedioic acid moiety attached to its α-amino group |
| Lys *13 | Lys residue with the C terminus of peptide sequence Glu*-Gly-Ser-Gly [SEQ ID NO: 14] attached to its ε-amino group, wherein Glu* is a Glu residue with an eicosanedioic acid moiety attached to its α-amino group |
| Lys *14 | Lys residue with the C terminus of peptide sequence Gly*-Thr attached to its ε-amino group, wherein Gly* is a Gly residue with an octadecanedioic acid moiety attached to its α-amino group |
| Lys *15 | Lys residue with the C terminus of peptide sequence Gly*-Tyr-Thr attached to its ε-amino group, wherein Gly* is a Gly residue with an octadecanedioic acid moiety attached to its α-amino group |

TABLE 1-continued

| | |
|---|---|
| Lys *16 | Lys residue with the C terminus of peptide sequence Gly*-Asn-Thr attached to its ε-amino group, wherein Gly* is a Gly residue with an octadecanedioic acid moiety attached to its α-amino group |
| Lys *17 | Lys residue with the C terminus of peptide residue γGlu* attached to its ε-amino group, wherein γGlu* is a γGlu residue with an octadecanedioic acid moiety attached to its α-amino group |
| Lys *18 | Lys residue with the C terminus of peptide residue γGlu* attached to its ε-amino group, wherein γGlu* is a γGlu residue with an eicosanedioic acid moiety attached to its α-amino group |
| Gly *18 | Gly residue with the C terminus of peptide residue γGlu* attached to its α-amino group, wherein γGlu* is a γGlu residue with an eicosanedioic acid moiety attached to its α-amino group |
| Lys *19 | Lys residue with an eicosanedioic acid moiety attached to its ε-amino group |
| Glu *19 | γGlu residue with an eicosanedioic acid moiety attached to its α-amino group |
| Lys *20 | Lys residue with the C terminus of peptide residue Gly* attached to its ε-amino group, wherein Gly* is a Gly residue with an eicosanedioic acid moiety attached to its α-amino group |
| Lys *21 | Lys residue with the C terminus of peptide sequence γGlu*-Ser-Gly attached to its ε-amino group, wherein γGlu* is a γGlu residue with an octadecanedioic acid moiety attached to its α-amino group |
| Lys *22 | Lys residue with the C terminus of peptide sequence γGlu*-Ser-Gly attached to its ε-amino group, wherein γGlu* is a γGlu residue with an eicosanedioic acid moiety attached to its α-amino group |
| Glu *23 | γGlu residue with the C terminus of peptide residue Lys* attached to its α-amino group, wherein Lys* is a Lys residue with an octadecanedioic acid moiety attached to its ε-amino group |
| Cys *24 | Cys residue attached via a disulfide bridge to peptide γGlu*-Cys, wherein γGlu* is a γGlu residue with an octadecanedioic acid moiety attached to its α-amino group |
| Lys *25 | Lys residue with the C terminus of peptide sequence γGlu*-Asn attached to its ε-amino group, wherein γGlu* is a γGlu residue with an octadecanedioic acid moiety attached to its α-amino group |
| Lys *26 | Lys residue with the C terminus of peptide sequence γGlu*-Ser-Gly-Thr [SEQ ID NO: 15] attached to its ε-amino group, wherein γGlu* is a γGlu residue with an octadecanedioic acid moiety attached to its α-amino group |
| Lys *27 | Lys residue with the C terminus of peptide sequence γGlu*-Gly-Ser-Ser-Gly [SEQ ID NO: 16] attached to its ε-amino group, wherein γGlu* is a γGlu residue with a hexadecanedioic acid moiety attached to its α-amino group |
| Lys *28 | Lys residue with the C terminus of peptide sequence γGlu*-Ser-Gly-Thr [SEQ ID NO: 15] attached to its ε-amino group, wherein γGlu* is a γGlu residue with an eicosanedioic acid moiety attached to its α-amino group |
| Lys *29 | Lys residue with the C terminus of peptide sequence γGlu*-Gly-Ser-Ser-Gly [SEQ ID NO: 16] attached to its ε-amino group, wherein γGlu* is a γGlu residue with an eicosanedioic acid moiety attached to its α-amino group |
| Lys *30 | Lys residue with the C terminus of peptide sequence γGlu*-Gly-Ser-Gly-Ser [SEQ ID NO: 8] attached to its ε-amino group, wherein γGlu* is a γGlu residue with an eicosanedioic acid moiety attached to its α-amino group |
| Lys *31 | Lys residue with the C terminus of peptide sequence γGlu*-Thr-His attached to its ε-amino group, wherein γGlu* is a γGlu residue with an eicosanedioic acid moiety attached to its α-amino group |
| Lys *32 | Lys residue with the C terminus of peptide sequence γGlu*-Gly-Ser attached to its ε-amino group, wherein γGlu* is a γGlu residue with an eicosanedioic acid moiety attached to its α-amino group |
| Lys *33 | Lys residue with the C terminus of peptide sequence γGlu*-Gly-Thr attached to its ε-amino group, wherein γGlu* is a γGlu residue with a hexadecanedioic acid moiety attached to its α-amino group |
| Lys *34 | Lys residue with the C terminus of peptide sequence γGlu*-Thr-Gly-Ser-Gly [SEQ ID NO: 17] attached to its ε-amino group, wherein γGlu* is a γGlu residue with an octadecanedioic acid moiety attached to its α-amino group |
| Lys *35 | Lys residue with the C terminus of peptide sequence γGlu*-Thr-Gly-Thr [SEQ ID NO: 18] attached to its ε-amino group, wherein γGlu* is a γGlu residue with an eicosanedioic acid moiety attached to its α-amino group |
| Cys *36 | Cys residue attached via a disulfide bridge to peptide γGlu*-Cys, wherein γGlu* is a γGlu residue with an eicosanedioic acid moiety attached to its α-amino group |
| Lys *37 | Lys residue with the C terminus of peptide sequence γGlu*-Gly-Ser-Gly [SEQ ID NO: 7] attached to its ε-amino group, wherein γGlu* is a γGlu residue the peptide sequence Lys-Lys-Lys attached to its γ-amino group |
| Lys *38 | Lys residue with the C terminus of peptide sequence γGlu*-Gly-Ser-Gly [SEQ ID NO: 7] attached to its ε-amino group, wherein γGlu* is a γGlu residue the peptide sequence Tyr-Tyr-Tyr attached to its γ-amino group |
| Lys *39 | Lys residue with the C terminus of peptide sequence γGlu*-Gly-Ser-Gly-Ser-Gly [SEQ ID NO: 19] attached to its ε-amino group, wherein γGlu* is a γGlu residue with an eicosanedioic acid moiety attached to its α-amino group |
| Lys *40 | Lys residue with the C terminus of peptide sequence γGlu*-Gln attached to its ε-amino group, wherein γGlu* is a γGlu residue with an eicosanedioic acid moiety attached to its α-amino group |
| Lys *41 | Lys residue with the C terminus of peptide sequence γGlu*-Gly-Ser attached to its ε-amino group, wherein γGlu* is a γGlu residue with an octadecanedioic acid moiety attached to its α-amino group |

TABLE 1-continued

| | |
|---|---|
| Lys *42 | Lys residue with the C terminus of peptide sequence γGlu*-Asn-His attached to its ε-amino group, wherein γGlu* is a γGlu residue with an octadecanedioic acid moiety attached to its α-amino group |
| Lys *43 | Lys residue with the C terminus of peptide sequence Glu*-Ser-Gly-Thr [SEQ ID NO: 20] attached to its ε-amino group, wherein Glu* is a Glu residue with an eicosanedioic acid moiety attached to its α-amino group |
| Lys *44 | Lys residue with the C terminus of peptide sequence Glu*-Ser-Gly-Thr [SEQ ID NO: 20] attached to its ε-amino group, wherein Glu* is a Glu residue with an octadecanedioic acid moiety attached to its α-amino group |
| Glu *45 | γGlu residue with the C terminus of peptide residue Lys* attached to its α-amino group, wherein Lys* is a Lys residue with an eicosanedioic acid moiety attached to its ε-amino group |
| Lys *46 | Lys residue with the C terminus of peptide sequence γGlu*-Asn-His attached to its ε-amino group, wherein γGlu* is a γGlu residue with an eicosanedioic acid moiety attached to its α-amino group |
| Lys *47 | Lys residue with the C terminus of peptide sequence γGlu*-Asn-His attached to its ε-amino group, wherein γGlu* is a γGlu residue with a hexadecanedioic acid moiety attached to its α-amino group |
| Lys *48 | Lys residue with the C terminus of peptide sequence γGlu*-Thr-Gly-Ser-Gly [SEQ ID NO: 17] attached to its ε-amino group, wherein γGlu* is a γGlu residue with a hexadecanedioic acid moiety attached to its α-amino group |
| Lys *49 | Lys residue with the C terminus of peptide sequence γGlu*-Thr-Gly-Ser-Gly [SEQ ID NO: 17] attached to its ε-amino group, wherein γGlu* is a γGlu residue with an eicosanedioic acid moiety attached to its α-amino group |
| Lys *50 | Lys residue with the C terminus of peptide sequence Glu*-Gly-Ser-Gly [SEQ ID NO: 14] attached to its ε-amino group, wherein Glu* is a Glu residue with a hexadecanedioic acid moiety attached to its α-amino group |
| Glu *51 | γGlu residue with the C terminus of peptide sequence Gly*-Ser-γLys attached to its α-amino group, wherein Gly* is a Gly residue with an octadecanedioic acid moiety attached to its α-amino group |
| Lys *52 | Lys residue with the C terminus of peptide sequence γGlu*-Gln attached to its ε-amino group, wherein γGlu* is a γGlu residue with an octadecanedioic acid moiety attached to its α-amino group |
| Lys *53 | Lys residue with the C terminus of peptide sequence Glu*-Gly-Ser-Gly [SEQ ID NO: 14] attached to its ε-amino group, wherein Glu* is a Glu residue with an octadecanedioic acid moiety attached to its α-amino group |
| Lys *54 | Lys residue with the C terminus of peptide sequence γGlu*-Trp-Gly attached to its ε-amino group, wherein γGlu* is a γGlu residue with an octadecanedioic acid moiety attached to its α-amino group |
| Lys *55 | Lys residue with the C terminus of peptide sequence Glu*-Gly-Ser-Gly-Ser [SEQ ID NO: 21] attached to its ε-amino group, wherein Glu* is a Glu residue with an octadecanedioic acid moiety attached to its α-amino group |
| Lys *56 | Lys residue with the C terminus of peptide sequence Glu*-Gly-Thr attached to its ε-amino group, wherein Glu* is a Glu residue with an octadecanedioic acid moiety attached to its α-amino group |
| Lys *57 | Lys residue with the C terminus of peptide sequence Glu*-Tyr-Gly attached to its ε-amino group, wherein Glu* is a Glu residue with an octadecanedioic acid moiety attached to its α-amino group |
| Lys *58 | Lys residue with the C terminus of peptide residue Glu* attached to its ε-amino group, wherein Glu* is a Glu residue with an octadecanedioic acid moiety attached to its α-amino group |
| Lys *59 | Lys residue with the C terminus of peptide residue Glu* attached to its ε-amino group, wherein Glu* is a Glu residue with an eicosanedioic acid moiety attached to its α-amino group |
| Lys *60 | Lys residue with the C terminus of peptide sequence Glu*-Asn attached to its ε-amino group, wherein Glu* is a Glu residue with an octadecanedioic acid moiety attached to its α-amino group |
| Lys *61 | Lys residue with the C terminus of peptide sequence Glu*-Gly-Thr attached to its ε-amino group, wherein Glu* is a Glu residue with a hexadecanedioic acid moiety attached to its α-amino group |
| Lys *62 | Lys residue with the C terminus of peptide sequence γGlu*-Gly-Ser-Gly [SEQ ID NO: 7] attached to its ε-amino group, wherein γGlu* is a γGlu residue with a hexadecanedioic acid moiety attached to its α-amino group |
| Lys *63 | Lys residue with the C terminus of peptide sequence γGlu*-Gly-Ser-Gly [SEQ ID NO: 7] attached to its ε-amino group, wherein γGlu* is a γGlu residue with an eicosanedioic acid moiety attached to its α-amino group |

It should be noted that as used above the symbol "γGlu" indicates a Glu residue which is attached to its adjacent amino acid residue not via the usual eupeptide bond but rather via an isopeptide bond between the α-amino group of the adjacent amino acid residue and the carboxylic acid group on the γ-carbon (C-4) of Glu.

FIG. 2 is a table showing the results of human cAMP inhibition studies and solubility scores for example compounds of the invention and certain control or reference compounds, and the results of feeding studies in rats which were administered example compounds of the invention or certain control or reference compounds.

SEQUENCE LISTING

This application is accompanied by a machine-readable sequence listing. The invention in certain embodiments encompasses the sequences of the sequence listing, peptides comprising or consisting of those sequences and all related uses, methods and products described therein.

Definitions

In order to facilitate review of the various embodiments of this disclosure, the following explanations of specific terms are provided:

Animal: Living multi-cellular vertebrate organisms, a category that includes, for example, mammals and birds. The term mammal includes both human and non-human mammals. Similarly, the term "subject" includes both human and veterinary subjects.

Appetite: A natural desire, or longing for food. In one embodiment, appetite is measured by a survey to assess the desire for food. Increased appetite generally leads to increased feeding behavior.

Appetite Suppressants: Compounds that decrease the desire for food. Commercially available appetite suppressants include, but are not limited to, amfepramone (diethylpropion), phentermine, mazindol, phenylpropanolamine fenfluramine, dexfenfluramine, and fluoxetine.

Body Mass Index (BMI): A mathematical formula for measuring body mass, also sometimes called Quetelet's Index. BMI is calculated by dividing weight (in kg) by height (in meters). The current standards for both men and women accepted as "normal" are a BMI of 20-24.9 kg/$m^2$. In one embodiment, a BMI of greater than 25 kg/$m^2$ can be used to identify an obese subject. Grade I obesity corresponds to a BMI of 25-29.9 kg/$m^2$. Grade II obesity corresponds to a BMI of 30-40 kg/$m^2$; and Grade III obesity corresponds to a BMI greater than 40 kg/$m^2$ (Jequier, *Am. J Clin. Nutr.* 45:1035-47, 1987). Ideal body weight will vary among species and individuals based on height, body build, bone structure, and sex.

Conservative substitutions: The replacement of an amino acid residue by another, biologically similar residue in a polypeptide. The term "conservative variation" also includes the use of a substituted amino acid, i.e. an amino acid with one or more atoms replaced with another atom or group, in place of a parent amino acid provided that the polypeptide retains its activity or provided that antibodies raised to the substituted polypeptide also immunoreact with the unsubstituted polypeptide. Typical but not limiting conservative substitutions are the replacements, for one another, among the aliphatic amino acids Ala, Val, Leu and Ile; interchange of hydroxyl-containing residues Ser and Thr, interchange of the acidic residues Asp and Glu, interchange between the amide-containing residues Asn and Gln, interchange of the basic residues Lys and Arg, interchange of the aromatic residues Phe and Tyr, and interchange of the small-sized amino acids Ala, Ser, Thr, Met and Gly. Additional conservative substitutions include the replacement of an amino acid by another of similar spatial or steric configuration, for example the interchange of Asn for Asp, or Gln for Glu.

Non-limiting examples of conservative amino acid substitutions

| Original Residue | Conservative Substitutions |
|---|---|
| Ala | Gly, Val, Leu, Ile, Ser, Thr, Met |
| Arg | Lys |
| Asn | Asp, Gln, His |
| Asp | Glu, Asn |
| Cys | Ser |
| Gln | Asn, His, Lys, Glu |
| Glu | Asp, Gln |
| Gly | Ala, Ser, Thr, Met |
| His | Asn, Gln |
| Ile | Ala, Leu, Val, Met |

-continued

| Original Residue | Conservative Substitutions |
|---|---|
| Leu | Ala, He, Val, Met, |
| Lys | Arg |
| Met | Leu, Ile, Ala, Ser, Thr, Gly |
| Phe | Leu, Tyr, Trp |
| Ser | Thr, Cys, Ala, Met, Gly |
| Thr | Ser, Ala, Ser, Met, Gly |
| Trp | Tyr, Phe |
| Tyr | Trp, Phe |
| Val | Ala, Ile, Leu |

Non-conservative substitutions: The replacement, in a polypeptide, of an amino acid residue by another residue which is not biologically similar. For example, the replacement of an amino acid residue with another residue that has a substantially different charge, a substantially different hydrophobicity or a substantially different spatial or steric configuration.

Diabetes: A failure of cells to transport endogenous glucose across their membranes either because of an endogenous deficiency of insulin and/or a defect in insulin sensitivity.

Diabetes is a chronic syndrome of impaired carbohydrate, protein, and fat metabolism owing to insufficient secretion of insulin or to target tissue insulin resistance. It occurs in two major forms: insulin-dependent diabetes mellitus (IDDM, type 1) and non-insulin dependent diabetes mellitus (NIDDM, type 2) which differ in etiology, pathology, genetics, age of onset, and treatment.

The two major forms of diabetes are both characterized by an inability to deliver insulin in an amount and with the precise timing that is needed for control of glucose homeostasis. Diabetes type 1, or insulin dependent diabetes mellitus (IDDM) is caused by the destruction of β cells, which results in insufficient levels of endogenous insulin. Diabetes type 2, or non-insulin dependent diabetes, results from a defect in both the body's sensitivity to insulin, and a relative deficiency in insulin production.

Food intake: The amount of food consumed by an individual. Food intake can be measured by volume or by weight. For example, food intake may be the total amount of food consumed by an individual. Or, food intake may be the amount of proteins, fat, carbohydrates, cholesterol, vitamins, minerals, or any other food component, of the individual. "Protein intake" refers to the amount of protein consumed by an individual. Similarly, "fat intake," "carbohydrate intake," "cholesterol intake," "vitamin intake," and "mineral intake" refer to the amount of proteins, fat, carbohydrates, cholesterol, vitamins, or minerals consumed by an individual.

Normal Daily Diet: The average food intake for an individual of a given species. A normal daily diet can be expressed in terms of caloric intake, protein intake, carbohydrate intake, and/or fat intake. A normal daily diet in humans generally comprises the following: about 2,000, about 2,400, or about 2,800 to significantly more calories. In addition, a normal daily diet in humans generally includes about 12 g to about 45 g of protein, about 120 g to about 610 g of carbohydrate, and about 11 g to about 90 g of fat. A low calorie diet would be no more than about 85%, and preferably no more than about 70%, of the normal caloric intake of a human individual.

In animals, the caloric and nutrient requirements vary depending on the species and size of the animal. For example, in cats, the total caloric intake per pound, as well as the percent distribution of protein, carbohydrate and fat varies with the age of the cat and the reproductive state. A general guideline for cats, however, is 40 cal/lb/day (18.2 cal/kg/day). About 30% to about 40% should be protein, about 7% to about 10% should be from carbohydrate, and about 50% to about 62.5% should be derived from fat intake. One of skill in the art can readily identify the normal daily diet of an individual of any species.

Obesity: A condition in which excess body fat may put a person at health risk (see Barlow and Dietz, *Pediatrics* 102:E29, 1998; National Institutes of Health, National Heart, Lung, and Blood Institute (NHLBI), *Obes. Res.* 6 (suppl. 2):51S-209S, 1998). Excess body fat is a result of an imbalance of energy intake and energy expenditure. For example, the Body Mass Index (BMI) may be used to assess obesity. In one commonly used convention, a BMI of 25.0 $kg/m^2$ to 29.9 $kg/m^2$ is overweight, while a BMI of 30 $kg/m^2$ or greater is obese.

In another convention, waist circumference is used to assess obesity. In this convention, in men a waist circumference of 102 cm or more is considered obese, while in women a waist circumference of 89 cm or more is considered obese. Strong evidence shows that obesity affects both the morbidity and mortality of individuals. For example, an obese individual is at increased risk for heart disease, non-insulin dependent (type-2) diabetes, hypertension, stroke, cancer (e.g. endometrial, breast, prostate, and colon cancer), dyslipidemia, gall bladder disease, sleep apnea, reduced fertility, and osteoarthritis, amongst others (see Lyznicki et al., *Am. Fam. Phys.* 63:2185, 2001).

Overweight: An individual who weighs more than their ideal body weight. An overweight individual can be obese, but is not necessarily obese. For example, an overweight individual is any individual who desires to decrease their weight. In one convention, an overweight individual is an individual with a BMI of 25.0 $kg/m^2$ to 29.9 $kg/m^2$.

Pegylated and pegylation: the process of reacting a poly (alkylene glycol), preferably an activated poly(alkylene glycol) to form a covalent bond. A facilitator may be used, for example an amino acid, e.g. lysine. Although "pegylation" is often carried out using poly(ethylene glycol) or derivatives thereof, such as methoxy poly(ethylene glycol), the term is not limited herein to the use of methoxy poly(ethylene glycol) but also includes the use of any other useful poly (alkylene glycol), for example poly(propylene glycol).

pI: pI is an abbreviation for isoelectric point. An alternative abbreviation sometimes used is IEP. It is the pH at which a particular molecule carries no net electric charge. At a pH below its pI a protein or peptide carries a net positive charge. At a pH above its pI a protein or peptide carries a net negative charge. Proteins and peptides can be separated according to their isoelectric points using a technique called isoelectric focussing which is an electrophoretic method that utilises a pH gradient contained within a polyacrylimide gel.

Peptide YY (PYY): The term PYY as used herein refers to a peptide YY polypeptide, a hormone secreted into the blood by cells lining the lower small intestine (the ileum) and the colon. Naturally occurring wild type PYY sequences for various species are shown in Table 2.

TABLE 2

PPY sequence of various species

| PEPTIDE YY | AA SEQUENCE | SEQ ID NO |
|---|---|---|
| Human | YPIKPEAPGEDASPEELNRYYASLRHYLNLVTRQRY<br>TyrProIleLysProGluAlaProGlyGluAspAlaSerProGluGluLeuAsnArg<br>TyrTyrAlaSerLeuArgHisTyrLeuAsnLeuValThrArgGlnArgTyr | 22 |
| Human 3-36 | IKPEAPGEDASPEELNRYYASLRHYLNLVTRQRY<br>IleLysProGluAlaProGlyGluAspAlaSerProGluGluLeuAsnArgTyrTyr<br>AlaSerLeuArgHisTyrLeuAsnLeuValThrArgGlnArgTyr | 23 |
| Rat (*Rattus norvegicus*) | YPAKPEAPGEDASPEELSRYYASLRHYLNLVTRQRY<br>TyrProAlaLysProGluAlaProGlyGluAspAlaSerProGluGluLeuSerArg<br>TyrTyrAlaSerLeuArgHisTyrLeuAsnLeuValThrArgGlnArgTyr | 24 |
| Mouse (*Mus musculus*) | YPAKPEAPGEDASPEELSRYYASLRHYLNLVTRQRY<br>TyrProAlaLysProGluAlaProGlyGluAspAlaSerProGluGluLeuSerArg<br>TyrTyrAlaSerLeuArgHisTyrLeuAsnLeuValThrArgGlnArgTyr | 25 |
| Pig | YPAKPEAPGEDASPEELSRYYASLRHYLNLVTRQRY<br>TyrProAlaLysProGluAlaProGlyGluAspAlaSerProGluGluLeuSerArg<br>TyrTyrAlaSerLeuArgHisTyrLeuAsnLeuValThrArgGlnArgTyr | 26 |
| Guinea pig | YPSKPEAPGSDASPEELARYYASLRHYLNLVTRQRY<br>TyrProSerLysProGluAlaProGlySerAspAlaSerProGluGluLeuAlaArg<br>TyrTyrAlaSerLeuArgHisTyrLeuAsnLeuValThrArgGlnArgTyr | 27 |
| Frog | YPPKPENPGEDASPEEMTKYLTALRHYINLVTRQRY<br>TyrProProLysProGluAsnProGlyGluAspAlaSerProGluGluMetThrLys<br>TyrLeuThrAlaLeuArgHisTyrIleAsnLeuValThrArgGlnArgTyr | 28 |
| Raja | YPPKPENPGDDAAPEELAKYYSALRHYINLITRQRY<br>TyrProProLysProGluAsnProGlyAspAspAlaAlaProGluGluLeuAlaLys<br>TyrTyrSerAlaLeuArgHisTyrIleAsnLeuIleThrArgGlnArgTyr | 29 |

TABLE 2-continued

| PPY sequence of various species | | |
|---|---|---|
| PEPTIDE YY | AA SEQUENCE | SEQ ID NO |
| Dogfish | YPPKPENPGEDAPPEELAKYYSALRHYINLITRQRY<br>TyrProProLysProGluAsnProGlyGluAspAlaProProGluGluLeuAlaLys<br>TyrTyrSerAlaLeuArgHisTyrIleAsnLeuIleThrArgGlnArgTyr | 30 |
| Lampetra | FPPKPDNPGDNASPEQMARYKAAVRHYINLITRQRY<br>PheProProLysProAspAsnProGlyAspAsnAlaSerProGluGlnMetAlaArg<br>TyrLysAlaAlaValArgHisTyrIleAsnLeuIleThrArgGlnArgTyr | 31 |
| Petromyzon | MPPKPDNPSPDASPEELSKYMLAVRNYINLITRQRY<br>MetProProLysProAspAsnProSerProAspAlaSerProGluGluLeuSerLys<br>TyrMetLeuAlaValArgAsnTyrIleAsnLeuIleThrArgGlnArgTyr | 32 |
| Dog (*Canis familiaris*) | YPAKPEAPGEDASPEELSRYYASLRHYLNLVTRQRY<br>TyrProAlaLysProGluAlaProGlyGluAspAlaSerProGluGluLeuSerArg<br>TyrTyrAlaSerLeuArgHisTyrLeuAsnLeuValThrArgGlnArgTyr | 33 |
| Rhesus monkey (*Macaca mulatta*) | YPIKPEAPGEDASPEELSRYYASLRHYLNLVTRQRY<br>TyrProIleLysProGluAlaProGlyGluAspAlaSerProGluGluLeuSerArg<br>TyrTyrAlaSerLeuArgHisTyrLeuAsnLeuValThrArgGlnArgTyr | 34 |
| Pipid frog (*Xenopus tropicaiis*) | YPTKPENPGNDASPEEMAKYLTALRHYINLVTRQRY<br>TyrProThrLysProGluAsnProGlyAsnAspAlaSerProGluGluMetAlaLys<br>TyrLeuThrAlaLeuArgHisTyrIleAsnLeuValThrArgGlnArgTyr | 35 |
| Atlantic salmon (*Salmosalar*) | YPPKPENPGEDAPPEELAKYYTALRHYINLITRQRY<br>TyrProProLysProGluAsnProGlyGluAspAlaProProGluGluLeuAlaLys<br>TyrTyrThrAlaLeuArgHisTyrIleAsnLeuIleThrArgGlnArgTyr | 36 |
| Cattle (*bos taurus*) | YPAKPQAPGEHASPDELNRYYTSLRHYLNLVTRQRF<br>TyrProAlaLysProGlnAlaProGlyGluHisAlaSerProAspGluLeuAsnArg<br>TyrTyrThrSerLeuArgHisTyrLeuAsnLeuValThrArgGlnArgPhe | 37 |

Peripheral Administration: Administration outside of the central nervous system. Peripheral administration does not include direct administration to the brain. Peripheral administration includes, but is not limited to intravascular, intramuscular, subcutaneous, inhalation, oral, rectal, transdermal or intra-nasal administration.

Polypeptide: A polymer in which the monomers are amino acid residues which are joined together through amide bonds. When the amino acids are alpha-amino acids, either the L-optical isomer or the D-optical isomer can be used, the L-isomers being preferred. The terms "polypeptide" or "protein" as used herein encompass any amino acid sequence and include modified sequences such as glycoproteins. The term "polypeptide" is specifically covers naturally occurring proteins, as well as those which are recombinantly or synthetically produced. The term "polypeptide fragment" refers to a portion of a polypeptide, for example a fragment which exhibits at least one useful sequence in binding a receptor. The term "functional fragments of a polypeptide" refers to all fragments of a polypeptide that retain an activity of the polypeptide. Biologically functional peptides can also include fusion proteins, in which the peptide of interest has been fused to another peptide that does not decrease its desired activity.

Subcutaneous administration: Subcutaneous administration is administration of a substance to the subcutaneous layer of fat which is found between the dermis of the skin and the underlying tissue. Subcutaneous administration may be by an injection using a hypodermic needle fitted, for example, to a syringe or a "pen" type injection device. Other administration methods may be used for example microneedles. Injection with a hypodermic needle typically involves a degree of pain on behalf of the recipient. Such pain may be masked by use of a local anaesthetic or analgesic. However, the usual method used to reduce the perceived pain of injections is to merely distract the subject immediately prior to and during the injection. Pain may be minimised by using a relatively small gauge hypodermic needle, by injecting a relatively small volume of substance and by avoiding excessively acidic or alkali compositions which may cause the subject to experience a "stinging" sensation at the injection site. Compositions having a pH of between pH4 and pH10 are usually regarded as tolerably comfortable.

Therapeutically effective amount: A dose sufficient to prevent advancement, or to cause regression of a disorder, or which is capable of relieving a sign or symptom of a disorder, or which is capable of achieving a desired result. In several embodiments, a therapeutically effective amount of a compound of the invention is an amount sufficient to inhibit or halt weight gain, or an amount sufficient to decrease appetite, or an amount sufficient to reduce caloric intake or food intake.

Sequence Listing

The amino acid sequences herein are shown with the N-terminus to the left, and where sequences are set out across multiple lines, the N-terminus is to the top left. Unless indicated otherwise, the amino acid residues in the sequences are L-amino acids.

DETAILED DESCRIPTION

Compounds of the Invention

The compound relating to all aspects of the invention are PYY analogues having a 30 to 42 residue primary amino acid sequence which is derived (via residue substitutions, deletions and additions) from a native PYY sequence (preferably from the native human sequence) wherein an amino acid residue of that primary sequence is derivatised by means of the attachment of a substituent derived from a fatty dioic acid. This substituent may be a fatty dioic acid attached directly to the residue of the primary amino acid sequence or it may comprise a short (for example 1 to 6 residue) peptide on which the fatty dioic acid is carried.

According to all aspects of the invention, the substituent is selected from:

(a) a group of the formula:

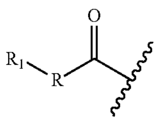

wherein the substituent is attached to the a-amino group of said substituted residue or wherein the substituted residue is Lys and the substituent is attached to the y-amino group of the Lys residue; R is a $C_8$-$C_{28}$ alkylene or alkenylene chain and $R_1$ is $CO_2H$;

(b) Z—Cys-S— wherein Z is a group of the formula

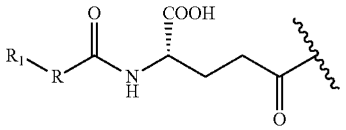

wherein R is a $C_8$-$C_{28}$ alkylene or alkenylene chain and $R_1$ is $CO_2H$, (c) Z—Cys-S— wherein Z is a group of the formula

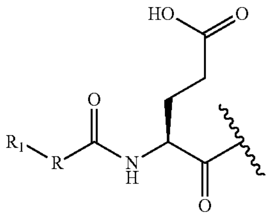

wherein R is a $C_8$-$C_{28}$ alkylene or alkenylene chain and $R_1$ is $CO_2H$; or (d) X-Q-;

wherein Q is a peptide sequence or single amino acid residue selected from:

```
                                [SEQ ID NO: 5]
Xaa65-Xaa64-Xaa63-Xaa62-Xaa61,

                                [SEQ ID NO: 6]
Xaa64-Xaa63-Xaa62-Xaa61,

Xaa63-Xaa62-Xaa61,

Xaa62-Xaa61
and

Xaa61;
```

and X is a group of the formula

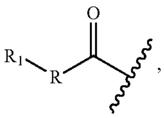

,

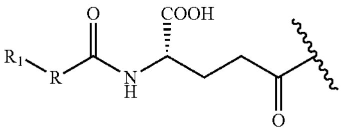

or

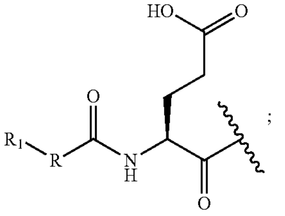

;

or wherein R is a $C_8$-$C_{28}$ alkylene or alkenylene chain and $R_1$ is $CO_2H$.

According to some embodiments a substituent may preferably be selected from one of the derivatives described above in Table 1.

Option (a) above represents the situation wherein the substituent is a fatty dioic acid attached directly to the primary peptide sequence. According to certain preferred embodiments that fatty dioic acid is hexadecadioic acid, octadecadioic acid or eicosandioic acid (i.e. R is respectively 14, 16 or 18, noting that an additional carbon atom is present in the $R_1$ moeity and the C═O group to make, respectively 16, 18 or 20 carbon atoms in the dioic acid chain).

It is understood that attachment of such a dioic acid is via one of the two CO(OH) groups of the acid to a $NH_2$ group on the primary peptide sequence. That $NH_2$ may be a non-α-$NH_2$ group (for example the ε-$NH_2$ group of the side chain of a Lysine residue). Alternatively it may be via an α-$NH_2$ group at the N-terminus of the primary peptide sequence. According to certain embodiments, attachment of the substituent is facilitated by the substitution of a naturally-occurring PYY amino acid residue with a residue having an $NH_2$-bearing side chain (for example Arg or Lys, most preferably Lys).

Option (b) above represents the situation wherein the substituent comprises a fatty dioic acid derived moiety and is attached to the primary peptide sequence via a Glu residue. According to certain preferred embodiments that fatty dioic acid is hexadecadioic acid, octadecadioic acid or eicosandioic acid (i.e. R is respectively 14, 16 or 18, noting that an additional carbon atom is present in the $R_1$ moeity and C═O group to make, respectively 16, 18 or 20 carbon atoms in the dioic acid chain). It is understood that attachment of such a dioic acid is via one of the two CO(OH) groups of the acid to the α-$NH_2$ group of the Glu residue. The Glu residue in turn is attached to the primary peptide sequence via its α-CO(OH) group attaching to an $NH_2$ group on the primary peptide sequence. That $NH_2$ may be a non-α-$NH_2$ group (for example the ε-$NH_2$ group of the side chain of a Lysine residue). Alternatively it may be via an α—$NH_2$ group at the N-terminus of the primary peptide sequence. According to certain embodiments, attachment of the substituent is facilitated by the substitution of a naturally-occurring PYY amino acid residue with a residue having an $NH_2$-bearing side chain (for example Arg or Lys, most preferably Lys).

Option (c) above represents the situation wherein the substituent comprises a fatty dioic acid derived moiety attached to the dipeptide Glu-Cys via a Glu residue. According to certain preferred embodiments that fatty dioic acid is hexadecadioic acid, octadecadioic acid or eicosandioic acid (i.e. R is respectively 14, 16 or 18, noting that an additional carbon atom is present in the $R_1$ moeity and C═O group to make, respectively 16, 18 or 20 carbon atoms in the dioic acid chain). The substituent may be attached by providing sufficiently reducing conditions for a —S—S— bridge to form between the Cys residue of the dipeptide and a Cys residue of the primary peptide sequence. According to certain embodiments, attachment of the substituent is facilitated by the substitution of a naturally-occurring PYY amino acid residue with a Cys residue.

Attachment of Derivatives

According to the invention, the substituent may be attached at any of the positions in the primary peptide sequence permitted by the claims. That is to say at one of positions Xaa51, Xaa52, Xaa53, Xaa54, Xaa55, Xaa56, Xaa3, Xaa4, Xaa6, Xaa7, Xaa9, Xaa10, Xaa11, Xaa12, Xaa13, Xaa14, Xaa15, Xaa16, Xaa18, Xaa19, Xaa22, Xaa23, Xaa25, Xaa26, Xaa27 or Xaa30. Preferred positions are selected from Xaa51, Xaa52, Xaa53, Xaa54, Xaa55, Xaa56, Xaa6, Xaa7, Xaa9, Xaa10, Xaa11, Xaa12, Xaa13, Xaa14, Xaa15, Xaa16, Xaa18, Xaa19, Xaa26 or Xaa30; for example selected from Xaa6, Xaa7, Xaa9, Xaa10, Xaa11, Xaa12, Xaa13, Xaa14, Xaa15, Xaa16, Xaa18, Xaa19, Xaa26 or Xaa30; or selected from, Xaa7, Xaa9 or Xaa 10 or from Xaa7, Xaa9, Xaa 10 or Xaa30.

It is preferred that the substituent is attached at one of positions Glu51, Glu52, Glu53, Glu54, Glu55, Glu56, Glu3, Glu4, Glu6, Glu7, Glu9, Glu10, Glu11, Glu12, Glu13, Glu14, Glu15, Glu16, Glu18, Glu19, Glu22, Glu23, Glu25, Glu26, Glu27, Lys51, Lys52, Lys53, Lys54, Lys55, Lys56, Lys3, Lys4, Lys6, Lys7, Lys9, Lys10, Lys11, Lys12, Lys13, Lys14, Lys15, Lys16, Lys18, Lys19, Lys22, Lys23, Lys25, Lys26, Lys27 or Lys30. Preferred positions are selected from Glu51, Glu52, Glu53, Glu54, Glu55, Glu56, Glu6, Glu7, Glu9, Glu10, Glu11, Glu12, Glu13, Glu14, Glu15, Glu16, Glu18, Glu19, Glu26, Lys51, Lys52, Lys53, Lys54, Lys55, Lys56, Lys6, Lys7, Lys9, Lys10, Lys11, Lys12, Lys13, Lys14, Lys15, Lys16, Lys18, Lys19, Lys26 or Lys30; for example selected from Glu6, Glu7, Glu9, Glu10, Glu11, Glu12, Glu13, Glu14, Glu15, Glu16, Glu18, Glu19, Glu26, or Lys 30; Lys6, Lys7, Lys9, Lys10, Lys11, Lys12, Lys13, Lys14, Lys15, Lys16, Lys18, Lys19, Lys26 or Lys30 or selected from Glu7, Glu9, Glu10, Lys7, Lys9, Lys10 or Lys30. In other embodiments the positions are selected from Glu51, Glu52, Glu53, Glu54, Glu55, Glu56, Glu6, Glu7, Glu9, Glu10, Glu11, Glu12, Glu13, Glu14, Glu15, Glu16, Glu18, Glu19, Glu26, Lys51, Lys52, Lys53, Lys54, Lys55, Lys56, Lys6, Lys7, Lys9, Lys10, Lys11, Lys12, Lys13, Lys14, Lys15, Lys16, Lys18, Lys19 or Lys26; for example selected from Glu6, Glu7, Glu9, Glu10, Glu11, Glu12, Glu13, Glu14, Glu15, Glu16, Glu18, Glu19 or Glu26; Lys6, Lys7, Lys9, Lys10, Lys11, Lys12, Lys13, Lys14, Lys15, Lys16, Lys18, Lys19, or Lys26; or selected from Glu7, Glu9, Glu10, Lys7, Lys9 or Lys10.

According to certain preferred embodiments the compound according the invention is such that at least one of the further features listed below apply:

1, Xaa2 is Pro;
2, Xaa3 is Ile;
3, Xaa4 is Lys;
4, Xaa5 is Pro;
5, Xaa6 is Lys substituted at its ε-amino group or Glu;
6, Xaa7 is Lys substituted at its ε-amino group or Ala;
7, Xaa9 is Lys substituted at its ε-amino group or Gly;
8, Xaa10 Lys substituted at its ε-amino group or Glu;
9, Xaa11 is Lys substituted at its ε-amino group, Asp, Gly or Glu;
10, Xaa12 is Lys substituted at its ε-amino group or Ala;
12, Xaa13 is Lys substituted at its ε-amino group or Ser;
13, Xaa14 is Lys substituted at its ε-amino group or Pro;
14, Xaa15 is Lys substituted at its ε-amino group or Glu;
15, Xaa16 is Lys substituted at its ε-amino group or Glu;
16, Xaa17 is Leu or Ile;
17, Xaa18 is Lys substituted at its ε-amino group, Leu or Val;
18, Xaa19 is Arg, Lys or His;
19, Xaa22 is Ala, or Ile;
20, Xaa23 is Ala or Glu;
21, Xaa24 is Leu;
22, Xaa25 is Arg;
23, Xaa26 is Lys substituted at its ε-amino group or His;
24, Xaa27 is Phe;
25, Xaa is Lys substituted at its ε-amino group or His;
26, Xaa31 is Val or Leu.

According to some embodiments 1, 2, 3, 4, 5, 6, 7, 8, 9 or 10 of criteria 1 to 26 above apply (with the proviso that compound comprises no more than a single fatty dioic acid-derived substituent). According to other embodiments all of criteria 1 to 25 above apply (with the proviso that compound comprises no more than a single fatty dioic acid-derived substituent). According to other embodiments all of criteria 1 to 25 above apply except that no more than 1 or no more than 2 of residues 2 to 36 are subject to a conservative substitution (and with the proviso that compound comprises no more than a single fatty dioic acid-derived substituent).

Further Derivatisation

In addition to attachment of dioic acid moieties, either directly or together with a short peptide moiety as described herein, the compounds of the invention may be incorporate further derivatisations selected from amidation, glycosylation, carbamylation, acylation, sulfation, phosphorylation, cyclization, lipidization, pegylation and fusion to another peptide or protein to form a fusion protein. In many embodiments it is especially preferred that the primary peptide chain of compounds of the invention may be amidated at their C-terminal. Such a modification is very common in nature with approximately half of naturally occurring peptides, including PYY in many cases, being susceptible to amidation at their C-terminal. The present invention encompasses all of the generic and specific sequences disclosed herein, including in the sequence listing and drawings, in both amidated and non-amidated forms, the amidation, where present being especially preferred on the C-terminal of the primary peptide sequence.

The N Terminus of the Primary Sequence

According to certain preferred embodiments the compound of the invention is of formula I (i.e. the primary peptide sequence starts with Xaa2). Compounds of formula II wherein B is Lys (preferably substituted in accordance with the present disclosure) are also preferred.

According to other embodiments the compounds of the invention are in accordance with formula III and A is a peptide sequence:

```
                                    [SEQ ID NO: 38]
Xaa51-Xaa52-Xaa53-Xaa54-Xaa55-Xaa56;

                                    [SEQ ID NO: 39]
Xaa52-Xaa53-Xaa54-Xaa55-Xaa56;

                                    [SEQ ID NO: 40]
Xaa53-Xaa54-Xaa55-Xaa56;

Xaa54-Xaa55-Xaa56;

Xaa55-Xaa56;
or

Xaa56;
```

Wherein:

Xaa51 is Glu substituted at its a-amino group;

Xaa52 is Glu substituted at its α-amino group or Lys substituted at its ε-amino group;

Xaa53 is Glu substituted at its α-amino group or Gly;

Xaa54 is Ser, or Pro;

Xaa55 is Lys substituted at its ε-amino group, Gly or Pro;

Xaa56 is Lys substituted at its ε-amino group, Glu substituted at its γ-carboxylic acid group, Ser, Pro or Thr;

It is preferred, when the compound of the invention is in accordance with formula III that B is Gly, Ser or Tyr, and A is substituted Lys or substituted Glu.

According to certain embodiments it is preferred that the substituent is attached to the ε-amino group of a Lys residue at position Xaa10.

Where Q is present in accordance with formula I, II or III it is preferably Gly65-Ser64-Gly63-Ser62-Gly61 [SEQ ID NO: 41]. Alternatively, Q may be Xaa64-Xaa63-Xaa62-Xaa61 [SEQ ID NO: 42], wherein Xaa64 is Gly, Ser or Thr; Xaa63 is Ser, Thr or Gly; Xaa62 is Gly or Ser and Xaa61 is Ser, Thr, Gly or Asp. Alternatively, Q may be Xaa63-Xaa62-Xaa61, wherein Xaa63 is Gly, Pro, Glu, Ser or Thr; Xaa62 is Ser, Thr or Gly and Xaa61 is Gly or Thr. Alternatively Q may be Xaa62-Xaa61, wherein Xaa62 is Ser, Gly, Tyr, Thr or Asn and Xaa61 is Gly, Thr, His or Ser. Alternatively, Q may be Xaa61, wherein Zaa61 is Gly, Glu, Lys, Asn or Gln. Alternatively, Q may be Gly63-Ser62-Gly61. Alternatively, Q may be Glu63-Gly62-Ser61. Alternatively, Q may be Glu63-Gly62-Thr61. Alternatively, Q may be Asn62-His61. Alternatively, Q may be Glu61. Alternatively, Q may be Gly61.

Attachment of Substituents

It should be noted that all compounds of all aspects of the invention comprise a single substituent which is derived from a fatty dioic acid in accordance with the invention. That moiety may be attached to part A, B or C of a compound of the invention.

In accordance with the invention, the substituent is attached (for example via a condensation reaction or a —S—S— bridge) to a group on an indicated amino acid residue of the primary peptide sequence. Those groups are indicated in accordance with the invention using, where appropriate, the IUPAC numbering convention for the carbon atoms as shown below using the amino acids Glu and Lys respectively as examples:

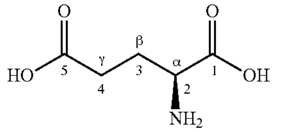

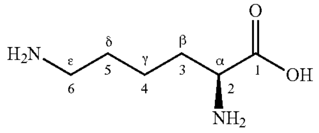

Cyclic Compounds

Compounds of the invention may have the substituent attached to a Cys residue via a —S—S— bridge as described above. Alternatively or additionally, the primary peptide sequence may contain two or more further Cys residues having a —S—S— bridge between them. Such residues are preferably at positions Xaa2, Xaa3, Xaa5, Xaa24 or Xaa27, allowing for a —S—S— bridge between Cys2 or Cys5 and Cys24 or Cys27. If the substituent is not attached to a Cys residue it is attached to another residue as described herein. According to certain embodiments, such cyclic compounds are not preferred.

A compound, derivative or salt according to the invention may have one or more of the following additional features:

A, B of formula II or III is a Lys residue, optionally substituted at its ε-amino group, B, Xaa2 is Pro,

```
                                    [SEQ ID NO: 43]
C, Xaa2-Xaa3-Xaa4-Xaa5-Xaa6 is

                                    [SEQ ID NO: 44]
Pro2-Ile3-Lys4-Pro5-Glu6,
```

D, Xaa7 is Lys substituted at its ε-amino group or Ala,

E, Xaa9 is Lys substituted at its ε-amino group or Gly,

F, Xaa10 is Lys substituted at its ε-amino group or Glu,

G, Xaa11 is Gly, Asn or Glu,

```
                                    [SEQ ID NO: 45]
H, Xaa12-Xaa13-Xaa14-Xaa15-Xaa16 is

                                    [SEQ ID NO: 46]
Ala12-Ser13-Pro14-Glu15-Glu16,
```

I, Xaa18 is Asn, Leu, Ala or Val, preferably Leu,

J, Xaa19 is His,

K, Xaa22 is Ala, or Ile,

L, Xaa23 is Ala or Glu,

M, Xaa24 is Leu or Cys,

N, Xaa25 is Arg,

O, Xaa26 is His,

P, Xaa27 is Phe.

Preferably, a compound has a combinations of features H, I, J, K, L, M, N, O and P, optionally in further combination with feature C and one of features D, E or F. Other preferred combinations of features include:

B, D, E, F, G, H, I, J, K, L, M, N, O and P

C, D, E, F, G, H, I, J, K, L, M, N, O and P

B, C, E, F, G, H, I, J, K, L, M, N, O and P

B, C, D, F, G, H, I, J, K, L, M, N, O and P

B, C, D, E, G, H, I, J, K, L, M, N, O and P

B, C, D, E, F, H, I, J, K, L, M, N, O and P

B, C, D, E, F, G, I, J, K, L, M, N, O and P
B, C, D, E, F, G, H, J, K, L, M, N, O and P
B, C, D, E, F, G, H, I, K, L, M, N, O and P
B, C, D, E, F, G, H, I, J, L, M, N, O and P
B, C, D, E, F, G, H, I, J, K, M, N, O and P
B, C, D, E, F, G, H, I, J, K, L, N, O and P
B, C, D, E, F, G, H, I, J, K, L, M, O and P
B, C, D, E, F, G, H, I, J, K, L, M, N and P
B, C, D, E, F, G, H, I, J, K, L, M, N and O
A, B, D, E, F, G, H, I, J, K, L, M, N, O and P
A, C, D, E, F, G, H, I, J, K, L, M, N, O and P
A, B, C, E, F, G, H, I, J, K, L, M, N, O and P
A, B, C, D, F, G, H, I, J, K, L, M, N, O and P
A, B, C, D, E, G, H, I, J, K, L, M, N, O and P
A, B, C, D, E, F, H, I, J, K, L, M, N, O and P
A, B, C, D, E, F, G, I, J, K, L, M, N, O and P
A, B, C, D, E, F, G, H, J, K, L, M, N, O and P
A, B, C, D, E, F, G, H, I, K, L, M, N, O and P
A, B, C, D, E, F, G, H, I, J, L, M, N, O and P
A, B, C, D, E, F, G, H, I, J, K, M, N, O and P
A, B, C, D, E, F, G, H, I, J, K, L, N, O and P
A, B, C, D, E, F, G, H, I, J, K, L, M, O and P
A, B, C, D, E, F, G, H, I, J, K, L, M, N and P
A, B, C, D, E, F, G, H, I, J, K, L, M, N and O Preferred specific compounds include those listed in FIG. 1 and also compounds differing from those disclosed in FIG. 1 by virtue of a single or double conservative amino acid residue change at a position which is not substituted.

Particularly preferred compounds include Y1596, Y1597, Y1603, Y1606, Y1619, Y1621, Y1622, Y1631, Y1632, Y1638, Y1642, Y1644, Y1650, Y1660, Y1661, Y1662, Y1663, Y1665, Y1674, Y1679, Y1683, Y1695, Y1726, Y1733, Y1734, Y1735, Y1739, Y1740, Y1741, Y1746, Y1747, Y1748, Y1749, Y1751, Y1753, Y1754, Y1764, Y1768, Y1769, Y1770, Y1771, Y1772, Y1773, Y1775, Y1776, Y1777, Y1778, Y1779, Y1781, Y1782, Y1783, Y1784, Y1785, Y1786, Y1787, Y1788, Y1789, Y1790, Y1791, Y1792, Y1793, Y1794, Y1795, Y1796, Y1797, Y1798, Y1799, Y, Y1800, Y1801, Y1802, Y1803, Y1804, Y1805, Y1806, Y1807, Y1816, Y1818, Y1819, Y1820, Y1821, Y1822, Y1823, Y1824, Y1825, Y1826, and Y1827 as disclosed in FIG. 1 and also compounds differing from those compounds by virtue of a single or double conservative amino acid residue change at a position which is not substituted.

Salts

Salts of PYY analogue compounds of the invention that are suitable for use in a medicament are those wherein a counterion is pharmaceutically acceptable. However, salts having non-pharmaceutically acceptable counterions are within the scope of the present invention, for example, for use as intermediates in the preparation of PYY analogues of the invention and their pharmaceutically acceptable salts and/or derivatives thereof.

Suitable salts according to the invention include those formed with organic or inorganic acids or bases. Pharmaceutically acceptable acid addition salts include those formed with hydrochloric, hydrobromic, sulphuric, nitric, citric, tartaric, acetic, phosphoric, lactic, pyruvic, acetic, trifluoroacetic, succinic, perchloric, fumaric, maleic, glycollic, lactic, salicylic, oxaloacetic, methanesulfonic, ethanesulfonic, p-toluenesulfonic, formic, benzoic, malonic, naphthalene-2-sulfonic, benzenesulfonic, and isethionic acids.Other acids such as oxalic acid may be useful as intermediates in obtaining the compounds of the invention.

Pharmaceutically acceptable salts with bases include ammonium salts, alkali metal salts, for example potassium and sodium salts, alkaline earth metal salts, for example calcium and magnesium salts, and salts with organic bases, for example dicyclohexylamine and N-methyl-D-glucomine.

Solvates

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Solvates, such as hydrates, exist when the drug substance incorporates solvent, such as water, in the crystal lattice in either stoichiometric or non-stoichiometric amounts. Drug substances are routinely screened for the existence of hydrates since these may be encountered at any stage of the drug manufacturing process or upon storage of the drug substance or dosage form. Solvates are described in S. Byrn et al, Pharmaceutical Research 12(7), 1995, 954-954, and Water-Insoluble Drug Formulation, 2nd ed. R. Liu, CRC Press, page 553, which are incorporated herein by reference. Accordingly, it will be understood by the skilled person that PYY analogues of the invention, as well as derivatives and/or salts thereof may therefore be present in the form of solvates. Solvates of PYY analogues of the invention which are suitable for use in medicine are those wherein the associated solvent is pharmaceutically acceptable. For example, a hydrate is an example of a pharmaceutically acceptable solvate.

Biological Activity

Compounds of the invention have agonistic activity at the human Y2R receptor and thus can be considered to be Y2R agonists. This may be assessed by, for example, an in vitro or cellular binding assay or by a reporter assay. Preferred compounds of the invention exhibit an activity at the human Y2R receptor which is at least 1/10th that of human PYY(3-36), preferably an activity which is at least 1/5th, 1/3rd or 1/2 that of human PYY(3-36), for example when tested in accordance with the assay described in the examples section below. More certain preferred compounds of the invention exhibit an activity at the human Y2R receptor which is at least equivalent to that of human PYY(3-36).

Methods of assessing activity at the 2YR receptor are well known.

Compounds, solvates, derivatives and salts of the invention fulfil some, or more preferably all, of the following criteria:

1) Sustained bioactivity at the human Y2R receptor resulting in inhibition of appetite;
2) Low incidence of side effects such as nausea and vomiting, particularly at therapeutically effective dosage levels;
3) High solubility in aqueous solution at pH 5 to allow an effective dose to be administered in a low volume injection (thereby resulting in lower pain of injection). Solubility may be easily assessed by simple in vitro tests;
4) Long period of activity in vivo (as assessed in humans or an animal model) so as to permit injections no more frequently than daily and preferably no more than twice, or more preferably no more than once a week, whilst still producing acceptable therapeutic or cosmetic benefits;

5) Low antigenicity in humans. This may be assessed in humans or animal models (in particular mice which have been experimentally reconstituted with a human immune system so as to mimic human antibody repertoire) or predicted using predictive software such as that incorporating the "antigenic index" algorithm ((Jameson & Wolf (1988) Comput. Appl. Biosci. 4(1): 181-6), or the PREDITOP algorithm (Pellequer & Westhof, (1993) J. Mol. Graph. 11(3):204-10), or using the methods of Kolaskar & Tongankar (1990) FEBS Leu. 10:276(1-2):172-4, the contents of which are incorporated herein by reference).

According to certain embodiments of the invention, especially embodiments relating to weight loss, obesity, carbohydrate metabolism and diabetes, the compounds, derivatives, solvates and salts of the invention have one, several or all of the following features:

A) Sufficient solubility between pH 4 and pH 5 to permit an effective dose to be administered in a volume of less than lml, less than 0.5 ml or less than 0.3 ml;

B) Inhibition of cAMP signalling in human embryonic kidney cells over-expressing the human Y2R Receptor;

C) One, several or all of the further 1 to 5 features listed above.

Pharmacokinetics, Duration of Action and Solubility

Compounds of the present invention exhibit potent and prolonged duration of action in vivo following subcutaneous administration. In order to achieve this, the compounds are required to have both good activity at the biological target, and excellent pharmacokinetic properties. Incorporation of His residue(s) into peptides having poor aqueous solubility typically leads to peptides having enhanced solubility at acidic pH (e.g. pH 5) due to the presence of charged His side-chain groups, but which are less soluble at physiological pH (pH 7.4). The pI of the side-chain group of histidine is about 6.0. Such properties enable formulation of His-containing peptides in weakly acidic media. Upon subcutaneous injection of such formulations, the solubility falls leading to subcutaneous precipitation of peptide which resolubilises over time. Zinc-containing formulations of His-containing peptides enhance this effect, because at pH 7.4 but not at pH 5 zinc ions co-ordinate with histidine residues and result in a further reduction in solubility which can contribute to increased precipitation at a subcutaneous injection site, or which can contribute to increased stability of the precipitate. However, where precipitation of peptide is not sufficiently rapid following subcutaneous administration, there may still be an initial "spike" or "burst" in blood concentration levels of the peptide. Such properties are undesirable since they increase the possibility of subjects experiencing side effects associated with high concentration levels of the peptides, such as nausea, even if only temporary

Conditions

The invention also provides an analogue of PYY according to the invention, or a pharmaceutical composition comprising the analogue of PYY, for use as a medicament. The PYY analogue and pharmaceutical composition find use in the treatment and/or prevention of conditions such as diabetes and obesity. The PYY analogue, and pharmaceutical composition comprising the PYY analogue, also find use in reducing appetite in a subject, reducing food intake in a subject, and/or reducing calorie intake in a subject.

The invention also provides the use of an analogue of PYY according to the invention for the manufacture of a medicament for the prevention or treatment of diabetes and/or obesity. The invention also provides the use of an analogue of PYY according to the invention for the manufacture of a medicament for reducing appetite in a subject, reducing food intake in a subject, and/or reducing calorie intake in a subject.

The invention also provides a method of treating or preventing a disease or disorder or other non-desired physiological state in a subject, comprising administering a therapeutically effective amount of an analogue of PYY according to the invention, or a pharmaceutical composition comprising the PYY analogue, to the subject.

The invention also provides a method of preventing or treating diabetes and/or obesity, reducing appetite, reducing food intake, and/or reducing calorie intake in a subject, comprising administering a therapeutically effective amount of an analogue of PYY according to the invention, or a pharmaceutical composition comprising the PYY analogue, to the subject.

In one embodiment, the PYY analogue or pharmaceutical composition is administered parentally. In one embodiment, the PYY analogue or pharmaceutical composition is administered subcutaneously. In one embodiment, the PYY analogue or pharmaceutical composition is administered intravenously, intramuscularly, intranasally, transdermally or sublingually.

The subject to whom the PYY analogue according to the invention, or pharmaceutical composition comprising the PYY analogue, is administered may be overweight, for example they may be obese. Alternatively, or in addition, the subject may be diabetic, for example having insulin resistance or glucose intolerance, or both. The subject may have diabetes mellitus, for example, the subject may have Type 2 diabetes. The subject may be overweight, for example, obese and have diabetes mellitus, for example, Type 2 diabetes. Alternatively, the subject may have Type 1 diabetes.

The PYY analogues of the invention are thought to protect islet of Langerhans cells, in particular beta cells, allowing them to retain their normal physiological function, for example the ability to secrete insulin in response to appropriate stimuli, when challenged by toxins (e.g. streptozotocin), pathogens or by an autoimmune response. The PYY analogues of the invention are also thought to be effective in recovering or rescuing pancreatic islet function, and, in particular, beta cell function, following deterioration of physiological function following exposure to a toxin, pathogen or an autoimmune response. Recovery of function may be to at least 10, 20, 30, 40, 50, 60, 70, 80, 90 or 100% of the function exhibited prior to deterioration. Accordingly, the invention also provides a PYY analogue of the invention, or a pharmaceutical composition comprising the PYY analogue, for use in preventing loss of pancreatic islet function (for example beta cell function) and/or recovering pancreatic islet function (for example beta cell function). The invention further provides the use of a PYY analogue of the invention for the manufacture of a medicament for preventing loss of pancreatic islet function (for example beta cell function) and/or for recovering pancreatic islet function (for example beta cell function). The invention further provides a method of preventing loss of pancreatic islet function (for example beta cell function) and/or recovering pancreatic islet function (for example beta cell function) in a subject comprising administering to the subject an effective amount of a PYY analogue of the invention, or a pharmaceutical composition comprising the PYY analogue, to the subject.

The pancreatic islet-protecting properties of the PYY analogues of the invention render them useful for administration in combination with further therapeutic agents which have as a side-effect islet toxicity. An example of such a therapeutic agent is streptozotocin. Accordingly, the invention also provides a PYY analogue according to the invention in combination with a further therapeutic agent which has islet toxicity as a side-effect. The invention also provides a pharmaceutical composition comprising a PYY analogue according to the invention and a further therapeutic agent which has islet toxicity as a side-effect, together with a pharmaceutically acceptable carrier.

In addition, or alternatively, the subject may have, or may be at risk of having, a disorder in which obesity or being overweight is a risk factor. Such disorders include, but are not limited to, cardiovascular disease, for example hypertension, atherosclerosis, congestive heart failure, and dyslipidemia; stroke; gallbladder disease; osteoarthritis; sleep apnea; reproductive disorders for example, polycystic ovarian syndrome; cancers, for example breast, prostate, colon, endometrial, kidney, and esophagus cancer; varicose veins; acnthosis nigricans; eczema; exercise intolerance; insulin resistance; hypertension hypercholesterolemia; cholithiasis; osteoarthritis; orthopedic injury; insulin resistance, for example, type-2 diabetes and syndrome X; and thromboembolic disease (see Kopelman, *Nature* 404:635-43, 2000; Rissanen et al., *British Med. J.* 301, 835, 1990).

Other disorders associated with obesity include depression, anxiety, panic attacks, migraine headaches, PMS, chronic pain states, fibromyalgia, insomnia, impulsivity, obsessive compulsive disorder, and myoclonus. Furthermore, obesity is a recognized risk factor for increased incidence of complications of general anesthesia. (See e. g., Kopelman, *Nature* 404:635-43, 2000). In general, obesity reduces life span and carries a serious risk of co-morbidities such as those listed above.

Other diseases or disorders associated with obesity are birth defects, maternal obesity being associated with increased incidence of neural tube defects, carpal tunnel syndrome (CTS); chronic venous insufficiency (CVI); daytime sleepiness; deep vein thrombosis (DVT); end stage renal disease (ESRD); gout; heat disorders; impaired immune response; impaired respiratory function; infertility; liver disease; lower back pain; obstetric and gynecologic complications; pancreatitis; as well as abdominal hernias; acanthosis nigricans; endocrine abnormalities; chronic hypoxia and hypercapnia; dermatological effects; elephantitis; gastroesophageal reflux; heel spurs; lower extremity edema; mammegaly which causes considerable problems such as bra strap pain, skin damage, cervical pain, chronic odors and infections in the skin folds under the breasts, etc.; large anterior abdominal wall masses, for example abdominal panniculitis with frequent panniculitis, impeding walking, causing frequent infections, odors, clothing difficulties, low back pain; musculoskeletal disease; pseudo tumor cerebri (or benign intracranial hypertension); and sliding hiatal hernia.

The invention also provides a method for improving a lipid profile in a subject comprising administration of a PYY analogue according to the invention, or a pharmaceutical composition comprising the PYY analogue, to the subject. The invention also provides a method for alleviating a condition or disorder that can be alleviated by reducing nutrient availability, comprising administration of a PYY analogue according to the invention, or a pharmaceutical composition comprising the PYY analogue, to the subject.

Appetite can be measured by any means known to one of skill in the art. For example, decreased appetite can be assessed by a psychological assessment. For example, administration of a compound of the invention results in a change in perceived hunger, satiety, and/or fullness. Hunger can be assessed by any means known to one of skill in the art. For example, hunger is assessed using psychological assays, such as by an assessment of hunger feelings and sensory perception using a questionnaire, such as, but not limited to, a Visual Analog Score (VAS) questionnaire. In one specific, non-limiting example, hunger is assessed by answering questions relating to desire for food, drink, prospective food consumption, nausea, and perceptions relating to smell or taste.

A PYY analogue of the invention may be used for weight control and treatment, for example reduction or prevention of obesity, in particular any one or more of the following: preventing and reducing weight gain; inducing and promoting weight loss; and reducing obesity as measured by the Body Mass Index. A PYY analogue of the invention may be used in the control of any one or more of appetite, satiety and hunger, in particular any one or more of the following: reducing, suppressing and inhibiting appetite; inducing, increasing, enhancing and promoting satiety and sensations of satiety; and reducing, inhibiting and suppressing hunger and sensations of hunger. A PYY analogue of the invention may be used in maintaining any one or more of a desired body weight, a desired Body Mass Index, a desired appearance and good health. Accordingly, the invention also provides a method of causing weight loss or preventing weight gain in a subject for cosmetic purposes, comprising administering an effective amount of an analogue of PYY according to the invention, or a composition comprising the PYY analogue, to the subject.

A subject may be a subject who desires weight loss, for example female and male subjects who desire a change in their appearance. A subject may desire decreased feelings of hunger, for example the subject may be a person involved in a lengthy task that requires a high level of concentration, for example soldiers on active duty, air traffic controllers, or truck drivers on long distance routes, etc.

The present invention may also be used in treating, prevention, ameliorating or alleviating conditions or disorders caused by, complicated by, or aggravated by a relatively high nutrient availability. The term "condition or disorder which can be alleviated by reducing caloric (or nutrient) availability" is used herein to denote any condition or disorder in a subject that is either caused by, complicated by, or aggravated by a relatively high nutrient availability, or that can be alleviated by reducing nutrient availability, for example by decreasing food intake. Subjects who are insulin resistant, glucose intolerant, or have any form of diabetes mellitus, for example, type 1, 2 or gestational diabetes, can also benefit from methods in accordance with the present invention.

The invention relates to the treatment of metabolic disorders, for example disorders of energy metabolism. Such disorders include conditions or disorders associated with increased caloric intake include, but are not limited to, insulin resistance, glucose intolerance, obesity, diabetes, including type-2 diabetes, eating disorders, insulin-resistance syndromes, and Alzheimer's disease.

According to the present invention, the PYY analogue is preferably used in the treatment of a human. However, while the compounds of the invention will typically be used to treat human subjects they may also be used to treat similar or identical conditions in other vertebrates for example other primates; farm animals for example swine, cattle and poultry; sport animals for example horses; companion animals for example dogs and cats.

Compositions

While it is possible for the active ingredient to be administered alone, it is preferable for it to be present in a pharmaceutical formulation or composition. Accordingly, the invention also provides a pharmaceutical composition comprising an analogue of PYY according to the invention together with a pharmaceutically acceptable carrier and optionally other therapeutic ingredients. Pharmaceutical compositions of the invention may take the form of a pharmaceutical formulation as described below.

The pharmaceutical formulations according to the invention include those suitable for oral, parenteral (including subcutaneous, intradermal, intramuscular, intravenous, and intraarticular), inhalation (including fine particle dusts or mists which may be generated by means of various types of metered dose pressurized aerosols, nebulizers or insufflators), rectal and topical (including dermal, transdermal, transmucosal, buccal, sublingual, and intraocular) administration, although the most suitable route may depend upon, for example, the condition and disorder of the recipient.

The formulations may conveniently be presented in unit dosage form and may be prepared by any of the methods well known in the art of pharmacy. All methods include the step of bringing the active ingredient into association with the carrier which constitutes one or more accessory ingredients. In general the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, sachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste. Various pharmaceutically acceptable carriers and their formulation are described in standard formulation treatises, e.g., *Remington's Pharmaceutical Sciences* by E. W. Martin. See also Wang, Y. J. and Hanson, M. A., *Journal of Parenteral Science and Technology*, Technical Report No. 10, Supp. 42:2S, 1988.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein. The present compounds can, for example, be administered in a form suitable for immediate release or extended release. Immediate release or extended release can be achieved by the use of suitable pharmaceutical compositions comprising the present compounds, or, particularly in the case of extended release, by the use of devices such as subcutaneous implants or osmotic pumps. The present compounds can also be administered liposomally.

Preferably, compositions according to the invention are suitable for subcutaneous administration, for example by injection. According to certain embodiments the composition may contain metal ion for example copper, iron, aluminium, zinc, nickel or cobalt ions. The presence of such ions may limit solubility and thus delay absorption into the circulatory system from the site of subcutaneous administration. In a particularly preferred embodiment, the composition contains zinc ions. Zinc ions may be present at any suitable concentration for example at a molar ratio to peptide molecules of 10:1 to 1:10, 8:1 to 1:8, 5:1 to 1:5, 4:1 to 1:4, 3:1 to 1:3, 2:1 to 1:2 or 1:1. In one embodiment, the pharmaceutical composition has a pH of less than 5 and the pharmaceutical composition comprises zinc ions.

Exemplary compositions for oral administration include suspensions which can contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which can contain, for example, microcrystalline cellulose, dicalcium phosphate, starch, magnesium stearate and/or lactose and/or other excipients, binders, extenders, disintegrants, diluents and lubricants such as those known in the art. PYY analogues of the invention or variants, derivatives, salts or solvates thereof can also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations can also include an excipient to aid mucosal adhesion such as hydroxypropyl cellulose (HPC), hydroxypropyl methyl cellulose (HPMC), sodium carboxy methyl cellulose (SCMC), maleic anhydride copolymer (e.g., Gantrez), and agents to control release such as polyacrylic copolymer (e.g. Carbopol 934). Lubricants, glidants, flavors, coloring agents and stabilizers may also be added for ease of fabrication and use.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example saline or water-for-injection, immediately prior to use. Extemporaneous injection solutions and suspensions may be prepared from sterile powders, granules and tablets of the kind previously described. Exemplary compositions for parenteral administration include injectable solutions or suspensions which can contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid, or Cremaphor. An aqueous carrier may be, for example, an isotonic buffer solution at a pH of from about 3.0 to about 8.0, preferably at a pH of from about 3.5 to about 7.4, for example from 3.5 to 6.0, for example from 3.5 to about 5.0. Useful buffers include sodium citrate-citric acid and sodium phosphate-phosphoric acid, and sodium acetate/acetic acid buffers. The composition preferably does not include oxidizing agents and other compounds that are known to be deleterious to PYY and related molecules. Excipients that can be included are, for instance, other proteins, such as human serum albumin or plasma preparations. If desired, the pharmaceutical composition may also contain minor amounts of non-toxic auxiliary substances, such as wetting or emulsifying agents, preservatives, and pH buffering agents and the like, for example sodium acetate or sorbitan monolaurate.

In one embodiment, the pharmaceutical composition is present in a syringe or other administration device for subcutaneous administration to humans.

Exemplary compositions for nasal aerosol or inhalation administration include solutions in saline, which can contain, for example, benzyl alcohol or other suitable preservatives, absorption promoters to enhance bioavailability, and/or other solubilizing or dispersing agents such as those known in the art. Conveniently in compositions for nasal aerosol or inhalation administration the compound of the invention is delivered in the form of an aerosol spray presentation from a pressurized pack or a nebulizer, with the use of a suitable propellant, e.g., dichlorodifluoro-methane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of e.g., gelatin for use in an inhaler or insufflator can be formulated to contain a powder mix of the compound and a suitable powder base, for example lactose or starch. In one specific, non-limiting example, a compound of the invention is administered as an aerosol from a metered dose valve, through an aerosol adapter also known as an actuator. Optionally, a stabilizer is also included, and/or porous particles for deep lung delivery are included (e.g., see U.S. Pat. No. 6,447,743).

Formulations for rectal administration may be presented as a retention enema or a suppository with the usual carriers such as cocoa butter, synthetic glyceride esters or polyethylene glycol. Such carriers are typically solid at ordinary temperatures, but liquefy and/or dissolve in the rectal cavity to release the drug.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerine or sucrose and acacia. Exemplary compositions for topical administration include a topical carrier such as Plastibase (mineral oil gelled with polyethylene).

Preferred unit dosage formulations are those containing an effective dose, as hereinbefore recited, or an appropriate fraction thereof, of the PYY analogue.

It should be understood that in addition to the ingredients particularly mentioned above, the formulations of this invention may include other agents conventional in the art having regard to the type of formulation in question, for example those suitable for oral administration may include flavouring agents.

The PYY analogues of the invention are also suitably administered as sustained-release systems. Suitable examples of sustained-release systems of the invention include suitable polymeric materials, for example semi-permeable polymer matrices in the form of shaped articles, e.g., films, or mirocapsules; suitable hydrophobic materials, for example as an emulsion in an acceptable oil; or ion exchange resins; and sparingly soluble derivatives of the compound of the invention, for example, a sparingly soluble salt. Sustained-release systems may be administered orally; rectally; parenterally; intracistemally; intravaginally; intraperitoneally; topically, for example as a powder, ointment, gel, drop or transdermal patch; bucally; or as an oral or nasal spray.

Preparations for administration can be suitably formulated to give controlled release of compounds of the invention. For example, the pharmaceutical compositions may be in the form of particles comprising one or more of biodegradable polymers, polysaccharide jellifying and/or bioadhesive polymers, amphiphilic polymers, agents capable of modifying the interface properties of the particles of the compound of formula (I). These compositions exhibit certain biocompatibility features which allow a controlled release of the active substance. See U.S. Pat. No. 5,700,486.

A PYY analogue of the invention may be delivered by way of a pump (see Langer, supra; Sefton, *CRC Crit. Ref. Biomed. Eng.* 14:201, 1987; Buchwald et al., *Surgery* 88:507, 1980; Saudek et al., *N Engl. J. Med.* 321:574, 1989) or by a continuous subcutaneous infusions, for example, using a mini-pump. An intravenous bag solution may also be employed. The key factor in selecting an appropriate dose is the result obtained, as measured by decreases in total body weight or ratio of fat to lean mass, or by other criteria for measuring control or prevention of obesity or prevention of obesity-related conditions, as are deemed appropriate by the practitioner. Other controlled release systems are discussed in the review by Langer (*Science* 249:1527-1533, 1990). In another aspect of the disclosure, compounds of the invention are delivered by way of an implanted pump, described, for example, in U.S. Pat. Nos. 6,436,091; 5,939,380; 5,993,414.

Implantable drug infusion devices are used to provide patients with a constant and long term dosage or infusion of a drug or any other therapeutic agent. Essentially such device may be categorized as either active or passive. A compound of the present invention may be formulated as a depot preparation. Such a long acting depot formulation can be administered by implantation, for example subcutaneously or intramuscularly; or by intramuscular injection. Thus, for example, the compounds can be formulated with suitable polymeric or hydrophobic materials, for example as an emulsion in an acceptable oil; or ion exchange resins; or as a sparingly soluble derivatives, for example, as a sparingly soluble salt.

A therapeutically effective amount of a PYY analogue of the invention may be administered as a single pulse dose, as a bolus dose, or as pulse doses administered over time. Thus, in pulse doses, a bolus administration of a PYY analogue of the invention is provided, followed by a time period wherein no a compound of the invention is administered to the subject, followed by a second bolus administration. In specific, non-limiting examples, pulse doses of a compound of the invention are administered during the course of a day, during the course of a week, or during the course of a month.

The invention also provides an analogue of PYY according to the invention together with a further therapeutic agent, for simultaneous, sequential or separate administration. The invention also provides a pharmaceutical composition comprising the PYY analogue according to the invention and a further therapeutic agent. Examples of further therapeutic agents include an additional appetite suppressant, a food-intake-reducing, plasma glucose-lowering or plasma lipid-altering agent. Specific, non-limiting examples of an additional appetite suppressant include amfepramone (diethylpropion), phentermine, mazindol and phenylpropanolamine, fenfluramine, dexfenfluramine, and fluoxetine. As mentioned above, the PYY analogue of the invention can be administered simultaneously with the additional appetite suppressant, or it may be administered sequentially or separately. In one embodiment, the compound of the invention is formulated and administered with an appetite suppressant in a single dose.

A PYY analogue of the invention may be administered whenever the effect, e.g., appetite suppression, decreased food intake, or decreased caloric intake, is desired, or slightly before to whenever the effect is desired, such as, but not limited to about 10 minutes, about 15 minutes, about 30 minutes, about 60 minutes, about 90 minutes, or about 120 minutes, before the time the effect is desired.

The therapeutically effective amount of a PYY analogue of the invention will be dependent on the molecule utilized, the subject being treated, the severity and type of the affliction, and the manner and route of administration. For example, a therapeutically effective amount of a PYY analogue of the invention may vary from about 0.01 μg per kilogram (kg) body weight to about 1 g per kg body weight, for example about 0.1 μg to about 20 mg per kg body weight, for example about 1 μg to about 5 mg per kg body weight, or about 5 μg to about 1 mg per kg body weight.

In one embodiment of the invention, a PYY analogue of the invention may be administered to a subject at from 5 to 1000 nmol per kg bodyweight, for example at from 10 to 750 nmol per kg bodyweight, for example at from 20 to 500 nmol per kg bodyweight, in particular at from 30 to 240 nmol per kg bodyweight. For a 75 kg subject, such doses correspond to dosages of from 375 nmol to 75 μmol, for example from 750 nmol to 56.25 μmol, for example from 1.5 to 37.5 μmol, in particular from 2.25 to 18 μmol.

In an alternative embodiment, a PYY analogue of the invention may be administered to a subject at 0.5 to 135 picomole (pmol) per kg body weight, for example 5 to 100 picomole (pmol) per kg body weight, for example 10 to 90 picomole (pmol) per kg body weight, for example about 72 pmol per kg body weight. In one specific, non-limiting example, a PYY analogue of the invention is administered in a dose of about 1 nmol or more, 2 nmol or more, or 5 nmol or more. In this example, the dose of the PYY analogue of the invention is generally not more than 100 nmol, for example, the dose is 90 nmols or less, 80 nmols or less, 70 nmols or less, 60 nmols or less, 50 nmols or less, 40 nmols or less, 30 nmols or less, 20 nmols or less, 10 nmols. For example, a dosage range may comprise any combination of any of the specified lower dose limits with any of the specified upper dose limits. Thus, examples of non-limiting dose ranges of compounds of the invention are within the range of from 1 to 100 nmols, from 2 to 90 mols, from 5 to 80 nmols.

In one specific, non-limiting example, from about 1 to about 50 nmol of a PYY analogue of the invention is administered, for example about 2 to about 20 nmol, for example about 10 nmol is administered as a subcutaneous injection. The exact dose is readily determined by one of skill in the art based on the potency of the specific PYY analogue utilized, the route of delivery of the PYY analogue and the age, weight, sex and physiological condition of the subject.

Suitable doses of PYY analogue of the invention also include those that result in a reduction in calorie intake, food intake, or appetite, caused by the normal postprandial level of PYY. Examples of doses include, but are not limited to doses that produce the effect demonstrated when the serum levels of PYY are from about 40 pM to about 60 pM, or from about 40 pM to about 45 pM, or about 43 pM.

The doses discussed above may be given, for example, once, twice, three-times or four-times a day. Alternatively, they may be give once every 2, 3 or 4 days. In a slow release formulation containing zinc, it may be possible to give a dose once every 3, 6, 7, 8, 9, 10, 11, 12, 13, 14, 15, 16, 17, 18, 19, 20 or 21 days. According to certain embodiments they may be administered once shortly before each meal to be taken.

Specific sequences of the invention According to certain specific embodiments of the invention the analogue of PYY has an amino acid sequence given in one of the specific sequences set out in FIG. 1.

EXAMPLES

The invention is illustrated by the following non-limiting Examples.

Materials and Methods

Peptide Synthesis

Peptides were synthesised using a standard fluorenylmethoxycarbonyl (Fmoc) solid phase peptide synthesis (SPPS) method. Peptide synthesis was carried out on a tricyclic amide linker resin. Amino acids were attached using the Fmoc strategy. Each amino acid was added sequentially from the C- to the N-termini. Peptide couplings were mediated by reagents such as TBTU. Peptide cleavage from the resin was achieved with trifluoracetic acid in the presence of scavengers.

Peptides were purified by reverse phase HPLC. Quality control was performed on all purified peptides and peptides were shown in most cases to be greater than 90% pure by HPLC in two buffer systems. MALDI-MS showed the expected molecular ion.

Example Synthesis

Example compound Y1592 was prepared as follows using standard Fmoc chemistry:

1. Resin preparation: To 2Cl-Trt resin (0.30 mmol, 1.00 eq) was added FMOC-TYR(TBU)-OH (137.86 mg, 300.00 μmol, 1.00 eq) and DIEA (232.63 mg, 1.80 mmol, 313.52 μL, 6.00 eq) in DCM (10.0 mL). The mixture was agitated with $N_2$ for 2 h at 20° C., then MeOH (0.3 mL) was added and the mixture was agitated with $N_2$ for another 30 min. The resin was washed with DMF (3×15.0 mL), and then 20% piperidine in DMF (5.00 mL) was added and the mixture was agitated with $N_2$ for 30 min at 20° C. The mixture was filtered to get the resin. The resin was washed with DMF (5×15.0 mL) and the mixture was filtered to get the resin.
2. Coupling: A solution of FMOC-ARG(PBF)-OH (583.89 mg, 900.00 μmol, 3.00 eq), DIEA (232.63 mg, 1.80 mmol, 313.52 μL, 6.00 eq) and HBTU (324.25 mg, 855.00 μmol, 2.85 eq) in DMF (5.00 mL) were added to the resin and agitated with $N_2$ for 30 min at 20° C. The resin was then washed with DMF (3×15.0 mL).
3. Deprotection: 20% piperidine in DMF (5.00 mL) was added to the resin and the mixture was agitated with $N_2$ for 30 min at 20° C. The resin was washed with DMF (5×15.0 mL) and filtered to get the resin.

4. Steps 2 and 3 were repeated using the reagents in Table 3 until the last amino acid had been added (reaction iteration #1 in Table 3 is the first added Arg residue, as set out in step 2 above).

TABLE 3

| # | Materials | Coupling reagents |
|---|---|---|
| 1 | FMOC-ARG(PBF)-OH (3.00 eq) | HBTU (2.85 eq) and DIEA (6.00 eq) |
| 2 | FMOC-GLN(TRT)-OH (3.00 eq) | HBTU (2.85 eq) and DIEA (6.00 eq) |
| 3 | FMOC-ARG(PBF)-OH (3.00 eq) | HBTU (2.85 eq) and DIEA (6.00 eq) |
| 4 | FMOC-THR(TBU)-OH (3.00 eq) | HBTU (2.85 eq) and DIEA (6.00 eq) |
| 5 | FMOC-VAL-OH (3.00 eq) | HBTU (2.85 eq) and DIEA (6.00 eq) |
| 6 | FMOC-HIS(TRT)-OH (3.00 eq) | HBTU (2.85 eq) and DIEA (6.00 eq) |
| 7 | FMOC-ASN(TRT)-OH (3.00 eq) | HBTU (2.85 eq) and DIEA (6.00 eq) |
| 8 | FMOC-LEU-OH (3.00 eq) | HBTU (2.85 eq) and DIEA (6.00 eq) |
| 9 | FMOC-PHE-OH (3.00 eq) | HBTU (2.85 eq) and DIEA (6.00 eq) |
| 10 | FMOC-HIS(TRT)-OH (3.00 eq) | HBTU (2.85 eq) and DIEA (6.00 eq) |
| 11 | FMOC-ARG(PBF)-OH (3.00 eq) | HBTU (2.85 eq) and DIEA (6.00 eq) |
| 12 | FMOC-LEU-OH (3.00 eq) | HBTU (2.85 eq) and DIEA (6.00 eq) |
| 13 | FMOC-ALA-OH (3.00 eq) | HBTU (2.85 eq) and DIEA (6.00 eq) |
| 14 | FMOC-ALA-OH (3.00 eq) | HBTU (2.85 eq) and DIEA (6.00 eq) |
| 15 | FMOC-TYR(TBU)-OH (3.00 eq) | HBTU (2.85 eq) and DIEA (6.00 eq) |
| 16 | FMOC-TYR(TBU)-OH (3.00 eq) | HBTU (2.85 eq) and DIEA (6.00 eq) |
| 17 | FMOC-HIS(TRT)-OH (3.00 eq) | HBTU (2.85 eq) and DIEA (6.00 eq) |
| 18 | FMOC-LEU-OH (3.00 eq) | HBTU (2.85 eq) and DIEA (6.00 eq) |
| 19 | FMOC-LEU-OH (3.00 eq) | HBTU (2.85 eq) and DIEA (6.00 eq) |
| 20 | FMOC-GLU(OTBU)-OH (3.00 eq) | HBTU (2.85 eq) and DIEA (6.00 eq) |
| 21 | FMOC-GLU(OTBU)-OH (3.00 eq) | HBTU (2.85 eq) and DIEA (6.00 eq) |
| 22 | FMOC-PRO-OH (3.00 eq) | HBTU (2.85 eq) and DIEA (6.00 eq) |
| 23 | FMOC-SER(TBU)-OH (3.00 eq) | HBTU (2.85 eq) and DIEA (6.00 eq) |
| 24 | FMOC-ALA-OH (3.00 eq) | HBTU (2.85 eq) and DIEA (6.00 eq) |
| 25 | FMOC-GLY-OH (3.00 eq) | HBTU (2.85 eq) and DIEA (6.00 eq) |
| 26 | FMOC-GLU(OTBU)-OH (3.00 eq) | HBTU (2.85 eq) and DIEA (6.00 eq) |
| 27 | FMOC-GLY-OH (3.00 eq) | HBTU (2.85 eq) and DIEA (6.00 eq) |
| 28 | FMOC-PRO-OH (3.00 eq) | HBTU (2.85 eq) and DIEA (6.00 eq) |
| 29 | FMOC-ALA-OH (3.00 eq) | HBTU (2.85 eq) and DIEA (6.00 eq) |
| 30 | FMOC-GLU(OTBU)-OH (3.00 eq) | HBTU (2.85 eq) and DIEA (6.00 eq) |
| 31 | FMOC-PRO-OH (3.00 eq) | HBTU (2.85 eq) and DIEA (6.00 eq) |
| 32 | FMOC-LYS(BOC)-OH (3.00 eq) | HBTU (2.85 eq) and DIEA (6.00 eq) |
| 33 | FMOC-ILE-OH (3.00 eq) | HBTU (2.85 eq) and DIEA (6.00 eq) |
| 34 | FMOC-PRO-OH (3.00 eq) | HBTU (2.85 eq) and DIEA (6.00 eq) |
| 35 | FMOC-GLY-OH (3.00 eq) | HBTU (2.85 eq) and DIEA (6.00 eq) |
| 36 | FMOC-LYS(DDE)-OH (3.00 eq) | HBTU (2.85 eq) and DIEA (6.00 eq) |
| 37 | tert-butoxycarbonyl tert-butyl carbonate (3.00 eq) | DIEA (6.00 eq) |

5. After the coupling of tert-butoxycarbonyl tert-butyl carbonate in iteration #37, 3% $H_2NH_2$/DMF was added and reacted for 30 min to remove DDE, and then repeated. The mixture was then drained and washed with DMF (5×20.0 mL).

6. The reactions of steps 2 and 3 were then carried out using 16-(tert-butoxy)-16-oxohexadecanoic acid (3.00 eq) in HBTU (2.85 eq) and DIEA (6.00 eq).

Peptide Cleavage and Purification

The resin was washed with MeOH (2×30.0 mL) and dried under vacuum to get 2.20 g peptide resin. Then 25.0 mL of cleavage buffer (92.5% TFA/2.5% Mpr/2.5% TIS/2.5% $H_2O$) was added to the flask containing the side chain-protected peptide resin at 20° C. and the mixture was stirred for 2 h. The peptide was precipitated with cold tert-butyl methyl ether (300 mL) and centrifuged (3 min at 5000 rpm). The peptide precipitation was washed with tert-butyl methyl ether (150 mL) twice more. The crude peptide was dried under vacuum for 2 h, and confirmed by LCMS (EW18009-1-P1A1).

The residue was purified by preparative HPLC (TFA, conditions: 30° C., A: 0.075% TFA/$H_2O$, B: $CH_3CN$) to give the compound as a white solid, which was confirmed by LCMS (EW18009-1-P1A) and HPLC (EW18009-1-P1B).

FIG. 1 discloses a number of specific sequences encompassed by the scope of the present invention in all its aspects. Each of these sequences is a specific embodiment of the invention. It also discloses, on the first line, the sequence of naturally occurring human PYY for reference.

Human Y2 Receptor, In Vitro Receptor Potency Studies

DiscoverX® hY2 CHO-K1 cells (10,000 cells per well in a 96 well plate) were resuspended in media containing 0.1% (v/v) BSA and 0.01 mM forskolin and test peptides at a range of concentrations, for 30 minutes. The reaction was stopped by lysing the cells and cAMP quantified 60 minutes later using Cisbio cAMP dynamic 2 kit. Y2R agonists inhibit the forskolin-stimulated cAMP production. ICso values are calculated for control peptide ($PYY_{3-36}$) and test peptides of the invention. A ratio of test peptide: $PYY_{3-36}$ is calculated, where 1=as potent as $PYY_{3-36}$, 0.1=10 fold greater potency and 10=10 fold lower potency. The average (mean) ratio is calculated from independent tests.

Inhibition of cAMP production, expressed as a ratio of test compound: $PYY_{3-36}$ is shown in FIG. 2 in the column headed "human cAMP inhibition"

Solubility Studies

Solubility of compounds of the invention were assessed by preparing a solution of the compounds at 50 mg/mL by dissolving 2 mg of material in 0.04 mL water for injection. The pH of the solution was adjusted to pH 4. Solubility is assessed by a visual inspection where:

1=freely soluble, clear solution visibility identical to diluent

2=soluble with small number (<less than 3) visible particles

3=soluble with moderate number (3-10) visible particles

4=numerous insoluble particles in suspension, non-transparent

5=insoluble, precipitate present

The results of this study are shown in FIG. 2 in the column headed "solubility at 50 mg/ml pH4"

In Vivo Efficacy Studies, Single Dose Feeding Studies in Male Wistar Rats

Animals

Ad libitum fed Male Wistar rats (Charles River Ltd, Margate, UK) were used for animal experiments Feeding Studies in Rats Rats were individually housed in IVC cages. Animals were randomised into treatment groups, with stratification by body weight. All peptide solutions were prepared freshly immediately prior to administration. The vehicle used for all studies was 5% v/v water and 95% NaCl (0.9% w/v). Compounds of the invention (at either 100, 200 or 400 nmol/kg body weight) were resuspended in water for injection. Peptide and vehicle were administered in the early light phase (0900 hr-1000 hr) by subcutaneous injection and animals provided a known amount of food.

Animals were given free access to food and water during the study period. Animal body weight and remaining food were weighed throughout the study, typically 24, 48, 72 96 and 168 h post dosing.

Results

Results are calculated by comparison of individual rats food intake and change of body weight to the mean change in saline control animals and expressed as treatment group average (mean). For example a food intake value of '−16' represents an average of a 16 g reduction of food intake compared to the average food intake of control animals in the study for the same time interval.

FIG. 2 shows the results of rat feeding studies in which male Wistar rats were administered example compounds of the invention. The values shown are the differences in food intake and weight loss between rats which received control saline or peptide in water for injection over 24 hours, 48 hours, 72 hours, 96 hours, and 7 days. The longevity values represent a score indicating the longevity of the effect of the example peptide on food intake and weight loss; a larger value indicates a more long-lasting effect.

The invention claimed is:

1. A compound, or a salt thereof, having an amino acid sequence of Y1596 (SEQ ID NO: 51), Y1622 (SEQ ID NO: 77), Y1642 (SEQ ID NO: 97), Y1739 (SEQ ID NO: 194), Y1740 (SEQ ID NO: 195), Y1741 (SEQ ID NO: 196), Y1783 (SEQ ID NO: 238), Y1786 (SEQ ID NO: 241), Y1788 (SEQ ID NO: 243), Y1797 (SEQ ID NO: 252), Y1798 (SEQ ID NO: 253), Y1799 (SEQ ID NO: 254), Y1800 (SEQ ID NO: 255), Y1801 (SEQ ID NO: 256), Y1802 (SEQ ID NO: 257), Y1803 (SEQ ID NO: 258), Y1804 (SEQ ID NO: 259), Y1805 (SEQ ID NO: 260), Y1821 (SEQ ID NO: 276), Y1822 (SEQ ID NO: 277), Y1823 (SEQ ID NO: 278), Y1824 (SEQ ID NO: 279), Y1826 (SEQ ID NO: 281), or Y1827 (SEQ ID NO: 282).

2. The compound of claim 1, or the salt thereof, together with a further therapeutic agent, for simultaneous, sequential or separate administration.

3. A composition comprising the compound of claim 1 or the salt thereof, and a pharmaceutically acceptable carrier and optionally a further therapeutic agent.

4. The composition of claim 3, wherein the composition is contained in a syringe or other administration device for subcutaneous administration to humans.

5. A method of promoting weight loss or preventing weight gain in a subject in need thereof, comprising administering to the subject a therapeutically effective amount of the compound of claim 1.

* * * * *

SEQUENCE LISTING

```
<160> NUMBER OF SEQ ID NOS: 282

<210> SEQ ID NO 1
<211> LENGTH: 35
<212> TYPE: PRT
<213> ORGANISM: Artificial Sequence
<220> FEATURE:
<223> OTHER INFORMATION: component of appetite suppressant
<220> FEATURE:
<221> NAME/KEY: VARIANT
<222> LOCATION: (1)..(1)
<223> OTHER INFORMATION: Pro or Cys
<220> FEATURE:
<221> NAME/KEY: VARIANT
<222> LOCATION: (2)..(2)
<223> OTHER INFORMATION: residue is Ile or Lys substituated at its
      epsilon-amino group
<220> FEATURE:
<221> NAME/KEY: VARIANT
<222> LOCATION: (3)..(3)
<223> OTHER INFORMATION: residue is Lys or Lys substituated at its
      epsilon-amino group
<220> FEATURE:
<221> NAME/KEY: VARIANT
<222> LOCATION: (4)..(4)
<223> OTHER INFORMATION: Pro or Cys
<220> FEATURE:
<221> NAME/KEY: VARIANT
<222> LOCATION: (5)..(5)
<223> OTHER INFORMATION: residue is Glu or Glu substituted at its gamma-
      carboxylic acid group or Lys substituted at its epsilon-amino
      agroup
<220> FEATURE:
<221> NAME/KEY: VARIANT
<222> LOCATION: (6)..(6)
<223> OTHER INFORMATION: residue is Lys substituted at its epsilon-amino
      group, Cys substituted at its beta-thiol group or Ala or Cys
<220> FEATURE:
<221> NAME/KEY: VARIANT
<222> LOCATION: (6)..(6)
<223> OTHER INFORMATION: residue is Lys substituted at its epsilon-amino
      group, Cys substituted at its beta-thiol group or Ala or Cys
<220> FEATURE:
<221> NAME/KEY: VARIANT
<222> LOCATION: (8)..(8)
<223> OTHER INFORMATION: residue is Lys substituted at its epsilon-amino
      group, Cys substituted at its beta-thiol group or Gly or Cys
<220> FEATURE:
<221> NAME/KEY: VARIANT
<222> LOCATION: (9)..(9)
```

<223> OTHER INFORMATION: residue is Glu substituted at its gamma carboxylic acid group, Lys substituted at its epsilon-amino, Cys substituted at its beta thiol group, Lys, Glu or Cys
<220> FEATURE:
<221> NAME/KEY: VARIANT
<222> LOCATION: (10)..(10)
<223> OTHER INFORMATION: residue is Lys substituted at its epsilon-amino, Asp, Gly, Asn or Glu
<220> FEATURE:
<221> NAME/KEY: VARIANT
<222> LOCATION: (11)..(11)
<223> OTHER INFORMATION: residue is Lys substituted at its epsilon-amino group or Ala;
<220> FEATURE:
<221> NAME/KEY: VARIANT
<222> LOCATION: (12)..(12)
<223> OTHER INFORMATION: residue is Lys substituted at its epsilon-amino group or Ser
<220> FEATURE:
<221> NAME/KEY: VARIANT
<222> LOCATION: (13)..(13)
<223> OTHER INFORMATION: residue is Lys substituted at its epsilon-amino group or Pro
<220> FEATURE:
<221> NAME/KEY: VARIANT
<222> LOCATION: (14)..(14)
<223> OTHER INFORMATION: residue is Lys substituted at its epsilon-amino group or Glu
<220> FEATURE:
<221> NAME/KEY: VARIANT
<222> LOCATION: (15)..(15)
<223> OTHER INFORMATION: residue is Lys substituted at its epsilon-amino group or Glu
<220> FEATURE:
<221> NAME/KEY: VARIANT
<222> LOCATION: (16)..(16)
<223> OTHER INFORMATION: Leu or Ile
<220> FEATURE:
<221> NAME/KEY: VARIANT
<222> LOCATION: (17)..(17)
<223> OTHER INFORMATION: residue is Lys substituted at its epsilon-amino group, Asn, Leu,
Ala or Val
<220> FEATURE:
<221> NAME/KEY: VARIANT
<222> LOCATION: (18)..(18)
<223> OTHER INFORMATION: residue is Lys substituted at its epsilon-amino group, Arg, Lys or His
<220> FEATURE:
<221> NAME/KEY: VARIANT
<222> LOCATION: (21)..(21)
<223> OTHER INFORMATION: residue is Lys substituted at its epsilon-amino group, Ala or Ile
<220> FEATURE:
<221> NAME/KEY: VARIANT
<222> LOCATION: (22)..(22)
<223> OTHER INFORMATION: residue is Lys substituted at its epsilon-amino group, Ala or Glu
<220> FEATURE:
<221> NAME/KEY: VARIANT
<222> LOCATION: (23)..(23)
<223> OTHER INFORMATION: Leu or Cys
<220> FEATURE:
<221> NAME/KEY: VARIANT
<222> LOCATION: (23)..(23)
<223> OTHER INFORMATION: Leu or Cys
<220> FEATURE:
<221> NAME/KEY: VARIANT
<222> LOCATION: (24)..(24)
<223> OTHER INFORMATION: residue is Lys substituted at its epsilon-amino group or Arg
<220> FEATURE:
<221> NAME/KEY: VARIANT
<222> LOCATION: (24)..(24)
<223> OTHER INFORMATION: residue is Lys substituted at its epsilon-amino group or Arg
<220> FEATURE:
<221> NAME/KEY: VARIANT
<222> LOCATION: (25)..(25)

```
<223> OTHER INFORMATION: residue is Lys substituted at its epsilon-amino
      group or His
<220> FEATURE:
<221> NAME/KEY: VARIANT
<222> LOCATION: (26)..(26)
<223> OTHER INFORMATION: residue is Lys substituted at its epsilon-amino
      group or Tyr, Phe or Cys
<220> FEATURE:
<221> NAME/KEY: VARIANT
<222> LOCATION: (26)..(26)
<223> OTHER INFORMATION: residue is Lys substituted at its epsilon-amino
      group or Tyr, Phe or Cys
<220> FEATURE:
<221> NAME/KEY: VARIANT
<222> LOCATION: (29)..(29)
<223> OTHER INFORMATION: residue is Lys substituted at its epsilon-amino
      group or Arg, Lys or His
<220> FEATURE:
<221> NAME/KEY: VARIANT
<222> LOCATION: (30)..(30)
<223> OTHER INFORMATION: Val or Leu

<400> SEQUENCE: 1

Cys Lys Ile Cys Glu Ala Pro Cys Cys Asn Ala Lys Lys Glu Glu Ile
1               5                   10                  15

Ala Arg Tyr Tyr Ala Ala Cys Arg His Cys Leu Asn Arg Leu Thr Arg
            20                  25                  30

Gln Arg Tyr
        35


<210> SEQ ID NO 2
<211> LENGTH: 6
<212> TYPE: PRT
<213> ORGANISM: Artificial Sequence
<220> FEATURE:
<223> OTHER INFORMATION: component of appetite suppressant
<220> FEATURE:
<221> NAME/KEY: VARIANT
<222> LOCATION: (1)..(1)
<223> OTHER INFORMATION: residue is is Glu substituted at its alpha-
      amino group or Glu
<220> FEATURE:
<221> NAME/KEY: VARIANT
<222> LOCATION: (2)..(2)
<223> OTHER INFORMATION: residue is Glu substituted at its alpha-amino
      group, Lys substituted at its alpha-amino group, Gly or Tyr;
<220> FEATURE:
<221> NAME/KEY: VARIANT
<222> LOCATION: (3)..(3)
<223> OTHER INFORMATION: residue is Glu substituted at its alpha-amino
      group, Gly substituted at its alpha-amino group, Ser, Asn, Gly,
      Glu or Tyr
<220> FEATURE:
<221> NAME/KEY: VARIANT
<222> LOCATION: (4)..(4)
<223> OTHER INFORMATION: residue is Glu substituted at its gamma-
      carboxylic acid group, Glu or Asn or Ser substituted at its alpha-
      amino group, Lys substituted at its epsilon amino group, Ser, Gly,
      Glu, Tyr, Pro, Asn or His
<220> FEATURE:
<221> NAME/KEY: VARIANT
<222> LOCATION: (5)..(5)
<223> OTHER INFORMATION: residue is Glu substituted at its gamma-
      carboxylic acid group, Glu substituted at its alpha-amino group,
      Lys substituted at its epsilon-amino group, Ser substituted at its
      alpha-amino group, Gly, Ser, Glu, Pro, His, Asn or Thr
<220> FEATURE:
<221> NAME/KEY: VARIANT
<222> LOCATION: (6)..(6)
<223> OTHER INFORMATION: residue is Lys substituted at its epsilon-amino
      group, Glu substituted at its gamma-carboxylic acid group, Gly
      substituted at its alpha-amino group, Gly, Ser, Pro, His, Thr, Tyr
      or Glu

<400> SEQUENCE: 2
```

Glu Glu Asn Asn Asn Glu
1 5

<210> SEQ ID NO 3
<211> LENGTH: 5
<212> TYPE: PRT
<213> ORGANISM: Artificial Sequence
<220> FEATURE:
<223> OTHER INFORMATION: component of appetite suppressant
<220> FEATURE:
<221> NAME/KEY: VARIANT
<222> LOCATION: (1)..(1)
<223> OTHER INFORMATION: residue is Glu substituted at its alpha-amino group, Lys substituted at its alpha-amino group, Gly or Tyr;
<220> FEATURE:
<221> NAME/KEY: VARIANT
<222> LOCATION: (2)..(2)
<223> OTHER INFORMATION: residue is Glu substituted at its alpha-amino group, Gly substituted at its alpha-amino group, Ser, Asn, Gly, Glu or Tyr
<220> FEATURE:
<221> NAME/KEY: VARIANT
<222> LOCATION: (3)..(3)
<223> OTHER INFORMATION: residue is Glu substituted at its gamma-carboxylic acid group, Glu or Asn or Ser substituted at its alpha-amino group, Lys substituted at its epsilon amino group, Ser, Gly, Glu, Tyr, Pro, Asn or His
<220> FEATURE:
<221> NAME/KEY: VARIANT
<222> LOCATION: (4)..(4)
<223> OTHER INFORMATION: residue is Glu substituted at its gamma-carboxylic acid group, Glu substituted at its alpha-amino group, Lys substituted at its epsilon-amino group, Ser substituted at its alpha-amino group, Gly, Ser, Glu, Pro, His, Asn or Thr
<220> FEATURE:
<221> NAME/KEY: VARIANT
<222> LOCATION: (5)..(5)
<223> OTHER INFORMATION: residue is Lys substituted at its epsilon-amino group, Glu substituted at its gamma-carboxylic acid group, Gly substituted at its alpha-amino group, Gly, Ser, Pro, His, Thr, Tyr or Glu

<400> SEQUENCE: 3

Glu Asn Asn Asn Glu
1 5

<210> SEQ ID NO 4
<211> LENGTH: 4
<212> TYPE: PRT
<213> ORGANISM: Artificial Sequence
<220> FEATURE:
<223> OTHER INFORMATION: component of appetite suppressant
<220> FEATURE:
<221> NAME/KEY: VARIANT
<222> LOCATION: (1)..(1)
<223> OTHER INFORMATION: residue is Glu substituted at its alpha-amino group, Gly substituted at its alpha-amino group, Ser, Asn, Gly, Glu or Tyr
<220> FEATURE:
<221> NAME/KEY: VARIANT
<222> LOCATION: (2)..(2)
<223> OTHER INFORMATION: residue is Glu substituted at its gamma-carboxylic acid group, Glu or Asn or Ser substituted at its alpha-amino group, Lys substituted at its epsilon amino group, Ser, Gly, Glu, Tyr, Pro, Asn or His
<220> FEATURE:
<221> NAME/KEY: VARIANT
<222> LOCATION: (3)..(3)
<223> OTHER INFORMATION: residue is Glu substituted at its gamma-carboxylic acid group, Glu substituted at its alpha-amino group, Lys substituted at its epsilon-amino group, Ser substituted at its alpha-amino group, Gly, Ser, Glu, Pro, His, Asn or Thr
<220> FEATURE:
<221> NAME/KEY: VARIANT
<222> LOCATION: (4)..(4)

<223> OTHER INFORMATION: residue is Lys substituted at its epsilon-amino group, Glu substituted at its gamma-carboxylic acid group, Gly substituted at its alpha-amino group, Gly, Ser, Pro, His, Thr, Tyr or Glu

<400> SEQUENCE: 4

Asn Asn Asn Glu
1

<210> SEQ ID NO 5
<211> LENGTH: 5
<212> TYPE: PRT
<213> ORGANISM: Artificial Sequence
<220> FEATURE:
<223> OTHER INFORMATION: component of appetite suppressant
<220> FEATURE:
<221> NAME/KEY: VARIANT
<222> LOCATION: (2)..(2)
<223> OTHER INFORMATION: Gly, Ser or Thr
<220> FEATURE:
<221> NAME/KEY: VARIANT
<222> LOCATION: (3)..(3)
<223> OTHER INFORMATION: Gly, Ser or Thr
<220> FEATURE:
<221> NAME/KEY: VARIANT
<222> LOCATION: (4)..(4)
<223> OTHER INFORMATION: Ser, Gly, Tyr, Thr or Asn
<220> FEATURE:
<221> NAME/KEY: VARIANT
<222> LOCATION: (5)..(5)
<223> OTHER INFORMATION: Gly, Glu, Lys, Asn or Gln

<400> SEQUENCE: 5

Gly Gly Gly Gly Asp
1 5

<210> SEQ ID NO 6
<211> LENGTH: 4
<212> TYPE: PRT
<213> ORGANISM: Artificial Sequence
<220> FEATURE:
<223> OTHER INFORMATION: component of appetite suppressant
<220> FEATURE:
<221> NAME/KEY: VARIANT
<222> LOCATION: (1)..(1)
<223> OTHER INFORMATION: Gly, Ser or Thr
<220> FEATURE:
<221> NAME/KEY: VARIANT
<222> LOCATION: (2)..(2)
<223> OTHER INFORMATION: Gly, Ser or Thr
<220> FEATURE:
<221> NAME/KEY: VARIANT
<222> LOCATION: (3)..(3)
<223> OTHER INFORMATION: Ser, Gly, Tyr, Thr or Asn
<220> FEATURE:
<221> NAME/KEY: VARIANT
<222> LOCATION: (4)..(4)
<223> OTHER INFORMATION: Gly, Glu, Lys, Asn or Gln

<400> SEQUENCE: 6

Gly Gly Gly Asp
1

<210> SEQ ID NO 7
<211> LENGTH: 4
<212> TYPE: PRT
<213> ORGANISM: Artificial Sequence
<220> FEATURE:
<223> OTHER INFORMATION: component of appetite suppressant
<220> FEATURE:
<221> NAME/KEY: MOD_RES
<222> LOCATION: (1)..(1)
<223> OTHER INFORMATION: gamma Glu residue with the peptide sequence Lys-Lys-Lys attached to its epsilon-amino group

<400> SEQUENCE: 7

Glu Gly Ser Gly
1

<210> SEQ ID NO 8
<211> LENGTH: 5
<212> TYPE: PRT
<213> ORGANISM: Artificial Sequence
<220> FEATURE:
<223> OTHER INFORMATION: component of appetite suppressant
<220> FEATURE:
<221> NAME/KEY: MOD_RES
<222> LOCATION: (1)..(1)
<223> OTHER INFORMATION: gamma Glu residue with an octadecanedioc acid moiety attached to its alpha-amino group

<400> SEQUENCE: 8

Glu Gly Ser Gly Ser
1 5

<210> SEQ ID NO 9
<211> LENGTH: 4
<212> TYPE: PRT
<213> ORGANISM: Artificial Sequence
<220> FEATURE:
<223> OTHER INFORMATION: component of appetite suppressant
<220> FEATURE:
<221> NAME/KEY: MOD_RES
<222> LOCATION: (1)..(1)
<223> OTHER INFORMATION: gamma Glu residue with an octadecanedioc acid moiety attached to its alpha-amino group

<400> SEQUENCE: 9

Glu Pro Thr Gly
1

<210> SEQ ID NO 10
<211> LENGTH: 5
<212> TYPE: PRT
<213> ORGANISM: Artificial Sequence
<220> FEATURE:
<223> OTHER INFORMATION: component of appetite suppressant
<220> FEATURE:
<221> NAME/KEY: MOD_RES
<222> LOCATION: (1)..(1)
<223> OTHER INFORMATION: gamma Glu residue with an octadecanedioc acid moiety attached to its alpha-amino group

<400> SEQUENCE: 10

Glu Gly Thr Gly Thr
1 5

<210> SEQ ID NO 11
<211> LENGTH: 5
<212> TYPE: PRT
<213> ORGANISM: Artificial Sequence
<220> FEATURE:
<223> OTHER INFORMATION: component of appetite suppressant
<220> FEATURE:
<221> NAME/KEY: MOD_RES
<222> LOCATION: (1)..(1)
<223> OTHER INFORMATION: gamma Glu residue with an octadecanedioc acid moiety attached to its alpha-amino group

<400> SEQUENCE: 11

Glu Ser Gly Gly Gly
1 5

<210> SEQ ID NO 12
<211> LENGTH: 5
<212> TYPE: PRT
<213> ORGANISM: Artificial Sequence
<220> FEATURE:
<223> OTHER INFORMATION: component of appetite suppressant
<220> FEATURE:
<221> NAME/KEY: MOD_RES
<222> LOCATION: (1)..(1)
<223> OTHER INFORMATION: gamma Glu residue with an octadecanedioc acid
      moiety attached to its alpha-amino group

<400> SEQUENCE: 12

```
Glu Gly Ser Gly Glu
1               5
```

<210> SEQ ID NO 13
<211> LENGTH: 5
<212> TYPE: PRT
<213> ORGANISM: Artificial Sequence
<220> FEATURE:
<223> OTHER INFORMATION: component of appetite suppressant
<220> FEATURE:
<221> NAME/KEY: MOD_RES
<222> LOCATION: (1)..(1)
<223> OTHER INFORMATION: gamma Glu residue with an octadecanedioc acid
      moiety attached to its alpha-amino group

<400> SEQUENCE: 13

```
Glu Gly Ser Gly Asp
1               5
```

<210> SEQ ID NO 14
<211> LENGTH: 4
<212> TYPE: PRT
<213> ORGANISM: Artificial Sequence
<220> FEATURE:
<223> OTHER INFORMATION: component of appetite suppressant
<220> FEATURE:
<221> NAME/KEY: MOD_RES
<222> LOCATION: (1)..(1)
<223> OTHER INFORMATION: Glu residue with an eicosanedioc acid moiety
      attached to its alpha-amino group

<400> SEQUENCE: 14

```
Glu Gly Ser Gly
1
```

<210> SEQ ID NO 15
<211> LENGTH: 4
<212> TYPE: PRT
<213> ORGANISM: Artificial Sequence
<220> FEATURE:
<223> OTHER INFORMATION: component of appetite suppressant
<220> FEATURE:
<221> NAME/KEY: MOD_RES
<222> LOCATION: (1)..(1)
<223> OTHER INFORMATION: gamma Glu residue with an octadecanedioc acid
      moiety attached to its alpha-amino group

<400> SEQUENCE: 15

```
Glu Ser Gly Thr
1
```

<210> SEQ ID NO 16
<211> LENGTH: 5
<212> TYPE: PRT
<213> ORGANISM: Artificial Sequence
<220> FEATURE:
<223> OTHER INFORMATION: component of appetite suppressant -continued
<220> FEATURE:
<221> NAME/KEY: MOD_RES
<222> LOCATION: (1)..(1)
<223> OTHER INFORMATION: gamma Glu residue with an eicosanedioc acid
      moiety attached to its alpha-amino group

<400> SEQUENCE: 16

Glu Gly Ser Ser Gly
1               5

<210> SEQ ID NO 17
<211> LENGTH: 5
<212> TYPE: PRT
<213> ORGANISM: Artificial Sequence
<220> FEATURE:
<223> OTHER INFORMATION: component of appetite suppressant
<220> FEATURE:
<221> NAME/KEY: MOD_RES
<222> LOCATION: (1)..(1)
<223> OTHER INFORMATION: gamma Glu residue with an octadecanedioc acid
      moiety attached to its alpha-amino group

<400> SEQUENCE: 17

Glu Thr Gly Ser Gly
1               5

<210> SEQ ID NO 18
<211> LENGTH: 4
<212> TYPE: PRT
<213> ORGANISM: Artificial Sequence
<220> FEATURE:
<223> OTHER INFORMATION: component of appetite suppressant
<220> FEATURE:
<221> NAME/KEY: MOD_RES
<222> LOCATION: (1)..(1)
<223> OTHER INFORMATION: gamma Glu residue with an eicosanedioc acid
      moiety attached to its alpha-amino group

<400> SEQUENCE: 18

Glu Thr Gly Thr
1

<210> SEQ ID NO 19
<211> LENGTH: 6
<212> TYPE: PRT
<213> ORGANISM: Artificial Sequence
<220> FEATURE:
<223> OTHER INFORMATION: component of appetite suppressant
<220> FEATURE:
<221> NAME/KEY: MOD_RES
<222> LOCATION: (1)..(1)
<223> OTHER INFORMATION: gamma Glu residue with an eicosanedioc acid
      moiety attached to its alpha-amino group

<400> SEQUENCE: 19

Glu Gly Ser Gly Ser Gly
1               5

<210> SEQ ID NO 20
<211> LENGTH: 4
<212> TYPE: PRT
<213> ORGANISM: Artificial Sequence
<220> FEATURE:
<223> OTHER INFORMATION: component of appetite suppressant
<220> FEATURE:
<221> NAME/KEY: MOD_RES
<222> LOCATION: (1)..(1)
<223> OTHER INFORMATION: Glu residue with an eicosanedioc acid moiety
      attached to its alpha amino group

<400> SEQUENCE: 20

```
Glu Ser Gly Thr
1


<210> SEQ ID NO 21
<211> LENGTH: 5
<212> TYPE: PRT
<213> ORGANISM: Artificial Sequence
<220> FEATURE:
<223> OTHER INFORMATION: component of appetite suppressant
<220> FEATURE:
<221> NAME/KEY: MOD_RES
<222> LOCATION: (1)..(1)
<223> OTHER INFORMATION: Glu residue with an octadecanedioc acid moiety
      attached to its alpha-amino group

<400> SEQUENCE: 21

Glu Gly Ser Gly Ser
1               5


<210> SEQ ID NO 22
<211> LENGTH: 36
<212> TYPE: PRT
<213> ORGANISM: Homo sapiens

<400> SEQUENCE: 22

Tyr Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg Gln Arg Tyr
        35


<210> SEQ ID NO 23
<211> LENGTH: 34
<212> TYPE: PRT
<213> ORGANISM: Homo sapiens

<400> SEQUENCE: 23

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr


<210> SEQ ID NO 24
<211> LENGTH: 36
<212> TYPE: PRT
<213> ORGANISM: Rattus norvegicus

<400> SEQUENCE: 24

Tyr Pro Ala Lys Pro Glu Ala Pro Gly Glu Asp Ala Ser Pro Glu Glu
1               5                   10                  15

Leu Ser Arg Tyr Tyr Ala Ser Leu Arg His Tyr Leu Asn Leu Val Thr
            20                  25                  30

Arg Gln Arg Tyr
        35


<210> SEQ ID NO 25
<211> LENGTH: 36
<212> TYPE: PRT
<213> ORGANISM: Mus musculus

<400> SEQUENCE: 25
```

```
Tyr Pro Ala Lys Pro Glu Ala Pro Gly Glu Asp Ala Ser Pro Glu Glu
1               5                   10                  15

Leu Ser Arg Tyr Tyr Ala Ser Leu Arg His Tyr Leu Asn Leu Val Thr
            20                  25                  30

Arg Gln Arg Tyr
        35


<210> SEQ ID NO 26
<211> LENGTH: 36
<212> TYPE: PRT
<213> ORGANISM: Sus scrofa

<400> SEQUENCE: 26

Tyr Pro Ala Lys Pro Glu Ala Pro Gly Glu Asp Ala Ser Pro Glu Glu
1               5                   10                  15

Leu Ser Arg Tyr Tyr Ala Ser Leu Arg His Tyr Leu Asn Leu Val Thr
            20                  25                  30

Arg Gln Arg Tyr
        35


<210> SEQ ID NO 27
<211> LENGTH: 36
<212> TYPE: PRT
<213> ORGANISM: Cavia porcellus

<400> SEQUENCE: 27

Tyr Pro Ser Lys Pro Glu Ala Pro Gly Ser Asp Ala Ser Pro Glu Glu
1               5                   10                  15

Leu Ala Arg Tyr Tyr Ala Ser Leu Arg His Tyr Leu Asn Leu Val Thr
            20                  25                  30

Arg Gln Arg Tyr
        35


<210> SEQ ID NO 28
<211> LENGTH: 36
<212> TYPE: PRT
<213> ORGANISM: Rana spp.

<400> SEQUENCE: 28

Tyr Pro Pro Lys Pro Glu Asn Pro Gly Glu Asp Ala Ser Pro Glu Glu
1               5                   10                  15

Met Thr Lys Tyr Leu Thr Ala Leu Arg His Tyr Ile Asn Leu Val Thr
            20                  25                  30

Arg Gln Arg Tyr
        35


<210> SEQ ID NO 29
<211> LENGTH: 36
<212> TYPE: PRT
<213> ORGANISM: Raja spp.

<400> SEQUENCE: 29

Tyr Pro Pro Lys Pro Glu Asn Pro Gly Asp Asp Ala Ala Pro Glu Glu
1               5                   10                  15

Leu Ala Lys Tyr Tyr Ser Ala Leu Arg His Tyr Ile Asn Leu Ile Thr
            20                  25                  30

Arg Gln Arg Tyr
        35
```

-continued

```
<210> SEQ ID NO 30
<211> LENGTH: 36
<212> TYPE: PRT
<213> ORGANISM: Greliorhinus starlaris

<400> SEQUENCE: 30

Tyr Pro Pro Lys Pro Glu Asn Pro Gly Glu Asp Ala Pro Pro Glu Glu
1               5                   10                  15

Leu Ala Lys Tyr Tyr Ser Ala Leu Arg His Tyr Ile Asn Leu Ile Thr
            20                  25                  30

Arg Gln Arg Tyr
        35


<210> SEQ ID NO 31
<211> LENGTH: 36
<212> TYPE: PRT
<213> ORGANISM: Lampetra spp.

<400> SEQUENCE: 31

Phe Pro Pro Lys Pro Asp Asn Pro Gly Asp Asn Ala Ser Pro Glu Gln
1               5                   10                  15

Met Ala Arg Tyr Lys Ala Ala Val Arg His Tyr Ile Asn Leu Ile Thr
            20                  25                  30

Arg Gln Arg Tyr
        35


<210> SEQ ID NO 32
<211> LENGTH: 36
<212> TYPE: PRT
<213> ORGANISM: Petromyzon spp.

<400> SEQUENCE: 32

Met Pro Pro Lys Pro Asp Asn Pro Ser Pro Asp Ala Ser Pro Glu Glu
1               5                   10                  15

Leu Ser Lys Tyr Met Leu Ala Val Arg Asn Tyr Ile Asn Leu Ile Thr
            20                  25                  30

Arg Gln Arg Tyr
        35


<210> SEQ ID NO 33
<211> LENGTH: 36
<212> TYPE: PRT
<213> ORGANISM: Canis familiaris

<400> SEQUENCE: 33

Tyr Pro Ala Lys Pro Glu Ala Pro Gly Glu Asp Ala Ser Pro Glu Glu
1               5                   10                  15

Leu Ser Arg Tyr Tyr Ala Ser Leu Arg His Tyr Leu Asn Leu Val Thr
            20                  25                  30

Arg Gln Arg Tyr
        35


<210> SEQ ID NO 34
<211> LENGTH: 36
<212> TYPE: PRT
<213> ORGANISM: Macaca mulatta

<400> SEQUENCE: 34

Tyr Pro Ile Lys Pro Glu Ala Pro Gly Glu Asp Ala Ser Pro Glu Glu
1               5                   10                  15

Leu Ser Arg Tyr Tyr Ala Ser Leu Arg His Tyr Leu Asn Leu Val Thr
```

```
            20                  25                  30

Arg Gln Arg Tyr
        35


<210> SEQ ID NO 35
<211> LENGTH: 36
<212> TYPE: PRT
<213> ORGANISM: Xenopus tropicalis

<400> SEQUENCE: 35

Tyr Pro Thr Lys Pro Glu Asn Pro Gly Asn Asp Ala Ser Pro Glu Glu
1               5                   10                  15

Met Ala Lys Tyr Leu Thr Ala Leu Arg His Tyr Ile Asn Leu Val Thr
            20                  25                  30

Arg Gln Arg Tyr
        35


<210> SEQ ID NO 36
<211> LENGTH: 36
<212> TYPE: PRT
<213> ORGANISM: Salmo salar

<400> SEQUENCE: 36

Tyr Pro Pro Lys Pro Glu Asn Pro Gly Glu Asp Ala Pro Pro Glu Glu
1               5                   10                  15

Leu Ala Lys Tyr Tyr Thr Ala Leu Arg His Tyr Ile Asn Leu Ile Thr
            20                  25                  30

Arg Gln Arg Tyr
        35


<210> SEQ ID NO 37
<211> LENGTH: 36
<212> TYPE: PRT
<213> ORGANISM: Bos Taurus

<400> SEQUENCE: 37

Tyr Pro Ala Lys Pro Gln Ala Pro Gly Glu His Ala Ser Pro Asp Glu
1               5                   10                  15

Leu Asn Arg Tyr Tyr Thr Ser Leu Arg His Tyr Leu Asn Leu Val Thr
            20                  25                  30

Arg Gln Arg Phe
        35


<210> SEQ ID NO 38
<211> LENGTH: 6
<212> TYPE: PRT
<213> ORGANISM: Artificial Sequence
<220> FEATURE:
<223> OTHER INFORMATION: component of appetite suppressant
<220> FEATURE:
<221> NAME/KEY: MOD_RES
<222> LOCATION: (1)..(1)
<223> OTHER INFORMATION: Glu substituted at its alpha amino group
<220> FEATURE:
<221> NAME/KEY: VARIANT
<222> LOCATION: (2)..(2)
<223> OTHER INFORMATION: Glu substituted at its alpha-amino group or Lys
      substituted at its epsilon-amino group
<220> FEATURE:
<221> NAME/KEY: VARIANT
<222> LOCATION: (3)..(3)
<223> OTHER INFORMATION: Glu substituted at its alpha-amino group or Gly
<220> FEATURE:
<221> NAME/KEY: VARIANT
<222> LOCATION: (4)..(4)
```

<223> OTHER INFORMATION: Ser or Pro
<220> FEATURE:
<221> NAME/KEY: VARIANT
<222> LOCATION: (5)..(5)
<223> OTHER INFORMATION: Lys substituted at its epsilon-amino group, Gly or Pro
<220> FEATURE:
<221> NAME/KEY: VARIANT
<222> LOCATION: (6)..(6)
<223> OTHER INFORMATION: Lys substituted at its epsilon-amino group, Glu substituted at its gamma-carboxylic acid group, Ser, Pro or Thr

<400> SEQUENCE: 38

Glu Glu Gly Pro Gly Glu
1 5

<210> SEQ ID NO 39
<211> LENGTH: 5
<212> TYPE: PRT
<213> ORGANISM: Artificial sequence
<220> FEATURE:
<223> OTHER INFORMATION: component of appetite suppressant
<220> FEATURE:
<221> NAME/KEY: VARIANT
<222> LOCATION: (1)..(1)
<223> OTHER INFORMATION: Glu substituted at its alpha-amino group or Lys substituted at its epsilon-amino group
<220> FEATURE:
<221> NAME/KEY: VARIANT
<222> LOCATION: (2)..(2)
<223> OTHER INFORMATION: Glu substituted at its alpha-amino group or Gly
<220> FEATURE:
<221> NAME/KEY: VARIANT
<222> LOCATION: (3)..(3)
<223> OTHER INFORMATION: Ser or Pro
<220> FEATURE:
<221> NAME/KEY: VARIANT
<222> LOCATION: (4)..(4)
<223> OTHER INFORMATION: Lys substituted at its epsilon-amino group, Gly or Pro
<220> FEATURE:
<221> NAME/KEY: VARIANT
<222> LOCATION: (5)..(5)
<223> OTHER INFORMATION: Lys substituted at its epsilon-amino group, Glu substituted at its gamma-carboxylic acid group, Ser, Pro or Thr

<400> SEQUENCE: 39

Glu Gly Pro Gly Glu
1 5

<210> SEQ ID NO 40
<211> LENGTH: 4
<212> TYPE: PRT
<213> ORGANISM: Artificial sequence
<220> FEATURE:
<223> OTHER INFORMATION: component of appetite suppressant
<220> FEATURE:
<221> NAME/KEY: VARIANT
<222> LOCATION: (1)..(1)
<223> OTHER INFORMATION: Glu substituted at its alpha-amino group or Gly
<220> FEATURE:
<221> NAME/KEY: VARIANT
<222> LOCATION: (2)..(2)
<223> OTHER INFORMATION: Ser or Pro
<220> FEATURE:
<221> NAME/KEY: VARIANT
<222> LOCATION: (3)..(3)
<223> OTHER INFORMATION: Lys substituted at its epsilon-amino group, Gly or Pro
<220> FEATURE:
<221> NAME/KEY: VARIANT
<222> LOCATION: (4)..(4)
<223> OTHER INFORMATION: Lys substituted at its epsilon-amino group, Glu substituted at its gamma-carboxylic acid group, Ser, Pro or Thr

<400> SEQUENCE: 40

Gly Pro Gly Glu
1

<210> SEQ ID NO 41
<211> LENGTH: 5
<212> TYPE: PRT
<213> ORGANISM: Artificial sequence
<220> FEATURE:
<223> OTHER INFORMATION: component of appetite suppressant

<400> SEQUENCE: 41

Gly Ser Gly Ser Gly
1 5

<210> SEQ ID NO 42
<211> LENGTH: 4
<212> TYPE: PRT
<213> ORGANISM: Artificial sequence
<220> FEATURE:
<223> OTHER INFORMATION: component of appetite suppressant
<220> FEATURE:
<221> NAME/KEY: VARIANT
<222> LOCATION: (1)..(1)
<223> OTHER INFORMATION: Gly, Ser or Thr
<220> FEATURE:
<221> NAME/KEY: VARIANT
<222> LOCATION: (2)..(2)
<223> OTHER INFORMATION: Ser, Thr or Gly
<220> FEATURE:
<221> NAME/KEY: VARIANT
<222> LOCATION: (3)..(3)
<223> OTHER INFORMATION: Gly or Ser
<220> FEATURE:
<221> NAME/KEY: VARIANT
<222> LOCATION: (4)..(4)
<223> OTHER INFORMATION: Ser, Thr, Gly or Asp

<400> SEQUENCE: 42

Gly Gly Gly Asp
1

<210> SEQ ID NO 43
<211> LENGTH: 5
<212> TYPE: PRT
<213> ORGANISM: Artificial sequence
<220> FEATURE:
<223> OTHER INFORMATION: component of appetite suppressant
<220> FEATURE:
<221> NAME/KEY: VARIANT
<222> LOCATION: (1)..(1)
<223> OTHER INFORMATION: Pro or Cys
<220> FEATURE:
<221> NAME/KEY: VARIANT
<222> LOCATION: (2)..(2)
<223> OTHER INFORMATION: Lys substituted at its epsilon-amino group or Ile
<220> FEATURE:
<221> NAME/KEY: VARIANT
<222> LOCATION: (3)..(3)
<223> OTHER INFORMATION: Lys substituted at its epsilon-amino group or Lys
<220> FEATURE:
<221> NAME/KEY: VARIANT
<222> LOCATION: (4)..(4)
<223> OTHER INFORMATION: Pro or Cys
<220> FEATURE:
<221> NAME/KEY: VARIANT
<222> LOCATION: (5)..(5)
<223> OTHER INFORMATION: Glu substituted at its gamma carboxylic acid group, Lys substituted at its epsilon-amino group or Glu

<400> SEQUENCE: 43

Cys Ile Lys Cys Glu
1 5

<210> SEQ ID NO 44
<211> LENGTH: 5
<212> TYPE: PRT
<213> ORGANISM: Artificial sequence
<220> FEATURE:
<223> OTHER INFORMATION: component of appetite suppressant

<400> SEQUENCE: 44

Pro Ile Lys Pro Glu
1 5

<210> SEQ ID NO 45
<211> LENGTH: 5
<212> TYPE: PRT
<213> ORGANISM: Artificial sequence
<220> FEATURE:
<223> OTHER INFORMATION: component of appetite suppressant
<220> FEATURE:
<221> NAME/KEY: VARIANT
<222> LOCATION: (1)..(1)
<223> OTHER INFORMATION: Lys substituted at its epsilon-amino group or Ala
<220> FEATURE:
<221> NAME/KEY: VARIANT
<222> LOCATION: (2)..(2)
<223> OTHER INFORMATION: Lys substituted at its epsilon -amino group or Ser
<220> FEATURE:
<221> NAME/KEY: VARIANT
<222> LOCATION: (3)..(3)
<223> OTHER INFORMATION: Lys substituted at its epsilon-amino group or Pro
<220> FEATURE:
<221> NAME/KEY: VARIANT
<222> LOCATION: (4)..(4)
<223> OTHER INFORMATION: Lys substituted at its epsilon-amino group or Glu
<220> FEATURE:
<221> NAME/KEY: VARIANT
<222> LOCATION: (5)..(5)
<223> OTHER INFORMATION: Lys substituted at its epsilon-amino group or Glu

<400> SEQUENCE: 45

Ala Lys Lys Lys Glu
1 5

<210> SEQ ID NO 46
<211> LENGTH: 5
<212> TYPE: PRT
<213> ORGANISM: Artificial sequence
<220> FEATURE:
<223> OTHER INFORMATION: component of appetite suppressant

<400> SEQUENCE: 46

Ala Ser Pro Glu Glu
1 5

<210> SEQ ID NO 47
<211> LENGTH: 37
<212> TYPE: PRT
<213> ORGANISM: Artificial Sequence
<220> FEATURE:
<223> OTHER INFORMATION: component of appetite suppressant
<220> FEATURE:
<221> NAME/KEY: MOD_RES
<222> LOCATION: (1)..(1)
<223> OTHER INFORMATION: Lys residue with a hexadecanedioc acid moiety attached to its epsilon-amino group
<220> FEATURE:
<221> NAME/KEY: MOD_RES
<222> LOCATION: (37)..(37)
<223> OTHER INFORMATION: AMIDATION

<400> SEQUENCE: 47

Lys Gly Pro Ile Lys Pro Glu Ala Pro Gly Glu Gly Ala Ser Pro Glu
1 5 10 15

Glu Leu Leu His Tyr Tyr Ala Ala Leu Arg His Phe Leu Asn His Val
20 25 30

Thr Arg Gln Arg Tyr
35

<210> SEQ ID NO 48
<211> LENGTH: 36
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (1)..(1)
<223> OTHER INFORMATION: Lys residue with a hexadecanedioc acid moiety attached to its epsilon-amino group
<220> FEATURE:
<221> NAME/KEY: MOD_RES
<222> LOCATION: (36)..(36)
<223> OTHER INFORMATION: AMIDATION

<400> SEQUENCE: 48

Lys Pro Ile Lys Pro Glu Ala Pro Gly Glu Gly Ala Ser Pro Glu Glu
1 5 10 15

Leu Leu His Tyr Tyr Ala Ala Leu Arg His Phe Leu Asn His Val Thr
20 25 30

Arg Gln Arg Tyr
35

<210> SEQ ID NO 49
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (5)..(5)
<223> OTHER INFORMATION: Lys residue with a hexadecanedioc acid moiety attached to its epsilon-amino group
<220> FEATURE:
<221> NAME/KEY: MOD_RES
<222> LOCATION: (35)..(35)
<223> OTHER INFORMATION: AMIDATION

<400> SEQUENCE: 49

Pro Ile Lys Pro Lys Ala Pro Gly Glu Gly Ala Ser Pro Glu Glu Leu
1 5 10 15

Leu His Tyr Tyr Ala Ala Leu Arg His Phe Leu Asn His Val Thr Arg
20 25 30

Gln Arg Tyr
35

<210> SEQ ID NO 50
<211> LENGTH: 35
<212> TYPE: PRT
<213> ORGANISM: Artificial sequence
<220> FEATURE:

<223> OTHER INFORMATION: component of appetite suppressant
<220> FEATURE:
<221> NAME/KEY: MOD_RES
<222> LOCATION: (6)..(6)
<223> OTHER INFORMATION: Lys residue with a hexadecanedioc acid moiety
attached to its epsilon-amino group
<220> FEATURE:
<221> NAME/KEY: MOD_RES
<222> LOCATION: (35)..(35)
<223> OTHER INFORMATION: AMIDATION

<400> SEQUENCE: 50

```
Pro Ile Lys Pro Glu Lys Pro Gly Glu Gly Ala Ser Pro Glu Glu Leu
1               5                   10                  15

Leu His Tyr Tyr Ala Ala Leu Arg His Phe Leu Asn His Val Thr Arg
            20                  25                  30

Gln Arg Tyr
        35
```

<210> SEQ ID NO 51
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (9)..(9)
<223> OTHER INFORMATION: Lys residue with a hexadecanedioc acid moiety
attached to its epsilon-amino group
<220> FEATURE:
<221> NAME/KEY: MOD_RES
<222> LOCATION: (35)..(35)
<223> OTHER INFORMATION: AMIDATION

<400> SEQUENCE: 51

```
Pro Ile Lys Pro Glu Ala Pro Gly Lys Gly Ala Ser Pro Glu Glu Leu
1               5                   10                  15

Leu His Tyr Tyr Ala Ala Leu Arg His Phe Leu Asn His Val Thr Arg
            20                  25                  30

Gln Arg Tyr
        35
```

<210> SEQ ID NO 52
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (10)..(10)
<223> OTHER INFORMATION: Lys residue with a hexadecanedioc acid moiety
attached to its epsilon-amino group
<220> FEATURE:
<221> NAME/KEY: MOD_RES
<222> LOCATION: (35)..(35)
<223> OTHER INFORMATION: AMIDATION

<400> SEQUENCE: 52

```
Pro Ile Lys Pro Glu Ala Pro Gly Glu Lys Ala Ser Pro Glu Glu Leu
1               5                   10                  15

Leu His Tyr Tyr Ala Ala Leu Arg His Phe Leu Asn His Val Thr Arg
            20                  25                  30

Gln Arg Tyr
        35
```

<210> SEQ ID NO 53
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (17)..(17)
<223> OTHER INFORMATION: Lys residue with a hexadecanedioc acid moiety attached to its epsilon-amino group
<220> FEATURE:
<221> NAME/KEY: MOD_RES
<222> LOCATION: (35)..(35)
<223> OTHER INFORMATION: AMIDATION

<400> SEQUENCE: 53

```
Pro Ile Lys Pro Glu Ala Pro Gly Glu Gly Ala Ser Pro Glu Glu Leu
1               5                   10                  15

Lys His Tyr Tyr Ala Ala Leu Arg His Phe Leu Asn His Val Thr Arg
            20                  25                  30

Gln Arg Tyr
        35
```

<210> SEQ ID NO 54
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (18)..(18)
<223> OTHER INFORMATION: Lys residue with a hexadecanedioc acid moiety attached to its epsilon-amino group
<220> FEATURE:
<221> NAME/KEY: MOD_RES
<222> LOCATION: (35)..(35)
<223> OTHER INFORMATION: AMIDATION

<400> SEQUENCE: 54

```
Pro Ile Lys Pro Glu Ala Pro Gly Glu Gly Ala Ser Pro Glu Glu Leu
1               5                   10                  15

Leu Lys Tyr Tyr Ala Ala Leu Arg His Phe Leu Asn His Val Thr Arg
            20                  25                  30

Gln Arg Tyr
        35
```

<210> SEQ ID NO 55
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (21)..(21)
<223> OTHER INFORMATION: Lys residue with a hexadecanedioc acid moiety attached to its epsilon-amino group
<220> FEATURE:
<221> NAME/KEY: MOD_RES
<222> LOCATION: (35)..(35)
<223> OTHER INFORMATION: AMIDATION

<400> SEQUENCE: 55

```
Pro Ile Lys Pro Glu Ala Pro Gly Glu Gly Ala Ser Pro Glu Glu Leu
1               5                   10                  15

Leu His Tyr Tyr Lys Ala Leu Arg His Phe Leu Asn His Val Thr Arg
            20                  25                  30
```

```
Gln Arg Tyr
        35


<210> SEQ ID NO 56
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (22)..(22)
<223> OTHER INFORMATION: Lys residue with a hexadecanedioc acid moiety
      attached to its epsilon-amino group
<220> FEATURE:
<221> NAME/KEY: MOD_RES
<222> LOCATION: (35)..(35)
<223> OTHER INFORMATION: AMIDATION

<400> SEQUENCE: 56

Pro Ile Lys Pro Glu Ala Pro Gly Glu Gly Ala Ser Pro Glu Glu Leu
1               5                   10                  15

Leu His Tyr Tyr Ala Lys Leu Arg His Phe Leu Asn His Val Thr Arg
            20                  25                  30

Gln Arg Tyr
        35


<210> SEQ ID NO 57
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (24)..(24)
<223> OTHER INFORMATION: Lys residue with a hexadecanedioc acid moiety
      attached to its epsilon-amino group
<220> FEATURE:
<221> NAME/KEY: MOD_RES
<222> LOCATION: (35)..(35)
<223> OTHER INFORMATION: AMIDATION

<400> SEQUENCE: 57

Pro Ile Lys Pro Glu Ala Pro Gly Glu Gly Ala Ser Pro Glu Glu Leu
1               5                   10                  15

Leu His Tyr Tyr Ala Ala Leu Lys His Phe Leu Asn His Val Thr Arg
            20                  25                  30

Gln Arg Tyr
        35


<210> SEQ ID NO 58
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (25)..(25)
<223> OTHER INFORMATION: Lys residue with a hexadecanedioc acid moiety
      attached to its epsilon-amino group
<220> FEATURE:
<221> NAME/KEY: MOD_RES
<222> LOCATION: (35)..(35)
<223> OTHER INFORMATION: AMIDATION

<400> SEQUENCE: 58
```

-continued

```
Pro Ile Lys Pro Glu Ala Pro Gly Glu Gly Ala Ser Pro Glu Glu Leu
1               5                   10                  15

Leu His Tyr Tyr Ala Ala Leu Arg Lys Phe Leu Asn His Val Thr Arg
            20                  25                  30

Gln Arg Tyr
        35


<210> SEQ ID NO 59
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (26)..(26)
<223> OTHER INFORMATION: Lys residue with a hexadecanedioc acid moiety
      attached to its epsilon-amino group
<220> FEATURE:
<221> NAME/KEY: MOD_RES
<222> LOCATION: (35)..(35)
<223> OTHER INFORMATION: AMIDATION

<400> SEQUENCE: 59

Pro Ile Lys Pro Glu Ala Pro Gly Glu Gly Ala Ser Pro Glu Glu Leu
1               5                   10                  15

Leu His Tyr Tyr Ala Ala Leu Arg His Lys Leu Asn His Val Thr Arg
            20                  25                  30

Gln Arg Tyr
        35


<210> SEQ ID NO 60
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (29)..(29)
<223> OTHER INFORMATION: Lys residue with a hexadecanedioc acid moiety
      attached to its epsilon-amino group
<220> FEATURE:
<221> NAME/KEY: MOD_RES
<222> LOCATION: (35)..(35)
<223> OTHER INFORMATION: AMIDATION

<400> SEQUENCE: 60

Pro Ile Lys Pro Glu Ala Pro Gly Glu Gly Ala Ser Pro Glu Glu Leu
1               5                   10                  15

Leu His Tyr Tyr Ala Ala Leu Arg His Phe Leu Asn Lys Val Thr Arg
            20                  25                  30

Gln Arg Tyr
        35


<210> SEQ ID NO 61
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (29)..(29)
<223> OTHER INFORMATION: Lys residue with the C terminus of peptide
      sequence gamma Glu*-Gly-Ser-Gly attached to its epsilon-amino
      group, wherein gamma Glu* is a gamma Glu residue with an
      octadecanedioc acid moiety attached to its alpha-amino group
```

<220> FEATURE:
<221> NAME/KEY: MOD_RES
<222> LOCATION: (35)..(35)
<223> OTHER INFORMATION: AMIDATION

<400> SEQUENCE: 61

```
Pro Ile Lys Pro Glu Ala Pro Gly Glu Gly Ala Ser Pro Glu Glu Leu
1               5                   10                  15

Leu His Tyr Tyr Ala Ala Leu Arg His Phe Leu Asn Lys Val Thr Arg
            20                  25                  30

Gln Arg Tyr
        35
```

<210> SEQ ID NO 62
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (6)..(6)
<223> OTHER INFORMATION: Lys residue with the C terminus of peptide sequence Glu*-Gly-Ser-Gly attached to its epsilon-amino group, wherein Glu* is a Glu residue with an octadecanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 62

```
Pro Ile Lys Pro Glu Lys Pro Gly Glu Gly Ala Ser Pro Glu Glu Leu
1               5                   10                  15

Leu His Tyr Tyr Ala Ala Leu Arg His Phe Leu Asn His Val Thr Arg
            20                  25                  30

Gln Arg Tyr
        35
```

<210> SEQ ID NO 63
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (6)..(6)
<223> OTHER INFORMATION: Lys residue with the C terminus of peptide sequence gamma Glu*-Gly-Ser-Gly attached to its epsilon-amino group, wherein gamma Glu* is a gamma Glu residue with an octadecanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 63

```
Pro Ile Lys Pro Glu Lys Pro Gly Glu Gly Ala Ser Pro Glu Glu Leu
1               5                   10                  15

Leu His Tyr Tyr Ala Ala Leu Arg His Phe Leu Asn His Val Thr Arg
            20                  25                  30

Gln Arg Tyr
        35
```

<210> SEQ ID NO 64
<211> LENGTH: 35

<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (6)..(6)
<223> OTHER INFORMATION: Lys residue with the C terminus of peptide sequence gamma Glu*-Gly-Ser-Gly-Ser attached to its epsilon-amino group, wherein gamma Glu* is a gamma Glu residue with an octadecanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 64

```
Pro Ile Lys Pro Glu Lys Pro Gly Glu Gly Ala Ser Pro Glu Glu Leu
1               5                   10                  15

Leu His Tyr Tyr Ala Ala Leu Arg His Phe Leu Asn His Val Thr Arg
            20                  25                  30

Gln Arg Tyr
        35
```

<210> SEQ ID NO 65
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (6)..(6)
<223> OTHER INFORMATION: Lys residue with the C terminus of peptide sequence gamma Glu*-Pro-Thr-Gly attached to its epsilon-amino group, wherein gamma Glu* is a gamma Glu residue with an octadecanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 65

```
Pro Ile Lys Pro Glu Lys Pro Gly Glu Gly Ala Ser Pro Glu Glu Leu
1               5                   10                  15

Leu His Tyr Tyr Ala Ala Leu Arg His Phe Leu Asn His Val Thr Arg
            20                  25                  30

Gln Arg Tyr
        35
```

<210> SEQ ID NO 66
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (6)..(6)
<223> OTHER INFORMATION: Lys residue with the C terminus of peptide sequence Ser*-Gly attached to its epsilon-amino group, wherein Ser* is a Ser residue with an octadecanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 66

```
Pro Ile Lys Pro Glu Lys Pro Gly Glu Gly Ala Ser Pro Glu Glu Ile
```

```
1               5                   10                  15

Leu Lys Tyr Tyr Ile Glu Leu Arg His Phe Leu Asn His Leu Thr Arg
            20                  25                  30

Gln Arg Tyr
        35


<210> SEQ ID NO 67
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (6)..(6)
<223> OTHER INFORMATION: Lys residue with the C terminus of peptide
      sequence gamma Glu*-Gly-Ser-Gly attached to its epsilon-amino
      group, wherein gamma Glu* is a gamma Glu residue with an
      octadecanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 67

Pro Ile Lys Pro Glu Lys Pro Gly Glu Gly Ala Ser Pro Glu Glu Ile
1               5                   10                  15

Leu Lys Tyr Tyr Ile Glu Leu Arg His Phe Leu Asn His Leu Thr Arg
            20                  25                  30

Gln Arg Tyr
        35


<210> SEQ ID NO 68
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (6)..(6)
<223> OTHER INFORMATION: Lys residue with the C terminus of peptide
      sequence gamma Glu*-Gly-Ser-Gly-Ser attached to its epsilon-amino
      group, wherein gamma Glu* is a gamma Glu residue with an
      octadecanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 68

Pro Ile Lys Pro Glu Lys Pro Gly Glu Gly Ala Ser Pro Glu Glu Ile
1               5                   10                  15

Leu Lys Tyr Tyr Ile Glu Leu Arg His Phe Leu Asn His Leu Thr Arg
            20                  25                  30

Gln Arg Tyr
        35


<210> SEQ ID NO 69
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (6)..(6)
<223> OTHER INFORMATION: Lys residue with the C terminus of peptide
```

```
      sequence gamma Glu*-Gly-Thr-Gly-Thr attached to its epsilon-amino
      group, wherein gamma Glu* is a gamma Glu residue with an
      octadecanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 69

Pro Ile Lys Pro Glu Lys Pro Gly Glu Gly Ala Ser Pro Glu Glu Ile
1               5                   10                  15

Leu Lys Tyr Tyr Ile Glu Leu Arg His Phe Leu Asn His Leu Thr Arg
            20                  25                  30

Gln Arg Tyr
        35


<210> SEQ ID NO 70
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (6)..(6)
<223> OTHER INFORMATION: Lys residue with the C terminus of peptide
      sequence gamma Glu*-Gly-Thr attached to its epsilon-amino group,
      wherein gamma Glu* is a gamma Glu residue with an octadecanedioc
      acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 70

Pro Ile Lys Pro Glu Lys Pro Gly Glu Gly Ala Ser Pro Glu Glu Ile
1               5                   10                  15

Leu Lys Tyr Tyr Ile Glu Leu Arg His Phe Leu Asn His Leu Thr Arg
            20                  25                  30

Gln Arg Tyr
        35


<210> SEQ ID NO 71
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (6)..(6)
<223> OTHER INFORMATION: Lys residue with the C terminus of peptide
      sequence gamma Glu*-Tyr-Gly attached to its epsilon-amino group,
      wherein gamma Glu* is a gamma Glu residue with an octadecanedioc
      acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 71

Pro Ile Lys Pro Glu Lys Pro Gly Glu Gly Ala Ser Pro Glu Glu Ile
1               5                   10                  15

Leu Lys Tyr Tyr Ile Glu Leu Arg His Phe Leu Asn His Leu Thr Arg
            20                  25                  30

Gln Arg Tyr
        35
```

```
<210> SEQ ID NO 72
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (6)..(6)
<223> OTHER INFORMATION: Lys residue with the C terminus of peptide
      sequence gamma Glu*-Trp-Gly attached to its epsilon-amino group,
      wherein gamma Glu* is a gamma Glu residue with an octadecanedioc
      acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 72

Pro Ile Lys Pro Glu Lys Pro Gly Glu Gly Ala Ser Pro Glu Glu Ile
1               5                   10                  15

Leu Lys Tyr Tyr Ile Glu Leu Arg His Phe Leu Asn His Leu Thr Arg
            20                  25                  30

Gln Arg Tyr
        35


<210> SEQ ID NO 73
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (6)..(6)
<223> OTHER INFORMATION: Lys residue with the C terminus of peptide
      sequence gamma Glu*-Ser-Gly-Gly-Gly attached to its epsilon-amino
      group, wherein gamma Glu* is a gamma Glu residue with an
      octadecanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 73

Pro Ile Lys Pro Glu Lys Pro Gly Glu Gly Ala Ser Pro Glu Glu Ile
1               5                   10                  15

Leu Lys Tyr Tyr Ile Glu Leu Arg His Phe Leu Asn His Leu Thr Arg
            20                  25                  30

Gln Arg Tyr
        35


<210> SEQ ID NO 74
<211> LENGTH: 37
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (1)..(1)
<223> OTHER INFORMATION: Lys residue with the C terminus of peptide
      sequence gamma Glu*-Gly-Ser-Gly attached to its epsilon-amino
      group, wherein gamma Glu* is a gamma Glu residue with an
       octadecanedioc acid moiety attached to its alpha-amino group
<220> FEATURE:
<221> NAME/KEY: MOD_RES
<222> LOCATION: (37)..(37)
<223> OTHER INFORMATION: AMIDATION
```

<400> SEQUENCE: 74

Lys Gly Pro Ile Lys Pro Glu Ala Pro Gly Glu Gly Ala Ser Pro Glu
1 5 10 15

Glu Leu Leu His Tyr Tyr Ala Ala Leu Arg His Phe Leu Asn His Val
20 25 30

Thr Arg Gln Arg Tyr
35

<210> SEQ ID NO 75
<211> LENGTH: 36
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (1)..(1)
<223> OTHER INFORMATION: Lys residue with the C terminus of peptide sequence gamma Glu*-Gly-Ser-Gly attached to its epsilon-amino group, wherein gamma Glu* is a gamma Glu residue with an octadecanedioc acid moiety attached to its alpha-amino group
<220> FEATURE:
<221> NAME/KEY: MOD_RES
<222> LOCATION: (36)..(36)
<223> OTHER INFORMATION: AMIDATION

<400> SEQUENCE: 75

Lys Pro Ile Lys Pro Glu Ala Pro Gly Glu Gly Ala Ser Pro Glu Glu
1 5 10 15

Leu Leu His Tyr Tyr Ala Ala Leu Arg His Phe Leu Asn His Val Thr
20 25 30

Arg Gln Arg Tyr
35

<210> SEQ ID NO 76
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (5)..(5)
<223> OTHER INFORMATION: Lys residue with the C terminus of peptide sequence gamma Glu*-Gly-Ser-Gly attached to its epsilon-amino group, wherein gamma Glu* is a gamma Glu residue with an octadecanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 76

Pro Ile Lys Pro Lys Ala Pro Gly Glu Gly Ala Ser Pro Glu Glu Leu
1 5 10 15

Leu His Tyr Tyr Ala Ala Leu Arg His Phe Leu Asn His Val Thr Arg
20 25 30

Gln Arg Tyr
35

<210> SEQ ID NO 77
<211> LENGTH: 35
<212> TYPE: PRT
<213> ORGANISM: Artificial sequence
<220> FEATURE:
<223> OTHER INFORMATION: component of appetite suppressant
<220> FEATURE:

<221> NAME/KEY: MOD_RES
<222> LOCATION: (9)..(9)
<223> OTHER INFORMATION: Lys residue with the C terminus of peptide
      sequence gamma Glu*-Gly-Ser-Gly attached to its epsilon-amino
      group, wherein gamma Glu* is a gamma Glu residue with an
      octadecanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 77

Pro Ile Lys Pro Glu Ala Pro Gly Lys Gly Ala Ser Pro Glu Glu Leu
1               5                   10                  15

Leu His Tyr Tyr Ala Ala Leu Arg His Phe Leu Asn His Val Thr Arg
            20                  25                  30

Gln Arg Tyr
        35

<210> SEQ ID NO 78
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (10)..(10)
<223> OTHER INFORMATION: Lys residue with the C terminus of peptide
      sequence gamma Glu*-Gly-Ser-Gly attached to its epsilon-amino
      group, wherein gamma Glu* is a gamma Glu residue with an
      octadecanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 78

Pro Ile Lys Pro Glu Ala Pro Gly Glu Lys Ala Ser Pro Glu Glu Leu
1               5                   10                  15

Leu His Tyr Tyr Ala Ala Leu Arg His Phe Leu Asn His Val Thr Arg
            20                  25                  30

Gln Arg Tyr
        35

<210> SEQ ID NO 79
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (17)..(17)
<223> OTHER INFORMATION: Lys residue with the C terminus of peptide
      sequence gamma Glu*-Gly-Ser-Gly attached to its epsilon-amino
      group, wherein gamma Glu* is a gamma Glu residue with an
      octadecanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 79

Pro Ile Lys Pro Glu Ala Pro Gly Glu Gly Ala Ser Pro Glu Glu Leu
1               5                   10                  15

Lys His Tyr Tyr Ala Ala Leu Arg His Phe Leu Asn His Val Thr Arg
            20                  25                  30

Gln Arg Tyr
35

<210> SEQ ID NO 80
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (18)..(18)
<223> OTHER INFORMATION: Lys residue with the C terminus of peptide sequence gamma Glu*-Gly-Ser-Gly attached to its epsilon-amino group, wherein gamma Glu* is a gamma Glu residue with an octadecanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 80

Pro Ile Lys Pro Glu Ala Pro Gly Glu Gly Ala Ser Pro Glu Glu Leu
1 5 10 15

Leu Lys Tyr Tyr Ala Ala Leu Arg His Phe Leu Asn His Val Thr Arg
20 25 30

Gln Arg Tyr
35

<210> SEQ ID NO 81
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (21)..(21)
<223> OTHER INFORMATION: Lys residue with the C terminus of peptide sequence gamma Glu*-Gly-Ser-Gly attached to its epsilon-amino group, wherein gamma Glu* is a gamma Glu residue with an octadecanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 81

Pro Ile Lys Pro Glu Ala Pro Gly Glu Gly Ala Ser Pro Glu Glu Leu
1 5 10 15

Leu His Tyr Tyr Lys Ala Leu Arg His Phe Leu Asn His Val Thr Arg
20 25 30

Gln Arg Tyr
35

<210> SEQ ID NO 82
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (22)..(22)
<223> OTHER INFORMATION: Lys residue with the C terminus of peptide sequence gamma Glu*-Gly-Ser-Gly attached to its epsilon-amino group, wherein gamma Glu* is a gamma Glu residue with an octadecanedioc acid moiety attached to its alpha-amino group
<220> FEATURE:
<221> NAME/KEY: MOD_RES -continued

<222> LOCATION: (35)..(35)
<223> OTHER INFORMATION: AMIDATION

<400> SEQUENCE: 82

Pro Ile Lys Pro Glu Ala Pro Gly Glu Gly Ala Ser Pro Glu Glu Leu
1 5 10 15

Leu His Tyr Tyr Ala Lys Leu Arg His Phe Leu Asn His Val Thr Arg
20 25 30

Gln Arg Tyr
35

<210> SEQ ID NO 83
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (24)..(24)
<223> OTHER INFORMATION: Lys residue with the C terminus of peptide sequence gamma Glu*-Gly-Ser-Gly attached to its epsilon-amino group, wherein gamma Glu* is a gamma Glu residue with an octadecanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 83

Pro Ile Lys Pro Glu Ala Pro Gly Glu Gly Ala Ser Pro Glu Glu Leu
1 5 10 15

Leu His Tyr Tyr Ala Ala Leu Lys His Phe Leu Asn His Val Thr Arg
20 25 30

Gln Arg Tyr
35

<210> SEQ ID NO 84
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (25)..(25)
<223> OTHER INFORMATION: Lys residue with the C terminus of peptide sequence gamma Glu*-Gly-Ser-Gly attached to its epsilon-amino group, wherein gamma Glu* is a gamma Glu residue with an octadecanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 84

Pro Ile Lys Pro Glu Ala Pro Gly Glu Gly Ala Ser Pro Glu Glu Leu
1 5 10 15

Leu His Tyr Tyr Ala Ala Leu Arg Lys Phe Leu Asn His Val Thr Arg
20 25 30

Gln Arg Tyr
35

<210> SEQ ID NO 85
<211> LENGTH: 35
<212> TYPE: PRT
<213> ORGANISM: Artificial sequence -continued
<220> FEATURE:
<223> OTHER INFORMATION: component of appetite suppressant
<220> FEATURE:
<221> NAME/KEY: MOD_RES
<222> LOCATION: (26)..(26)
<223> OTHER INFORMATION: Lys residue with the C terminus of peptide sequence gamma Glu*-Gly-Ser-Gly attached to its epsilon-amino group, wherein gamma Glu* is a gamma Glu residue with an octadecanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 85

```
Pro Ile Lys Pro Glu Ala Pro Gly Glu Gly Ala Ser Pro Glu Glu Leu
1               5                   10                  15

Leu His Tyr Tyr Ala Ala Leu Arg His Lys Leu Asn His Val Thr Arg
            20                  25                  30

Gln Arg Tyr
        35
```

<210> SEQ ID NO 86
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (29)..(29)
<223> OTHER INFORMATION: Lys residue with the C terminus of peptide sequence gamma Glu*-Gly-Ser-Gly attached to its epsilon-amino group, wherein gamma Glu* is a gamma Glu residue with an octadecanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 86

```
Pro Ile Lys Pro Glu Ala Pro Gly Glu Gly Ala Ser Pro Glu Glu Leu
1               5                   10                  15

Leu His Tyr Tyr Ala Ala Leu Arg His Phe Leu Asn Lys Val Thr Arg
            20                  25                  30

Gln Arg Tyr
        35
```

<210> SEQ ID NO 87
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (5)..(5)
<223> OTHER INFORMATION: Lys residue with the C terminus of peptide sequence gamma Glu*-Gly-Ser-Gly-Glu attached to its epsilon-amino group, wherein gamma Glu* is a gamma Glu residue with an octadecanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 87

```
Pro Ile Lys Pro Lys Ala Pro Gly Glu Gly Ala Ser Pro Glu Glu Leu
1               5                   10                  15
```

-continued

```
Leu His Tyr Tyr Ala Ala Leu Arg His Phe Leu Asn His Val Thr Arg
            20                  25                  30

Gln Arg Tyr
        35


<210> SEQ ID NO 88
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (9)..(9)
<223> OTHER INFORMATION: Lys residue with the C terminus of peptide
      sequence gamma Glu*-Gly-Ser-Gly-Glu attached to its epsilon-amino
      group, wherein gamma Glu* is a gamma Glu residue with an
      octadecanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 88

Pro Ile Lys Pro Glu Ala Pro Gly Lys Gly Ala Ser Pro Glu Glu Leu
1               5                   10                  15

Leu His Tyr Tyr Ala Ala Leu Arg His Phe Leu Asn His Val Thr Arg
            20                  25                  30

Gln Arg Tyr
        35


<210> SEQ ID NO 89
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (10)..(10)
<223> OTHER INFORMATION: Lys residue with the C terminus of peptide
      sequence gamma Glu*-Gly-Ser-Gly-Asp attached to its epsilon-amino
      group, wherein gamma Glu* is a gamma Glu residue with an
      octadecanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 89

Pro Ile Lys Pro Glu Ala Pro Gly Glu Lys Ala Ser Pro Glu Glu Leu
1               5                   10                  15

Leu His Tyr Tyr Ala Ala Leu Arg His Phe Leu Asn His Val Thr Arg
            20                  25                  30

Gln Arg Tyr
        35


<210> SEQ ID NO 90
<211> LENGTH: 35
<212> TYPE: PRT
<213> ORGANISM: Artificial Sequence
<220> FEATURE:
<223> OTHER INFORMATION: component of appetite suppressant
<220> FEATURE:
<221> NAME/KEY: MOD_RES
<222> LOCATION: (6)..(6)
<223> OTHER INFORMATION: Lys residue with the C terminus of peptide
      sequence gamma Glu*-Gly-Ser-Gly-Asp attached to its epsilon-amino
      group, wherein gamma Glu* is a gamma Glu residue with an
```

-continued

```
      octadecanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 90

Pro Ile Lys Pro Glu Lys Pro Gly Glu Gly Ala Ser Pro Glu Glu Ile
1               5                   10                  15

Leu Lys Tyr Tyr Ile Glu Leu Arg His Phe Leu Asn His Leu Thr Arg
            20                  25                  30

Gln Arg Tyr
        35


<210> SEQ ID NO 91
<211> LENGTH: 40
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (1)..(1)
<223> OTHER INFORMATION: gamma Glu residue with an octadecanedioc acid
      moiety attached to its alpha-amino group
<220> FEATURE:
<221> NAME/KEY: MOD_RES
<222> LOCATION: (40)..(40)
<223> OTHER INFORMATION: AMIDATION

<400> SEQUENCE: 91

Glu Gly Ser Gly Gly Pro Ile Lys Pro Glu Ala Pro Gly Glu Gly Ala
1               5                   10                  15

Ser Pro Glu Glu Leu Leu His Tyr Tyr Ala Ala Leu Arg His Phe Leu
            20                  25                  30

Asn His Val Thr Arg Gln Arg Tyr
        35                  40


<210> SEQ ID NO 92
<211> LENGTH: 40
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (1)..(1)
<223> OTHER INFORMATION: gamma Glu residue with an octadecanedioc acid
      moiety attached to its alpha-amino group
<220> FEATURE:
<221> NAME/KEY: MOD_RES
<222> LOCATION: (40)..(40)
<223> OTHER INFORMATION: AMIDATION

<400> SEQUENCE: 92

Glu Gly Ser Gly Gly Pro Ile Lys Pro Glu Ala Pro Gly Glu Gly Ala
1               5                   10                  15

Ser Pro Glu Glu Ile Leu Lys Tyr Tyr Ile Glu Leu Arg His Phe Leu
            20                  25                  30

Asn His Leu Thr Arg Gln Arg Tyr
        35                  40


<210> SEQ ID NO 93
<211> LENGTH: 37
<212> TYPE: PRT
<213> ORGANISM: Artificial sequence
<220> FEATURE:
```

<223> OTHER INFORMATION: component of appetite suppressant
<220> FEATURE:
<221> NAME/KEY: MOD_RES
<222> LOCATION: (1)..(1)
<223> OTHER INFORMATION: Lys residue with the C terminus of peptide sequence Glu*-Gly-Ser-Gly attached to its epsilon-amino group, wherein Glu* is a Glu residue with an octadecanedioc acid moiety attached to its alpha-amino group
<220> FEATURE:
<221> NAME/KEY: MOD_RES
<222> LOCATION: (37)..(37)
<223> OTHER INFORMATION: AMIDATION

<400> SEQUENCE: 93

```
Lys Gly Pro Ile Lys Pro Glu Ala Pro Gly Glu Gly Ala Ser Pro Glu
1               5                   10                  15

Glu Leu Leu His Tyr Tyr Ala Ala Leu Arg His Phe Leu Asn His Val
            20                  25                  30

Thr Arg Gln Arg Tyr
        35
```

<210> SEQ ID NO 94
<211> LENGTH: 37
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (1)..(1)
<223> OTHER INFORMATION: Lys residue with the C terminus of peptide sequence Glu*-Gly-Ser-Gly attached to its epsilon-amino group, wherein Glu* is a Glu residue with an octadecanedioc acid moiety attached to its alpha-amino group
<220> FEATURE:
<221> NAME/KEY: MOD_RES
<222> LOCATION: (37)..(37)
<223> OTHER INFORMATION: AMIDATION

<400> SEQUENCE: 94

```
Lys Gly Pro Ile Lys Pro Glu Ala Pro Gly Glu Gly Ala Ser Pro Glu
1               5                   10                  15

Glu Ile Leu Lys Tyr Tyr Ile Glu Leu Arg His Phe Leu Asn His Leu
            20                  25                  30

Thr Arg Gln Arg Tyr
        35
```

<210> SEQ ID NO 95
<211> LENGTH: 36
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (1)..(1)
<223> OTHER INFORMATION: Lys residue with the C terminus of peptide sequence Glu*-Gly-Ser-Gly attached to its epsilon-amino group, wherein Glu* is a Glu residue with an octadecanedioc acid moiety attached to its alpha-amino group
<220> FEATURE:
<221> NAME/KEY: MOD_RES
<222> LOCATION: (36)..(36)
<223> OTHER INFORMATION: AMIDATION

<400> SEQUENCE: 95

```
Lys Pro Ile Lys Pro Glu Ala Pro Gly Glu Gly Ala Ser Pro Glu Glu
1               5                   10                  15

Leu Leu His Tyr Tyr Ala Ala Leu Arg His Phe Leu Asn His Val Thr
```

```
            20                  25                  30

Arg Gln Arg Tyr
        35


<210> SEQ ID NO 96
<211> LENGTH: 36
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (1)..(1)
<223> OTHER INFORMATION: Lys residue with the C terminus of peptide
      sequence Glu*-Gly-Ser-Gly attached to its epsilon-amino group,
      wherein Glu* is a Glu residue with an octadecanedioc acid moiety
      attached to its alpha-amino group
<220> FEATURE:
<221> NAME/KEY: MOD_RES
<222> LOCATION: (36)..(36)
<223> OTHER INFORMATION: AMIDATION

<400> SEQUENCE: 96

Lys Pro Ile Lys Pro Glu Ala Pro Gly Glu Gly Ala Ser Pro Glu Glu
1               5                   10                  15

Ile Leu Lys Tyr Tyr Ile Glu Leu Arg His Phe Leu Asn His Leu Thr
            20                  25                  30

Arg Gln Arg Tyr
        35


<210> SEQ ID NO 97
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (9)..(9)
<223> OTHER INFORMATION: Lys residue with the C terminus of peptide
      sequence Glu*-Gly-Ser-Gly attached to its epsilon-amino group,
      wherein Glu* is a Glu residue with an octadecanedioc acid moiety
      attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 97

Pro Ile Lys Pro Glu Ala Pro Gly Lys Gly Ala Ser Pro Glu Glu Leu
1               5                   10                  15

Leu His Tyr Tyr Ala Ala Leu Arg His Phe Leu Asn His Val Thr Arg
            20                  25                  30

Gln Arg Tyr
        35


<210> SEQ ID NO 98
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (9)..(9)
<223> OTHER INFORMATION: Lys residue with the C terminus of peptide
      sequence Glu*-Gly-Ser-Gly attached to its epsilon-amino group,
      wherein Glu* is a Glu residue with an octadecanedioc acid moiety
      attached to its alpha-amino group
```

<220> FEATURE:
<221> NAME/KEY: MOD_RES
<222> LOCATION: (35)..(35)
<223> OTHER INFORMATION: AMIDATION

<400> SEQUENCE: 98

Pro Ile Lys Pro Glu Ala Pro Gly Lys Gly Ala Ser Pro Glu Glu Ile
1               5                   10                  15

Leu Lys Tyr Tyr Ile Glu Leu Arg His Phe Leu Asn His Leu Thr Arg
            20                  25                  30

Gln Arg Tyr
        35

<210> SEQ ID NO 99
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (17)..(17)
<223> OTHER INFORMATION: Lys residue with the C terminus of peptide sequence Glu*-Gly-Ser-Gly attached to its epsilon-amino group, wherein Glu* is a Glu residue with an octadecanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 99

Pro Ile Lys Pro Glu Ala Pro Gly Glu Gly Ala Ser Pro Glu Glu Leu
1               5                   10                  15

Lys His Tyr Tyr Ala Ala Leu Arg His Phe Leu Asn His Val Thr Arg
            20                  25                  30

Gln Arg Tyr
        35

<210> SEQ ID NO 100
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (17)..(17)
<223> OTHER INFORMATION: Lys residue with the C terminus of peptide sequence Glu*-Gly-Ser-Gly attached to its epsilon-amino group, wherein Glu* is a Glu residue with an octadecanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 100

Pro Ile Lys Pro Glu Ala Pro Gly Glu Gly Ala Ser Pro Glu Glu Ile
1               5                   10                  15

Lys Lys Tyr Tyr Ile Glu Leu Arg His Phe Leu Asn His Leu Thr Arg
            20                  25                  30

Gln Arg Tyr
        35

<210> SEQ ID NO 101
<211> LENGTH: 35

-continued

<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (6)..(6)
<223> OTHER INFORMATION: Lys residue with the C terminus of peptide sequence Glu*-Gly-Ser-Gly attached to its epsilon-amino group, wherein Glu* is a Glu residue with an octadecanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 101

```
Pro Ile Lys Pro Glu Lys Pro Gly Glu Gly Ala Ser Pro Glu Glu Ile
1               5                   10                  15

Leu Lys Tyr Tyr Ile Glu Leu Arg His Phe Leu Asn His Leu Thr Arg
            20                  25                  30

Gln Arg Tyr
        35
```

<210> SEQ ID NO 102
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (6)..(6)
<223> OTHER INFORMATION: Lys residue with the C terminus of peptide sequence Glu*-Gly-Ser-Gly-Ser attached to its epsilon-amino group, wherein Glu* is a Glu residue with an octadecanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 102

```
Pro Ile Lys Pro Glu Lys Pro Gly Glu Gly Ala Ser Pro Glu Glu Ile
1               5                   10                  15

Leu Lys Tyr Tyr Ile Glu Leu Arg His Phe Leu Asn His Leu Thr Arg
            20                  25                  30

Gln Arg Tyr
        35
```

<210> SEQ ID NO 103
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (6)..(6)
<223> OTHER INFORMATION: Lys residue with the C terminus of peptide sequence Glu*-Gly-Ser-Gly attached to its epsilon-amino group, wherein Glu* is a Glu residue with an eicosanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 103

```
Pro Ile Lys Pro Glu Lys Pro Gly Glu Gly Ala Ser Pro Glu Glu Ile
```

-continued

```
1               5                   10                  15

Leu Lys Tyr Tyr Ile Glu Leu Arg His Phe Leu Asn His Leu Thr Arg
            20                  25                  30

Gln Arg Tyr
        35


<210> SEQ ID NO 104
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (6)..(6)
<223> OTHER INFORMATION: Lys residue with the C terminus of peptide
      sequence Gly*-Thr attached to its epsilon-amino group, wherein
      Gly* is a Gly residue with an octadecanedioc acid moiety attached
      to its alpha-amino group
<220> FEATURE:
<221> NAME/KEY: MOD_RES
<222> LOCATION: (35)..(35)
<223> OTHER INFORMATION: AMIDATION

<400> SEQUENCE: 104

Pro Ile Lys Pro Glu Lys Pro Gly Glu Gly Ala Ser Pro Glu Glu Ile
1               5                   10                  15

Leu Lys Tyr Tyr Ile Glu Leu Arg His Phe Leu Asn His Leu Thr Arg
            20                  25                  30

Gln Arg Tyr
        35


<210> SEQ ID NO 105
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (6)..(6)
<223> OTHER INFORMATION: Lys residue with the C terminus of peptide
      sequence gamma Glu*-Gly-Thr attached to its epsilon-amino group,
      wherein gamma Glu* is a gamma Glu residue with an octadecanedioc
      acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 105

Pro Ile Lys Pro Glu Lys Pro Gly Lys Gly Ala Ser Pro Glu Glu Leu
1               5                   10                  15

Ala His Tyr Tyr Ile Glu Leu Arg His Phe Leu Asn Lys Val Thr Arg
            20                  25                  30

Gln Arg Tyr
        35


<210> SEQ ID NO 106
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (6)..(6)
<223> OTHER INFORMATION: Lys residue with the C terminus of peptide
```

sequence gamma Glu*-Gly-Thr attached to its epsilon-amino group, wherein gamma Glu* is a gamma Glu residue with an octadecanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 106

Pro Ile Lys Pro Glu Lys Pro Gly Lys Asp Ala Ser Pro Glu Glu Ile
1 5 10 15

Leu Arg Tyr Tyr Ile Glu Leu Arg His Phe Leu Asn His Leu Thr Arg
20 25 30

Gln Arg Tyr
35

<210> SEQ ID NO 107
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (6)..(6)
<223> OTHER INFORMATION: Lys residue with the C terminus of peptide sequence gamma Glu*-Gly-Thr attached to its epsilon-amino group, wherein gamma Glu* is a gamma Glu residue with an octadecanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 107

Pro Ile Lys Pro Glu Lys Pro Gly Glu Gly Ala Ser Pro Glu Glu Ile
1 5 10 15

Leu His Tyr Tyr Ala Ala Leu Arg His Phe Leu Asn His Leu Thr Arg
20 25 30

Gln Arg Tyr
35

<210> SEQ ID NO 108
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (6)..(6)
<223> OTHER INFORMATION: Lys residue with the C terminus of peptide sequence gamma Glu*-Gly-Thr attached to its epsilon-amino group, wherein gamma Glu* is a gamma Glu residue with an octadecanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 108

Pro Ile Lys Pro Glu Lys Pro Gly Glu Asn Ala Ser Pro Glu Glu Ile
1 5 10 15

Leu Lys Tyr Tyr Ile Glu Leu Arg His Phe Leu Asn His Leu Thr Arg
20 25 30

Gln Arg Tyr
35

<210> SEQ ID NO 109
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (8)..(8)
<223> OTHER INFORMATION: Lys residue with the C terminus of peptide sequence Glu*-Gly-Ser-Gly attached to its epsilon-amino group, wherein Glu* is a Glu residue with an octadecanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 109

```
Pro Ile Lys Pro Glu Ala Pro Lys Glu Gly Ala Ser Pro Glu Glu Ile
1               5                   10                  15

Leu Lys Tyr Tyr Ile Glu Leu Arg His Phe Leu Asn His Leu Thr Arg
            20                  25                  30

Gln Arg Tyr
        35
```

<210> SEQ ID NO 110
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (11)..(11)
<223> OTHER INFORMATION: Lys residue with the C terminus of peptide sequence Glu*-Gly-Ser-Gly attached to its epsilon-amino group, wherein Glu* is a Glu residue with an octadecanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 110

```
Pro Ile Lys Pro Glu Ala Pro Gly Glu Gly Lys Ser Pro Glu Glu Ile
1               5                   10                  15

Leu Lys Tyr Tyr Ile Glu Leu Arg His Phe Leu Asn His Leu Thr Arg
            20                  25                  30

Gln Arg Tyr
        35
```

<210> SEQ ID NO 111
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (6)..(6)
<223> OTHER INFORMATION: Lys residue with the C terminus of peptide sequence Glu*-Gly-Thr attached to its epsilon-amino group, wherein Glu* is a Glu residue with an octadecanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 111

Pro Ile Lys Pro Glu Lys Pro Gly Glu Gly Ala Ser Pro Glu Glu Ile
1 5 10 15

Leu Lys Tyr Tyr Ile Glu Leu Arg His Phe Leu Asn His Leu Thr Arg
20 25 30

Gln Arg Tyr
35

<210> SEQ ID NO 112
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (6)..(6)
<223> OTHER INFORMATION: Lys residue with the C terminus of peptide sequence Gly*-Tyr-Thr attached to its epsilon-amino group, wherein Gly* is a Gly residue with an octadecanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 112

Pro Ile Lys Pro Glu Lys Pro Gly Glu Gly Ala Ser Pro Glu Glu Ile
1 5 10 15

Leu Lys Tyr Tyr Ile Glu Leu Arg His Phe Leu Asn His Leu Thr Arg
20 25 30

Gln Arg Tyr
35

<210> SEQ ID NO 113
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (6)..(6)
<223> OTHER INFORMATION: Lys residue with the C terminus of peptide sequence Gly*-Asn-Thr attached to its epsilon-amino group, wherein Gly* is a Gly residue with an octadecanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 113

Pro Ile Lys Pro Glu Lys Pro Gly Glu Gly Ala Ser Pro Glu Glu Ile
1 5 10 15

Leu Lys Tyr Tyr Ile Glu Leu Arg His Phe Leu Asn His Leu Thr Arg
20 25 30

Gln Arg Tyr
35

<210> SEQ ID NO 114
<211> LENGTH: 35
<212> TYPE: PRT
<213> ORGANISM: Artificial sequence
<220> FEATURE:
<223> OTHER INFORMATION: component of appetite suppressant
<220> FEATURE:

<221> NAME/KEY: MOD_RES
<222> LOCATION: (6)..(6)
<223> OTHER INFORMATION: Lys residue with the C terminus of peptide sequence Glu*-Tyr-Gly attached to its epsilon-amino group, wherein Glu* is a Glu residue with an octadecanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 114

Pro Ile Lys Pro Glu Lys Pro Gly Glu Gly Ala Ser Pro Glu Glu Ile
1 5 10 15

Leu Lys Tyr Tyr Ile Glu Leu Arg His Phe Leu Asn His Leu Thr Arg
20 25 30

Gln Arg Tyr
35

<210> SEQ ID NO 115
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (15)..(15)
<223> OTHER INFORMATION: Lys residue with the C terminus of peptide sequence gamma Glu*-Gly-Ser-Gly attached to its epsilon-amino group, wherein gamma Glu* is a gamma Glu residue with an octadecanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 115

Pro Ile Lys Pro Glu Ala Pro Gly Glu Gly Ala Ser Pro Glu Lys Leu
1 5 10 15

Leu His Tyr Tyr Ala Ala Leu Arg His Phe Leu Asn His Val Thr Arg
20 25 30

Gln Arg Tyr
35

<210> SEQ ID NO 116
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (14)..(14)
<223> OTHER INFORMATION: Lys residue with the C terminus of peptide sequence gamma Glu*-Gly-Ser-Gly attached to its epsilon-amino group, wherein gamma Glu* is a gamma Glu residue with an octadecanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 116

Pro Ile Lys Pro Glu Ala Pro Gly Glu Gly Ala Ser Pro Lys Glu Leu
1 5 10 15

Leu His Tyr Tyr Ala Ala Leu Arg His Phe Leu Asn His Val Thr Arg
20 25 30

Gln Arg Tyr
35

<210> SEQ ID NO 117
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (13)..(13)
<223> OTHER INFORMATION: Lys residue with the C terminus of peptide sequence gamma Glu*-Gly-Ser-Gly attached to its epsilon-amino group, wherein gamma Glu* is a gamma Glu residue with an octadecanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 117

Pro Ile Lys Pro Glu Ala Pro Gly Glu Gly Ala Ser Lys Glu Glu Leu
1 5 10 15

Leu His Tyr Tyr Ala Ala Leu Arg His Phe Leu Asn His Val Thr Arg
20 25 30

Gln Arg Tyr
35

<210> SEQ ID NO 118
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (12)..(12)
<223> OTHER INFORMATION: Lys residue with the C terminus of peptide sequence gamma Glu*-Gly-Ser-Gly attached to its epsilon-amino group, wherein gamma Glu* is a gamma Glu residue with an octadecanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 118

Pro Ile Lys Pro Glu Ala Pro Gly Glu Gly Ala Lys Pro Glu Glu Leu
1 5 10 15

Leu His Tyr Tyr Ala Ala Leu Arg His Phe Leu Asn His Val Thr Arg
20 25 30

Gln Arg Tyr
35

<210> SEQ ID NO 119
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (11)..(11)
<223> OTHER INFORMATION: Lys residue with the C terminus of peptide sequence gamma Glu*-Gly-Ser-Gly attached to its epsilon-amino group, wherein gamma Glu* is a gamma Glu residue with an octadecanedioc acid moiety attached to its alpha-amino group
<220> FEATURE:
<221> NAME/KEY: MOD_RES

<222> LOCATION: (35)..(35)
<223> OTHER INFORMATION: AMIDATION

<400> SEQUENCE: 119

Pro Ile Lys Pro Glu Ala Pro Gly Glu Gly Lys Ser Pro Glu Glu Leu
1               5                   10                  15

Leu His Tyr Tyr Ala Ala Leu Arg His Phe Leu Asn His Val Thr Arg
            20                  25                  30

Gln Arg Tyr
        35

<210> SEQ ID NO 120
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (8)..(8)
<223> OTHER INFORMATION: Lys residue with the C terminus of peptide sequence gamma Glu*-Gly-Ser-Gly attached to its epsilon-amino group, wherein gamma Glu* is a gamma Glu residue with an octadecanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 120

Pro Ile Lys Pro Glu Ala Pro Lys Glu Gly Ala Ser Pro Glu Glu Leu
1               5                   10                  15

Leu His Tyr Tyr Ala Ala Leu Arg His Phe Leu Asn His Val Thr Arg
            20                  25                  30

Gln Arg Tyr
        35

<210> SEQ ID NO 121
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (2)..(2)
<223> OTHER INFORMATION: Lys residue with the C terminus of peptide sequence gamma Glu*-Gly-Ser-Gly attached to its epsilon-amino group, wherein gamma Glu* is a gamma Glu residue with an octadecanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 121

Pro Ile Lys Pro Glu Ala Pro Gly Glu Gly Ala Ser Pro Glu Glu Leu
1               5                   10                  15

Leu His Tyr Tyr Ala Ala Leu Arg His Phe Leu Asn His Val Thr Arg
            20                  25                  30

Gln Arg Tyr
        35

<210> SEQ ID NO 122
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (2)..(2)
<223> OTHER INFORMATION: Lys residue with the C terminus of peptide sequence gamma Glu*-Gly-Ser-Gly attached to its epsilon-amino group, wherein gamma Glu* is a gamma Glu residue with an octadecanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 122

```
Pro Lys Lys Pro Glu Ala Pro Gly Glu Gly Ala Ser Pro Glu Glu Leu
1               5                   10                  15

Leu His Tyr Tyr Ala Ala Leu Arg His Phe Leu Asn His Val Thr Arg
            20                  25                  30

Gln Arg Tyr
        35
```

<210> SEQ ID NO 123
<211> LENGTH: 37
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (1)..(1)
<223> OTHER INFORMATION: Gly residue with an octadecanedioc acid moiety attached to its alpha-amino group
<220> FEATURE:
<221> NAME/KEY: MOD_RES
<222> LOCATION: (37)..(37)
<223> OTHER INFORMATION: AMIDATION

<400> SEQUENCE: 123

```
Gly Ser Pro Ile Lys Pro Glu Ala Pro Gly Glu Gly Ala Ser Pro Glu
1               5                   10                  15

Glu Leu Leu His Tyr Tyr Ala Ala Leu Arg His Phe Leu Asn His Val
            20                  25                  30

Thr Arg Gln Arg Tyr
        35
```

<210> SEQ ID NO 124
<211> LENGTH: 37
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (1)..(1)
<223> OTHER INFORMATION: Gly residue with an octadecanedioc acid moiety attached to its alpha-amino group
<220> FEATURE:
<221> NAME/KEY: MOD_RES
<222> LOCATION: (37)..(37)
<223> OTHER INFORMATION: AMIDATION

<400> SEQUENCE: 124

```
Gly Thr Pro Ile Lys Pro Glu Ala Pro Gly Glu Gly Ala Ser Pro Glu
1               5                   10                  15

Glu Leu Leu His Tyr Tyr Ala Ala Leu Arg His Phe Leu Asn His Val
            20                  25                  30

Thr Arg Gln Arg Tyr
```

35

<210> SEQ ID NO 125
<211> LENGTH: 37
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (1)..(1)
<223> OTHER INFORMATION: Gly residue with an octadecanedioc acid moiety attached to its alpha-amino group
<220> FEATURE:
<221> NAME/KEY: MOD_RES
<222> LOCATION: (37)..(37)
<223> OTHER INFORMATION: AMIDATION

<400> SEQUENCE: 125

```
Gly Tyr Pro Ile Lys Pro Glu Ala Pro Gly Glu Gly Ala Ser Pro Glu
1               5                   10                  15

Glu Leu Leu His Tyr Tyr Ala Ala Leu Arg His Phe Leu Asn His Val
            20                  25                  30

Thr Arg Gln Arg Tyr
        35
```

<210> SEQ ID NO 126
<211> LENGTH: 38
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (1)..(1)
<223> OTHER INFORMATION: gamma Glu residue with an octadecanedioc acid moiety attached to its alpha-amino group
<220> FEATURE:
<221> NAME/KEY: MOD_RES
<222> LOCATION: (38)..(38)
<223> OTHER INFORMATION: AMIDATION

<400> SEQUENCE: 126

```
Glu Gly Ser Pro Ile Lys Pro Glu Ala Pro Gly Glu Gly Ala Ser Pro
1               5                   10                  15

Glu Glu Leu Leu His Tyr Tyr Ala Ala Leu Arg His Phe Leu Asn His
            20                  25                  30

Val Thr Arg Gln Arg Tyr
        35
```

<210> SEQ ID NO 127
<211> LENGTH: 39
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (1)..(1)
<223> OTHER INFORMATION: Ser residue with an octadecanedioc acid moiety attached to its alpha-amino group
<220> FEATURE:
<221> NAME/KEY: MOD_RES
<222> LOCATION: (39)..(39)
<223> OTHER INFORMATION: AMIDATION

<400> SEQUENCE: 127

```
Ser Gly Gly Ser Pro Ile Lys Pro Glu Ala Pro Gly Glu Gly Ala Ser
1               5                   10                  15
```

Pro Glu Glu Leu Leu His Tyr Tyr Ala Ala Leu Arg His Phe Leu Asn
20 25 30

His Val Thr Arg Gln Arg Tyr
35

<210> SEQ ID NO 128
<211> LENGTH: 38
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (1)..(1)
<223> OTHER INFORMATION: Lys residue with the C terminus of peptide residue gamma Glu* attached to its epsilon-amino group, wherein gamma Glu* is a gamma Glu residue with an octadecanedioc acid moiety attached to its alpha-amino group
<220> FEATURE:
<221> NAME/KEY: MOD_RES
<222> LOCATION: (38)..(38)
<223> OTHER INFORMATION: AMIDATION

<400> SEQUENCE: 128

Lys Gly Ser Pro Ile Lys Pro Glu Ala Pro Gly Glu Gly Ala Ser Pro
1 5 10 15

Glu Glu Leu Leu His Tyr Tyr Ala Ala Leu Arg His Phe Leu Asn His
20 25 30

Val Thr Arg Gln Arg Tyr
35

<210> SEQ ID NO 129
<211> LENGTH: 36
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (1)..(1)
<223> OTHER INFORMATION: Lys residue with an octadecanedioc acid moiety attached to its epsilon-amino group
<220> FEATURE:
<221> NAME/KEY: MOD_RES
<222> LOCATION: (36)..(36)
<223> OTHER INFORMATION: AMIDATION

<400> SEQUENCE: 129

Lys Pro Ile Lys Pro Glu Ala Pro Gly Glu Gly Ala Ser Pro Glu Glu
1 5 10 15

Leu Leu His Tyr Tyr Ala Ala Leu Arg His Phe Leu Asn His Val Thr
20 25 30

Arg Gln Arg Tyr
35

<210> SEQ ID NO 130
<211> LENGTH: 36
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (1)..(1)
<223> OTHER INFORMATION: Lys residue with the C terminus of peptide residue gamma Glu* attached to its epsilon-amino group, wherein gamma Glu* is a gamma Glu residue with an octadecanedioc acid moiety attached to its alpha-amino group

```
<220> FEATURE:
<221> NAME/KEY: MOD_RES
<222> LOCATION: (36)..(36)
<223> OTHER INFORMATION: AMIDATION

<400> SEQUENCE: 130

Lys Pro Ile Lys Pro Glu Ala Pro Gly Glu Gly Ala Ser Pro Glu Glu
1               5                   10                  15

Leu Leu His Tyr Tyr Ala Ala Leu Arg His Phe Leu Asn His Val Thr
            20                  25                  30

Arg Gln Arg Tyr
        35


<210> SEQ ID NO 131
<211> LENGTH: 37
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (1)..(1)
<223> OTHER INFORMATION: Lys residue with the C terminus of peptide
      residue gamma Glu* attached to its epsilon-amino group, wherein
      gamma Glu* is a gamma Glu residue with an octadecanedioc acid
      moiety attached to its alpha-amino group
<220> FEATURE:
<221> NAME/KEY: MOD_RES
<222> LOCATION: (37)..(37)
<223> OTHER INFORMATION: AMIDATION

<400> SEQUENCE: 131

Lys Gly Pro Ile Lys Pro Glu Ala Pro Gly Glu Gly Ala Ser Pro Glu
1               5                   10                  15

Glu Leu Leu His Tyr Tyr Ala Ala Leu Arg His Phe Leu Asn His Val
            20                  25                  30

Thr Arg Gln Arg Tyr
        35


<210> SEQ ID NO 132
<211> LENGTH: 37
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (1)..(1)
<223> OTHER INFORMATION: Lys residue with the C terminus of peptide
      residue gamma Glu* attached to its epsilon-amino group, wherein
      gamma Glu* is a gamma Glu residue with an octadecanedioc acid
      moiety attached to its alpha-amino group
<220> FEATURE:
<221> NAME/KEY: MOD_RES
<222> LOCATION: (37)..(37)
<223> OTHER INFORMATION: AMIDATION

<400> SEQUENCE: 132

Lys Ser Pro Ile Lys Pro Glu Ala Pro Gly Glu Gly Ala Ser Pro Glu
1               5                   10                  15

Glu Leu Leu His Tyr Tyr Ala Ala Leu Arg His Phe Leu Asn His Val
            20                  25                  30

Thr Arg Gln Arg Tyr
        35


<210> SEQ ID NO 133
<211> LENGTH: 38
```

```
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (1)..(1)
<223> OTHER INFORMATION: Lys residue with the C terminus of peptide
      residue gamma Glu* attached to its epsilon-amino group, wherein
      gamma Glu* is a gamma Glu residue with an octadecanedioc acid
      moiety attached to its alpha-amino group
<220> FEATURE:
<221> NAME/KEY: MOD_RES
<222> LOCATION: (38)..(38)
<223> OTHER INFORMATION: AMIDATION

<400> SEQUENCE: 133

Lys Ser Gly Pro Ile Lys Pro Glu Ala Pro Gly Glu Gly Ala Ser Pro
1               5                   10                  15

Glu Glu Leu Leu His Tyr Tyr Ala Ala Leu Arg His Phe Leu Asn His
            20                  25                  30

Val Thr Arg Gln Arg Tyr
        35


<210> SEQ ID NO 134
<211> LENGTH: 38
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (1)..(1)
<223> OTHER INFORMATION: Lys residue with the C terminus of peptide
      residue gamma Glu* attached to its epsilon-amino group, wherein
      gamma Glu* is a gamma Glu residue with an octadecanedioc acid
      moiety attached to its alpha-amino group
<220> FEATURE:
<221> NAME/KEY: MOD_RES
<222> LOCATION: (38)..(38)
<223> OTHER INFORMATION: AMIDATION

<400> SEQUENCE: 134

Lys Thr Gly Pro Ile Lys Pro Glu Ala Pro Gly Glu Gly Ala Ser Pro
1               5                   10                  15

Glu Glu Leu Leu His Tyr Tyr Ala Ala Leu Arg His Phe Leu Asn His
            20                  25                  30

Val Thr Arg Gln Arg Tyr
        35


<210> SEQ ID NO 135
<211> LENGTH: 38
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (1)..(1)
<223> OTHER INFORMATION: Lys residue with the C terminus of peptide
      residue gamma Glu* attached to its epsilon-amino group, wherein
      gamma Glu* is a gamma Glu residue with an eicosanedioc acid moiety
      attached to its alpha-amino group
<220> FEATURE:
<221> NAME/KEY: MOD_RES
<222> LOCATION: (38)..(38)
<223> OTHER INFORMATION: AMIDATION

<400> SEQUENCE: 135

Lys Ser Gly Pro Ile Lys Pro Glu Ala Pro Gly Glu Gly Ala Ser Pro
```

```
1               5                   10                  15

Glu Glu Leu Leu His Tyr Tyr Ala Ala Leu Arg His Phe Leu Asn His
            20                  25                  30

Val Thr Arg Gln Arg Tyr
        35


<210> SEQ ID NO 136
<211> LENGTH: 37
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (1)..(1)
<223> OTHER INFORMATION: Lys residue with an octadecanedioc acid moiety
      attached to its epsilon-amino group
<220> FEATURE:
<221> NAME/KEY: MOD_RES
<222> LOCATION: (37)..(37)
<223> OTHER INFORMATION: AMIDATION

<400> SEQUENCE: 136

Lys Gly Pro Ile Lys Pro Glu Ala Pro Gly Glu Gly Ala Ser Pro Glu
1               5                   10                  15

Glu Leu Leu His Tyr Tyr Ala Ala Leu Arg His Phe Leu Asn His Val
            20                  25                  30

Thr Arg Gln Arg Tyr
        35


<210> SEQ ID NO 137
<211> LENGTH: 37
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (1)..(1)
<223> OTHER INFORMATION: Lys residue with an eicosanedioc acid moiety
      attached to its epsilon-amino group
<220> FEATURE:
<221> NAME/KEY: MOD_RES
<222> LOCATION: (37)..(37)
<223> OTHER INFORMATION: AMIDATION

<400> SEQUENCE: 137

Lys Gly Pro Ile Lys Pro Glu Ala Pro Gly Glu Gly Ala Ser Pro Glu
1               5                   10                  15

Glu Leu Leu His Tyr Tyr Ala Ala Leu Arg His Phe Leu Asn His Val
            20                  25                  30

Thr Arg Gln Arg Tyr
        35


<210> SEQ ID NO 138
<211> LENGTH: 37
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (1)..(1)
<223> OTHER INFORMATION: Lys residue with the C terminus of peptide
      residue Gly* attached to its epsilon-amino group, wherein Gly* is
      a Gly residue with an eicosanedioc acid moiety attached to its
      alpha-amino group
<220> FEATURE:
```

<221> NAME/KEY: MOD_RES
<222> LOCATION: (37)..(37)
<223> OTHER INFORMATION: AMIDATION

<400> SEQUENCE: 138

Lys Gly Pro Ile Lys Pro Glu Ala Pro Gly Glu Gly Ala Ser Pro Glu
1 5 10 15

Glu Leu Leu His Tyr Tyr Ala Ala Leu Arg His Phe Leu Asn His Val
20 25 30

Thr Arg Gln Arg Tyr
35

<210> SEQ ID NO 139
<211> LENGTH: 38
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (1)..(1)
<223> OTHER INFORMATION: Lys residue with the C terminus of peptide residue Glu* attached to its epsilon-amino group, wherein Glu* is a Glu residue with an octadecanedioc acid moiety attached to its alpha-amino group
<220> FEATURE:
<221> NAME/KEY: MOD_RES
<222> LOCATION: (38)..(38)
<223> OTHER INFORMATION: AMIDATION

<400> SEQUENCE: 139

Lys Ser Gly Pro Ile Lys Pro Glu Ala Pro Gly Glu Gly Ala Ser Pro
1 5 10 15

Glu Glu Leu Leu His Tyr Tyr Ala Ala Leu Arg His Phe Leu Asn His
20 25 30

Val Thr Arg Gln Arg Tyr
35

<210> SEQ ID NO 140
<211> LENGTH: 38
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (1)..(1)
<223> OTHER INFORMATION: Lys residue with the C terminus of peptide residue Glu* attached to its epsilon-amino group, wherein Glu* is a Glu residue with an octadecanedioc acid moiety attached to its alpha-amino group
<220> FEATURE:
<221> NAME/KEY: MOD_RES
<222> LOCATION: (38)..(38)
<223> OTHER INFORMATION: AMIDATION

<400> SEQUENCE: 140

Lys Thr Gly Pro Ile Lys Pro Glu Ala Pro Gly Glu Gly Ala Ser Pro
1 5 10 15

Glu Glu Leu Leu His Tyr Tyr Ala Ala Leu Arg His Phe Leu Asn His
20 25 30

Val Thr Arg Gln Arg Tyr
35

<210> SEQ ID NO 141
<211> LENGTH: 38
<212> TYPE: PRT

<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (1)..(1)
<223> OTHER INFORMATION: Lys residue with the C terminus of peptide residue Glu* attached to its epsilon-amino group, wherein Glu* is a Glu residue with an eicosanedioc acid moiety attached to its alpha-amino group
<220> FEATURE:
<221> NAME/KEY: MOD_RES
<222> LOCATION: (38)..(38)
<223> OTHER INFORMATION: AMIDATION

<400> SEQUENCE: 141

```
Lys Ser Gly Pro Ile Lys Pro Glu Ala Pro Gly Glu Gly Ala Ser Pro
1               5                   10                  15

Glu Glu Leu Leu His Tyr Tyr Ala Ala Leu Arg His Phe Leu Asn His
            20                  25                  30

Val Thr Arg Gln Arg Tyr
        35
```

<210> SEQ ID NO 142
<211> LENGTH: 36
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (1)..(1)
<223> OTHER INFORMATION: Lys residue with the C terminus of peptide sequence gamma Glu*-Ser-Gly attached to its epsilon-amino group, wherein gamma Glu* is a gamma Glu residue with an octadecanedioc acid moiety attached to its alpha-amino group
<220> FEATURE:
<221> NAME/KEY: MOD_RES
<222> LOCATION: (36)..(36)
<223> OTHER INFORMATION: AMIDATION

<400> SEQUENCE: 142

```
Lys Pro Ile Lys Pro Glu Ala Pro Gly Glu Gly Ala Ser Pro Glu Glu
1               5                   10                  15

Leu Leu His Tyr Tyr Ala Ala Leu Arg His Phe Leu Asn His Val Thr
            20                  25                  30

Arg Gln Arg Tyr
        35
```

<210> SEQ ID NO 143
<211> LENGTH: 36
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (1)..(1)
<223> OTHER INFORMATION: Lys residue with the C terminus of peptide sequence gamma Glu*-Ser-Gly attached to its epsilon-amino group, wherein gamma Glu* is a gamma Glu residue with an eicosanedioc acid moiety attached to its alpha-amino group
<220> FEATURE:
<221> NAME/KEY: MOD_RES
<222> LOCATION: (36)..(36)
<223> OTHER INFORMATION: AMIDATION

<400> SEQUENCE: 143

```
Lys Pro Ile Lys Pro Glu Ala Pro Gly Glu Gly Ala Ser Pro Glu Glu
1               5                   10                  15
```

Leu Leu His Tyr Tyr Ala Ala Leu Arg His Phe Leu Asn His Val Thr
20 25 30

Arg Gln Arg Tyr
35

<210> SEQ ID NO 144
<211> LENGTH: 38
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (1)..(1)
<223> OTHER INFORMATION: gamma Glu residue with an octadecanedioc acid moiety attached to its alpha-amino group
<220> FEATURE:
<221> NAME/KEY: MOD_RES
<222> LOCATION: (38)..(38)
<223> OTHER INFORMATION: AMIDATION

<400> SEQUENCE: 144

Glu Ser Gly Pro Ile Lys Pro Glu Ala Pro Gly Glu Gly Ala Ser Pro
1 5 10 15

Glu Glu Leu Leu His Tyr Tyr Ala Ala Leu Arg His Phe Leu Asn His
20 25 30

Val Thr Arg Gln Arg Tyr
35

<210> SEQ ID NO 145
<211> LENGTH: 38
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (1)..(1)
<223> OTHER INFORMATION: gamma Glu residue with an eicosanedioc acid moiety attached to its alpha-amino group
<220> FEATURE:
<221> NAME/KEY: MOD_RES
<222> LOCATION: (38)..(38)
<223> OTHER INFORMATION: AMIDATION

<400> SEQUENCE: 145

Glu Ser Gly Pro Ile Lys Pro Glu Ala Pro Gly Glu Gly Ala Ser Pro
1 5 10 15

Glu Glu Leu Leu His Tyr Tyr Ala Ala Leu Arg His Phe Leu Asn His
20 25 30

Val Thr Arg Gln Arg Tyr
35

<210> SEQ ID NO 146
<211> LENGTH: 38
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (1)..(1)
<223> OTHER INFORMATION: gamma Glu residue with an octadecanedioc acid moiety attached to its alpha-amino group
<220> FEATURE:
<221> NAME/KEY: MOD_RES
<222> LOCATION: (38)..(38)
<223> OTHER INFORMATION: AMIDATION

<400> SEQUENCE: 146

Glu Thr Gly Pro Ile Lys Pro Glu Ala Pro Gly Glu Gly Ala Ser Pro
1               5                   10                  15

Glu Glu Leu Leu His Tyr Tyr Ala Ala Leu Arg His Phe Leu Asn His
            20                  25                  30

Val Thr Arg Gln Arg Tyr
        35

<210> SEQ ID NO 147
<211> LENGTH: 41
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (4)..(4)
<223> OTHER INFORMATION: Lys residue with an octadecanedioc acid moiety attached to its epsilon-amino group
<220> FEATURE:
<221> NAME/KEY: MOD_RES
<222> LOCATION: (41)..(41)
<223> OTHER INFORMATION: AMIDATION

<400> SEQUENCE: 147

Glu Tyr Glu Lys Glu Tyr Pro Ile Lys Pro Glu Ala Pro Gly Glu Gly
1               5                   10                  15

Ala Ser Pro Glu Glu Ile Leu Lys Tyr Tyr Ile Glu Leu Arg His Phe
            20                  25                  30

Leu Asn His Leu Thr Arg Gln Arg Tyr
        35                  40

<210> SEQ ID NO 148
<211> LENGTH: 37
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (1)..(1)
<223> OTHER INFORMATION: Lys residue with the C terminus of peptide sequence Glu*-Gly-Ser-Gly attached to its epsilon-amino group, wherein Glu* is a Glu residue with an octadecanedioc acid moiety attached to its alpha-amino group
<220> FEATURE:
<221> NAME/KEY: MOD_RES
<222> LOCATION: (37)..(37)
<223> OTHER INFORMATION: AMIDATION

<400> SEQUENCE: 148

Lys Gly Pro Ile Lys Pro Glu Ala Pro Gly Glu Gly Ala Ser Pro Glu
1               5                   10                  15

Glu Ile Leu His Tyr Tyr Ala Ala Leu Arg His Phe Leu Asn His Leu
            20                  25                  30

Thr Arg Gln Arg Tyr
        35

<210> SEQ ID NO 149
<211> LENGTH: 37
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (1)..(1)
<223> OTHER INFORMATION: Lys residue with the C terminus of peptide sequence Glu*-Gly-Ser-Gly attached to its epsilon-amino group, wherein Glu* is a Glu residue with an octadecanedioc acid moiety attached to its alpha-amino group
<220> FEATURE:
<221> NAME/KEY: MOD_RES
<222> LOCATION: (37)..(37)
<223> OTHER INFORMATION: AMIDATION

<400> SEQUENCE: 149

```
Lys Gly Pro Ile Lys Pro Glu Ala Pro Gly Glu Asn Ala Ser Pro Glu
1               5                   10                  15

Glu Ile Leu Lys Tyr Tyr Ile Glu Leu Arg His Phe Leu Asn His Leu
            20                  25                  30

Thr Arg Gln Arg Tyr
        35
```

<210> SEQ ID NO 150
<211> LENGTH: 37
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (1)..(1)
<223> OTHER INFORMATION: Lys residue with the C terminus of peptide sequence Glu*-Gly-Ser-Gly attached to its epsilon-amino group, wherein Glu* is a Glu residue with an octadecanedioc acid moiety attached to its alpha-amino group
<220> FEATURE:
<221> NAME/KEY: MOD_RES
<222> LOCATION: (37)..(37)
<223> OTHER INFORMATION: AMIDATION

<400> SEQUENCE: 150

```
Lys Gly Pro Ile Lys Pro Glu Ala Pro Gly Lys Asp Ala Ser Pro Glu
1               5                   10                  15

Glu Ile Leu Arg Tyr Tyr Ile Ala Leu Arg His Phe Leu Asn His Leu
            20                  25                  30

Thr Arg Gln Arg Tyr
        35
```

<210> SEQ ID NO 151
<211> LENGTH: 41
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (41)..(41)
<223> OTHER INFORMATION: AMIDATION

<400> SEQUENCE: 151

```
Glu Tyr Glu Lys Glu Tyr Pro Ile Lys Pro Glu Ala Pro Gly Glu Gly
1               5                   10                  15

Ala Ser Pro Glu Glu Ile Leu Lys Tyr Tyr Ile Glu Leu Arg His Phe
            20                  25                  30

Leu Asn His Leu Thr Arg Gln Arg Tyr
        35                  40
```

<210> SEQ ID NO 152
<211> LENGTH: 41
<212> TYPE: PRT
<213> ORGANISM: Artificial sequence -continued
<220> FEATURE:
<223> OTHER INFORMATION: component of appetite suppressant
<220> FEATURE:
<221> NAME/KEY: MOD_RES
<222> LOCATION: (41)..(41)
<223> OTHER INFORMATION: AMIDATION

<400> SEQUENCE: 152

Glu Tyr Glu Lys Glu Tyr Pro Ile Lys Pro Glu Ala Pro Gly Glu Gly
1               5                   10                  15

Ala Ser Pro Glu Glu Ile Leu Lys Tyr Tyr Ile Glu Leu Arg His Phe
            20                  25                  30

Leu Asn His Leu Thr Arg Gln Arg Tyr
        35                  40

<210> SEQ ID NO 153
<211> LENGTH: 38
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (1)..(1)
<223> OTHER INFORMATION: Lys residue with an octadecanedioc acid moiety
attached to its epsilon-amino group
<220> FEATURE:
<221> NAME/KEY: MOD_RES
<222> LOCATION: (38)..(38)
<223> OTHER INFORMATION: AMIDATION

<400> SEQUENCE: 153

Lys Glu Tyr Pro Ile Lys Pro Glu Ala Pro Gly Glu Gly Ala Ser Pro
1               5                   10                  15

Glu Glu Ile Leu Lys Tyr Tyr Ile Glu Leu Arg His Phe Leu Asn His
            20                  25                  30

Leu Thr Arg Gln Arg Tyr
        35

<210> SEQ ID NO 154
<211> LENGTH: 38
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (38)..(38)
<223> OTHER INFORMATION: AMIDATION

<400> SEQUENCE: 154

Lys Glu Tyr Pro Ile Lys Pro Glu Ala Pro Gly Glu Gly Ala Ser Pro
1               5                   10                  15

Glu Glu Ile Leu Lys Tyr Tyr Ile Glu Leu Arg His Phe Leu Asn His
            20                  25                  30

Leu Thr Arg Gln Arg Tyr
        35

<210> SEQ ID NO 155
<211> LENGTH: 37
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (1)..(1)

<223> OTHER INFORMATION: gamma Glu residue with the C terminus of peptide residue Lys* attached to its alpha-amino group, wherein Lys* is a Lys residue with an octadecanedioc acid moiety attached to its epsilon-amino group
<220> FEATURE:
<221> NAME/KEY: MOD_RES
<222> LOCATION: (37)..(37)
<223> OTHER INFORMATION: AMIDATION

<400> SEQUENCE: 155

```
Glu Tyr Pro Ile Lys Pro Glu Ala Pro Gly Glu Gly Ala Ser Pro Glu
1               5                   10                  15

Glu Ile Leu Lys Tyr Tyr Ile Glu Leu Arg His Phe Leu Asn His Leu
            20                  25                  30

Thr Arg Gln Arg Tyr
        35
```

<210> SEQ ID NO 156
<211> LENGTH: 41
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (4)..(4)
<223> OTHER INFORMATION: Lys residue with the C terminus of peptide sequence gamma Glu*-Gly-Ser-Gly attached to its epsilon-amino group, wherein gamma Glu* is a gamma Glu residue with an octadecanedioc acid moiety attached to its alpha-amino group
<220> FEATURE:
<221> NAME/KEY: MOD_RES
<222> LOCATION: (41)..(41)
<223> OTHER INFORMATION: AMIDATION

<400> SEQUENCE: 156

```
Tyr Glu Lys Glu Tyr Glu Pro Ile Lys Pro Glu Ala Pro Gly Glu Gly
1               5                   10                  15

Ala Ser Pro Glu Glu Ile Leu Lys Tyr Tyr Ile Glu Leu Arg His Phe
            20                  25                  30

Leu Asn His Leu Thr Arg Gln Arg Tyr
        35                  40
```

<210> SEQ ID NO 157
<211> LENGTH: 41
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (4)..(4)
<223> OTHER INFORMATION: Lys residue with an octadecanedioc acid moiety attached to its epsilon-amino group
<220> FEATURE:
<221> NAME/KEY: MOD_RES
<222> LOCATION: (41)..(41)
<223> OTHER INFORMATION: AMIDATION

<400> SEQUENCE: 157

```
Tyr Glu Lys Glu Tyr Glu Pro Ile Lys Pro Glu Ala Pro Gly Glu Gly
1               5                   10                  15

Ala Ser Pro Glu Glu Ile Leu Lys Tyr Tyr Ile Glu Leu Arg His Phe
            20                  25                  30

Leu Asn His Leu Thr Arg Gln Arg Tyr
        35                  40
```

<210> SEQ ID NO 158
<211> LENGTH: 39
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (1)..(1)
<223> OTHER INFORMATION: Lys residue with an octadecanedioc acid moiety
attached to its epsilon-amino group
<220> FEATURE:
<221> NAME/KEY: MOD_RES
<222> LOCATION: (39)..(39)
<223> OTHER INFORMATION: AMIDATION

<400> SEQUENCE: 158

```
Lys Glu Tyr Glu Pro Ile Lys Pro Glu Ala Pro Gly Glu Gly Ala Ser
1               5                   10                  15

Pro Glu Glu Ile Leu Lys Tyr Tyr Ile Glu Leu Arg His Phe Leu Asn
            20                  25                  30

His Leu Thr Arg Gln Arg Tyr
        35
```

<210> SEQ ID NO 159
<211> LENGTH: 40
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (4)..(4)
<223> OTHER INFORMATION: Lys residue with an octadecanedioc acid moiety
attached to its epsilon-amino group
<220> FEATURE:
<221> NAME/KEY: MOD_RES
<222> LOCATION: (40)..(40)
<223> OTHER INFORMATION: AMIDATION

<400> SEQUENCE: 159

```
Glu Tyr Glu Lys Glu Pro Ile Lys Pro Glu Ala Pro Gly Glu Gly Ala
1               5                   10                  15

Ser Pro Glu Glu Ile Leu Lys Tyr Tyr Ile Glu Leu Arg His Phe Leu
            20                  25                  30

Asn His Leu Thr Arg Gln Arg Tyr
        35                  40
```

<210> SEQ ID NO 160
<211> LENGTH: 38
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (1)..(1)
<223> OTHER INFORMATION: Gly residue with an octadecanedioc acid moiety
attached to its alpha-amino group
<220> FEATURE:
<221> NAME/KEY: MOD_RES
<222> LOCATION: (38)..(38)
<223> OTHER INFORMATION: AMIDATION

<400> SEQUENCE: 160

```
Gly Gly Thr Pro Ile Lys Pro Glu Ala Pro Gly Glu Gly Ala Ser Pro
1               5                   10                  15

Glu Glu Ile Leu Lys Tyr Tyr Ile Glu Leu Arg His Phe Leu Asn His
            20                  25                  30
```

Leu Thr Arg Gln Arg Tyr
35

<210> SEQ ID NO 161
<211> LENGTH: 41
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (1)..(1)
<223> OTHER INFORMATION: Glu residue with an octadecanedioc acid moiety attached to its alpha-amino group
<220> FEATURE:
<221> NAME/KEY: MOD_RES
<222> LOCATION: (41)..(41)
<223> OTHER INFORMATION: AMIDATION

<400> SEQUENCE: 161

Glu Gly Ser Gly Gly Ala Pro Ile Lys Pro Glu Ala Pro Gly Glu Gly
1 5 10 15

Ala Ser Pro Glu Glu Ile Leu Lys Tyr Tyr Ile Glu Leu Arg His Phe
20 25 30

Leu Asn His Leu Thr Arg Gln Arg Tyr
35 40

<210> SEQ ID NO 162
<211> LENGTH: 41
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (1)..(1)
<223> OTHER INFORMATION: Glu residue with an octadecanedioc acid moiety attached to its alpha-amino group
<220> FEATURE:
<221> NAME/KEY: MOD_RES
<222> LOCATION: (41)..(41)
<223> OTHER INFORMATION: AMIDATION

<400> SEQUENCE: 162

Glu Gly Ser Gly Gly Val Pro Ile Lys Pro Glu Ala Pro Gly Glu Gly
1 5 10 15

Ala Ser Pro Glu Glu Ile Leu Lys Tyr Tyr Ile Glu Leu Arg His Phe
20 25 30

Leu Asn His Leu Thr Arg Gln Arg Tyr
35 40

<210> SEQ ID NO 163
<211> LENGTH: 40
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (1)..(1)
<223> OTHER INFORMATION: Glu residue with an octadecanedioc acid moiety attached to its alpha-amino group
<220> FEATURE:
<221> NAME/KEY: MOD_RES
<222> LOCATION: (40)..(40)
<223> OTHER INFORMATION: AMIDATION

<400> SEQUENCE: 163

-continued

Glu Gly Ser Gly Ala Pro Ile Lys Pro Glu Ala Pro Gly Glu Gly Ala
1 5 10 15

Ser Pro Glu Glu Ile Leu Lys Tyr Tyr Ile Glu Leu Arg His Phe Leu
20 25 30

Asn His Leu Thr Arg Gln Arg Tyr
35 40

<210> SEQ ID NO 164
<211> LENGTH: 39
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (1)..(1)
<223> OTHER INFORMATION: Glu residue with an octadecanedioc acid moiety attached to its alpha-amino group
<220> FEATURE:
<221> NAME/KEY: MOD_RES
<222> LOCATION: (39)..(39)
<223> OTHER INFORMATION: AMIDATION

<400> SEQUENCE: 164

Glu Gly Ser Ala Pro Ile Lys Pro Glu Ala Pro Gly Glu Gly Ala Ser
1 5 10 15

Pro Glu Glu Ile Leu Lys Tyr Tyr Ile Glu Leu Arg His Phe Leu Asn
20 25 30

His Leu Thr Arg Gln Arg Tyr
35

<210> SEQ ID NO 165
<211> LENGTH: 41
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (4)..(4)
<223> OTHER INFORMATION: Lys residue with an octadecanedioc acid moiety attached to its epsilon-amino group
<220> FEATURE:
<221> NAME/KEY: MOD_RES
<222> LOCATION: (41)..(41)
<223> OTHER INFORMATION: AMIDATION

<400> SEQUENCE: 165

Tyr Glu Lys Glu Tyr Ala Pro Ile Lys Pro Glu Ala Pro Gly Glu Gly
1 5 10 15

Ala Ser Pro Glu Glu Ile Leu Lys Tyr Tyr Ile Glu Leu Arg His Phe
20 25 30

Leu Asn His Leu Thr Arg Gln Arg Tyr
35 40

<210> SEQ ID NO 166
<211> LENGTH: 36
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (1)..(1)
<223> OTHER INFORMATION: Lys residue with an octadecanedioc acid moiety attached to its alpha-amino group
<220> FEATURE:
<221> NAME/KEY: MOD_RES

<222> LOCATION: (36)..(36)
<223> OTHER INFORMATION: AMIDATION

<400> SEQUENCE: 166

Ala Pro Ile Lys Pro Glu Ala Pro Gly Glu Gly Ala Ser Pro Glu Glu
1 5 10 15

Ile Leu Lys Tyr Tyr Ile Glu Leu Arg His Phe Leu Asn His Leu Thr
20 25 30

Arg Gln Arg Tyr
35

<210> SEQ ID NO 167
<211> LENGTH: 38
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (1)..(1)
<223> OTHER INFORMATION: Ser residue with an octadecanedioc acid moiety attached to its alpha-amino group
<220> FEATURE:
<221> NAME/KEY: MOD_RES
<222> LOCATION: (38)..(38)
<223> OTHER INFORMATION: AMIDATION

<400> SEQUENCE: 167

Ser Gly Ala Pro Ile Lys Pro Glu Ala Pro Gly Glu Gly Ala Ser Pro
1 5 10 15

Glu Glu Ile Leu Lys Tyr Tyr Ile Glu Leu Arg His Phe Leu Asn His
20 25 30

Leu Thr Arg Gln Arg Tyr
35

<210> SEQ ID NO 168
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (5)..(5)
<223> OTHER INFORMATION: gamma Glu residue with the C terminus of peptide residue Lys* attached to its alpha-amino group, wherein Lys* is a Lys residue with an octadecanedioc acid moiety attached to its epsilon-amino group
<220> FEATURE:
<221> NAME/KEY: MOD_RES
<222> LOCATION: (35)..(35)
<223> OTHER INFORMATION: AMIDATION

<400> SEQUENCE: 168

Pro Ile Lys Pro Glu Ala Pro Gly Glu Gly Ala Ser Pro Glu Glu Ile
1 5 10 15

Leu Lys Tyr Tyr Ile Glu Leu Arg His Phe Leu Asn His Leu Thr Arg
20 25 30

Gln Arg Tyr
35

<210> SEQ ID NO 169
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (9)..(9)
<223> OTHER INFORMATION: gamma Glu residue with the C terminus of peptide residue Lys* attached to its alpha-amino group, wherein Lys* is a Lys residue with an octadecanedioc acid moiety attached to its epsilon-amino group
<220> FEATURE:
<221> NAME/KEY: MOD_RES
<222> LOCATION: (35)..(35)
<223> OTHER INFORMATION: AMIDATION

<400> SEQUENCE: 169

```
Pro Ile Lys Pro Glu Ala Pro Gly Glu Gly Ala Ser Pro Glu Glu Ile
1               5                   10                  15

Leu Lys Tyr Tyr Ile Glu Leu Arg His Phe Leu Asn His Leu Thr Arg
            20                  25                  30

Gln Arg Tyr
        35
```

<210> SEQ ID NO 170
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (14)..(14)
<223> OTHER INFORMATION: gamma Glu residue with the C terminus of peptide residue Lys* attached to its alpha-amino group, wherein Lys* is a Lys residue with an octadecanedioc acid moiety attached to its epsilon-amino group
<220> FEATURE:
<221> NAME/KEY: MOD_RES
<222> LOCATION: (35)..(35)
<223> OTHER INFORMATION: AMIDATION

<400> SEQUENCE: 170

```
Pro Ile Lys Pro Glu Ala Pro Gly Glu Gly Ala Ser Pro Glu Glu Ile
1               5                   10                  15

Leu Lys Tyr Tyr Ile Glu Leu Arg His Phe Leu Asn His Leu Thr Arg
            20                  25                  30

Gln Arg Tyr
        35
```

<210> SEQ ID NO 171
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (15)..(15)
<223> OTHER INFORMATION: gamma Glu residue with the C terminus of peptide residue Lys* attached to its alpha-amino group, wherein Lys* is a Lys residue with an octadecanedioc acid moiety attached to its epsilon-amino group
<220> FEATURE:
<221> NAME/KEY: MOD_RES
<222> LOCATION: (35)..(35)
<223> OTHER INFORMATION: AMIDATION

<400> SEQUENCE: 171

```
Pro Ile Lys Pro Glu Ala Pro Gly Glu Gly Ala Ser Pro Glu Glu Ile
1               5                   10                  15

Leu Lys Tyr Tyr Ile Glu Leu Arg His Phe Leu Asn His Leu Thr Arg
            20                  25                  30
```

Gln Arg Tyr
35

<210> SEQ ID NO 172
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (6)..(6)
<223> OTHER INFORMATION: Cys residue attached via a disulfide bridge to peptide gamma Glu*-Cys, wherein gamma Glu* is a gamma Glu residue with an octadecanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 172

Pro Ile Lys Pro Glu Cys Pro Gly Glu Gly Ala Ser Pro Glu Glu Ile
1 5 10 15

Leu Lys Tyr Tyr Ile Glu Leu Arg His Phe Leu Asn His Leu Thr Arg
20 25 30

Gln Arg Tyr
35

<210> SEQ ID NO 173
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (9)..(9)
<223> OTHER INFORMATION: Lys residue with the C terminus of peptide sequence Glu*-Gly-Ser-Gly attached to its epsilon-amino group, wherein Glu* is a Glu residue with an octadecanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 173

Pro Ile Lys Pro Glu Ala Pro Gly Lys Asp Ala Ser Pro Glu Glu Leu
1 5 10 15

Asn His Tyr Tyr Ala Ala Leu Arg His Phe Leu Asn Arg Val Thr Arg
20 25 30

Gln Arg Tyr
35

<210> SEQ ID NO 174
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (9)..(9)
<223> OTHER INFORMATION: Lys residue with the C terminus of peptide sequence Glu*-Gly-Ser-Gly attached to its epsilon-amino group, wherein Glu* is a Glu residue with an octadecanedioc acid moiety attached to its alpha-amino group
<220> FEATURE:

```
<221> NAME/KEY: MOD_RES
<222> LOCATION: (35)..(35)
<223> OTHER INFORMATION: AMIDATION

<400> SEQUENCE: 174

Pro Ile Lys Pro Glu Ala Pro Gly Lys Asp Ala Ser Pro Glu Glu Leu
1               5                   10                  15

Val His Tyr Tyr Ile Ala Leu Arg His Phe Leu Asn His Val Thr Arg
            20                  25                  30

Gln Arg Tyr
        35


<210> SEQ ID NO 175
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (9)..(9)
<223> OTHER INFORMATION: Lys residue with the C terminus of peptide
      sequence Glu*-Gly-Ser-Gly attached to its epsilon-amino group,
      wherein Glu* is a Glu residue with an octadecanedioc acid moiety
      attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 175

Pro Ile Lys Pro Glu Ala Pro Gly Lys Asp Ala Ser Pro Glu Glu Ile
1               5                   10                  15

Leu His Tyr Tyr Ala Ala Leu Arg His Tyr Leu Asn His Leu Thr Arg
            20                  25                  30

Gln Arg Tyr
        35


<210> SEQ ID NO 176
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (9)..(9)
<223> OTHER INFORMATION: Lys residue with the C terminus of peptide
      sequence Glu*-Gly-Ser-Gly attached to its epsilon-amino group,
      wherein Glu* is a Glu residue with an octadecanedioc acid moiety
      attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 176

Pro Ile Lys Pro Glu Ala Pro Gly Lys Glu Ala Ser Pro Glu Glu Ile
1               5                   10                  15

Leu Lys Tyr Tyr Ile Glu Leu Arg His Phe Leu Asn His Leu Thr Arg
            20                  25                  30

Gln Arg Tyr
        35


<210> SEQ ID NO 177
<211> LENGTH: 35
<212> TYPE: PRT
```

<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (9)..(9)
<223> OTHER INFORMATION: Lys residue with the C terminus of peptide sequence Glu*-Gly-Ser-Gly attached to its epsilon-amino group, wherein Glu* is a Glu residue with an octadecanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 177

```
Pro Ile Lys Pro Glu Ala Pro Gly Lys Asn Ala Ser Pro Glu Glu Ile
1               5                   10                  15

Leu Lys Tyr Tyr Ile Glu Leu Arg His Phe Leu Asn His Leu Thr Arg
            20                  25                  30

Gln Arg Tyr
        35
```

<210> SEQ ID NO 178
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (9)..(9)
<223> OTHER INFORMATION: Lys residue with the C terminus of peptide sequence Glu*-Gly-Ser-Gly attached to its epsilon-amino group, wherein Glu* is a Glu residue with an eicosanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 178

```
Pro Ile Lys Pro Glu Ala Pro Gly Lys Asn Ala Ser Pro Glu Glu Ile
1               5                   10                  15

Leu Lys Tyr Tyr Ile Glu Leu Arg His Phe Leu Asn His Leu Thr Arg
            20                  25                  30

Gln Arg Tyr
        35
```

<210> SEQ ID NO 179
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (9)..(9)
<223> OTHER INFORMATION: Lys residue with the C terminus of peptide sequence Glu*-Gly-Ser-Gly attached to its epsilon-amino group, wherein Glu* is a Glu residue with an octadecanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 179

```
Pro Ile Lys Pro Glu Ala Pro Gly Lys Gly Ala Ser Pro Glu Glu Ile
1               5                   10                  15
```

Leu His Tyr Tyr Ala Ala Leu Arg His Phe Leu Asn His Leu Thr Arg
20 25 30

Gln Arg Tyr
35

<210> SEQ ID NO 180
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (6)..(6)
<223> OTHER INFORMATION: Lys residue with the C terminus of peptide sequence Glu*-Gly-Ser-Gly attached to its epsilon-amino group, wherein Glu* is a Glu residue with an octadecanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 180

Pro Ile Lys Pro Glu Lys Pro Gly Glu Gly Ala Ser Pro Glu Glu Leu
1 5 10 15

Leu His Tyr Tyr Ala Ala Leu Arg His Phe Leu Asn His Val Thr Arg
20 25 30

Gln Arg Tyr
35

<210> SEQ ID NO 181
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (6)..(6)
<223> OTHER INFORMATION: Lys residue with the C terminus of peptide sequence Glu*-Gly-Ser-Gly attached to its epsilon-amino group, wherein Glu* is a Glu residue with an octadecanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 181

Pro Ile Lys Pro Glu Lys Pro Gly Glu Asp Ala Ser Pro Glu Glu Leu
1 5 10 15

Asn His Tyr Tyr Ala Ala Leu Arg His Phe Leu Asn Arg Val Thr Arg
20 25 30

Gln Arg Tyr
35

<210> SEQ ID NO 182
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (6)..(6)
<223> OTHER INFORMATION: Lys residue with the C terminus of peptide sequence Glu*-Gly-Ser-Gly attached to its epsilon-amino group, wherein Glu* is a Glu residue with an octadecanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 182

Pro Ile Lys Pro Glu Lys Pro Gly Glu Asp Ala Ser Pro Glu Glu Leu
1 5 10 15

Val His Tyr Tyr Ile Ala Leu Arg His Phe Leu Asn His Val Thr Arg
20 25 30

Gln Arg Tyr
35

<210> SEQ ID NO 183
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (6)..(6)
<223> OTHER INFORMATION: Lys residue with the C terminus of peptide sequence Glu*-Gly-Ser-Gly attached to its epsilon-amino group, wherein Glu* is a Glu residue with an octadecanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 183

Pro Ile Lys Pro Glu Lys Pro Gly Glu Asp Ala Ser Pro Glu Glu Ile
1 5 10 15

Leu His Tyr Tyr Ala Ala Leu Arg His Tyr Leu Asn His Leu Thr Arg
20 25 30

Gln Arg Tyr
35

<210> SEQ ID NO 184
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (6)..(6)
<223> OTHER INFORMATION: Lys residue with the C terminus of peptide sequence Glu*-Gly-Ser-Gly attached to its epsilon-amino group, wherein Glu* is a Glu residue with an octadecanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 184

Pro Ile Lys Pro Glu Lys Pro Gly Glu Glu Ala Ser Pro Glu Glu Ile
1 5 10 15

Leu Lys Tyr Tyr Ile Glu Leu Arg His Phe Leu Asn His Leu Thr Arg
20 25 30

Gln Arg Tyr
35

```
<210> SEQ ID NO 185
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (6)..(6)
<223> OTHER INFORMATION: Lys residue with the C terminus of peptide
      sequence Glu*-Gly-Ser-Gly attached to its epsilon-amino group,
      wherein Glu* is a Glu residue with an octadecanedioc acid moiety
      attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 185

Pro Ile Lys Pro Glu Lys Pro Gly Glu Asn Ala Ser Pro Glu Glu Ile
1               5                   10                  15

Leu Lys Tyr Tyr Ile Glu Leu Arg His Phe Leu Asn His Leu Thr Arg
            20                  25                  30

Gln Arg Tyr
        35


<210> SEQ ID NO 186
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (6)..(6)
<223> OTHER INFORMATION: Lys residue with the C terminus of peptide
      sequence Glu*-Gly-Ser-Gly attached to its epsilon-amino group,
      wherein Glu* is a Glu residue with an octadecanedioc acid moiety
      attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 186

Pro Ile Lys Pro Glu Lys Pro Gly Glu Asn Ala Ser Pro Glu Glu Ile
1               5                   10                  15

Leu Lys Tyr Tyr Ile Glu Leu Arg His Phe Leu Asn His Leu Thr Arg
            20                  25                  30

Gln Arg Tyr
        35


<210> SEQ ID NO 187
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (6)..(6)
<223> OTHER INFORMATION: Lys residue with the C terminus of peptide
      sequence Glu*-Gly-Ser-Gly attached to its epsilon-amino group,
      wherein Glu* is a Glu residue with an octadecanedioc acid moiety
      attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 187
```

Pro Ile Lys Pro Glu Lys Pro Gly Glu Gly Ala Ser Pro Glu Glu Ile
1 5 10 15

Leu His Tyr Tyr Ala Ala Leu Arg His Phe Leu Asn His Leu Thr Arg
20 25 30

Gln Arg Tyr
35

<210> SEQ ID NO 188
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (8)..(8)
<223> OTHER INFORMATION: Lys residue with the C terminus of peptide sequence gamma Glu*-Asn attached to its epsilon-amino group, wherein gamma Glu* is a gamma Glu residue with an octadecanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 188

Pro Ile Lys Pro Glu Ala Pro Lys Glu Gly Ala Ser Pro Glu Glu Leu
1 5 10 15

Leu His Tyr Tyr Ala Ala Leu Arg His Phe Leu Asn His Val Thr Arg
20 25 30

Gln Arg Tyr
35

<210> SEQ ID NO 189
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (8)..(8)
<223> OTHER INFORMATION: Lys residue with the C terminus of peptide sequence gamma Glu*-Ser-Gly-Thr attached to its epsilon-amino group, wherein gamma Glu* is a gamma Glu residue with an octadecanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 189

Pro Ile Lys Pro Glu Ala Pro Lys Glu Gly Ala Ser Pro Glu Glu Leu
1 5 10 15

Leu His Tyr Tyr Ala Ala Leu Arg His Phe Leu Asn His Val Thr Arg
20 25 30

Gln Arg Tyr
35

<210> SEQ ID NO 190
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES -continued
<222> LOCATION: (8)..(8)
<223> OTHER INFORMATION: Lys residue with the C terminus of peptide sequence gamma Glu*-Gly-Ser-Ser-Gly attached to its epsilon-amino group, wherein gamma Glu* is a gamma Glu residue with a hexadecanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 190

```
Pro Ile Lys Pro Glu Ala Pro Lys Glu Gly Ala Ser Pro Glu Glu Leu
1               5                   10                  15

Leu His Tyr Tyr Ala Ala Leu Arg His Phe Leu Asn His Val Thr Arg
            20                  25                  30

Gln Arg Tyr
        35
```

<210> SEQ ID NO 191
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (8)..(8)
<223> OTHER INFORMATION: Lys residue with the C terminus of peptide sequence Glu*-Asn attached to its epsilon-amino group, wherein Glu* is a Glu residue with an octadecanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 191

```
Pro Ile Lys Pro Glu Ala Pro Lys Glu Asn Ala Ser Pro Glu Glu Ile
1               5                   10                  15

Leu Lys Tyr Tyr Ile Glu Leu Arg His Phe Leu Asn His Leu Thr Arg
            20                  25                  30

Gln Arg Tyr
        35
```

<210> SEQ ID NO 192
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (8)..(8)
<223> OTHER INFORMATION: Lys residue with the C terminus of peptide sequence gamma Glu*-Ser-Gly-Thr attached to its epsilon-amino group, wherein gamma Glu* is a gamma Glu residue with an eicosanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 192

```
Pro Ile Lys Pro Glu Ala Pro Lys Glu Asn Ala Ser Pro Glu Glu Ile
1               5                   10                  15

Leu Lys Tyr Tyr Ile Glu Leu Arg His Phe Leu Asn His Leu Thr Arg
            20                  25                  30

Gln Arg Tyr
```

35

<210> SEQ ID NO 193
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (8)..(8)
<223> OTHER INFORMATION: Lys residue with the C terminus of peptide sequence gamma Glu*-Gly-Ser-Ser-Gly attached to its epsilon-amino group, wherein gamma Glu* is a gamma Glu residue with an eicosanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 193

Pro Ile Lys Pro Glu Ala Pro Lys Glu Asn Ala Ser Pro Glu Glu Ile
1 5 10 15

Leu Lys Tyr Tyr Ile Glu Leu Arg His Phe Leu Asn His Leu Thr Arg
20 25 30

Gln Arg Tyr
35

<210> SEQ ID NO 194
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (9)..(9)
<223> OTHER INFORMATION: Lys residue with the C terminus of peptide sequence gamma Glu*-Asn attached to its epsilon-amino group, wherein gamma Glu* is a gamma Glu residue with an octadecanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 194

Pro Ile Lys Pro Glu Ala Pro Gly Lys Gly Ala Ser Pro Glu Glu Leu
1 5 10 15

Leu His Tyr Tyr Ala Ala Leu Arg His Phe Leu Asn His Val Thr Arg
20 25 30

Gln Arg Tyr
35

<210> SEQ ID NO 195
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (9)..(9)
<223> OTHER INFORMATION: Lys residue with the C terminus of peptide sequence Glu*-Ser-Gly-Thr attached to its epsilon-amino group, wherein Glu* is a Glu residue with an octadecanedioc acid moiety attached to its alpha-amino group
<220> FEATURE:
<221> NAME/KEY: MOD_RES
<222> LOCATION: (35)..(35)

<223> OTHER INFORMATION: AMIDATION

<400> SEQUENCE: 195

```
Pro Ile Lys Pro Glu Ala Pro Gly Lys Gly Ala Ser Pro Glu Glu Leu
1               5                   10                  15

Leu His Tyr Tyr Ala Ala Leu Arg His Phe Leu Asn His Val Thr Arg
            20                  25                  30

Gln Arg Tyr
        35
```

<210> SEQ ID NO 196
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (9)..(9)
<223> OTHER INFORMATION: Lys residue with the C terminus of peptide sequence gamma Glu*-Gly-Ser-Ser-Gly attached to its epsilon-amino group, wherein gamma Glu* is a gamma Glu residue with a hexadecanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 196

```
Pro Ile Lys Pro Glu Ala Pro Gly Lys Gly Ala Ser Pro Glu Glu Leu
1               5                   10                  15

Leu His Tyr Tyr Ala Ala Leu Arg His Phe Leu Asn His Val Thr Arg
            20                  25                  30

Gln Arg Tyr
        35
```

<210> SEQ ID NO 197
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (9)..(9)
<223> OTHER INFORMATION: Lys residue with the C terminus of peptide sequence gamma Glu*-Asn attached to its epsilon-amino group, wherein gamma Glu* is a gamma Glu residue with an octadecanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 197

```
Pro Ile Lys Pro Glu Ala Pro Gly Lys Asn Ala Ser Pro Glu Glu Ile
1               5                   10                  15

Leu Lys Tyr Tyr Ile Glu Leu Arg His Phe Leu Asn His Leu Thr Arg
            20                  25                  30

Gln Arg Tyr
        35
```

<210> SEQ ID NO 198
<211> LENGTH: 35
<212> TYPE: PRT
<213> ORGANISM: Artificial sequence
<220> FEATURE:

<223> OTHER INFORMATION: component of appetite suppressant
<220> FEATURE:
<221> NAME/KEY: MOD_RES
<222> LOCATION: (9)..(9)
<223> OTHER INFORMATION: Lys residue with the C terminus of peptide sequence gamma Glu*-Ser-Gly-Thr attached to its epsilon-amino group, wherein gamma Glu* is a gamma Glu residue with an octadecanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 198

Pro Ile Lys Pro Glu Ala Pro Gly Lys Asn Ala Ser Pro Glu Glu Ile
1 5 10 15

Leu Lys Tyr Tyr Ile Glu Leu Arg His Phe Leu Asn His Leu Thr Arg
20 25 30

Gln Arg Tyr
35

<210> SEQ ID NO 199
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (9)..(9)
<223> OTHER INFORMATION: Lys residue with the C terminus of peptide sequence gamma Glu*-Gly-Ser-Ser-Gly attached to its epsilon-amino group, wherein gamma Glu* is a gamma Glu residue with a hexadecanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 199

Pro Ile Lys Pro Glu Ala Pro Gly Lys Asn Ala Ser Pro Glu Glu Ile
1 5 10 15

Leu Lys Tyr Tyr Ile Glu Leu Arg His Phe Leu Asn His Leu Thr Arg
20 25 30

Gln Arg Tyr
35

<210> SEQ ID NO 200
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (8)..(8)
<223> OTHER INFORMATION: Lys residue with the C terminus of peptide sequence gamma Glu*-Gly-Ser-Gly-Ser attached to its epsilon-amino group, wherein gamma Glu* is a gamma Glu residue with an eicosanedioc acid mo
<220> FEATURE:
<221> NAME/KEY: MOD_RES
<222> LOCATION: (35)..(35)
<223> OTHER INFORMATION: AMIDATION iety attached to its alpha-amino group

<400> SEQUENCE: 200

Pro Ile Lys Pro Glu Ala Pro Lys Glu Gly Ala Ser Pro Glu Glu Leu
1 5 10 15

-continued

```
Leu His Tyr Tyr Ala Ala Leu Arg His Phe Leu Asn His Val Thr Arg
            20                  25                  30

Gln Arg Tyr
        35


<210> SEQ ID NO 201
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (8)..(8)
<223> OTHER INFORMATION: Lys residue with the C terminus of peptide
      sequence gamma Glu*-Thr-His  attached to its epsilon-amino group,
      wherein gamma Glu* is a gamma Glu residue with an eicosanedioc
      acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 201

Pro Ile Lys Pro Glu Ala Pro Lys Glu Gly Ala Ser Pro Glu Glu Leu
1               5                   10                  15

Leu His Tyr Tyr Ala Ala Leu Arg His Phe Leu Asn His Val Thr Arg
            20                  25                  30

Gln Arg Tyr
        35


<210> SEQ ID NO 202
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (8)..(8)
<223> OTHER INFORMATION: Lys residue with the C terminus of peptide
      residue gamma Glu* attached to its epsilon-amino group, wherein
      gamma Glu* is a gamma Glu residue with an eicosanedioc acid moiety
      attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 202

Pro Ile Lys Pro Glu Ala Pro Lys Glu Gly Ala Ser Pro Glu Glu Leu
1               5                   10                  15

Leu His Tyr Tyr Ala Ala Leu Arg His Phe Leu Asn His Val Thr Arg
            20                  25                  30

Gln Arg Tyr
        35


<210> SEQ ID NO 203
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (8)..(8)
<223> OTHER INFORMATION: Lys residue with the C terminus of peptide
      sequence gamma Glu*-Ser-Gly-Thr attached to its epsilon-amino
      group, wherein gamma Glu* is a gamma Glu residue with an
```

eicosanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 203

Pro Ile Lys Pro Glu Ala Pro Lys Glu Gly Ala Ser Pro Glu Glu Leu
1 5 10 15

Leu His Tyr Tyr Ala Ala Leu Arg His Phe Leu Asn His Val Thr Arg
20 25 30

Gln Arg Tyr
35

<210> SEQ ID NO 204
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (8)..(8)
<223> OTHER INFORMATION: Lys residue with the C terminus of peptide sequence gamma Glu*-Gly-Ser attached to its epsilon-amino group, wherein gamma Glu* is a gamma Glu residue with an eicosanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 204

Pro Ile Lys Pro Glu Ala Pro Lys Glu Gly Ala Ser Pro Glu Glu Leu
1 5 10 15

Leu His Tyr Tyr Ala Ala Leu Arg His Phe Leu Asn His Val Thr Arg
20 25 30

Gln Arg Tyr
35

<210> SEQ ID NO 205
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (8)..(8)
<223> OTHER INFORMATION: Lys residue with the C terminus of peptide sequence gamma Glu*-Gly-Thr attached to its epsilon-amino group, wherein gamma Glu* is a gamma Glu residue with a hexadecanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 205

Pro Ile Lys Pro Glu Ala Pro Lys Glu Gly Ala Ser Pro Glu Glu Leu
1 5 10 15

Leu His Tyr Tyr Ala Ala Leu Arg His Phe Leu Asn His Val Thr Arg
20 25 30

Gln Arg Tyr
35

<210> SEQ ID NO 206

-continued

<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (8)..(8)
<223> OTHER INFORMATION: Lys residue with the C terminus of peptide sequence gamma Glu*-Thr-Gly-Ser-Gly attached to its epsilon-amino group, wherein gamma Glu* is a gamma Glu residue with an octadecanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 206

Pro Ile Lys Pro Glu Ala Pro Lys Glu Gly Ala Ser Pro Glu Glu Leu
1 5 10 15

Leu His Tyr Tyr Ala Ala Leu Arg His Phe Leu Asn His Val Thr Arg
20 25 30

Gln Arg Tyr
35

<210> SEQ ID NO 207
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (8)..(8)
<223> OTHER INFORMATION: Lys residue with the C terminus of peptide sequence Glu*-Gly-Thr attached to its epsilon-amino group, wherein Glu* is a Glu residue with a hexadecanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 207

Pro Ile Lys Pro Glu Ala Pro Lys Glu Gly Ala Ser Pro Glu Glu Leu
1 5 10 15

Leu His Tyr Tyr Ala Ala Leu Arg His Phe Leu Asn His Val Thr Arg
20 25 30

Gln Arg Tyr
35

<210> SEQ ID NO 208
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (8)..(8)
<223> OTHER INFORMATION: Lys residue with the C terminus of peptide sequence gamma Glu*-Thr-Gly-Thr attached to its epsilon-amino group, wherein gamma Glu* is a gamma Glu residue with an eicosanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 208

```
Pro Ile Lys Pro Glu Ala Pro Lys Glu Gly Ala Ser Pro Glu Glu Leu
1               5                   10                  15

Leu His Tyr Tyr Ala Ala Leu Arg His Phe Leu Asn His Val Thr Arg
            20                  25                  30

Gln Arg Tyr
        35


<210> SEQ ID NO 209
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (8)..(8)
<223> OTHER INFORMATION: Lys residue with the C terminus of peptide
      sequence gamma Glu*-Gly-Ser-Gly attached to its epsilon-amino
      group, wherein gamma Glu* is a gamma Glu residue with an
      octadecanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 209

Pro Ile Lys Pro Glu Ala Pro Lys Glu Glu Ala Ser Pro Glu Glu Ile
1               5                   10                  15

Leu Lys Tyr Tyr Ile Glu Leu Arg His Phe Leu Asn His Leu Thr Arg
            20                  25                  30

Gln Arg Tyr
        35


<210> SEQ ID NO 210
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (8)..(8)
<223> OTHER INFORMATION: Lys residue with the C terminus of peptide
      sequence gamma Glu*-Gly-Ser-Gly attached to its epsilon-amino
      group, wherein gamma Glu* is a gamma Glu residue with an
      octadecanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 210

Pro Ile Lys Pro Glu Ala Pro Lys Glu Gly Ala Ser Pro Glu Glu Ile
1               5                   10                  15

Leu Lys Tyr Tyr Ile Glu Leu Arg His Phe Leu Asn His Leu Thr Arg
            20                  25                  30

Gln Arg Tyr
        35


<210> SEQ ID NO 211
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (8)..(8)
```

<223> OTHER INFORMATION: Cys residue attached via a disulfide bridge to
      peptide gamma Glu*-Cys, wherein gamma Glu* is a gamma Glu residue
      with an eicosanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 211

Pro Ile Lys Pro Glu Ala Pro Cys Glu Gly Ala Ser Pro Glu Glu Leu
1               5                   10                  15

Leu His Tyr Tyr Ala Ala Leu Arg His Phe Leu Asn His Val Thr Arg
            20                  25                  30

Gln Arg Tyr
        35

<210> SEQ ID NO 212
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (8)..(8)
<223> OTHER INFORMATION: Cys residue attached via a disulfide bridge to
      peptide gamma Glu*-Cys, wherein gamma Glu* is a gamma Glu residue
      with an eicosanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 212

Pro Ile Lys Pro Glu Ala Pro Cys Glu Glu Ala Ser Pro Glu Glu Ile
1               5                   10                  15

Leu Lys Tyr Tyr Ile Glu Leu Arg His Phe Leu Asn His Leu Thr Arg
            20                  25                  30

Gln Arg Tyr
        35

<210> SEQ ID NO 213
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (8)..(8)
<223> OTHER INFORMATION: Cys residue attached via a disulfide bridge to
      peptide gamma Glu*-Cys, wherein gamma Glu* is a gamma Glu residue
      with an eicosanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 213

Pro Ile Lys Pro Glu Ala Pro Cys Glu Gly Ala Ser Pro Glu Glu Ile
1               5                   10                  15

Leu Lys Tyr Tyr Ile Glu Leu Arg His Phe Leu Asn His Leu Thr Arg
            20                  25                  30

Gln Arg Tyr
        35

<210> SEQ ID NO 214

```
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (9)..(9)
<223> OTHER INFORMATION: Cys residue attached via a disulfide bridge to
      peptide gamma Glu*-Cys, wherein gamma Glu* is a gamma Glu residue
      with an eicosanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 214

Pro Ile Lys Pro Glu Ala Pro Gly Cys Glu Ala Ser Pro Glu Glu Ile
1               5                   10                  15

Leu Lys Tyr Tyr Ile Glu Leu Arg His Phe Leu Asn His Leu Thr Arg
            20                  25                  30

Gln Arg Tyr
        35


<210> SEQ ID NO 215
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (8)..(8)
<223> OTHER INFORMATION: Lys residue with the C terminus of peptide
      sequence gamma Glu*-Gly-Ser-Gly attached to its epsilon-amino
      group, wherein gamma Glu* is a gamma Glu residue with an
      octadecanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 215

Cys Ile Lys Pro Glu Ala Pro Lys Glu Gly Ala Ser Pro Glu Glu Leu
1               5                   10                  15

Leu His Tyr Tyr Ala Ala Leu Arg His Cys Leu Asn His Val Thr Arg
            20                  25                  30

Gln Arg Tyr
        35


<210> SEQ ID NO 216
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (8)..(8)
<223> OTHER INFORMATION: Lys residue with the C terminus of peptide
      sequence gamma Glu*-Gly-Ser-Gly attached to its epsilon-amino
      group, wherein gamma Glu* is a gamma Glu residue with an
      octadecanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 216

Pro Ile Lys Cys Glu Ala Pro Lys Glu Gly Ala Ser Pro Glu Glu Leu
```

-continued

```
1               5                   10                  15

Leu His Tyr Tyr Ala Ala Cys Arg His Phe Leu Asn His Val Thr Arg
            20                  25                  30

Gln Arg Tyr
        35


<210> SEQ ID NO 217
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (8)..(8)
<223> OTHER INFORMATION: Lys residue with the C terminus of peptide
      sequence gamma Glu*-Gly-Ser-Gly attached to its epsilon-amino
      group, wherein gamma Glu* is a gamma Glu residue the peptide
      sequence Lys-Lys-Lys attached to its gamma-amino group
<220> FEATURE:
<221> NAME/KEY: MOD_RES
<222> LOCATION: (35)..(35)
<223> OTHER INFORMATION: AMIDATION

<400> SEQUENCE: 217

Pro Ile Lys Pro Glu Ala Pro Lys Glu Gly Ala Ser Pro Glu Glu Leu
1               5                   10                  15

Leu His Tyr Tyr Ala Ala Leu Arg His Phe Leu Asn His Val Thr Arg
            20                  25                  30

Gln Arg Tyr
        35


<210> SEQ ID NO 218
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (8)..(8)
<223> OTHER INFORMATION: Lys residue with the C terminus of peptide
      sequence gamma Glu*-Gly-Ser-Gly attached to its epsilon-amino
      group, wherein gamma Glu* is a gamma Glu residue the peptide
      sequence Tyr-Tyr-Tyr attached to its gamma-amino group
<220> FEATURE:
<221> NAME/KEY: MOD_RES
<222> LOCATION: (35)..(35)
<223> OTHER INFORMATION: AMIDATION

<400> SEQUENCE: 218

Pro Ile Lys Pro Glu Ala Pro Lys Glu Gly Ala Ser Pro Glu Glu Leu
1               5                   10                  15

Leu His Tyr Tyr Ala Ala Leu Arg His Phe Leu Asn His Val Thr Arg
            20                  25                  30

Gln Arg Tyr
        35


<210> SEQ ID NO 219
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (8)..(8)
<223> OTHER INFORMATION: Lys residue with the C terminus of peptide
```

sequence gamma Glu*-Gly-Ser-Gly attached to its epsilon-amino group, wherein gamma Glu* is a gamma Glu residue with an octadecanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 219

```
Pro Ile Lys Pro Glu Ala Pro Lys Glu Asp Ala Ser Pro Glu Glu Leu
1               5                   10                  15

Val His Tyr Tyr Ile Ala Leu Arg His Phe Leu Asn His Val Thr Arg
            20                  25                  30

Gln Arg Tyr
        35
```

<210> SEQ ID NO 220
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (8)..(8)
<223> OTHER INFORMATION: Lys residue with the C terminus of peptide sequence gamma Glu*-Gly-Ser-Gly attached to its epsilon-amino group, wherein gamma Glu* is a gamma Glu residue with an octadecanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 220

```
Pro Ile Lys Pro Glu Ala Pro Lys Glu Asp Ala Ser Pro Glu Glu Ile
1               5                   10                  15

Leu His Tyr Tyr Ala Ala Leu Arg His Tyr Leu Asn His Leu Thr Arg
            20                  25                  30

Gln Arg Tyr
        35
```

<210> SEQ ID NO 221
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (8)..(8)
<223> OTHER INFORMATION: Lys residue with the C terminus of peptide sequence gamma Glu*-Gly-Ser-Gly attached to its epsilon-amino group, wherein gamma Glu* is a gamma Glu residue with an octadecanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 221

```
Pro Ile Lys Pro Glu Ala Pro Lys Glu Asn Ala Ser Pro Glu Glu Ile
1               5                   10                  15

Leu Lys Tyr Tyr Ile Glu Leu Arg His Phe Leu Asn His Leu Thr Arg
            20                  25                  30

Gln Arg Tyr
        35
```

<210> SEQ ID NO 222
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (8)..(8)
<223> OTHER INFORMATION: Lys residue with the C terminus of peptide sequence gamma Glu*-Gly-Ser-Gly attached to its epsilon-amino group, wherein gamma Glu* is a gamma Glu residue with an octadecanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 222

```
Pro Ile Lys Pro Glu Ala Pro Lys Glu Asn Ala Ser Pro Glu Glu Ile
1               5                   10                  15

Leu Lys Tyr Tyr Ile Glu Leu Arg His Phe Leu Asn His Leu Thr Arg
            20                  25                  30

Gln Arg Tyr
        35
```

<210> SEQ ID NO 223
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (8)..(8)
<223> OTHER INFORMATION: Lys residue with the C terminus of peptide sequence gamma Glu*-Gly-Ser-Gly attached to its epsilon-amino group, wherein gamma Glu* is a gamma Glu residue with an octadecanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 223

```
Pro Ile Lys Pro Glu Ala Pro Lys Glu Gly Ala Ser Pro Glu Glu Ile
1               5                   10                  15

Leu His Tyr Tyr Ala Ala Leu Arg His Phe Leu Asn His Leu Thr Arg
            20                  25                  30

Gln Arg Tyr
        35
```

<210> SEQ ID NO 224
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (8)..(8)
<223> OTHER INFORMATION: Lys residue with the C terminus of peptide sequence gamma Glu*-Gly-Ser-Gly-Ser-Gly attached to its epsilon-amino group, wherein gamma Glu* is a gamma Glu residue with an eicosanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 224

Pro Ile Lys Pro Glu Ala Pro Lys Glu Gly Ala Ser Pro Glu Glu Leu
1 5 10 15

Leu His Tyr Tyr Ala Ala Leu Arg His Phe Leu Asn His Val Thr Arg
20 25 30

Gln Arg Tyr
35

<210> SEQ ID NO 225
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (6)..(6)
<223> OTHER INFORMATION: Lys residue with the C terminus of peptide sequence gamma Glu*-Gly-Ser-Gly-Ser-Gly attached to its epsilon-amino group, wherein gamma Glu* is a gamma Glu residue with an eicosanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 225

Pro Ile Lys Pro Glu Lys Pro Gly Glu Gly Ala Ser Pro Glu Glu Leu
1 5 10 15

Leu His Tyr Tyr Ala Ala Leu Arg His Phe Leu Asn His Val Thr Arg
20 25 30

Gln Arg Tyr
35

<210> SEQ ID NO 226
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (9)..(9)
<223> OTHER INFORMATION: Lys residue with the C terminus of peptide sequence gamma Glu*-Gly-Ser-Gly-Ser-Gly attached to its epsilon-amino group, wherein gamma Glu* is a gamma Glu residue with an eicosanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 226

Pro Ile Lys Pro Glu Ala Pro Gly Lys Gly Ala Ser Pro Glu Glu Leu
1 5 10 15

Leu His Tyr Tyr Ala Ala Leu Arg His Phe Leu Asn His Val Thr Arg
20 25 30

Gln Arg Tyr
35

<210> SEQ ID NO 227
<211> LENGTH: 35
<212> TYPE: PRT
<213> ORGANISM: Artificial sequence
<220> FEATURE:
<223> OTHER INFORMATION: component of appetite suppressant
<220> FEATURE:

-continued

<221> NAME/KEY: MOD_RES
<222> LOCATION: (10)..(10)
<223> OTHER INFORMATION: Lys residue with the C terminus of peptide sequence gamma Glu*-Gly-Ser-Gly-Ser-Gly attached to its epsilon-amino group, wherein gamma Glu* is a gamma Glu residue with an eicosanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 227

Pro Ile Lys Pro Glu Ala Pro Gly Glu Lys Ala Ser Pro Glu Glu Leu
1 5 10 15

Leu His Tyr Tyr Ala Ala Leu Arg His Phe Leu Asn His Val Thr Arg
20 25 30

Gln Arg Tyr
35

<210> SEQ ID NO 228
<211> LENGTH: 40
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (1)..(1)
<223> OTHER INFORMATION: Gly residue with the C terminus of peptide residue gamma Glu* attached to its alpha-amino group, wherein gamma Glu* is a gamma Glu residue with an eicosanedioc acid moiety attached to its alpha-amino group
<220> FEATURE:
<221> NAME/KEY: MOD_RES
<222> LOCATION: (40)..(40)
<223> OTHER INFORMATION: AMIDATION

<400> SEQUENCE: 228

Gly Ser Gly Ser Gly Pro Ile Lys Pro Glu Ala Pro Gly Glu Gly Ala
1 5 10 15

Ser Pro Glu Glu Leu Leu His Tyr Tyr Ala Ala Leu Arg His Phe Leu
20 25 30

Asn His Val Thr Arg Gln Arg Tyr
35 40

<210> SEQ ID NO 229
<211> LENGTH: 41
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (1)..(1)
<223> OTHER INFORMATION: Gly residue with the C terminus of peptide residue gamma Glu* attached to its alpha-amino group, wherein gamma Glu* is a gamma Glu residue with an eicosanedioc acid moiety attached to its alpha-amino group
<220> FEATURE:
<221> NAME/KEY: MOD_RES
<222> LOCATION: (41)..(41)
<223> OTHER INFORMATION: AMIDATION

<400> SEQUENCE: 229

Gly Ser Gly Ser Gly Tyr Pro Ile Lys Pro Glu Ala Pro Gly Glu Gly
1 5 10 15

Ala Ser Pro Glu Glu Leu Leu His Tyr Tyr Ala Ala Leu Arg His Phe
20 25 30

```
Leu Asn His Val Thr Arg Gln Arg Tyr
        35                  40


<210> SEQ ID NO 230
<211> LENGTH: 36
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (1)..(1)
<223> OTHER INFORMATION: Lys residue with the C terminus of peptide
      sequence gamma Glu*-Gly-Ser-Gly-Ser-Gly attached to its epsilon-
      amino group, wherein gamma Glu* is a gamma Glu residue with an
      eicosanedioc acid moiety attached to its alpha-amino group
<220> FEATURE:
<221> NAME/KEY: MOD_RES
<222> LOCATION: (36)..(36)
<223> OTHER INFORMATION: AMIDATION

<400> SEQUENCE: 230

Lys Pro Ile Lys Pro Glu Ala Pro Gly Glu Gly Ala Ser Pro Glu Glu
1               5                   10                  15

Leu Leu His Tyr Tyr Ala Ala Leu Arg His Phe Leu Asn His Val Thr
            20                  25                  30

Arg Gln Arg Tyr
        35


<210> SEQ ID NO 231
<211> LENGTH: 41
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (1)..(1)
<223> OTHER INFORMATION: Lys residue with the C terminus of peptide
      sequence gamma Glu*-Gln  attached to its epsilon-amino group,
      wherein gamma Glu* is a gamma Glu residue with an eicosanedioc
      acid moiety attached to its alpha-amino group
<220> FEATURE:
<221> NAME/KEY: MOD_RES
<222> LOCATION: (41)..(41)
<223> OTHER INFORMATION: AMIDATION

<400> SEQUENCE: 231

Lys Gly Pro Pro Pro Ser Pro Ile Lys Pro Glu Ala Pro Gly Glu Gly
1               5                   10                  15

Ala Ser Pro Glu Glu Leu Leu His Tyr Tyr Ala Ala Leu Arg His Phe
            20                  25                  30

Leu Asn His Val Thr Arg Gln Arg Tyr
        35                  40


<210> SEQ ID NO 232
<211> LENGTH: 41
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (1)..(1)
<223> OTHER INFORMATION: Lys residue with the C terminus of peptide
      sequence gamma Glu*-Gly-Ser  attached to its epsilon-amino group,
      wherein gamma Glu* is a gamma Glu residue with an octadecanedioc
      acid moiety attached to its alpha-amino group
<220> FEATURE:
<221> NAME/KEY: MOD_RES
```

<222> LOCATION: (41)..(41)
<223> OTHER INFORMATION: AMIDATION

<400> SEQUENCE: 232

Lys Gly Pro Pro Pro Ser Pro Ile Lys Pro Glu Ala Pro Gly Glu Gly
1               5                   10                  15

Ala Ser Pro Glu Glu Leu Leu His Tyr Tyr Ala Ala Leu Arg His Phe
            20                  25                  30

Leu Asn His Val Thr Arg Gln Arg Tyr
        35                  40

<210> SEQ ID NO 233
<211> LENGTH: 38
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (1)..(1)
<223> OTHER INFORMATION: Lys residue with the C terminus of peptide sequence gamma Glu*-Gln attached to its epsilon-amino group, wherein gamma Glu* is a gamma Glu residue with an eicosanedioc acid moiety attached to its alpha-amino group
<220> FEATURE:
<221> NAME/KEY: MOD_RES
<222> LOCATION: (38)..(38)
<223> OTHER INFORMATION: AMIDATION

<400> SEQUENCE: 233

Lys Ser Gly Pro Ile Lys Pro Glu Ala Pro Gly Glu Gly Ala Ser Pro
1               5                   10                  15

Glu Glu Leu Leu His Tyr Tyr Ala Ala Leu Arg His Phe Leu Asn His
            20                  25                  30

Val Thr Arg Gln Arg Tyr
        35

<210> SEQ ID NO 234
<211> LENGTH: 38
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (1)..(1)
<223> OTHER INFORMATION: Lys residue with the C terminus of peptide sequence gamma Glu*-Gly-Ser attached to its epsilon-amino group, wherein gamma Glu* is a gamma Glu residue with an octadecanedioc acid moiety attached to its alpha-amino group
<220> FEATURE:
<221> NAME/KEY: MOD_RES
<222> LOCATION: (38)..(38)
<223> OTHER INFORMATION: AMIDATION

<400> SEQUENCE: 234

Lys Ser Gly Pro Ile Lys Pro Glu Ala Pro Gly Glu Gly Ala Ser Pro
1               5                   10                  15

Glu Glu Leu Leu His Tyr Tyr Ala Ala Leu Arg His Phe Leu Asn His
            20                  25                  30

Val Thr Arg Gln Arg Tyr
        35

<210> SEQ ID NO 235
<211> LENGTH: 39
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (1)..(1)
<223> OTHER INFORMATION: Asn residue with an octadecanedioc acid moiety attached to its alpha-amino group
<220> FEATURE:
<221> NAME/KEY: MOD_RES
<222> LOCATION: (39)..(39)
<223> OTHER INFORMATION: AMIDATION

<400> SEQUENCE: 235

Asn Thr Ser Gly Pro Ile Lys Pro Glu Ala Pro Gly Glu Gly Ala Ser
1 5 10 15

Pro Glu Glu Leu Leu His Tyr Tyr Ala Ala Leu Arg His Phe Leu Asn
20 25 30

His Val Thr Arg Gln Arg Tyr
35

<210> SEQ ID NO 236
<211> LENGTH: 37
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (1)..(1)
<223> OTHER INFORMATION: Lys residue with the C terminus of peptide sequence gamma Glu*-Asn-His attached to its epsilon-amino group, wherein gamma Glu* is a gamma Glu residue with an octadecanedioc acid moiety attached to its alpha-amino group
<220> FEATURE:
<221> NAME/KEY: MOD_RES
<222> LOCATION: (37)..(37)
<223> OTHER INFORMATION: AMIDATION

<400> SEQUENCE: 236

Lys Tyr Pro Ile Lys Pro Glu Ala Pro Gly Glu Gly Ala Ser Pro Glu
1 5 10 15

Glu Leu Leu His Tyr Tyr Ala Ala Leu Arg His Phe Leu Asn His Val
20 25 30

Thr Arg Gln Arg Tyr
35

<210> SEQ ID NO 237
<211> LENGTH: 38
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (1)..(1)
<223> OTHER INFORMATION: Lys residue with the C terminus of peptide sequence gamma Glu*-Asn-His attached to its epsilon-amino group, wherein gamma Glu* is a gamma Glu residue with an octadecanedioc acid moiety attached to its alpha-amino group
<220> FEATURE:
<221> NAME/KEY: MOD_RES
<222> LOCATION: (38)..(38)
<223> OTHER INFORMATION: AMIDATION

<400> SEQUENCE: 237

Lys Pro Tyr Pro Ile Lys Pro Glu Ala Pro Gly Glu Gly Ala Ser Pro
1 5 10 15

Glu Glu Leu Leu His Tyr Tyr Ala Ala Leu Arg His Phe Leu Asn His
20 25 30

```
Val Thr Arg Gln Arg Tyr
        35


<210> SEQ ID NO 238
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (9)..(9)
<223> OTHER INFORMATION: Lys residue with the C terminus of peptide
      sequence gamma Glu*-Asn-His  attached to its epsilon-amino group,
      wherein gamma Glu* is a gamma Glu residue with an octadecanedioc
      acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 238

Pro Ile Lys Pro Glu Ala Pro Gly Lys Gly Ala Ser Pro Glu Glu Leu
1               5                   10                  15

Leu His Tyr Tyr Ala Ala Leu Arg His Phe Leu Asn His Val Thr Arg
            20                  25                  30

Gln Arg Tyr
        35


<210> SEQ ID NO 239
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (8)..(8)
<223> OTHER INFORMATION: Lys residue with the C terminus of peptide
      sequence gamma Glu*-Asn-His  attached to its epsilon-amino group,
      wherein gamma Glu* is a gamma Glu residue with an octadecanedioc
      acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 239

Pro Ile Lys Pro Glu Ala Pro Lys Glu Gly Ala Ser Pro Glu Glu Leu
1               5                   10                  15

Leu His Tyr Tyr Ala Ala Leu Arg His Phe Leu Asn His Val Thr Arg
            20                  25                  30

Gln Arg Tyr
        35


<210> SEQ ID NO 240
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (6)..(6)
<223> OTHER INFORMATION: Lys residue with the C terminus of peptide
      sequence gamma Glu*-Asn-His  attached to its epsilon-amino group,
      wherein gamma Glu* is a gamma Glu residue with an octadecanedioc
      acid moiety attached to its alpha-amino group
<220> FEATURE:
```

<221> NAME/KEY: MOD_RES
<222> LOCATION: (35)..(35)
<223> OTHER INFORMATION: AMIDATION

<400> SEQUENCE: 240

Pro Ile Lys Pro Glu Lys Pro Gly Glu Gly Ala Ser Pro Glu Glu Leu
1 5 10 15

Leu His Tyr Tyr Ala Ala Leu Arg His Phe Leu Asn His Val Thr Arg
20 25 30

Gln Arg Tyr
35

<210> SEQ ID NO 241
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (9)..(9)
<223> OTHER INFORMATION: Lys residue with the C terminus of peptide sequence gamma Glu*-Ser-Gly-Thr attached to its epsilon-amino group, wherein gamma Glu* is a gamma Glu residue with an eicosanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 241

Pro Ile Lys Pro Glu Ala Pro Gly Lys Gly Ala Ser Pro Glu Glu Leu
1 5 10 15

Leu His Tyr Tyr Ala Ala Leu Arg His Phe Leu Asn His Val Thr Arg
20 25 30

Gln Arg Tyr
35

<210> SEQ ID NO 242
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (6)..(6)
<223> OTHER INFORMATION: Lys residue with the C terminus of peptide sequence gamma Glu*-Ser-Gly-Thr attached to its epsilon-amino group, wherein gamma Glu* is a gamma Glu residue with an eicosanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 242

Pro Ile Lys Pro Glu Lys Pro Gly Glu Gly Ala Ser Pro Glu Glu Leu
1 5 10 15

Leu His Tyr Tyr Ala Ala Leu Arg His Phe Leu Asn His Val Thr Arg
20 25 30

Gln Arg Tyr
35

<210> SEQ ID NO 243
<211> LENGTH: 35
<212> TYPE: PRT

<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (9)..(9)
<223> OTHER INFORMATION: Lys residue with the C terminus of peptide sequence gamma Glu*-Thr-Gly-Ser-Gly attached to its epsilon-amino group, wherein gamma Glu* is a gamma Glu residue with an octadecanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 243

```
Pro Ile Lys Pro Glu Ala Pro Gly Lys Gly Ala Ser Pro Glu Glu Leu
1               5                   10                  15

Leu His Tyr Tyr Ala Ala Leu Arg His Phe Leu Asn His Val Thr Arg
            20                  25                  30

Gln Arg Tyr
        35
```

<210> SEQ ID NO 244
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (6)..(6)
<223> OTHER INFORMATION: Lys residue with the C terminus of peptide sequence gamma Glu*-Ser-Gly-Thr attached to its epsilon-amino group, wherein gamma Glu* is a gamma Glu residue with an octadecanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 244

```
Pro Ile Lys Pro Glu Lys Pro Gly Glu Gly Ala Ser Pro Glu Glu Leu
1               5                   10                  15

Leu His Tyr Tyr Ala Ala Leu Arg His Phe Leu Asn His Val Thr Arg
            20                  25                  30

Gln Arg Tyr
        35
```

<210> SEQ ID NO 245
<211> LENGTH: 36
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (1)..(1)
<223> OTHER INFORMATION: Lys residue with the C terminus of peptide sequence gamma Glu*-Asn-His attached to its epsilon-amino group, wherein gamma Glu* is a gamma Glu residue with an octadecanedioc acid moiety attached to its alpha-amino group
<220> FEATURE:
<221> NAME/KEY: MOD_RES
<222> LOCATION: (36)..(36)
<223> OTHER INFORMATION: AMIDATION

<400> SEQUENCE: 245

```
Lys Pro Ile Lys Pro Glu Ala Pro Gly Glu Gly Ala Ser Pro Glu Glu
1               5                   10                  15
```

Leu Leu His Tyr Tyr Ala Ala Leu Arg His Phe Leu Asn His Val Thr
20 25 30

Arg Gln Arg Tyr
35

<210> SEQ ID NO 246
<211> LENGTH: 36
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (1)..(1)
<223> OTHER INFORMATION: Lys residue with the C terminus of peptide sequence gamma Glu*-Ser-Gly-Thr attached to its epsilon-amino group, wherein gamma Glu* is a gamma Glu residue with an octadecanedioc acid moiety attached to its alpha-amino group
<220> FEATURE:
<221> NAME/KEY: MOD_RES
<222> LOCATION: (36)..(36)
<223> OTHER INFORMATION: AMIDATION

<400> SEQUENCE: 246

Lys Pro Ile Lys Pro Glu Ala Pro Gly Glu Gly Ala Ser Pro Glu Glu
1 5 10 15

Leu Leu His Tyr Tyr Ala Ala Leu Arg His Phe Leu Asn His Val Thr
20 25 30

Arg Gln Arg Tyr
35

<210> SEQ ID NO 247
<211> LENGTH: 36
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (1)..(1)
<223> OTHER INFORMATION: Lys residue with the C terminus of peptide sequence gamma Glu*-Ser-Gly-Thr attached to its epsilon-amino group, wherein gamma Glu* is a gamma Glu residue with an eicosanedioc acid moiety attached to its alpha-amino group
<220> FEATURE:
<221> NAME/KEY: MOD_RES
<222> LOCATION: (36)..(36)
<223> OTHER INFORMATION: AMIDATION

<400> SEQUENCE: 247

Lys Pro Ile Lys Pro Glu Ala Pro Gly Glu Gly Ala Ser Pro Glu Glu
1 5 10 15

Leu Leu His Tyr Tyr Ala Ala Leu Arg His Phe Leu Asn His Val Thr
20 25 30

Arg Gln Arg Tyr
35

<210> SEQ ID NO 248
<211> LENGTH: 37
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (1)..(1)
<223> OTHER INFORMATION: Lys residue with the C terminus of peptide sequence Glu*-Ser-Gly-Thr attached to its epsilon-amino group, wherein Glu* is a Glu residue with an octadecanedioc acid moiety attached to its alpha-amino group
<220> FEATURE:
<221> NAME/KEY: MOD_RES
<222> LOCATION: (37)..(37)
<223> OTHER INFORMATION: AMIDATION

<400> SEQUENCE: 248

Lys Tyr Pro Ile Lys Pro Glu Ala Pro Gly Glu Gly Ala Ser Pro Glu
1               5                   10                  15

Glu Leu Leu His Tyr Tyr Ala Ala Leu Arg His Phe Leu Asn His Val
            20                  25                  30

Thr Arg Gln Arg Tyr
        35

<210> SEQ ID NO 249
<211> LENGTH: 37
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (1)..(1)
<223> OTHER INFORMATION: Lys residue with the C terminus of peptide sequence Glu*-Ser-Gly-Thr attached to its epsilon-amino group, wherein Glu* is a Glu residue with an eicosanedioc acid moiety attached to its alpha-amino group
<220> FEATURE:
<221> NAME/KEY: MOD_RES
<222> LOCATION: (37)..(37)
<223> OTHER INFORMATION: AMIDATION

<400> SEQUENCE: 249

Lys Tyr Pro Ile Lys Pro Glu Ala Pro Gly Glu Gly Ala Ser Pro Glu
1               5                   10                  15

Glu Leu Leu His Tyr Tyr Ala Ala Leu Arg His Phe Leu Asn His Val
            20                  25                  30

Thr Arg Gln Arg Tyr
        35

<210> SEQ ID NO 250
<211> LENGTH: 37
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (1)..(1)
<223> OTHER INFORMATION: gamma Glu residue with the C terminus of peptide residue Lys* attached to its alpha-amino group, wherein Lys* is a Lys residue with an octadecanedioc acid moiety attached to its epsilon-amino group
<220> FEATURE:
<221> NAME/KEY: MOD_RES
<222> LOCATION: (37)..(37)
<223> OTHER INFORMATION: AMIDATION

<400> SEQUENCE: 250

Glu Tyr Pro Ile Lys Pro Glu Ala Pro Gly Glu Gly Ala Ser Pro Glu
1               5                   10                  15

Glu Leu Leu His Tyr Tyr Ala Ala Leu Arg His Phe Leu Asn His Val
            20                  25                  30

Thr Arg Gln Arg Tyr
        35

```
<210> SEQ ID NO 251
<211> LENGTH: 37
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (1)..(1)
<223> OTHER INFORMATION: gamma Glu residue with the C terminus of
      peptide residue Lys* attached to its alpha-amino group, wherein
      Lys* is a Lys residue with an eicosanedioc acid moiety attached to
      its epsilon-amino group
<220> FEATURE:
<221> NAME/KEY: MOD_RES
<222> LOCATION: (37)..(37)
<223> OTHER INFORMATION: AMIDATION

<400> SEQUENCE: 251

Glu Tyr Pro Ile Lys Pro Glu Ala Pro Gly Glu Gly Ala Ser Pro Glu
1               5                   10                  15

Glu Leu Leu His Tyr Tyr Ala Ala Leu Arg His Phe Leu Asn His Val
            20                  25                  30

Thr Arg Gln Arg Tyr
        35


<210> SEQ ID NO 252
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (9)..(9)
<223> OTHER INFORMATION: Lys residue with the C terminus of peptide
      sequence gamma Glu*-Asn-His attached to its epsilon-amino group,
      wherein gamma Glu* is a gamma Glu residue with an eicosanedioc
      acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 252

Pro Ile Lys Pro Glu Ala Pro Gly Lys Gly Ala Ser Pro Glu Glu Leu
1               5                   10                  15

Leu His Tyr Tyr Ala Ala Leu Arg His Phe Leu Asn His Val Thr Arg
            20                  25                  30

Gln Arg Tyr
        35


<210> SEQ ID NO 253
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (9)..(9)
<223> OTHER INFORMATION: Lys residue with the C terminus of peptide
      sequence gamma Glu*-Asn-His attached to its epsilon-amino group,
      wherein gamma Glu* is a gamma Glu residue with a hexadecanedioc
      acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 253
```

```
Pro Ile Lys Pro Glu Ala Pro Gly Lys Gly Ala Ser Pro Glu Glu Leu
1               5                   10                  15

Leu His Tyr Tyr Ala Ala Leu Arg His Phe Leu Asn His Val Thr Arg
            20                  25                  30

Gln Arg Tyr
        35


<210> SEQ ID NO 254
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (9)..(9)
<223> OTHER INFORMATION: Lys residue with the C terminus of peptide
      sequence gamma Glu*-Gly-Ser-Gly attached to its epsilon-amino
      group, wherein gamma Glu* is a gamma Glu residue with an
      octadecanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 254

Pro Ile Lys Pro Glu Ala Pro Gly Lys Gly Ala Ser Pro Glu Glu Leu
1               5                   10                  15

Leu His Tyr Tyr Ala Ala Leu Arg His Phe Leu Asn His Val Thr Arg
            20                  25                  30

Gln Arg Tyr
        35


<210> SEQ ID NO 255
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (9)..(9)
<223> OTHER INFORMATION: Lys residue with the C terminus of peptide
      sequence gamma Glu*-Thr-Gly-Ser-Gly attached to its epsilon-amino
      group, wherein gamma Glu* is a gamma Glu residue with a
      hexadecanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 255

Pro Ile Lys Pro Glu Ala Pro Gly Lys Gly Ala Ser Pro Glu Glu Leu
1               5                   10                  15

Leu His Tyr Tyr Ala Ala Leu Arg His Phe Leu Asn His Val Thr Arg
            20                  25                  30

Gln Arg Tyr
        35


<210> SEQ ID NO 256
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
```

<222> LOCATION: (9)..(9)
<223> OTHER INFORMATION: Lys residue with the C terminus of peptide sequence gamma Glu*-Thr-Gly-Ser-Gly attached to its epsilon-amino group, wherein gamma Glu* is a gamma Glu residue with an eicosanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 256

```
Pro Ile Lys Pro Glu Ala Pro Gly Lys Gly Ala Ser Pro Glu Glu Leu
1               5                   10                  15

Leu His Tyr Tyr Ala Ala Leu Arg His Phe Leu Asn His Val Thr Arg
            20                  25                  30

Gln Arg Tyr
        35
```

<210> SEQ ID NO 257
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (9)..(9)
<223> OTHER INFORMATION: Lys residue with the C terminus of peptide sequence Glu*-Gly-Ser-Gly attached to its epsilon-amino group, wherein Glu* is a Glu residue with a hexadecanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 257

```
Pro Ile Lys Pro Glu Ala Pro Gly Lys Gly Ala Ser Pro Glu Glu Leu
1               5                   10                  15

Leu His Tyr Tyr Ala Ala Leu Arg His Phe Leu Asn His Val Thr Arg
            20                  25                  30

Gln Arg Tyr
        35
```

<210> SEQ ID NO 258
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (9)..(9)
<223> OTHER INFORMATION: Lys residue with the C terminus of peptide sequence Glu*-Gly-Ser-Gly attached to its epsilon-amino group, wherein Glu* is a Glu residue with an eicosanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 258

```
Pro Ile Lys Pro Glu Ala Pro Gly Lys Gly Ala Ser Pro Glu Glu Leu
1               5                   10                  15

Leu His Tyr Tyr Ala Ala Leu Arg His Phe Leu Asn His Val Thr Arg
            20                  25                  30

Gln Arg Tyr
```

35

<210> SEQ ID NO 259
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (9)..(9)
<223> OTHER INFORMATION: Lys residue with the C terminus of peptide sequence gamma Glu*-Gly-Ser-Gly attached to its epsilon-amino group, wherein gamma Glu* is a gamma Glu residue with a hexadecanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 259

```
Pro Ile Lys Pro Glu Ala Pro Gly Lys Gly Ala Ser Pro Glu Glu Leu
1               5                   10                  15

Leu His Tyr Tyr Ala Ala Leu Arg His Phe Leu Asn His Val Thr Arg
            20                  25                  30

Gln Arg Tyr
        35
```

<210> SEQ ID NO 260
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (9)..(9)
<223> OTHER INFORMATION: Lys residue with the C terminus of peptide sequence gamma Glu*-Gly-Ser-Gly attached to its epsilon-amino group, wherein gamma Glu* is a gamma Glu residue with an eicosanedioic acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 260

```
Pro Ile Lys Pro Glu Ala Pro Gly Lys Gly Ala Ser Pro Glu Glu Leu
1               5                   10                  15

Leu His Tyr Tyr Ala Ala Leu Arg His Phe Leu Asn His Val Thr Arg
            20                  25                  30

Gln Arg Tyr
        35
```

<210> SEQ ID NO 261
<211> LENGTH: 36
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (1)..(1)
<223> OTHER INFORMATION: Lys residue with the C terminus of peptide sequence Glu*-Gly-Ser-Gly attached to its epsilon-amino group, wherein Glu* is a Glu residue with an octadecanedioc acid moiety attached to its alpha-amino group
<220> FEATURE:
<221> NAME/KEY: MOD_RES
<222> LOCATION: (35)..(35)

<223> OTHER INFORMATION: AMIDATION

<400> SEQUENCE: 261

Lys Pro Ile Lys Pro Glu Ala Pro Gly Glu Gly Ala Ser Pro Glu Glu
1               5                   10                  15

Leu Leu His Tyr Tyr Ala Ala Leu Arg His Phe Leu Asn His Val Thr
            20                  25                  30

Arg Gln Arg Tyr
        35

<210> SEQ ID NO 262
<211> LENGTH: 36
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (1)..(1)
<223> OTHER INFORMATION: Lys residue with the C terminus of peptide sequence Glu*-Gly-Ser-Gly attached to its epsilon-amino group, wherein Glu* is a Glu residue with an eicosanedioc acid moiety attached to its alpha-amino group
<220> FEATURE:
<221> NAME/KEY: MOD_RES
<222> LOCATION: (36)..(36)
<223> OTHER INFORMATION: AMIDATION

<400> SEQUENCE: 262

Lys Pro Ile Lys Pro Glu Ala Pro Gly Glu Gly Ala Ser Pro Glu Glu
1               5                   10                  15

Leu Leu His Tyr Tyr Ala Ala Leu Arg His Phe Leu Asn His Val Thr
            20                  25                  30

Arg Gln Arg Tyr
        35

<210> SEQ ID NO 263
<211> LENGTH: 36
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (1)..(1)
<223> OTHER INFORMATION: Lys residue with the C terminus of peptide sequence Glu*-Gly-Ser-Gly attached to its epsilon-amino group, wherein Glu* is a Glu residue with a hexadecanedioc acid moiety attached to its alpha-amino group
<220> FEATURE:
<221> NAME/KEY: MOD_RES
<222> LOCATION: (36)..(36)
<223> OTHER INFORMATION: AMIDATION

<400> SEQUENCE: 263

Lys Pro Ile Lys Pro Glu Ala Pro Gly Glu Gly Ala Ser Pro Glu Glu
1               5                   10                  15

Ile Leu Lys Tyr Tyr Ile Glu Leu Arg His Phe Leu Asn His Leu Thr
            20                  25                  30

Arg Gln Arg Tyr
        35

<210> SEQ ID NO 264
<211> LENGTH: 36
<212> TYPE: PRT
<213> ORGANISM: Artificial sequence
<220> FEATURE:

<223> OTHER INFORMATION: component of appetite suppressant
<220> FEATURE:
<221> NAME/KEY: MOD_RES
<222> LOCATION: (1)..(1)
<223> OTHER INFORMATION: Lys residue with the C terminus of peptide sequence Glu*-Gly-Ser-Gly attached to its epsilon-amino group, wherein Glu* is a Glu residue with an eicosanedioc acid moiety attached to its alpha-amino group
<220> FEATURE:
<221> NAME/KEY: MOD_RES
<222> LOCATION: (36)..(36)
<223> OTHER INFORMATION: AMIDATION

<400> SEQUENCE: 264

```
Lys Pro Ile Lys Pro Glu Ala Pro Gly Glu Gly Ala Ser Pro Glu Glu
1               5                   10                  15

Ile Leu Lys Tyr Tyr Ile Glu Leu Arg His Phe Leu Asn His Leu Thr
            20                  25                  30

Arg Gln Arg Tyr
        35
```

<210> SEQ ID NO 265
<211> LENGTH: 37
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (1)..(1)
<223> OTHER INFORMATION: gamma Glu residue with the C terminus of peptide sequence Gly*-Ser-gamma Lys attached to its alpha-amino group, wherein Gly* is a Gly residue with an octadecanedioc acid moiety attached to its alpha-amino group
<220> FEATURE:
<221> NAME/KEY: MOD_RES
<222> LOCATION: (37)..(37)
<223> OTHER INFORMATION: AMIDATION

<400> SEQUENCE: 265

```
Glu Tyr Pro Ile Lys Pro Glu Ala Pro Gly Glu Gly Ala Ser Pro Glu
1               5                   10                  15

Glu Ile Leu Lys Tyr Tyr Ile Glu Leu Arg His Phe Leu Asn His Leu
            20                  25                  30

Thr Arg Gln Arg Tyr
        35
```

<210> SEQ ID NO 266
<211> LENGTH: 36
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (1)..(1)
<223> OTHER INFORMATION: Lys residue with the C terminus of peptide sequence gamma Glu*-Gly-Ser-Gly attached to its epsilon-amino group, wherein gamma Glu* is a gamma Glu residue with an octadecanedioc acid moiety attached to its alpha-amino group
<220> FEATURE:
<221> NAME/KEY: MOD_RES
<222> LOCATION: (36)..(36)
<223> OTHER INFORMATION: AMIDATION

<400> SEQUENCE: 266

```
Lys Pro Ile Lys Pro Glu Ala Pro Gly Glu Gly Ala Ser Pro Glu Glu
1               5                   10                  15

Ile Leu Lys Tyr Tyr Ile Glu Leu Arg His Phe Leu Asn His Leu Thr
```

```
            20                  25                  30

Arg Gln Arg Tyr
        35


<210> SEQ ID NO 267
<211> LENGTH: 36
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (1)..(1)
<223> OTHER INFORMATION: Lys residue with the C terminus of peptide
      sequence gamma Glu*-Gln  attached to its epsilon-amino group,
      wherein gamma Glu* is a gamma Glu residue with an octadecanedioc
      acid moiety attached to its alpha-amino group
<220> FEATURE:
<221> NAME/KEY: MOD_RES
<222> LOCATION: (36)..(36)
<223> OTHER INFORMATION: AMIDATION

<400> SEQUENCE: 267

Lys Pro Ile Lys Pro Glu Ala Pro Gly Glu Gly Ala Ser Pro Glu Glu
1               5                   10                  15

Ile Leu Lys Tyr Tyr Ile Glu Leu Arg His Phe Leu Asn His Leu Thr
            20                  25                  30

Arg Gln Arg Tyr
        35


<210> SEQ ID NO 268
<211> LENGTH: 36
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (1)..(1)
<223> OTHER INFORMATION: Lys residue with the C terminus of peptide
      sequence gamma Glu*-Asn-His  attached to its epsilon-amino group,
      wherein gamma Glu* is a gamma Glu residue with an octadecanedioc
      acid moiety attached to its alpha-amino group
<220> FEATURE:
<221> NAME/KEY: MOD_RES
<222> LOCATION: (36)..(36)
<223> OTHER INFORMATION: AMIDATION

<400> SEQUENCE: 268

Lys Pro Ile Lys Pro Glu Ala Pro Gly Glu Gly Ala Ser Pro Glu Glu
1               5                   10                  15

Ile Leu Lys Tyr Tyr Ile Glu Leu Arg His Phe Leu Asn His Leu Thr
            20                  25                  30

Arg Gln Arg Tyr
        35


<210> SEQ ID NO 269
<211> LENGTH: 36
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (1)..(1)
<223> OTHER INFORMATION: Lys residue with the C terminus of peptide
      sequence gamma Glu*-Gly-Ser  attached to its epsilon-amino group,
      wherein gamma Glu* is a gamma Glu residue with an octadecanedioc
      acid moiety attached to its alpha-amino group
```

<220> FEATURE:
<221> NAME/KEY: MOD_RES
<222> LOCATION: (36)..(36)
<223> OTHER INFORMATION: AMIDATION

<400> SEQUENCE: 269

Lys Pro Ile Lys Pro Glu Ala Pro Gly Glu Gly Ala Ser Pro Glu Glu
1 5 10 15

Ile Leu Lys Tyr Tyr Ile Glu Leu Arg His Phe Leu Asn His Leu Thr
20 25 30

Arg Gln Arg Tyr
35

<210> SEQ ID NO 270
<211> LENGTH: 37
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (1)..(1)
<223> OTHER INFORMATION: Lys residue with the C terminus of peptide sequence gamma Glu*-Ser-Gly-Thr attached to its epsilon-amino group, wherein gamma Glu* is a gamma Glu residue with an eicosanedioc acid moiety attached to its alpha-amino group
<220> FEATURE:
<221> NAME/KEY: MOD_RES
<222> LOCATION: (37)..(37)
<223> OTHER INFORMATION: AMIDATION

<400> SEQUENCE: 270

Lys Tyr Pro Ile Lys Pro Glu Ala Pro Gly Glu Gly Ala Ser Pro Glu
1 5 10 15

Glu Ile Leu Lys Tyr Tyr Ile Glu Leu Arg His Phe Leu Asn His Leu
20 25 30

Thr Arg Gln Arg Tyr
35

<210> SEQ ID NO 271
<211> LENGTH: 36
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (1)..(1)
<223> OTHER INFORMATION: Lys residue with the C terminus of peptide sequence Glu*-Gly-Ser-Gly attached to its epsilon-amino group, wherein Glu* is a Glu residue with an octadecanedioc acid moiety attached to its alpha-amino group
<220> FEATURE:
<221> NAME/KEY: MOD_RES
<222> LOCATION: (36)..(36)
<223> OTHER INFORMATION: AMIDATION

<400> SEQUENCE: 271

Lys Pro Ile Lys Pro Glu Ala Pro Gly Glu Gly Ala Ser Pro Glu Glu
1 5 10 15

Ile Leu Lys Tyr Tyr Ile Glu Leu Arg His Phe Leu Asn His Leu Thr
20 25 30

Arg Gln Arg Tyr
35

<210> SEQ ID NO 272
<211> LENGTH: 36

<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (1)..(1)
<223> OTHER INFORMATION: Lys residue with the C terminus of peptide sequence Glu*-Gly-Ser-Gly attached to its epsilon-amino group, wherein Glu* is a Glu residue with an octadecanedioc acid moiety attached to its alpha-amino group
<220> FEATURE:
<221> NAME/KEY: MOD_RES
<222> LOCATION: (36)..(36)
<223> OTHER INFORMATION: AMIDATION

<400> SEQUENCE: 272

```
Lys Pro Ile Lys Pro Glu Ala Pro Gly Glu Gly Ala Ser Pro Glu Glu
1               5                   10                  15

Ile Leu Lys Tyr Tyr Ile Glu Leu Arg His Phe Leu Asn His Leu Thr
            20                  25                  30

Arg Gln Arg Tyr
        35
```

<210> SEQ ID NO 273
<211> LENGTH: 36
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (1)..(1)
<223> OTHER INFORMATION: Lys residue with the C terminus of peptide sequence Glu*-Gly-Ser-Gly attached to its epsilon-amino group, wherein Glu* is a Glu residue with an octadecanedioc acid moiety attached to its alpha-amino group
<220> FEATURE:
<221> NAME/KEY: MOD_RES
<222> LOCATION: (36)..(36)
<223> OTHER INFORMATION: AMIDATION

<400> SEQUENCE: 273

```
Lys Pro Ile Lys Pro Glu Ala Pro Gly Glu Asn Ala Ser Pro Glu Glu
1               5                   10                  15

Ile Leu Lys Tyr Tyr Ile Glu Leu Arg His Phe Leu Asn His Leu Thr
            20                  25                  30

Arg Gln Arg Tyr
        35
```

<210> SEQ ID NO 274
<211> LENGTH: 36
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (1)..(1)
<223> OTHER INFORMATION: Lys residue with the C terminus of peptide sequence Glu*-Gly-Ser-Gly attached to its epsilon-amino group, wherein Glu* is a Glu residue with an octadecanedioc acid moiety attached to its alpha-amino group
<220> FEATURE:
<221> NAME/KEY: MOD_RES
<222> LOCATION: (36)..(36)
<223> OTHER INFORMATION: AMIDATION

<400> SEQUENCE: 274

```
Lys Pro Ile Lys Pro Glu Ala Pro Gly Glu Gly Ala Ser Pro Glu Glu
```

1 5 10 15

Ile Leu His Tyr Tyr Ile Glu Leu Arg His Phe Leu Asn His Leu Thr
20 25 30

Arg Gln Arg Tyr
35

<210> SEQ ID NO 275
<211> LENGTH: 36
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (1)..(1)
<223> OTHER INFORMATION: Lys residue with the C terminus of peptide sequence Glu*-Gly-Ser-Gly attached to its epsilon-amino group, wherein Glu* is a Glu residue with an octadecanedioc acid moiety attached to its alpha-amino group
<220> FEATURE:
<221> NAME/KEY: MOD_RES
<222> LOCATION: (36)..(36)
<223> OTHER INFORMATION: AMIDATION

<400> SEQUENCE: 275

Lys Pro Ile Lys Pro Glu Ala Pro Gly Glu Gly Ala Ser Pro Glu Glu
1 5 10 15

Ile Leu Lys Tyr Tyr Ala Ala Leu Arg His Phe Leu Asn His Leu Thr
20 25 30

Arg Gln Arg Tyr
35

<210> SEQ ID NO 276
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (9)..(9)
<223> OTHER INFORMATION: Lys residue with the C terminus of peptide sequence Glu*-Gly-Ser-Gly attached to its epsilon-amino group, wherein Glu* is a Glu residue with a hexadecanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 276

Pro Ile Lys Pro Glu Ala Pro Gly Lys Gly Ala Ser Pro Glu Glu Leu
1 5 10 15

Leu His Tyr Tyr Ala Ala Leu Arg His Phe Leu Asn His Val Thr Arg
20 25 30

Gln Arg Tyr
35

<210> SEQ ID NO 277
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (9)..(9)
<223> OTHER INFORMATION: Lys residue with the C terminus of peptide -continued

```
      sequence Glu*-Gly-Ser-Gly attached to its epsilon-amino group,
      wherein Glu* is a Glu residue with a hexadecanedioc acid moiety
      attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 277

Pro Ile Lys Pro Glu Ala Pro Gly Lys Gly Ala Ser Pro Glu Glu Leu
1               5                   10                  15

Leu His Tyr Tyr Ala Ala Leu Arg His Phe Leu Asn His Leu Thr Arg
            20                  25                  30

Gln Arg Tyr
        35


<210> SEQ ID NO 278
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (9)..(9)
<223> OTHER INFORMATION: Lys residue with the C terminus of peptide
      sequence gamma Glu*-Gly-Ser-Gly attached to its epsilon-amino
      group, wherein gamma Glu* is a gamma Glu residue with an
      octadecanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 278

Pro Ile Lys Pro Glu Ala Pro Gly Lys Gly Ala Ser Pro Glu Glu Leu
1               5                   10                  15

Leu His Tyr Tyr Ala Ala Leu Arg His Phe Leu Asn His Val Thr Arg
            20                  25                  30

Gln Arg Tyr
        35


<210> SEQ ID NO 279
<211> LENGTH: 35
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (9)..(9)
<223> OTHER INFORMATION: Lys residue with the C terminus of peptide
      sequence gamma Glu*-Gly-Ser-Gly attached to its epsilon-amino
      group, wherein gamma Glu* is a gamma Glu residue with an
      octadecanedioc acid moiety attached to its alpha-amino group
<220> FEATURE:
<221> NAME/KEY: MOD_RES
<222> LOCATION: (35)..(35)
<223> OTHER INFORMATION: AMIDATION

<400> SEQUENCE: 279

Pro Ile Lys Pro Glu Ala Pro Gly Lys Gly Ala Ser Pro Glu Glu Leu
1               5                   10                  15

Leu His Tyr Tyr Ala Ala Leu Arg His Phe Leu Asn His Leu Thr Arg
            20                  25                  30

Gln Arg Tyr
        35
```

<210> SEQ ID NO 280
<211> LENGTH: 36
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (1)..(1)
<223> OTHER INFORMATION: Lys residue with the C terminus of peptide sequence Glu*-Gly-Ser-Gly attached to its epsilon-amino group, wherein Glu* is a Glu residue with an octadecanedioc acid moiety attached to its alpha-amino group
<220> FEATURE:
<221> NAME/KEY: MOD_RES
<222> LOCATION: (36)..(36)
<223> OTHER INFORMATION: AMIDATION

<400> SEQUENCE: 280

```
Lys Pro Ile Lys Pro Glu Ala Pro Gly Glu Gly Ala Ser Pro Glu Glu
1               5                   10                  15

Ile Leu Lys Tyr Tyr Ile Glu Leu Arg His Phe Leu Asn His Leu Thr
            20                  25                  30

Arg Gln Arg Tyr
        35
```

<210> SEQ ID NO 281
<211> LENGTH: 33
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (9)..(9)
<223> OTHER INFORMATION: Lys residue with the C terminus of peptide sequence gamma Glu*-Gly-Ser-Gly attached to its epsilon-amino group, wherein gamma Glu* is a gamma Glu residue with an octadecanedioc acid moiety attached to its alpha-amino group

<400> SEQUENCE: 281

```
Pro Ile Lys Pro Glu Ala Pro Gly Lys Gly Ala Ser Pro Glu Glu Leu
1               5                   10                  15

Leu His Tyr Tyr Ala Ala Leu Arg His Phe Leu Asn His Val Thr Arg
            20                  25                  30

Gln
```

<210> SEQ ID NO 282
<211> LENGTH: 33
<212> TYPE: PRT
<213> ORGANISM: Artificial sequence
<220> FEATURE:
<223> OTHER INFORMATION: component of appetite suppressant
<220> FEATURE:
<221> NAME/KEY: MOD_RES
<222> LOCATION: (9)..(9)
<223> OTHER INFORMATION: Lys residue with the C terminus of peptide sequence gamma Glu*-Gly-Ser-Gly attached to its epsilon-amino group, wherein gamma Glu* is a gamma Glu residue with an eicosanedioic acid moiety attached to its alpha-amino group -continued

```
<400> SEQUENCE: 282

Pro Ile Lys Pro Glu Ala Pro Gly Lys Gly Ala Ser Pro Glu Glu Leu
1               5                   10                  15

Leu His Tyr Tyr Ala Ala Leu Arg His Phe Leu Asn His Val Thr Arg
            20                  25                  30

Gln
```